(12) United States Patent
Engblom et al.

(10) Patent No.: US 11,692,218 B2
(45) Date of Patent: Jul. 4, 2023

(54) SPATIAL TRANSCRIPTOMICS FOR ANTIGEN-RECEPTORS

(71) Applicant: 10x Genomics, Inc., Pleasanton, CA (US)

(72) Inventors: Camilla Engblom, Solna (SE); Kim Thrane, Pleasanton, CA (US); Jeffrey Mold, Pleasanton, CA (US); Jonas Frisen, Stockholm (SE); Joakim Lundeberg, Stockholm (SE); Qirong Lin, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

(21) Appl. No.: 17/552,135

(22) Filed: Dec. 15, 2021

(65) Prior Publication Data

US 2022/0106633 A1    Apr. 7, 2022

Related U.S. Application Data

(63) Continuation of application No. PCT/US2021/035242, filed on Jun. 1, 2021.

(60) Provisional application No. 63/033,568, filed on Jun. 2, 2020.

(51) Int. Cl.
  *C12Q 1/6837* (2018.01)
  *C12Q 1/6881* (2018.01)
  *C12Q 1/6869* (2018.01)

(52) U.S. Cl.
  CPC ......... *C12Q 1/6837* (2013.01); *C12Q 1/6869* (2013.01); *C12Q 1/6881* (2013.01)

(58) Field of Classification Search
  CPC .............. C12Q 1/6869; C12Q 1/6881
  See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 5,002,882 A | 3/1991 | Lunnen |
| 5,130,238 A | 7/1992 | Malek |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |

(Continued)

FOREIGN PATENT DOCUMENTS

| | | |
|---|---|---|
| CN | 1680604 | 10/2005 |
| CN | 108676814 | 10/2018 |

(Continued)

OTHER PUBLICATIONS

Salmen et al. BioRxiv 358937; doi: https://doi.org/10.1101/358937. (Year: 2018).*

(Continued)

*Primary Examiner* — Joseph G. Dauner
(74) *Attorney, Agent, or Firm* — Fish & Richardson P.C.

(57) ABSTRACT

Provided herein are methods, compositions, and kits for the detection of immune cell clonotypes and immune cell analytes within a biological sample.

27 Claims, 36 Drawing Sheets

Specification includes a Sequence Listing.

(56) References Cited

U.S. PATENT DOCUMENTS

| | | |
|---|---|---|
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 6,013,440 A | 1/2000 | Lipshutz |
| 6,027,889 A | 2/2000 | Barany et al. |
| 6,060,240 A | 5/2000 | Kamb et al. |
| 6,130,073 A | 10/2000 | Eggerding |
| 6,143,496 A | 11/2000 | Brown |
| 6,153,389 A | 11/2000 | Haarer |
| 6,165,714 A | 12/2000 | Lane et al. |
| 6,210,891 B1 | 4/2001 | Nyren |
| 6,210,894 B1 | 4/2001 | Brennan |
| 6,214,587 B1 | 4/2001 | Dattagupta |
| 6,258,568 B1 | 7/2001 | Nyren |
| 6,266,459 B1 | 7/2001 | Walt |
| 6,274,320 B1 | 8/2001 | Rothberg |
| 6,300,063 B1 | 10/2001 | Lipshutz et al. |
| 6,309,824 B1 | 10/2001 | Drmanac |
| 6,344,316 B1 | 2/2002 | Lockhart |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,544,732 B1 | 4/2003 | Chee |
| 6,620,584 B1 | 9/2003 | Chee |
| 6,632,641 B1 | 10/2003 | Brennan |
| 6,699,710 B1 | 3/2004 | Kononen |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,859,570 B2 | 2/2005 | Walt |
| 6,864,052 B1 | 3/2005 | Drmanac |
| 6,878,515 B1 | 4/2005 | Landegren |
| 6,897,023 B2 | 5/2005 | Fu |
| 6,942,968 B1 | 9/2005 | Dickinson et al. |
| 6,969,589 B2 | 11/2005 | Patil |
| 7,057,026 B2 | 6/2006 | Barnes |
| 7,115,400 B1 | 10/2006 | Adessi |
| 7,118,883 B2 | 10/2006 | Inoue |
| 7,166,431 B2 | 1/2007 | Chee et al. |
| 7,211,414 B2 | 5/2007 | Hardin |
| 7,255,994 B2 | 8/2007 | Lao |
| 7,258,976 B2 | 8/2007 | Mitsuhashi |
| 7,297,518 B2 | 11/2007 | Quake |
| 7,329,492 B2 | 2/2008 | Hardin |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,537,897 B2 | 5/2009 | Brenner |
| 7,563,576 B2 | 7/2009 | Chee |
| 7,582,420 B2 | 9/2009 | Oliphant et al. |
| 7,601,498 B2 | 10/2009 | Mao |
| 7,635,566 B2 | 12/2009 | Brenner |
| 7,674,752 B2 | 3/2010 | He |
| 7,700,286 B2 | 4/2010 | Stroun et al. |
| 7,709,198 B2 | 5/2010 | Luo et al. |
| 7,776,567 B2 | 8/2010 | Mao |
| 7,803,943 B2 | 9/2010 | Mao |
| 7,910,304 B2 | 3/2011 | Drmanac |
| 7,955,794 B2 | 6/2011 | Shen et al. |
| 7,960,119 B2 | 6/2011 | Chee |
| 8,003,354 B2 | 8/2011 | Shen et al. |
| 8,148,068 B2 | 4/2012 | Brenner |
| 8,206,917 B2 | 6/2012 | Chee |
| 8,288,103 B2 | 10/2012 | Oliphant |
| 8,337,851 B2 | 12/2012 | Aukerman |
| 8,460,865 B2 | 6/2013 | Chee |
| 8,481,257 B2 | 7/2013 | Van Eijk |
| RE44,596 E | 11/2013 | Stroun et al. |
| 8,603,743 B2 | 12/2013 | Liu et al. |
| 8,604,182 B2 | 12/2013 | Luo et al. |
| 8,685,889 B2 | 4/2014 | Van Eijk |
| 8,748,103 B2 | 6/2014 | Faham et al. |
| 8,815,512 B2 | 8/2014 | Van Eijk |
| 8,835,358 B2 | 9/2014 | Fodor |
| 8,911,945 B2 | 12/2014 | Van Eijk |
| 8,951,726 B2 | 2/2015 | Luo et al. |
| 9,062,348 B1 | 6/2015 | Van Eijk |
| 9,121,069 B2 | 9/2015 | Lo |
| 9,194,001 B2 | 11/2015 | Brenner |
| 9,217,176 B2 | 12/2015 | Faham |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,340,830 B2 | 5/2016 | Lipson |
| 9,371,598 B2 | 6/2016 | Chee |
| 9,506,061 B2 | 11/2016 | Brown et al. |
| 9,512,487 B2 | 12/2016 | Faham et al. |
| 9,593,365 B2 | 3/2017 | Frisen et al. |
| 9,644,204 B2 | 5/2017 | Hindson et al. |
| 9,694,361 B2 | 7/2017 | Bharadwaj |
| 9,702,004 B2 | 7/2017 | Van Eijk |
| 9,727,810 B2 | 8/2017 | Fodor et al. |
| 9,777,324 B2 | 10/2017 | Van Eijk |
| 9,783,841 B2 | 10/2017 | Nolan et al. |
| 9,834,814 B2 | 12/2017 | Peter et al. |
| 9,850,536 B2 | 12/2017 | Oliphant et al. |
| 9,868,979 B2 | 1/2018 | Chee et al. |
| 9,879,313 B2 | 1/2018 | Chee et al. |
| 10,002,316 B2 | 6/2018 | Fodor et al. |
| 10,023,907 B2 | 7/2018 | Van Eijk |
| 10,030,261 B2 | 7/2018 | Frisen et al. |
| 10,041,949 B2 | 8/2018 | Bendall et al. |
| 10,049,770 B2 | 8/2018 | Madabhushi et al. |
| 10,059,990 B2 | 8/2018 | Boyden et al. |
| 10,078,895 B2 | 9/2018 | Madabhushi et al. |
| 10,196,691 B2 | 2/2019 | Harkin et al. |
| 10,208,982 B2 | 2/2019 | Bannish et al. |
| 10,221,461 B2 | 3/2019 | Robins et al. |
| 10,246,752 B2 | 4/2019 | Faham et al. |
| 10,273,541 B2 | 4/2019 | Hindson et al. |
| 10,357,771 B2 | 7/2019 | Bharadwaj |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,550,429 B2 | 2/2020 | Harada et al. |
| 10,590,244 B2 | 3/2020 | Delaney et al. |
| 10,633,648 B2 | 4/2020 | Seelig et al. |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,858,702 B2 | 12/2020 | Lucero et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |

(56) References Cited

U.S. PATENT DOCUMENTS

| | | |
|---|---|---|
| 11,008,607 B2 | 5/2021 | Chee |
| 11,046,996 B1 | 6/2021 | Chee et al. |
| 11,067,567 B2 | 7/2021 | Chee |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 11,479,809 B2 | 10/2022 | Frisen et al. |
| 11,479,810 B1 | 10/2022 | Chee |
| 11,492,612 B1 | 11/2022 | Dadhwal |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 | 12/2022 | Schnall-Levin et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 | 3/2023 | Galonska et al. |
| 11,613,773 B2 | 3/2023 | Frisen et al. |
| 2002/0006477 A1 | 1/2002 | Shishido et al. |
| 2002/0040275 A1 | 4/2002 | Cravatt |
| 2002/0132246 A1 | 9/2002 | Kallioniemi et al. |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0148335 A1 | 8/2003 | Shen et al. |
| 2003/0162216 A1 | 8/2003 | Gold |
| 2003/0170637 A1 | 9/2003 | Pirrung et al. |
| 2003/0224419 A1 | 12/2003 | Corcoran |
| 2003/0232348 A1 | 12/2003 | Jones et al. |
| 2003/0232382 A1 | 12/2003 | Brennan |
| 2004/0002090 A1 | 1/2004 | Mayer et al. |
| 2004/0019005 A1 | 1/2004 | Van Ness |
| 2004/0033499 A1 | 2/2004 | Ilsley et al. |
| 2004/0067492 A1 | 4/2004 | Peng et al. |
| 2004/0067493 A1 | 4/2004 | Matsuzaki |
| 2004/0096853 A1 | 5/2004 | Mayer |
| 2004/0106110 A1 | 6/2004 | Balasubramanian |
| 2005/0019776 A1 | 1/2005 | Callow et al. |
| 2005/0026188 A1 | 2/2005 | Van Kessel |
| 2005/0037362 A1 | 2/2005 | Remacle et al. |
| 2005/0037393 A1 | 2/2005 | Gunderson et al. |
| 2005/0048580 A1 | 3/2005 | Labaer |
| 2005/0100900 A1 | 5/2005 | Kawashima et al. |
| 2005/0130173 A1 | 6/2005 | Leamon et al. |
| 2005/0136414 A1 | 6/2005 | Gunderson et al. |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0260653 A1 | 11/2005 | LaBaer |
| 2006/0110739 A1 | 5/2006 | Heyduk |
| 2006/0188875 A1 | 8/2006 | Cox et al. |
| 2006/0211001 A1 | 9/2006 | Yu et al. |
| 2006/0216775 A1 | 9/2006 | Burkart et al. |
| 2006/0228758 A1 | 10/2006 | Muchhal et al. |
| 2006/0263789 A1 | 11/2006 | Kincaid |
| 2007/0020640 A1 | 1/2007 | McCloskey et al. |
| 2007/0054288 A1 | 3/2007 | Su et al. |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0161029 A1 | 7/2007 | Li et al. |
| 2007/0172873 A1 | 7/2007 | Brenner et al. |
| 2007/0178503 A1 | 8/2007 | Jiang |
| 2007/0207482 A1 | 9/2007 | Church et al. |
| 2007/0254305 A1 | 11/2007 | Paik et al. |
| 2007/0269805 A1 | 11/2007 | Hogers |
| 2008/0009420 A1 | 1/2008 | Schroth et al. |
| 2008/0108804 A1 | 5/2008 | Hayashizaki et al. |
| 2008/0153086 A1 | 6/2008 | Wong |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0202998 A1 | 8/2009 | Schlumpberger et al. |
| 2009/0215633 A1 | 8/2009 | van Eijk et al. |
| 2009/0233802 A1 | 9/2009 | Bignell et al. |
| 2009/0253581 A1 | 10/2009 | van Eijk et al. |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0120097 A1 | 5/2010 | Matz et al. |
| 2010/0120098 A1 | 5/2010 | Grunenwald et al. |
| 2010/0145037 A1 | 6/2010 | Brive et al. |
| 2011/0028685 A1 | 2/2011 | Purkayastha et al. |
| 2011/0059436 A1 | 3/2011 | Hardin et al. |
| 2011/0111409 A1 | 5/2011 | Sinicropi et al. |
| 2011/0207134 A1* | 8/2011 | Faham ............... C12Q 1/6883 435/6.11 |
| 2011/0245111 A1 | 10/2011 | Chee |
| 2012/0135871 A1 | 5/2012 | van Eijk et al. |
| 2012/0202698 A1 | 8/2012 | van Eijk et al. |
| 2012/0202704 A1 | 8/2012 | Fan et al. |
| 2012/0252702 A1 | 10/2012 | Muratani et al. |
| 2013/0065768 A1* | 3/2013 | Zheng .................. C40B 20/00 506/2 |
| 2013/0171621 A1 | 7/2013 | Luo et al. |
| 2013/0202718 A1* | 8/2013 | Pepin .................. C12Q 1/6886 424/649 |
| 2013/0302801 A1* | 11/2013 | Asbury .............. C12Q 1/6869 435/6.12 |
| 2014/0066318 A1 | 3/2014 | Frisen et al. |
| 2014/0080715 A1 | 3/2014 | Lo et al. |
| 2014/0270435 A1 | 9/2014 | Dunn |
| 2014/0274731 A1 | 9/2014 | Raymond et al. |
| 2014/0296081 A1 | 10/2014 | Diehn et al. |
| 2014/0323330 A1 | 10/2014 | Glezer et al. |
| 2015/0000854 A1 | 1/2015 | Gann-Fetter et al. |
| 2015/0051085 A1 | 2/2015 | Vogelstein et al. |
| 2015/0292988 A1 | 10/2015 | Bharadwaj et al. |
| 2015/0344942 A1 | 12/2015 | Frisen et al. |
| 2016/0108458 A1 | 4/2016 | Frei et al. |
| 2016/0138091 A1 | 5/2016 | Chee et al. |
| 2016/0145677 A1 | 5/2016 | Chee et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2017/0016053 A1 | 1/2017 | Beechem et al. |
| 2017/0029875 A1 | 2/2017 | Zhang et al. |
| 2017/0067096 A1 | 3/2017 | Wassie et al. |
| 2017/0089811 A1 | 3/2017 | Tillberg et al. |
| 2017/0220733 A1 | 8/2017 | Zhuang et al. |
| 2017/0241911 A1 | 8/2017 | Rockel et al. |

(56) References Cited

U.S. PATENT DOCUMENTS

| | | |
|---|---|---|
| 2018/0051322 A1 | 2/2018 | Church et al. |
| 2018/0057873 A1 | 3/2018 | Zhou et al. |
| 2018/0105808 A1 | 4/2018 | Mikkelsen et al. |
| 2018/0112209 A1 | 4/2018 | Eshoo |
| 2018/0112261 A1 | 4/2018 | Van Driel et al. |
| 2018/0156784 A1 | 6/2018 | Usmani et al. |
| 2018/0180601 A1 | 6/2018 | Pedersen et al. |
| 2018/0201980 A1 | 7/2018 | Chee et al. |
| 2018/0216161 A1 | 8/2018 | Chen et al. |
| 2018/0216162 A1 | 8/2018 | Belhocine et al. |
| 2018/0245142 A1 | 8/2018 | So et al. |
| 2018/0282803 A1* | 10/2018 | Belgrader ............ C12Q 1/6804 |
| 2018/0291439 A1 | 10/2018 | van Eijk et al. |
| 2018/0305681 A1 | 10/2018 | Jovanovich et al. |
| 2019/0055594 A1 | 2/2019 | Samusik et al. |
| 2019/0064173 A1 | 2/2019 | Bharadwaj et al. |
| 2019/0085383 A1 | 3/2019 | Church et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0194709 A1 | 6/2019 | Church et al. |
| 2019/0203275 A1 | 7/2019 | Frisen et al. |
| 2019/0233878 A1 | 8/2019 | Delaney et al. |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0330617 A1 | 10/2019 | Church et al. |
| 2019/0338353 A1 | 11/2019 | Belgrader et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0024641 A1 | 1/2020 | Nolan et al. |
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0224244 A1 | 7/2020 | Nilsson et al. |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0299757 A1 | 9/2020 | Chee et al. |
| 2020/0325531 A1 | 10/2020 | Chee |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0095331 A1 | 4/2021 | Fan et al. |
| 2021/0123040 A1 | 4/2021 | Macosko et al. |
| 2021/0140982 A1 | 5/2021 | Uytingco et al. |
| 2021/0150707 A1 | 5/2021 | Weisenfeid et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0090181 A1 | 3/2022 | Gallant et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389504 A1 | 12/2022 | Chew et al. |
| 2022/0403455 A1 | 12/2022 | Ramachandran Iyer et al. |

(56) References Cited

U.S. PATENT DOCUMENTS

| | | |
|---|---|---|
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |

FOREIGN PATENT DOCUMENTS

| | | | |
|---|---|---|---|
| EP | 1923471 | 5/2008 | |
| EP | 2002017 | 12/2008 | |
| EP | 2881465 | 6/2015 | |
| EP | 3013984 | 5/2016 | |
| EP | 3511423 | 7/2019 | |
| EP | 3541956 | 9/2019 | |
| RU | 2145635 | 2/2000 | |
| WO | WO 1989/010977 | 11/1989 | |
| WO | WO 1991/006678 | 5/1991 | |
| WO | WO 1995/025116 | 9/1995 | |
| WO | WO 1995/035505 | 12/1995 | |
| WO | WO 2002/059355 | 8/2002 | |
| WO | WO 2002/077283 | 10/2002 | |
| WO | WO 2003/002979 | 1/2003 | |
| WO | WO 2003/010176 | 2/2003 | |
| WO | WO 2004/055159 | 7/2004 | |
| WO | WO 2005/007814 | 1/2005 | |
| WO | WO 2007/073171 | 6/2007 | |
| WO | WO 2007/076726 | 7/2007 | |
| WO | WO 2007/145612 | 12/2007 | |
| WO | WO 2009/032167 | 3/2009 | |
| WO | WO 2009/152928 | 12/2009 | |
| WO | WO-2010053587 A2 * | 5/2010 | ......... C12N 15/1072 |
| WO | WO 2010/126614 | 11/2010 | |
| WO | WO 2011/008502 | 1/2011 | |
| WO | WO 2011/068088 | 6/2011 | |
| WO | WO-2012083225 A2 * | 6/2012 | ............ C07K 16/00 |
| WO | WO 2012/140224 | 10/2012 | |
| WO | WO 2012/159089 | 11/2012 | |
| WO | WO-2013033271 A2 * | 3/2013 | ............ A61K 35/17 |
| WO | WO-2013090390 A2 * | 6/2013 | ............ C12Q 1/6881 |
| WO | WO 2013/123442 | 8/2013 | |
| WO | WO 2013/131962 | 9/2013 | |
| WO | WO 2013/138510 | 9/2013 | |
| WO | WO 2013/150082 | 10/2013 | |
| WO | WO 2013/150083 | 10/2013 | |
| WO | WO-2013155119 A1 * | 10/2013 | ........... C12Q 1/6848 |
| WO | WO-2013158936 A1 * | 10/2013 | ........... C12Q 1/6886 |
| WO | WO 2014/060483 | 4/2014 | |
| WO | WO 2014/144713 | 9/2014 | |
| WO | WO 2014/210223 | 12/2014 | |
| WO | WO 2014/210225 | 12/2014 | |
| WO | WO 2016/138496 | 9/2016 | |
| WO | WO 2016/138500 | 9/2016 | |
| WO | WO 2016/166128 | 10/2016 | |
| WO | WO 2016/168825 | 10/2016 | |
| WO | WO 2.017/019456 | 2/2017 | |
| WO | WO 2017/075293 | 5/2017 | |
| WO | WO 2017/096158 | 7/2017 | |
| WO | WO-2017177308 A1 * | 10/2017 | ........... C12Q 1/6837 |
| WO | WO 2018/064640 | 4/2018 | |
| WO | WO-2018075693 A1 * | 4/2018 | ......... C12N 15/1003 |
| WO | WO 2018/085599 | 5/2018 | |
| WO | WO 2018/091676 | 5/2018 | |
| WO | WO 2019/213254 | 11/2019 | |
| WO | WO 2019/213294 | 11/2019 | |
| WO | WO 2020/028194 | 2/2020 | |
| WO | WO 2020/047002 | 3/2020 | |
| WO | WO 2020/047004 | 3/2020 | |
| WO | WO 2020/047005 | 3/2020 | |
| WO | WO 2020/047010 | 3/2020 | |
| WO | WO 2020/053655 | 3/2020 | |
| WO | WO 2020/061064 | 3/2020 | |
| WO | WO 2020/061066 | 3/2020 | |
| WO | WO 2020/061108 | 3/2020 | |
| WO | WO 2020/076979 | 4/2020 | |
| WO | WO 2020/099640 | 5/2020 | |
| WO | WO 2020/123301 | 6/2020 | |
| WO | WO 2020/123305 | 6/2020 | |
| WO | WO 2020/123309 | 6/2020 | |
| WO | WO 2020/123311 | 6/2020 | |
| WO | WO 2020/123316 | 6/2020 | |
| WO | WO 2020/123317 | 6/2020 | |
| WO | WO 2020/123318 | 6/2020 | |
| WO | WO 2020/123319 | 6/2020 | |
| WO | WO-2020123316 A2 * | 6/2020 | ........... C12Q 1/6837 |
| WO | WO 2020/123320 | 7/2020 | |
| WO | WO 2020/142490 | 7/2020 | |
| WO | WO 2020/160044 | 8/2020 | |
| WO | WO 2020/167862 | 8/2020 | |
| WO | WO 2020/176788 | 9/2020 | |
| WO | WO 2020/176882 | 9/2020 | |
| WO | WO 2020/190509 | 9/2020 | |
| WO | WO 2020/198071 | 10/2020 | |
| WO | WO 2020/206285 | 10/2020 | |
| WO | WO 2020/219901 | 10/2020 | |
| WO | WO 2020/243579 | 12/2020 | |
| WO | WO 2021/041974 | 3/2021 | |
| WO | WO 2021/067246 | 4/2021 | |
| WO | WO 2021/067514 | 4/2021 | |
| WO | WO 2021/091611 | 5/2021 | |
| WO | WO 2021/092433 | 5/2021 | |
| WO | WO 2021/097255 | 5/2021 | |
| WO | WO 2021/102003 | 5/2021 | |
| WO | WO 2021/102005 | 5/2021 | |
| WO | WO 2021/102039 | 5/2021 | |
| WO | WO 2021/133842 | 7/2021 | |
| WO | WO 2021/133845 | 7/2021 | |
| WO | WO 2021/133849 | 7/2021 | |
| WO | WO 2021/142233 | 7/2021 | |
| WO | WO 2021/168261 | 8/2021 | |
| WO | WO 2021/168278 | 8/2021 | |
| WO | WO 2021/216708 | 10/2021 | |
| WO | WO 2021/225900 | 11/2021 | |
| WO | WO 2021/236625 | 11/2021 | |
| WO | WO 2021/236929 | 11/2021 | |
| WO | WO 2021/237056 | 11/2021 | |
| WO | WO 2021/237087 | 11/2021 | |
| WO | WO 2021/242834 | 12/2021 | |
| WO | WO 2021/247543 | 12/2021 | |
| WO | WO 2021/252499 | 12/2021 | |
| WO | WO 2021/252576 | 12/2021 | |
| WO | WO 2021/252591 | 12/2021 | |
| WO | WO 2021/252747 | 12/2021 | |
| WO | WO 2021/263111 | 12/2021 | |
| WO | WO 2022/025965 | 2/2022 | |
| WO | WO 2022/060798 | 3/2022 | |
| WO | WO 2022/060953 | 3/2022 | |
| WO | WO 2022/061152 | 3/2022 | |
| WO | WO 2022/087273 | 4/2022 | |
| WO | WO 2022/099037 | 5/2022 | |
| WO | WO 2022/109181 | 5/2022 | |
| WO | WO 2022/140028 | 6/2022 | |
| WO | WO 2022/147005 | 7/2022 | |
| WO | WO 2022/147296 | 7/2022 | |
| WO | WO 2022/164615 | 8/2022 | |
| WO | WO 2022/178267 | 8/2022 | |
| WO | WO 2022/198068 | 9/2022 | |
| WO | WO 2022/221425 | 10/2022 | |
| WO | WO 2022/226057 | 10/2022 | |
| WO | WO 2022/236054 | 11/2022 | |
| WO | WO 2022/256503 | 12/2022 | |
| WO | WO 2022/271820 | 12/2022 | |

(56) References Cited

FOREIGN PATENT DOCUMENTS

| WO | WO 2023/287765 | 1/2023 |
| WO | WO 2023/018799 | 2/2023 |
| WO | WO 2023/034489 | 3/2023 |

OTHER PUBLICATIONS

Mulder et al. Blood Advances. 2018. 2(23):3506-3514. (Year: 2018).*
"Chromium Single Cell V(D)J Solution" 10x Genomics. May 2017. (Year: 2017).*
Chromium Single Cell V(D)J Reagent Kits—User Guide. 10x Genomics. 2018. (Year: 2018).*
Wang et al. Nat Chem. 2017. 9(12):1222-1228. (Year: 2017).*
Ranzoni et al. Essays in Biochemistry. 2019. 63:217-225. (Year: 2019).*
Bowen et al. Nucleic Acids Research. 2013. 41(8):4535-4548. (Year: 2013).*
"Inside Visium Spatial Capture Technology". 10x Genomics. 2021. (Year: 2021).*
Efremova et al. Annu Rev Immunol. 2020. 38:727-57. (Year: 2020).*
Luo et al. Computational and Structural Biotechnology Journal. 2020. 18:2962-2971. (Year: 2020).*
Teraguchi et al. Computational and Structural Biotechnology Journal. 2020. 18:2000-2011. (Year: 2020).*
Pasetto et al. Frontiers in Immunology. 2021. 12:689091. (Year: 2021).*
Davis et al. Current Opinion in Immunology. 2019. 59:109-114. (Year: 2019).*
Fan et al. "Single-cell RNA-seq and V(D)J profiling of immune cells in COVID-19 patients". 2020. https://doi.org/10.1101/2020.05.24.20101238. (Year: 2020).*
Villa et al. Cell. 1998. 93:885-896. (Year: 1998).*
Akatsuka et al. Tissue Antigens. 1999. 53:122-134. (Year: 1999).*
Akatsuka et al. Human Immunology. 1996. 48:125-134. (Year: 1996).*
Robins et al. Blood. 2009. 114(19):4099. (Year: 2009).*
Cole et al. Genome Research. 2020. 30:589-601. (Year: 2020).*
Kim et al. BMB Rep. 2019. 52(9):540-547. (Year: 2019).*
Heather et al. Briefings in Bioinformatics. 2018. 19(4):554-565. (Year: 2018).*
Hudson et al. STAR Protocols. 2022. 3:101391. (Year: 2022).*
Sudmeier et al. Cell Reports Medicine. 2022. 3:100620. (Year: 2022).*
Hou et al. Int J Clin Exp Med. 2016. 9(10):18868-18882. (Year: 2016).*
Stubbington et al. Nature Methods. 2016. 13(4):329. (Year: 2016).*
Asp et al., "Spatially Resolved Transcriptomes—Next Generation Tools for Tissue Exploration," Bioessays, Oct. 2020, 42(10):e1900221, 16 pages.
U.S. Appl. No. 61/902,105, filed Nov. 8, 2013, Kozlov et al.
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.
[No Author Listed], "HuSNP Mapping Assay User's Manual," Affymetrix Part No. 90094 (Alfyxnetrix, Santa Clara. Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0cHl7rEk0UXwdl9It/e54d99fb08a8f1500aba503005a04a56/CG000238_VisiumSpatialTissueOptimizationUserGuide_RevD.pdf>, 42 pages.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw51ee9/6a2ac61cf6388a72564eeb96bc294967/CG000238_VisiumSpatialTissueOptimizationUserGuide_Rev_A.pdf>, 46 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cHl7rEk0UXwdl9It/e54d99fb08a8f1500aba503005a04a56/CG000238_VisiumSpatialTissueOptimizationUserGuide_RevD.pdf>, 43 pages.
10xGenomics.com, [online], "Visimn Spatial Gene Expression Reagent Kits—User Guide," Jun. 2020, retrieved on May 25, 2021, retrieved from URL<https://assets.ctfassets.net/an68im79xiti/3GGIfH3RWpdlbFVhalpexR/8baa08d9007157592b65b2cdc7130990/CG000239_VisiumSpatialGeneExpression_UserGuide_RevD.pdf>, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpdlbFVhalpexR/8baa08d9007157592b65b2cdc7130990/CG000239_VisiumSpatialGeneExpression_UserGuide_RevD.pdf>, 70 pages.
Adessi et al., "Solid phase DNA amplification: characterisation of primer attachment and amplification mechanisms," Nucl. Acids Res., 2000, 28(20):E87, 8 pages.
Adiconis et al., "Comparative analysis of RNA sequencing methods for degraded or low-input samples," Nat Methods, Jul. 2013, 10(7):623-9.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GáT Mismatches in DNA," Biochemistry, 1996, 36(34):10581-10594.
Amgad et al., "Report on computational assessment of Tumor Infiltrating Lymphocytes from the International Immuno-Oncology Biomarker Working Group," Nature Partner Journals Breast Cancer, May 2020, 6:16, 13 pages.
Andresen et al., "Deciphering the Antibodyome—Peptide Arrays for Serum Antibody Biomarker Diagnostics," Current Proteomics, 6(1):1-12, 2009.
Armani et al. "2D-PCR: a method of mapping DNA in tissue sections," Lab Chip, 2009, 9(24):3526-34.
Asp et al., "Spatial detection of fetal marker genes expressed at low level in adult human heart tissue," Scientific Reports, 2017, 7(1):12941, 10 pages.
Atkinson et al., "An Updated Protocol for High Throughput Plant Tissue Sectioning." Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Barnes, "PCR amplification of up to 35-kb DNA with high fidelity and high yield from lambda bacteriophage templates," Proc. Natl. Acad. Sci USA, 1994, 91(6):2216-2220.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.

(56) References Cited

OTHER PUBLICATIONS

Bentley et al., "Accurate whole human genome sequencing using reversible terminator chemistry," Nature, 2008, 456(7218):53-59.
Bergenstråhle et al., "Seamless integration of image and molecular analysis for spatial transcriptomics workflows," BMC Genomics, Jul. 2020, 21(1):482, 7 pages.
Bielas et al., "Human cancers express a mutator phenotype," Proc. Natl. Acad. Sci, USA, 2006, 103(48): 18238-18242.
Birney et al., "Identification and analysis of functional elements in 1% of the human genome bv the ENCODE pilot project," Nature, 2007, 447(7146):799-816.
Blanchard et al., "High-density oligonucleotide arrays," Biosensors & Bioelectronics, 1996, 11(6-7):687-690.
Blandini et al., "Animal models of Parkinson's disease," FEBS J., Apr. 2012, 279(7):1156-66.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolotin et al., "MiXCR: software for comprehensive adaptive immunity profiling," Nat Methods., May 2015, 12(5):380-1.
Bowtell, "The genesis and evolution of high-grade serous ovarian cancer," Nat. Rev. Cancer, 2010, (11 ):803-808 Abstract.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown el al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat. Methods, Dec. 2013, 10(12):1213-1218.
Bullard et al., "Direct comparison of nick-joining activity of the nucleic acid ligases from bacteriophage T4," Biochem. J. 2006, 398(1):135-144.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burton et al., "Coverslip Mounted-Immeision Cycled in Situ RT-PCR for the Localization of mRNA in Tissue Sections," Biotechniques, 1998, 24(1):92-100.
Cerutti et al., "Generation of sequence-specific, high affinitv anti-DNA antibodies," Journal of Biological Chemistry, 2001, 276(16):12769-12773.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "A Homogeneous, Ligase-mediated DNA diagnostic test," Genome research, 1998, 8(5):549-556.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "μCB-seq: microfluidic cell barcoding and sequencing for high-resolution imaging and sequencing of single cells," Lab Chip, Nov. 2020, 20(21):3899-3913.

Constantine et al., "Use of genechip high-density oligonucleotide arrays for gene expression monitoring," Life Sceience News, Amersham Life Science, 1998, pp. 11-14.
Copeland et al., "Mitochondrial DNA Alterations in Cancer," Cancer Invest., 2002, 557-569.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Daubendiek et al., "Rolling-Circle RNA Synthesis: Circular Oligonucleotides as Efficient Substrates for 7 RNA Polymerase,"J. Am. Chem. Soc., 1995, 117(29):7818-7819.
Davies et al., "How best to identify chromosomal interactions: a comparison of approaches," Nat. Methods, 2017, 14(2):125-134.
Dawson et al., "Animal models of neurodegenerative diseases," Nat Neurosci., Oct. 2018, 21(10):1370-1379.
Dawson et al., "Genetic animal models of Parkinson's disease," Neuron, Jun. 2010, 66(5):646-661.
Dean et al. "Comprehensive human genome amplification using multiple displacement amplification," Proc Natl. Acad. Sci. USA, 2002, 99(8):5261-66.
Deng et al., "Spatial Epigenome Sequencing at Tissue Scale and Cellular Level," BioRxiv, Mar. 2021, 40 pages.
Drmanac et al., "Accurate sequencing by hybridization for DNA diagnostics and individual genomics," Nature Biotechnology, 16:54-58, 1998.
Duncan et al., "Affinity chromatography of a sequence-specific DNA binding protein using Teflon-linked oligonucleotides," Anal. Biochem., 1988, 169(1):104-108.
Eagen, "Principles of Chromosome Architecture Revealed by Hi-C," Trends in Biochemical Sciences, Jun. 2018, 43(6):469-478.
Eguiluz el al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Fire et al., "Rolling replication of short DNA circles," Proc. Natl. Acad. Sci., 1995, 92(10):4641-4645.
Fluidigm, "Hyperion Imaging System: Visualize a new path forward," Feb. 2018, retrieved from URL <https://www.fluidigm.com/binaries/content/documents/fluidigm/search/hippo%3Aresultset/hyperion-imaging-system-br-400326/fluidigm%3Afile>, 27 pages.
Fluidigm, "Immuno-Oncology Research with the Hyperion Imaging Svstem: A high-parameter imaging solution at subcellular resolution to characterize the immune repertoire in the tumor microenvironment," Apr. 2018, retrieved from URL <https://www.fluidigm.com/binaries/content/documents/fluidigm/search/hippo%3Aresultset/application-note-immuno-oncology-research-with-the-hyperion%E2%84%A2-imaging-system/flaidigm%3Afile>, 6 pages.
Fluidigm, "Immuno-Oncology Research with the Hyperion Imaging System: A high-parameter imaging solution at subcellular resolution to characterize the immune repertoire in the tumor microenvironment," Aug. 2018, retrieved from URL <https://www.fluidigm.com/binaries/content/documents/fluidigm/marketing/immuno-oncology-research-with-the-hyperion-imaging-system-appnote-400332/immuno-oncology-research-with-the-hyperion-imaging-system-appnote-400332/fluidigm%3Afile>, 6 pages.
Fluidigm, "Maxpar Antibodies for Imaging Mass Cytometry," Mar. 2018, retrieved from URL <https://www.fluidigm.com/binaries/content/documents/fluidigm/search/hippo%3Aresultset/hyperion-antibodies-for-imaging-mass-cvtometry-br-101-7115/fluidigm%3Afile>, 2 pages.
Fodor et al., "Light-directed, spatially addressable parallel chemical synthesis," Science, 1995, 251(4995):767-773.

(56) References Cited

OTHER PUBLICATIONS

Forster et al., "A human gut bacterial genome and culture collection for improved metagenomic analyses," Nature Biotechnology, 2019, 37(2):186-192.
Fredriksson et al., "Multiplexed protein detection by proximity ligation for cancer detection," Nature Methods, 4(4): 327-29, 2007.
Fredriksson et al., "Multiplexed proximity ligation assays to profile putative plasma biomarkers relevant io pancreatic and ovarian cancer," Clin. Chem., 5(3): 582-89, 2008.
Frese et ah, "Formylglycine aldehvde Tag-protein engineering through a novel post-translational modification," ChemBioChem., 2009, 10(3):425-27.
Fu et al., "Counting individual DNA molecules by the stochastic attachment of diverse labels," PNAS, 2011, 108(22):9026-9031.
Fu et al., "Continuous Polony Gels for Tissue Mapping with High Resolution and RNA Capture Efficiency," bioRxiv, 2021, 20 pages.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis irom tissue," Nat Commun., Jan. 2018, 9(1):202, 9 pages.
Gao et al., "Q&A: Expansion microscopy", BMC Biology, 15:50, 9 pages, 2017.
GenBank Accession No. M10098.1, "Human 18S rRNA gene, complete," Aug. 3, 1993, 2 pages.
GenBank Accession No. M11167.1, "Human 28S ribosomal RNA gene," Aug. 3, 1993, 2 pages.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Giacomello et al., "Spatially resolved transcriptome profiling in model plant species", Nature Plants 3, 17061, 11 pages, 2017.
Gilles et al., "Single nucleotide polymorphic discrimination by an electronic dot blot assay on semiconductor microchips," Nat Biotechnol, Apr. 1999, 17(4):365-70.
Gnanapragasam, "Unlocking the molecular archive: the emerging use of formalin-fixed paraffin-embedded tissue for biomarker research in urological cancer," BJU International, 2009, 105(2):274-278.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goltsev et al., "Deep Profiling of Mouse Splenic Architecture with CODEX Multiplexed Imaging", Cell, 2018, 174(4):968-981.
Gracia Villacampa et al., "Genome-wide Spatial Expression Profiling in FFPE Tissues," bioRxiv, 2020, pp. 38 pages.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hadley et al., "Determining composition of micron-scale protein deposits in neurodegenerative disease by spatially targeted optical microproteomics," Elife, 2015, 4(e09579):21 pages.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Han et al., "3C and 3C-based techniques: the powerful tools for spatial genome organization deciphering", Molecular Cytogenetics (2018) 11: 21, 10 pages, 2018.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He, "Cell-free protein synthesis: applications in proteomics and biotechnology," New Biotechnology, 2008, 25(2-3):126-132.
Hejatko et al., "In situ hybridization technique for mRNA detection in whole mount *Arabidopsis* samples," Nature Protocols, 2006, 1(4):1939-1946.
Hiatt et al., "Parallel, tag-directed assembly of locally derived short sequence reads," Nature Methods, 2010, 7(2):119-25.
Hlubek et al, "Heterogeneous expression of Wnt/b-catenin target genes within colorectal cancer," 2007, Int. J. Cancer: 2017, 1941-1948.
Inoue and Wittbrodt, "One for All—A Highly Efficient and Versatile Method for Fluorescent Immunostaining in Fish Embryos," PLoS One 6, e19713, 2011.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Kolovos et al.. "Investigation of the spatial structure and interactions of the genome at sub-kilobasepair resolution using T2C," Nat. Protoc. 13, 459-477, 2018.
Korbel et al., "Paired-end mapping reveals extensive structural variation in the human genome," Science, 2007, 318(5849):420-426.
Kozlov et al., "A highly scalable peptide-based assay system for proteomics," PLoS ONE, 2012, 7(6):e37441, 10 pages.
Kristensen et al., "High-Throughput Methods for Detection of Genetic Variation," BioTechniques, Feb. 2001, 30(2):318-332.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lage et al., "Whole genome analysis of genetic alterations in small DNA samples using hyperbranched strand displacement amplification and anay-CGH," Genome Research, 2003, 13(2):294-307.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Autoantigen discovery with a synthetic human peptidome," Nature Biotechnology, May 2011, 29(6):535-541.
Lassmann et al., A Novel Approach For Reliable Microarrav Analysis of Microdissected Tumor Cells From Formalin-Fixed and Paraffin-Embedded Colorectal Cancer Resection Specimens, J Mol Med, 87, 211-224, 2009.
Lee et al., "Fluorescent in situ sequencing (FISSEQ) of RNA for gene expression profiling in intact cells and tissues," Nature Protocols, 2015, 10(3):442-458.
Lee et al., "Identifying T Cell Receptors from High-Throughput Sequencing: Dealing with Promiscuity in TCRα and TCRβ Pairing," PLoS Comput Biol., Jan. 2017, 13(1):e1005313, 25 pages.
Lem et al., "The promise of spatial transcriptomics for neuroscience in the era of molecular cell typing", Science 358, 64-69, 2017.
Leriche et al., "Cleavable linkers in chemical biology," Bioorganic & Medicinal Chemistry, 2012, 20:571-582.
Lewczuk et al., "Cerebrospinal fluid and blood biomarkers for neurodegenerative dementias: An update of the Consensus of the Task Force on Biological Markers in Psychiatry of the World Federation of Societies of Biological Psychiatry," World J Biol Psychiatry, Jun. 2018, 19(4):244-328.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.

(56) References Cited

OTHER PUBLICATIONS

Lizardi et al., "Mutation detection and single-molecule counting using isothermal rolling-circle amplification," Nat. Genet., 1998, 19(3):225-232.
Lovatt et al., "Transcriptome in vivo analysis (TIVA) of spatially defined single cells in live tissue," Nature Methods, 2013, 11(2):190-196.
Lundberg et al., "Multiplexed homogeneous proximity ligation assays for high-throughput protein biomarker research in serological material," Mol Cell Proteomics, 2011, 10(4):M110.004978, 11 pages.
MacBeath et al., "Printing proteins as microarrays for high-throughput function determination," Science, Sep. 2000, 289(5485):1760-1763.
Maniatis et al., "Spatiotemporal Dynamics of Molecular Pathology in Amyotrophic Lateral Sclerosis", 54 pages, 2018.
Martin, "Cutadapt removes adaptor sequences from high-throughput sequencing reads," EMBnet Journal, 2011, 17(1):10-12.
Marx, "Method of the Year: spatially resolved transcriptomics," Nature Methods, 2021, 18(1):9-14.
McKernan et al., "Sequence and structural variation in a human genome uncovered by short-read, massively parallel ligation sequencing using two-base encoding," Genome Res., 19: 1527-41, 2009.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miller et al., "Basic concepts of microarrays and potential applications in clinical microbiology," Clinical Microbiology Reviews, 2009, 22(4):611-633.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Mizusawa et al., "A bacteriophage lambda vector for cloning with BamHI and Sau3A," Gene, 1982, 20(3):317-322.
Moncada et al., "Building a tumor atlas: integrating single-cell RNA-Seq data with spatial transcriptomics in pancreatic ductal adenocarcinoma", Institute for Computational Medicine, bioRxiv, 28 pages, 2018.
Moor et al., "Spatial transcriptomics: paving the way for tissue-level systems biology", Science Direct, Current Opinion in Biotechnology, 46: 126-133, 2017.
Morlan et al., "Selective depletion of rRNA enables whole transcriptome profiling of archival fixed tissue," PLoS One, Aug. 2012, 7(8):e42882, 8 pages.
Mortazavi et al., "Mapping and quantifying mammalian transcriptomes bv RNA-Seq," Nature Methods, 5(7): 621-8, 2008.
Nagahara et al., "Neuroprotective effects of brain-derived neurotrophic factor in rodent and primate models of Alzheimer's disease," Nat Med., Mar. 2009, 15(3):331-337.
Ng et al., "Massively parallel sequencing and rare disease," Human Malec. Genetics, 19(2): R119-R124, 2010.
Ng et al., "Multiplex sequencing of paired-end ditags (MS-PET): a strategy for the ultra-high-throughput analysis of transcriptomes and genomes," Nucleic Acids Research, Jul. 2006, 34(12): e84, 10 pages.
Nikiforov et al., "The use of 96-well polystyrene plates for DNA hybridization-based assays: an evaluation of different approaches to oligonucleotide immobilization," Anal Biochem, May 1995, 227(1):201-9.
Nowak et al., "Entering the Postgenome Era," Science, 1995, 270(5235):368-71.
Park et al., "The Estimation of Breast Cancer Disease—Probability by Difference of Individual Susceptibility," Cancer Res. Treat., Feb. 2003, 35(1):35-51, Abstract.
Paterson et al., "Cerebrospinal fluid in the differential diagnosis of Alzheimer's disease: clinical utility of an extended panel of biomarkers in a specialist cognitive clinic," Alzheimers Res Ther., Mar. 2018, 10(1):32, 11 pages.
PCT International Search Report and Written Opinion in International Appln. No. PCT/US2021/035242, dated Sep. 2, 2021, 13 pages.
Pemov et al., "DNA analysis with multiplex microarray-enhanced PCR," Nucl. Acids Res., Jan. 2005, 33(2):e11, 9 pages.
Perler et al., "Intervening sequences in an Archaea DNA polymerase gen," Proc Natl Acad Sci USA, Jun. 1992, 89(12):5577-5581.
Petterson et al., "Generations of sequencing technologies," Genomics, 2009, 93(2):105-111.
Picelli et al., "Full-length RNA-seq from single cells using Smart-seq2," Nat Protoc., Jan. 2014, 9(1):171-81.
Polsky-Cynkin et al., "Use of DNA immobilized on plastic and agarose supports to detect DNA by sandwich hybridization," Clin. Chem., 1985, 31(9):1438-1443.
U.S. Appl. No. 61/267,363, filed Dec. 7, 2009, 33 pages.
Rajeswari et al., "Multiple pathogen biomarker detection using an encoded bead array in droplet PCR," J. Microbial Methods, Aug. 2017, 139:22-28.
Ranki et al., "Sandwich hybridization as a convenient method for the detection of nucleic acids in crude samples," Gene, 1983, 21(1-2):77-85.
Reinartz et al.. "Massively parallel signature sequencing (MPSS) as a tool for in-depth quantitative gene expression profiling in all organisms," Brief Funct Genomic Proteomic, Feb. 2002, 1(1):95-104.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Rubin et al., "Whole-genome resequencing reveals loci under selection during chicken domestication.," Nature, Mar. 2010, 464: 587-591.
Salem et al., "Multidimensional transcriptomics provides detailed information about immune cell distribution and identity in HER2+ breast tumors", bioRxiv, 41 pages, 2018.
Salmén el al., "Barcoded solid-phase RNA capture for Spatial Transcriptomics profiling in mammalian tissue sections," Nature Protocols, Oct. 2018, 13(11):2501-2534.
Saxonov et al., "10x Genomics, Mastering Biology to Advance Human Health," PowerPoint, 10x, 2020, 41 pages.
Scheideler et al., "Recapitulating complex biological signaling environments using a multiplexed, DNA-patterning approach," Sci. Adv., 2020, 6:eay5696.
Schena et al., "Quantitative monitoring of gene expression patterns with a complementary DNA microarray," Science, Oct. 1995, 270(5235):467-470.
Schmitt et al., "Detection of ultra-rare mutations by next-generation sequencing," PNAS (2012) 109:14508-14523.
Segahny et al., "Functional TCR T cell screening using single-cell droplet microfluidics†," Lab Chip, 2018, 3733-3749.
Sergeeva et al., "Display technologies: Application for the discovery of drug and gene delivery agents," Advanced Drug Delivery Reviews, 2006, 58(15):1622-1654.
Shalon et al., "A DNA microarray system for analyzing complex DNA samples using two-color fluorescent probe hybridization," Genome Res., Jul. 1996, 6(7):639-45.
Sheth et al., "Spatial metagenomic characterization of microbial biogeography in the gut," Nature Biotechnology, Aug. 2019, 37:877-883.
Shi, "Enabling large-scale pharmacogenetic studies by high-throughput mutation detection and genotyping technologies," Clin. Chem., Feb. 2001, 47(2):164-172.

(56) References Cited

OTHER PUBLICATIONS

Shoemaker et al., "Quantitative phenotypic analysis of yeast deletion mutants using a highly parallel molecular bar-coding strategy," Nature genetics (1996) 14:450-456.

Sievertzon et al., "Transcriptome analysis in primary neural stem cells using a tag cDNA amplification method," BMC Neuroscience, Dec. 2005, 6: 28.

Singh et al., "High-throughput targeted long-read single cell sequencing reveals the clonal and transcriptional landscape of lymphocytes," Nat Commun., Jul. 2019, 10(1):3120, 13 pages.

Stahl et al., "Visualization and analysis of gene expression in tissue sections by spatial transcriptomics," Science, Jun. 2016, 353(6294):78-82.

Stahl et al., "Visualization and analysis of gene expression in tissue sections by spatial transcriptomics," Supplementary Materials, Science, Jul. 2016, 353(6294):78-82, 41 pages.

Stimpson et al., "Real-time detection of DNA hybridization and melting on oligonucleotide arrays by using optical wave guides," Proc Natl Acad Sci USA, Jul. 1995, 92(14):6379-83.

Strell et al., "Placing RNA in context and space—methods for spatially resolved transcriptomics," The FEBS Journal, 2019, 286(8):1468-1481.

Stuart et al., "Comprehensive Integration of Single-Cell Data," Cell, Jun. 2019, 177(7):1888-1902.

Tegtmeyer et al., "Alternative Interactions of the SV40 A Protein with DNA," Virology, 1981, 115:75-87.

Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.

Trejo et al., "Extraction-free whole transcriptome gene expression analvsis of FFPE sections and histology-directed subareas of tissue," PLoS ONE, Feb. 2019, 14(2):e0212031, 22 pages.

Tu et al., "TCR sequencing paired with massively parallel 3' RNA-seq reveals clonotypic T cell signatures," Nature Immunology, Dec. 2019, 20(12):1692-1699.

Twyman et al., "Techniques Patents for SNP Genotyping," Pharmacogenomics, Jan. 2003, 4(1):67-79.

Van Gelder et al., "Amplified RNA synthesized from limited quantities of heterogeneous cDNA," Proc. Natl. Acad. Sci. USA, 1990, 87(5):1663-1667.

Vasiliskov et al., "Fabrication of mic roarray of gel-immobilized compounds on a chip by copolymerization," Biotechniques, Sep. 1999, 27(3):592-606.

Vázquez Bernat et al., "High-Qualitv Library Preparation for NGS-Based Immunoglobulin Germline Gene Inference and Repertoire Expression Analysis," Front. Immunol., Apr. 2019, 10:660, 12 pages.

Vickovic et al., "High-definition spatial transcriptomics for in situ tissue profiling," Nat Methods, Oct. 2019, 16(10):987-990.

Vogelstein et al., "Digital PCR," Proceedings of the National Academy of Sciences, Aug. 1999, 96(16):9236-9241.

Wade et al., "Genome sequence, comparative analysis, and population genetics of the domestic horse.," Science., 326: 865-7, 2009.

Walker et al., "Strand displacement amplification—an isothermal, in vitro DNA amplification technique," Nucleic Acids Research, 1992, 20(7):1691-1696.

Wang et al., "Imaging-based pooled CRISPR screening reveals regulators of lncRNA localization," Proc Natl Acad Sci USA, May 2019, 116(22):10842-10851.

Wang et al., "High-fidelity mRNA amplification for gene profiling," Nature Biotechnology, Apr. 2000, 18(4):457-459.

Waxman et al., "De-regulation of common housekeeping genes in hepatocellular carcinoma," BMC Genomics, 2007, 1-9.

Willi-Monnerat et al., "Comprehensive spatiotemporal transcriptomic analyses of the ganglionic eminences demonstrate the uniqueness of its caudal subdivision," Molecular and Cellular Nueorsciences 37: 845-856, 2008.

Worthington et al., "Cloning of random oligonucleotides to create single-insert plasmid libraries," Anal Biochem, 2001, 294(2):169-175.

Xiao et al., "Direct determination of haplotypes from single DNA molecules," Nature Methods, 2009, 6(3):199-01.

Yershov et al., "DNA analysis and diagnostics on oligonucleotide microchips," Proc. Natl. Acad. Sci. USA, May 1996, 93(10):4913-4918.

Zhang et al., "Single-base mutational analysis of cancer and genetic diseases using membrane bound modified oligonucleotides," Nucleic Acids Res., Jul. 1991, 19(14):3929-33.

Zhu et al., "Reverse transcriptase template switching: a SMART approach for full-length cDNA library construction," Biotechniques, Apr. 2001, 30(4):892-897.

Zilberman et al., "Genome-wide analysis of DNA methylation patterns," Development (2007) 134: 3959-3965.

Zlobec et al., "Next-generation tissue microarrav (ngTMA) increases the quality of biomarker studies: an example using CD3, CD8, and CD45RO in the tumor microenviromnent of six different solid tumor types," Journal of Translational Medicine, 2013 11(104):1-7.

Burgess, "Spatial transcriptomics coming of age," Nat Rev Genet., Jun. 2019, 20(6):317, 1 page.

Dalma-Weiszhausz et al., "The aflymetrix GeneChip platform: an overview," Methods Enzymol., 2006, 410:3-28.

Miller et al., "Chapter 11—Solid and Suspension Microarrays for Microbial Diagnostics," Methods in Microbiology, 2015, 42:395-431.

Vickovic et al., "SM-Omics: An automated Platform for High-Throughput Spatial Multi-Omics," bioRxiv, Oct. 2020, 40 pages.

Baner et al., "Signal amplification of padlock probes by rolling circle replication," Nucleic Acids Res., 1998, 26(22):5073-5078.

Borm et al., "High throughput human embryo spatial transcriptome mapping by surface transfer of tissue RNA," Abstracts Selected Talks, Single Cell Genomics mtg, (SCG2019), 2019, 1 pages (Abstract Only).

Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.

Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.

Codeluppi et al., "Spatial organization of the somatosensory cortex revealed by osmFISH," Nature Methods, Nov. 2018, 15:932-935.

Dean et al., "Rapid Amplification Of Plasmid And Phage DNA Using Phi29 DNA Polymerase And Multiply-Primed Rolling Circle Amplification," Genome Research, Jun. 2001, 11:1095-1099.

Eng et al., "Transcriptome-scale super-resolved imaging in tissues by RNA seqFISH+," Nature, Apr. 2019, 568(7751):235-239, 37 pages.

Faruqi et al., "High-throughput genotyping of single nucleotide polymorphisms with rolling circle amplification," BMC Genomics, Aug. 2001, 2:4, 10 pages.

Gibson et al., "Enzymatic assembly of DNA molecules up to several hundred kilobases," Nat Methods., May 2009, 6(5):343-5.

Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.

Goh et al., "Highly Specific Multiplexed RNA Imaging In Tissues With Split-FISH," Nat Methods, Jun. 15, 2020, 17(7):689-693, 21 pages.

Goransson et al., "A single molecule array for digital targeted molecular analyses," Nucleic Acids Res., Nov. 25, 2009, 37(1):e7, 9 pages.

Li et al., "RNase H-dependent PCR-enabled T-cell receptor sequencing for highly speci!c and ef!cient targeted sequencing of T-cell receptor mRNA for single-cell and repertoire analysis," Nature Protocols, Aug. 2019, 14:2571-2594.

Liu et al., "High-Spatial-Resolution Multi-Omics Sequencing via Deterministic Barcoding in Tissue," Cell, Nov. 13, 2020, 183(6):1665-1681, 36 pages.

Liu et al., "Spatial transcriptome sequencing of FFPE tissues at cellular level," bioRxiv 788992, Oct. 14, 2020, 39 pages.

(56) References Cited

OTHER PUBLICATIONS

Mohsen et al., "The Discovery of Rolling Circle Amplification and Rolling Circle Transcription," Acc Chem Res., Nov. 15, 2016, 49(11):2540-2550, 25 pages.
Nam et al., "Somatic mutations and cell identity linked by Genotyping of Transcriptomes," Nature, Jul. 2019, 571(7765):355-360.
PCT International Preliminary Report on Patentability in International Appln. No. PCT/US2021/035211, dated Dec. 6, 2022, 17 pages.
PCT International Preliminary Report on Patentability in International Appln. No. PCT/US2021/035242, dated Dec. 6, 2022, 7 pages.
PCT International Search Report and Written Opinion in International Appln. No. PCT/US2021/035211, dated Sep. 30, 2021, 27 pages.
PCT Invitation to Pay Additional Fees in International Appln. No. PCT/US2021/035211, dated Oct. 12, 2021, 17 pages.
Raj et al., "Imaging individual mRNA molecules using multiple singly labeled probes," Nature Methods, Oct. 2008, 5(10):877-879, 9 pages.
Takei et al., "Integrated Spatial Genomics Reveals Global Architecture Of Single Nuclei," Nature, Jan. 27, 2021, 590(7845):344-350, 53 pages.
Tomita et al., "Attention-Based Deep Neural Networks for Detection of Cancerous and Precancerous Esophagus Tissue on Histopathological Slides," JAMA Network Open. Nov. 6, 2019, 2(11):e1914645, 13 pages.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.

* cited by examiner

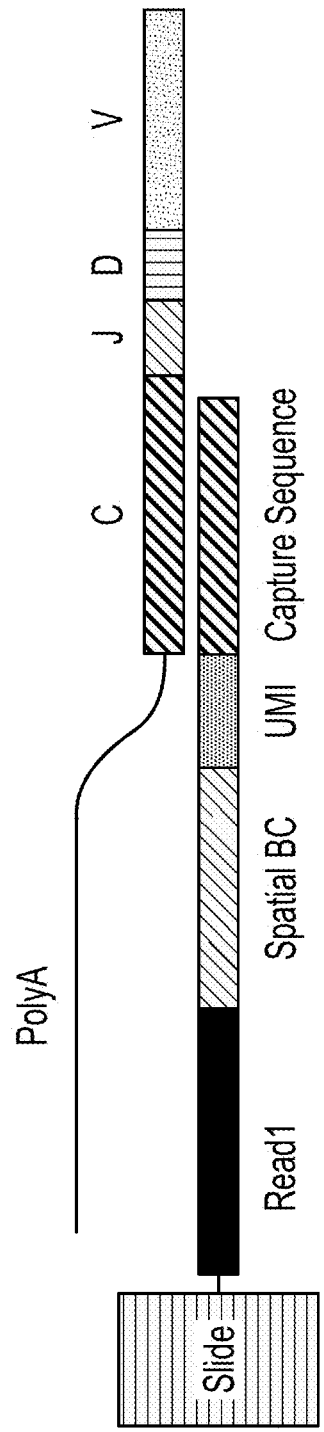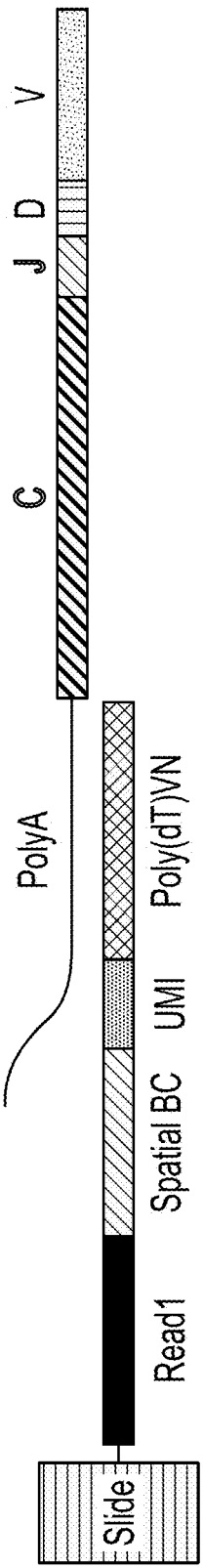
FIG. 3A
FIG. 3B

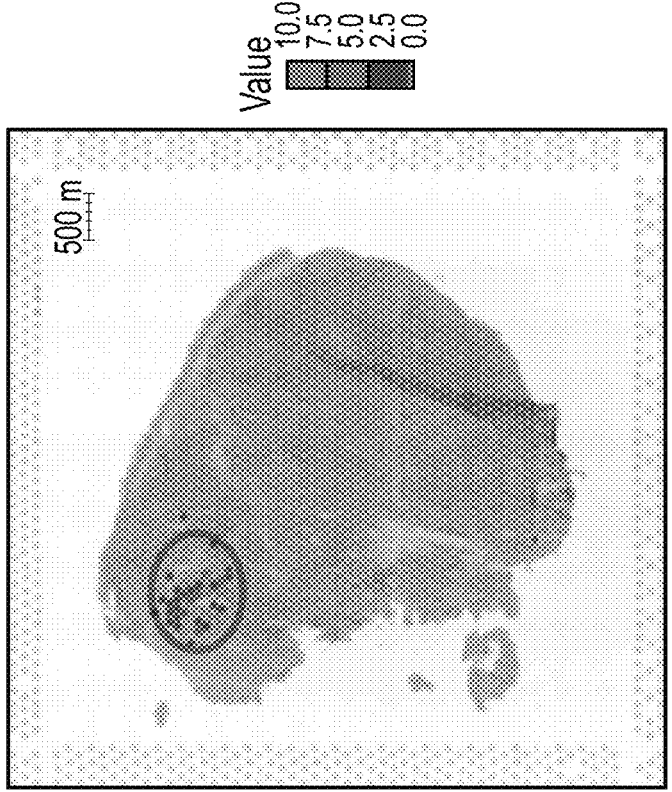
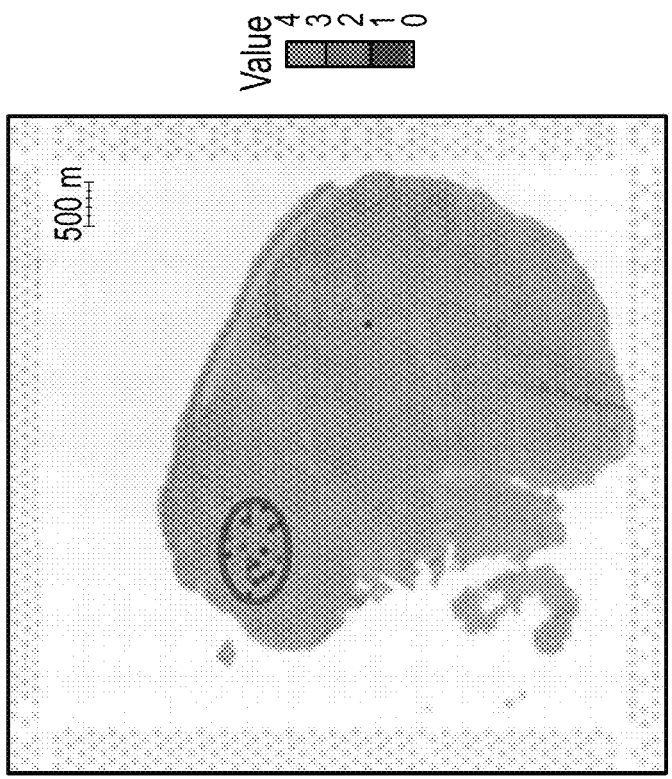
FIG. 18D

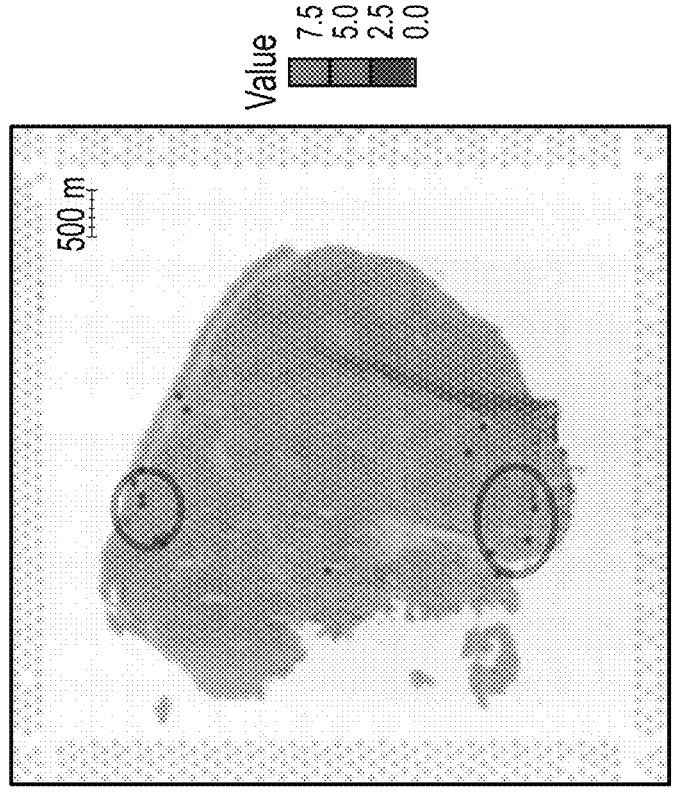
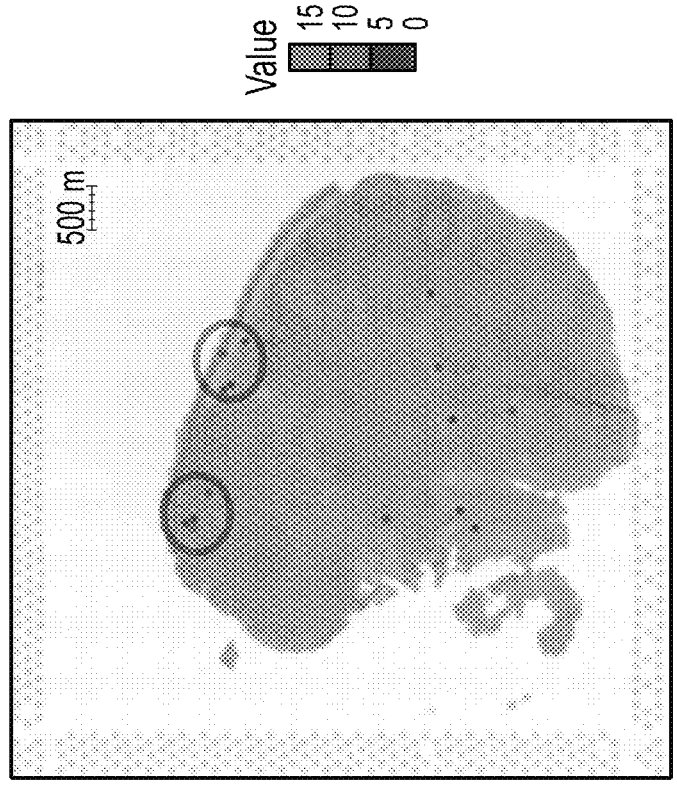
FIG.-18E

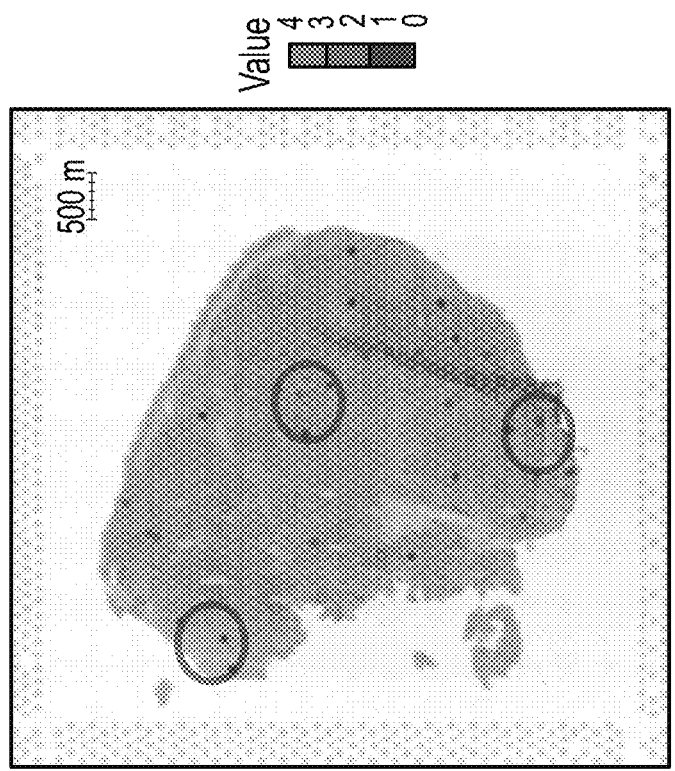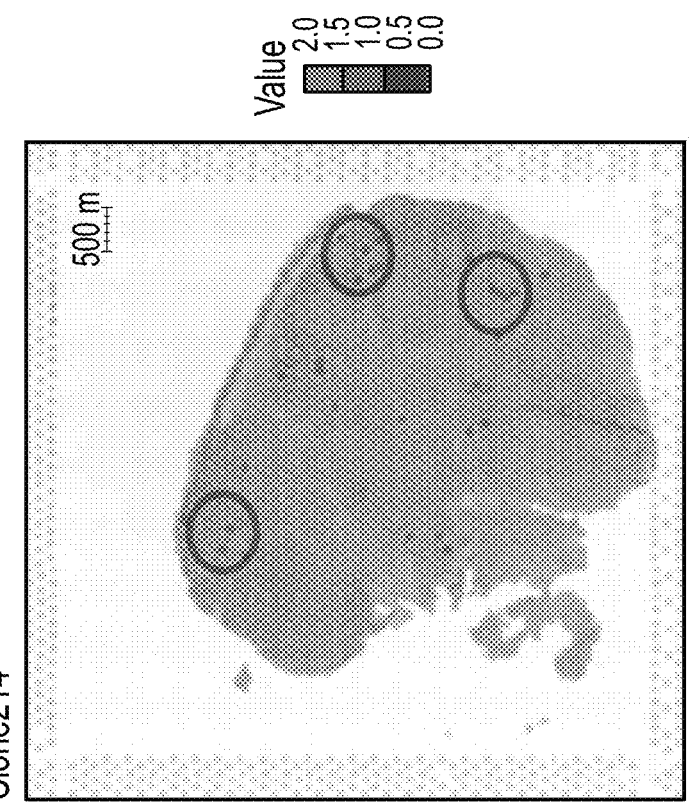
FIG.-18F

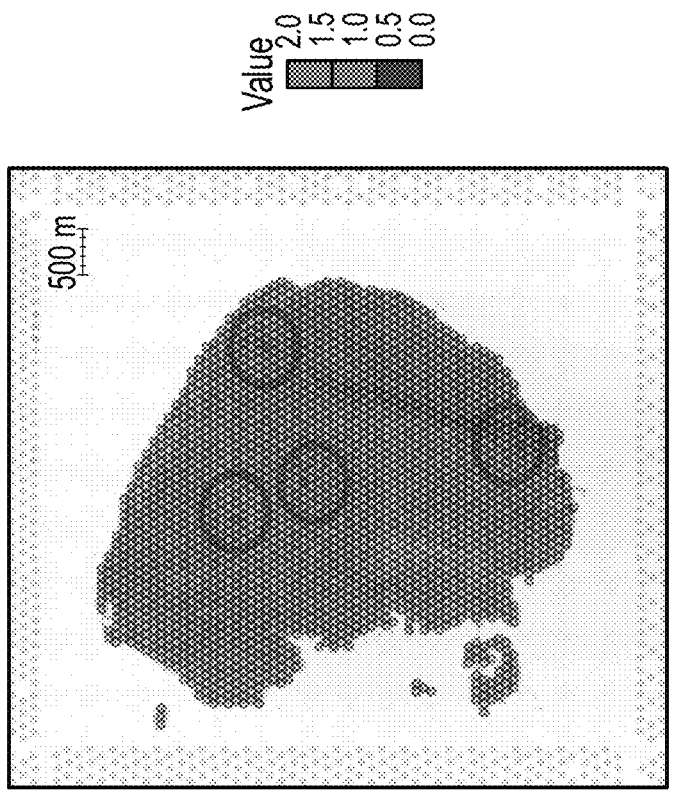
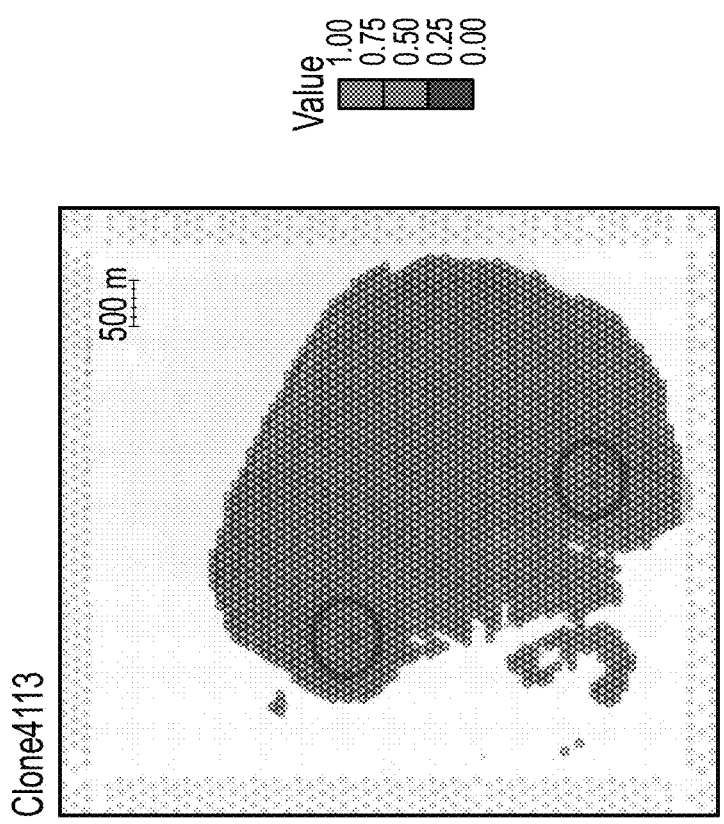
FIG.-18G

SEQUENCE LISTING

```
<160> NUMBER OF SEQ ID NOS: 640

<210> SEQ ID NO 1
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
tctgatggct caaacacagc                                            20

<210> SEQ ID NO 2
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
gccaggggga agaccgatgg g                                          21

<210> SEQ ID NO 3
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
cacgctgctc gtatccga                                              18

<210> SEQ ID NO 4
<211> LENGTH: 27
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 4
caacagggag aagaggatcc tcaggcc                                       27

<210> SEQ ID NO 5
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
ggacaaaaca ttgaccagcc cactgagat                                     29

<210> SEQ ID NO 6
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
aaaaaccaag tggagcagag tcctcagtcc                                    30

<210> SEQ ID NO 7
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
caacggaagg aggtggagca ggatc                                         25

<210> SEQ ID NO 8
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
caacagaagg aggtggagca gaattctgg                                     29

<210> SEQ ID NO 9
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
caacagaagg aggtggagca ggatcct                                       27
```

```
<210> SEQ ID NO 10
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
gagaatgtgg agcagcatcc ttcaacc                                         27

<210> SEQ ID NO 11
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
gagagtgtgg ggctgcatct tcctacc                                         27

<210> SEQ ID NO 12
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
cagaagataa ctcaaaccca accaggaatg ttc                                  33

<210> SEQ ID NO 13
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
cagagagtga ctcagcccga gaagctc                                         27

<210> SEQ ID NO 14
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
gactcggtta cccagacaga aggccc                                          26

<210> SEQ ID NO 15
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 15
cagaaggtaa ctcaagcgca gactgaaatt tct                                    33

<210> SEQ ID NO 16
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
aaggaccaag tgtttcagcc ttccacagtg                                        30

<210> SEQ ID NO 17
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
gaagaccagg tgacgcagag tcccg                                             25

<210> SEQ ID NO 18
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
aaacaggagg tgacgcagat tcctgc                                            26

<210> SEQ ID NO 19
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
atacaagtgg agcagagtcc tccagacctg a                                      31

<210> SEQ ID NO 20
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
caacagaagg agaaaagtga ccagcagca                                         29

<210> SEQ ID NO 21
<211> LENGTH: 33
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 21
atactgaacg tggaacaaag tcctcagtca ctg                                    33

<210> SEQ ID NO 22
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
caacaggtaa tgcaaattcc tcagtaccag c                                      31

<210> SEQ ID NO 23
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
aagaccaccc agcccccctc c                                                 21

<210> SEQ ID NO 24
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
aagaccacac agccaaattc aatggagagt aac                                    33

<210> SEQ ID NO 25
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
cagctgctgg agcagagccc tcagt                                             25

<210> SEQ ID NO 26
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
caacagaaga atgatgacca gcaagttaag caa                                    33
```

```
<210> SEQ ID NO 27
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
cagtcagtgg ctcagccgga agatc                                            25

<210> SEQ ID NO 28
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
caacaaccag tgcagagtcc tcaagcc                                          27

<210> SEQ ID NO 29
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
caagaactgg agcagagtcc tcagtccttg                                       30

<210> SEQ ID NO 30
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
caacagctga atcagagtcc tcaatctatg tttatc                                36

<210> SEQ ID NO 31
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
gaagacaagg tggtacaaag ccctctatct ctg                                   33

<210> SEQ ID NO 32
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 32
cagacagtca ctcagtctca accagagatg tct                           33

<210> SEQ ID NO 33
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
gagctgaaag tggaacaaaa ccctctgttc                               30

<210> SEQ ID NO 34
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
aagaccaccc agcccatctc catg                                     24

<210> SEQ ID NO 35
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
aattcagtca agcagacggg ccaaataac                                29

<210> SEQ ID NO 36
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
gccaaaaatg aagtggagca gagtcctc                                 28

<210> SEQ ID NO 37
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
gaggatgtgg agcagagtct tttcctgagt g                             31

<210> SEQ ID NO 38
<211> LENGTH: 30
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
caaaagatag aacagaattc cgaggccctg                                    30

<210> SEQ ID NO 39
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
gaaaaccagg tggagcacag ccctc                                         25

<210> SEQ ID NO 40
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
cagtctgtga gccagcataa ccaccac                                       27

<210> SEQ ID NO 41
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
cagtcggtga cccagcttga cagc                                          24

<210> SEQ ID NO 42
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
cagtcagtga cccagcctga catccac                                       27

<210> SEQ ID NO 43
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
cagtcggtga cccagcttgg cag                                           23
```

```
<210> SEQ ID NO 44
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
cagtctgtga cccagcttga cagcca                                          26

<210> SEQ ID NO 45
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
cagtcggtga cccagcttga tggc                                            24

<210> SEQ ID NO 46
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
gattcagtgg tccagacaga aggccaagt                                       29

<210> SEQ ID NO 47
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
aattcagtga cccagatgga agggcc                                          26

<210> SEQ ID NO 48
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
gaacctgaag tcacccagac tcccagc                                         27

<210> SEQ ID NO 49
<211> LENGTH: 30
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 49
gctgtttccc agactccaaa atacctggtc                                      30

<210> SEQ ID NO 50
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
gaagttaccc agacaccaaa acacctggtc                                      30

<210> SEQ ID NO 51
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
ggagtcactc aaactccaag atatctgatc aaaac                                35

<210> SEQ ID NO 52
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
ggtgtcactc agaccccaaa attccag                                         27

<210> SEQ ID NO 53
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
ggagtctccc agtccctgag acacaagg                                        28

<210> SEQ ID NO 54
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
ggagttacgc agacaccaag acacctgg                                        28
```

```
<210> SEQ ID NO 55
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
ggtgtcactc agaccccaaa attccg                                         26

<210> SEQ ID NO 56
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
ggagtctccc agtcccccag taacaag                                        27

<210> SEQ ID NO 57
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
gggatcaccc aggcaccaac atctc                                          25

<210> SEQ ID NO 58
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
ggagtctccc agaccccag taacaag                                         27

<210> SEQ ID NO 59
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
ggagtcaccc aaagtcccac acacct                                         26

<210> SEQ ID NO 60
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 60
ggagtcacac aaaccccaaa gcacct                                           26

<210> SEQ ID NO 61
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
gaaatcaccc agagcccaag acacaaga                                         28

<210> SEQ ID NO 62
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
gaagttgccc agtcccccag atataagatt a                                     31

<210> SEQ ID NO 63
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
ggaatcaccc agagcccaag atacaagat                                        29

<210> SEQ ID NO 64
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
ggagttgccc agtctcccag atataagatt atagag                                36

<210> SEQ ID NO 65
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
ggagtctccc agtccccaag gtacaaag                                         28

<210> SEQ ID NO 66
<211> LENGTH: 26
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 66
ggagtctccc agtccccaag gtacga                                          26

<210> SEQ ID NO 67
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
ggtgtcactc agaccccaaa attccac                                         27

<210> SEQ ID NO 68
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
ggagtctccc agtctcccag gtacaaagtc                                      30

<210> SEQ ID NO 69
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
ggtgtcactc agaccccaaa attccacat                                       29

<210> SEQ ID NO 70
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
ggagtctccc agtcccctag gtacaaagtc                                      30

<210> SEQ ID NO 71
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
ggagtcacac aaagtcccac acacctga                                        28
```

<210> SEQ ID NO 72
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
ggagtctccc agaaccccag acacaag                                           27

<210> SEQ ID NO 73
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
ggagtcatcc agtccccaag acatctgat                                         29

<210> SEQ ID NO 74
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
ggagttatcc agtcacccccg ccatg                                            25

<210> SEQ ID NO 75
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
ggagttatcc agtcacccccg gcac                                             24

<210> SEQ ID NO 76
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
agagtcaccc agacaccaag gcacaag                                           27

<210> SEQ ID NO 77
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
ggagttactc agttccccag ccacagc                                     27

<210> SEQ ID NO 78
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
atggtcatcc agaacccaag ataccaggtt                                  30

<210> SEQ ID NO 79
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
gagcctggag tcagccagac ccc                                         23

<210> SEQ ID NO 80
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
ggcgtcatgc agaacccaag acac                                        24

<210> SEQ ID NO 81
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
ggaatcactc agtccccaaa gtacctgttc a                                31

<210> SEQ ID NO 82
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
gctgtcgtct ctcaacatcc gagctg                                      26

<210> SEQ ID NO 83
<211> LENGTH: 24
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
attccagctc actggggctg gatg                                          24

<210> SEQ ID NO 84
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
aaagtcacac agactccagg acatttggtc a                                  31

<210> SEQ ID NO 85
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85
gatgttaccc agaccccaag gaataggatc                                    30

<210> SEQ ID NO 86
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
gacatctacc agaccccaag ataccttgtt atagg                              35

<210> SEQ ID NO 87
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
gtagttacac aattcccaag acacagaatc attgg                              35

<210> SEQ ID NO 88
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
caagtgaccc agaacccaag atacctcatc                                    30
```

```
<210> SEQ ID NO 89
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
ggtggcagca gtcacagatg cctactc                                         27

<210> SEQ ID NO 90
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
ggtggcagca gccacaggtg cccactc                                         27

<210> SEQ ID NO 91
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
ggtggcagca gctacaggtg tccagtc                                         27

<210> SEQ ID NO 92
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
ggtggsagca gcaacargwg cccactc                                         27

<210> SEQ ID NO 93
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
gctggctgta gctccaggtg ctcactc                                         27

<210> SEQ ID NO 94
<211> LENGTH: 33
<212> TYPE: DNA
<213> ORGANISM: Artificial Sequence
<220> FEATURE:
```

<221> NAME/KEY: source
<223> OTHER INFORMATION: /note="Description of Artificial Sequence:
       Synthetic oligonucleotide"

<400> SEQUENCE: 94
cctgctgctg accayccctt cmtgggtctt gtc         33

<210> SEQ ID NO 95
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 95
cctgctactg actgtcccgt cctgggtctt atc         33

<210> SEQ ID NO 96
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 96
gggttttcct cgttgctctt ttaagaggtg tccagtg     37

<210> SEQ ID NO 97
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 97
gggttttcct tgttgctatt ttaaaaggtg tccartg     37

<210> SEQ ID NO 98
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 98
ggattttcct tgctgctatt ttaaaaggtg tccagtg     37

<210> SEQ ID NO 99
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 99
gggttttcct tktkgctatw ttagaaggtg tccagtg     37

```
<210> SEQ ID NO 100
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
ggtggcrgct cccagatggg tcctgtc                                           27

<210> SEQ ID NO 101
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
ctggctgttc tccaaggagt ctgtg                                             25

<210> SEQ ID NO 102
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
ggcctcccat ggggtgtcct gtc                                               23

<210> SEQ ID NO 103
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103
ggtggcagca gcaacaggtg cccact                                            26

<210> SEQ ID NO 104
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
atggaactgg ggctccgctg ggttttcc                                          28

<210> SEQ ID NO 105
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 105
atggactgca cctggaggat cctcctc                                    27

<210> SEQ ID NO 106
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
tggctgagct gggtttycct tgttgc                                     26

<210> SEQ ID NO 107
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
ggagttkggg ctgmgctggg ttttcc                                     26

<210> SEQ ID NO 108
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
gcacctgtgg tttttcctcc tgctggtg                                   28

<210> SEQ ID NO 109
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
cacctgtggt tcttcctcct sctgg                                      25

<210> SEQ ID NO 110
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
ccaggatggg gtcaaccgcc atcctc                                     26

<210> SEQ ID NO 111
<211> LENGTH: 30
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 111
cagaggactc accatggagt ttgggctgag                                          30

<210> SEQ ID NO 112
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
ggactcacca tggagttggg actgagc                                             27

<210> SEQ ID NO 113
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
gggctgagct ggcttttct tgtggc                                               26

<210> SEQ ID NO 114
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
aagcagtggt atcaacgcag agtacatggg                                          30

<210> SEQ ID NO 115
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
tctgcgttga taccact                                                        17

<210> SEQ ID NO 116
<211> LENGTH: 30
<212> TYPE: DNA
<213> ORGANISM: Homo sapiens

<400> SEQUENCE: 116
gaaggagctc cagatgaaag actctgcctc                                          30

<210> SEQ ID NO 117
<211> LENGTH: 30
<212> TYPE: DNA
```

```
<213> ORGANISM: Homo sapiens

<400> SEQUENCE: 117
gttctcttca tcgctgctca tcctccaggt                                30

<210> SEQ ID NO 118
<211> LENGTH: 30
<212> TYPE: DNA
<213> ORGANISM: Homo sapiens

<400> SEQUENCE: 118
cttgtgagcg actccgcttt gtacttctgt                                30

<210> SEQ ID NO 119
<211> LENGTH: 30
<212> TYPE: DNA
<213> ORGANISM: Homo sapiens

<400> SEQUENCE: 119
ttatccctgc cgacagaaag tccagcactc                                30

<210> SEQ ID NO 120
<211> LENGTH: 31
<212> TYPE: DNA
<213> ORGANISM: Homo sapiens

<400> SEQUENCE: 120
aaggataaac atctgtctct gcgcattgca g                              31

<210> SEQ ID NO 121
<211> LENGTH: 30
<212> TYPE: DNA
<213> ORGANISM: Homo sapiens

<400> SEQUENCE: 121
ttgtttcata tcacagcctc ccagcctgca                                30

<210> SEQ ID NO 122
<211> LENGTH: 31
<212> TYPE: DNA
<213> ORGANISM: Homo sapiens

<400> SEQUENCE: 122
tacattacag ccgtgcagcc tgaagattca g                              31

<210> SEQ ID NO 123
<211> LENGTH: 30
<212> TYPE: DNA
<213> ORGANISM: Homo sapiens

<400> SEQUENCE: 123
aatctgagga aaccctctgt gcagtggagt                                30

<210> SEQ ID NO 124
<211> LENGTH: 30
<212> TYPE: DNA
<213> ORGANISM: Homo sapiens

<400> SEQUENCE: 124
gaaacctcct tccacctgac gaaaccctca                                30

<210> SEQ ID NO 125
<211> LENGTH: 30
```

<212> TYPE: DNA
<213> ORGANISM: Homo sapiens

<400> SEQUENCE: 125
caatctgagg aaaccctctg tgcattggag                             30

<210> SEQ ID NO 126
<211> LENGTH: 30
<212> TYPE: DNA
<213> ORGANISM: Homo sapiens

<400> SEQUENCE: 126
cacctgacga aaccctcagc ccatatgagc                             30

<210> SEQ ID NO 127
<211> LENGTH: 30
<212> TYPE: DNA
<213> ORGANISM: Homo sapiens

<400> SEQUENCE: 127
ggaaaccctc agtccatata agcgacacgg                             30

<210> SEQ ID NO 128
<211> LENGTH: 30
<212> TYPE: DNA
<213> ORGANISM: Homo sapiens

<400> SEQUENCE: 128
gaggaaacca tcaacccatg tgagtgatgc                             30

<210> SEQ ID NO 129
<211> LENGTH: 32
<212> TYPE: DNA
<213> ORGANISM: Homo sapiens

<400> SEQUENCE: 129
ggaaggaaca aaggttttga agccatgtac cg                          32

<210> SEQ ID NO 130
<211> LENGTH: 30
<212> TYPE: DNA
<213> ORGANISM: Homo sapiens

<400> SEQUENCE: 130
tccacttgga gaaaggctca gttcaagtgt                             30

<210> SEQ ID NO 131
<211> LENGTH: 30
<212> TYPE: DNA
<213> ORGANISM: Homo sapiens

<400> SEQUENCE: 131
gcagacacaa agcaaagctc tctgcacatc                             30

<210> SEQ ID NO 132
<211> LENGTH: 30
<212> TYPE: DNA
<213> ORGANISM: Homo sapiens

<400> SEQUENCE: 132
gccagccagt atatttccct gctcatcaga                             30

<210> SEQ ID NO 133

```
<211> LENGTH: 30
<212> TYPE: DNA
<213> ORGANISM: Homo sapiens

<400> SEQUENCE: 133
gccagccagt atgtttctct gctcatcaga                               30

<210> SEQ ID NO 134
<211> LENGTH: 30
<212> TYPE: DNA
<213> ORGANISM: Homo sapiens

<400> SEQUENCE: 134
ggtttacagc acaggtcgat aaatccagca                               30

<210> SEQ ID NO 135
<211> LENGTH: 30
<212> TYPE: DNA
<213> ORGANISM: Homo sapiens

<400> SEQUENCE: 135
gccaaacatt tctccctgca catcacagag                               30

<210> SEQ ID NO 136
<211> LENGTH: 30
<212> TYPE: DNA
<213> ORGANISM: Homo sapiens

<400> SEQUENCE: 136
tctgcaaatt gcagctactc aacctggaga                               30

<210> SEQ ID NO 137
<211> LENGTH: 30
<212> TYPE: DNA
<213> ORGANISM: Homo sapiens

<400> SEQUENCE: 137
gccaaccttg tcatctccgc ttcacaactg                               30

<210> SEQ ID NO 138
<211> LENGTH: 31
<212> TYPE: DNA
<213> ORGANISM: Homo sapiens

<400> SEQUENCE: 138
gaccttaaca aaggcgagac atctttccac c                             31

<210> SEQ ID NO 139
<211> LENGTH: 30
<212> TYPE: DNA
<213> ORGANISM: Homo sapiens

<400> SEQUENCE: 139
gtcacgcttg acacttccaa gaaaagcagt                               30

<210> SEQ ID NO 140
<211> LENGTH: 30
<212> TYPE: DNA
<213> ORGANISM: Homo sapiens

<400> SEQUENCE: 140
cctatcaaga gtgacagttc cttccacctg                               30
```

```
<210> SEQ ID NO 141
<211> LENGTH: 30
<212> TYPE: DNA
<213> ORGANISM: Homo sapiens

<400> SEQUENCE: 141
ggaacttcca gaaatccacc agttccttca                                    30

<210> SEQ ID NO 142
<211> LENGTH: 29
<212> TYPE: DNA
<213> ORGANISM: Homo sapiens

<400> SEQUENCE: 142
agaaggaaag ctttctgcac atcacagcc                                     29

<210> SEQ ID NO 143
<211> LENGTH: 30
<212> TYPE: DNA
<213> ORGANISM: Homo sapiens

<400> SEQUENCE: 143
caagtggaag acttaatgcc tcgctggata                                    30

<210> SEQ ID NO 144
<211> LENGTH: 30
<212> TYPE: DNA
<213> ORGANISM: Homo sapiens

<400> SEQUENCE: 144
gactgtcgct acggaacgct acagcttatt                                    30

<210> SEQ ID NO 145
<211> LENGTH: 30
<212> TYPE: DNA
<213> ORGANISM: Homo sapiens

<400> SEQUENCE: 145
tgccaagcag ttctcatcgc atatcatgga                                    30

<210> SEQ ID NO 146
<211> LENGTH: 30
<212> TYPE: DNA
<213> ORGANISM: Homo sapiens

<400> SEQUENCE: 146
gccactctta ataccaagga gggttacagc                                    30

<210> SEQ ID NO 147
<211> LENGTH: 30
<212> TYPE: DNA
<213> ORGANISM: Homo sapiens

<400> SEQUENCE: 147
cacatcacag ccacccagac tacagatgta                                    30

<210> SEQ ID NO 148
<211> LENGTH: 30
<212> TYPE: DNA
<213> ORGANISM: Homo sapiens

<400> SEQUENCE: 148
tcatcacaga agacagaaag tccagcacct                                    30
```

<210> SEQ ID NO 149
<211> LENGTH: 30
<212> TYPE: DNA
<213> ORGANISM: Homo sapiens

<400> SEQUENCE: 149
agaaagtcca gtaccttgat cctgcaccgt					30

<210> SEQ ID NO 150
<211> LENGTH: 30
<212> TYPE: DNA
<213> ORGANISM: Homo sapiens

<400> SEQUENCE: 150
gttctctcca catcactgca gcccagactg					30

<210> SEQ ID NO 151
<211> LENGTH: 30
<212> TYPE: DNA
<213> ORGANISM: Homo sapiens

<400> SEQUENCE: 151
aaagtgccaa gcacctctct ctgcacattg					30

<210> SEQ ID NO 152
<211> LENGTH: 30
<212> TYPE: DNA
<213> ORGANISM: Homo sapiens

<400> SEQUENCE: 152
ctgtacctta cggcctccca gctcagttac					30

<210> SEQ ID NO 153
<211> LENGTH: 30
<212> TYPE: DNA
<213> ORGANISM: Homo sapiens

<400> SEQUENCE: 153
gccaagttgg atgagaaaaa gcagcaaagt					30

<210> SEQ ID NO 154
<211> LENGTH: 30
<212> TYPE: DNA
<213> ORGANISM: Homo sapiens

<400> SEQUENCE: 154
gacctcaaat ggaagactga ctgctcagtt					30

<210> SEQ ID NO 155
<211> LENGTH: 30
<212> TYPE: DNA
<213> ORGANISM: Homo sapiens

<400> SEQUENCE: 155
tttcagcatc ctgaacatca cagccaccca					30

<210> SEQ ID NO 156
<211> LENGTH: 30
<212> TYPE: DNA
<213> ORGANISM: Homo sapiens

<400> SEQUENCE: 156
ccttcagtct caagatctca gactcacagc					30

<210> SEQ ID NO 157
<211> LENGTH: 29
<212> TYPE: DNA
<213> ORGANISM: Homo sapiens

<400> SEQUENCE: 157
aatggcctca cttgatacca aagcccgtc                              29

<210> SEQ ID NO 158
<211> LENGTH: 30
<212> TYPE: DNA
<213> ORGANISM: Homo sapiens

<400> SEQUENCE: 158
ctcccccatt gtgaaatatt cagtccaggt                             30

<210> SEQ ID NO 159
<211> LENGTH: 30
<212> TYPE: DNA
<213> ORGANISM: Homo sapiens

<400> SEQUENCE: 159
catacaggaa aagcacagct ccctgcacat                             30

<210> SEQ ID NO 160
<211> LENGTH: 31
<212> TYPE: DNA
<213> ORGANISM: Homo sapiens

<400> SEQUENCE: 160
atatcgcagc ctctcatctg ggagattcag c                           31

<210> SEQ ID NO 161
<211> LENGTH: 31
<212> TYPE: DNA
<213> ORGANISM: Homo sapiens

<400> SEQUENCE: 161
caggagctcc agatgaaaga ctctgcctct t                           31

<210> SEQ ID NO 162
<211> LENGTH: 32
<212> TYPE: DNA
<213> ORGANISM: Homo sapiens

<400> SEQUENCE: 162
acttccttcc acttgaggaa accctcagtc ca                          32

<210> SEQ ID NO 163
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
gtgactggag ttcagacgtg tgctcttccg atctgaagga gctccagatg aaagactctg   60
cctc                                                         64

<210> SEQ ID NO 164

```
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
gtgactggag ttcagacgtg tgctcttccg atctgttctc ttcatcgctg ctcatcctcc    60
aggt                                                                 64

<210> SEQ ID NO 165
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
gtgactggag ttcagacgtg tgctcttccg atctcttgtg agcgactccg ctttgtactt    60
ctgt                                                                 64

<210> SEQ ID NO 166
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
gtgactggag ttcagacgtg tgctcttccg atctttatcc ctgccgacag aaagtccagc    60
actc                                                                 64

<210> SEQ ID NO 167
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
gtgactggag ttcagacgtg tgctcttccg atctaaggat aaacatctgt ctctgcgcat    60
tgcag                                                                65

<210> SEQ ID NO 168
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
gtgactggag ttcagacgtg tgctcttccg atctttgttt catatcacag cctcccagcc    60
tgca                                                                 64
```

```
<210> SEQ ID NO 169
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
gtgactggag ttcagacgtg tgctcttccg atcttacatt acagccgtgc agcctgaaga    60
ttcag                                                                65

<210> SEQ ID NO 170
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
gtgactggag ttcagacgtg tgctcttccg atctaatctg aggaaaccct ctgtgcagtg    60
gagt                                                                 64

<210> SEQ ID NO 171
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
gtgactggag ttcagacgtg tgctcttccg atctgaaacc tccttccacc tgacgaaacc    60
ctca                                                                 64

<210> SEQ ID NO 172
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
gtgactggag ttcagacgtg tgctcttccg atctcaatct gaggaaaccc tctgtgcatt    60
ggag                                                                 64

<210> SEQ ID NO 173
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
gtgactggag ttcagacgtg tgctcttccg atctcacctg acgaaaccct cagcccatat    60
gagc                                                                 64
```

<210> SEQ ID NO 174
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
gtgactggag ttcagacgtg tgctcttccg atctggaaac cctcagtcca tataagcgac    60
acgg                                                                64

<210> SEQ ID NO 175
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
gtgactggag ttcagacgtg tgctcttccg atctgaggaa accatcaacc catgtgagtg    60
atgc                                                                64

<210> SEQ ID NO 176
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
gtgactggag ttcagacgtg tgctcttccg atctggaagg aacaaaggtt ttgaagccat    60
gtaccg                                                              66

<210> SEQ ID NO 177
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
gtgactggag ttcagacgtg tgctcttccg atcttccact tggagaaagg ctcagttcaa    60
gtgt                                                                64

<210> SEQ ID NO 178
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
gtgactggag ttcagacgtg tgctcttccg atctgcagac acaaagcaaa gctctctgca    60
catc                                                                64

<210> SEQ ID NO 179
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 179
gtgactggag ttcagacgtg tgctcttccg atctgccagc cagtatattt ccctgctcat    60
caga    64

<210> SEQ ID NO 180
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 180
gtgactggag ttcagacgtg tgctcttccg atctgccagc cagtatgttt ctctgctcat    60
caga    64

<210> SEQ ID NO 181
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 181
gtgactggag ttcagacgtg tgctcttccg atctggttta cagcacaggt cgataaatcc    60
agca    64

<210> SEQ ID NO 182
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 182
gtgactggag ttcagacgtg tgctcttccg atctgccaaa catttctccc tgcacatcac    60
agag    64

<210> SEQ ID NO 183
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 183
gtgactggag ttcagacgtg tgctcttccg atcttctgca aattgcagct actcaacctg    60
gaga                                                                 64

<210> SEQ ID NO 184
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
gtgactggag ttcagacgtg tgctcttccg atctgccaac cttgtcatct ccgcttcaca    60
actg                                                                 64

<210> SEQ ID NO 185
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
gtgactggag ttcagacgtg tgctcttccg atctgacctt aacaaaggcg agacatcttt    60
ccacc                                                                65

<210> SEQ ID NO 186
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
gtgactggag ttcagacgtg tgctcttccg atctgtcacg cttgacactt ccaagaaaag    60
cagt                                                                 64

<210> SEQ ID NO 187
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
gtgactggag ttcagacgtg tgctcttccg atctcctatc aagagtgaca gttccttcca    60
cctg                                                                 64

<210> SEQ ID NO 188
<211> LENGTH: 64
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 188
gtgactggag ttcagacgtg tgctcttccg atctggaact tccagaaatc caccagttcc    60
ttca                                                                 64

<210> SEQ ID NO 189
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
gtgactggag ttcagacgtg tgctcttccg atctagaagg aaagctttct gcacatcaca    60
gcc                                                                  63

<210> SEQ ID NO 190
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
gtgactggag ttcagacgtg tgctcttccg atctcaagtg gaagacttaa tgcctcgctg    60
gata                                                                 64

<210> SEQ ID NO 191
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
gtgactggag ttcagacgtg tgctcttccg atctgactgt cgctacggaa cgctacagct    60
tatt                                                                 64

<210> SEQ ID NO 192
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
gtgactggag ttcagacgtg tgctcttccg atcttgccaa gcagttctca tcgcatatca    60
tgga                                                                 64

<210> SEQ ID NO 193
<211> LENGTH: 64
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 193
gtgactggag ttcagacgtg tgctcttccg atctgccact cttaatacca aggagggtta    60
cagc                                                                 64

<210> SEQ ID NO 194
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
gtgactggag ttcagacgtg tgctcttccg atctcacatc acagccaccc agactacaga    60
tgta                                                                 64

<210> SEQ ID NO 195
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
gtgactggag ttcagacgtg tgctcttccg atcttcatca cagaagacag aaagtccagc    60
acct                                                                 64

<210> SEQ ID NO 196
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
gtgactggag ttcagacgtg tgctcttccg atctagaaag tccagtacct tgatcctgca    60
ccgt                                                                 64

<210> SEQ ID NO 197
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
gtgactggag ttcagacgtg tgctcttccg atctgttctc tccacatcac tgcagcccag    60
actg                                                                 64

<210> SEQ ID NO 198
<211> LENGTH: 64
<212> TYPE: DNA
```

<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 198
gtgactggag ttcagacgtg tgctcttccg atctaaagtg ccaagcacct ctctctgcac    60
attg    64

<210> SEQ ID NO 199
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 199
gtgactggag ttcagacgtg tgctcttccg atctctgtac cttacggcct cccagctcag    60
ttac    64

<210> SEQ ID NO 200
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 200
gtgactggag ttcagacgtg tgctcttccg atctgccaag ttggatgaga aaaagcagca    60
aagt    64

<210> SEQ ID NO 201
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 201
gtgactggag ttcagacgtg tgctcttccg atctgacctc aaatggaaga ctgactgctc    60
agtt    64

<210> SEQ ID NO 202
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 202
gtgactggag ttcagacgtg tgctcttccg atcttttcag catcctgaac atcacagcca    60
ccca    64

<210> SEQ ID NO 203
<211> LENGTH: 64

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
gtgactggag ttcagacgtg tgctcttccg atctccttca gtctcaagat ctcagactca    60
cagc                                                                64

<210> SEQ ID NO 204
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
gtgactggag ttcagacgtg tgctcttccg atctaatggc ctcacttgat accaaagccc    60
gtc                                                                 63

<210> SEQ ID NO 205
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
gtgactggag ttcagacgtg tgctcttccg atctctcccc cattgtgaaa tattcagtcc    60
aggt                                                                64

<210> SEQ ID NO 206
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
gtgactggag ttcagacgtg tgctcttccg atctcataca ggaaaagcac agctccctgc    60
acat                                                                64

<210> SEQ ID NO 207
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
gtgactggag ttcagacgtg tgctcttccg atctatatcg cagcctctca tctgggagat    60
tcagc                                                               65

<210> SEQ ID NO 208

```
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
gtgactggag ttcagacgtg tgctcttccg atctcaggag ctccagatga aagactctgc    60
ctctt                                                                65

<210> SEQ ID NO 209
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
gtgactggag ttcagacgtg tgctcttccg atctacttcc ttccacttga ggaaaccctc    60
agtcca                                                               66

<210> SEQ ID NO 210
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
gtgactggag ttcagacgtg tgctcttccg atct                                34

<210> SEQ ID NO 211
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
aaaaaccaag tggagcagag tcctcagtcc ctg                                 33

<210> SEQ ID NO 212
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
aaacaggagg tgacgcagat tcctgcagct c                                   31

<210> SEQ ID NO 213
<211> LENGTH: 32
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 213
aaggaccaag tgtttcagcc ttccacagtg gc                                  32

<210> SEQ ID NO 214
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
acccagcttg acagccaagt ccctgtct                                       28

<210> SEQ ID NO 215
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
acccagcttg atggccacat cactgtctct                                     30

<210> SEQ ID NO 216
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
acccagcttg gcagccacgt ctctg                                          25

<210> SEQ ID NO 217
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
actcaagcgc agactgaaat ttctgtggtg g                                   31

<210> SEQ ID NO 218
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
agaaggaggt ggagcaggat cctggacca                                      29

<210> SEQ ID NO 219
```

```
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
agaattccga ggctctgaac attcaggagg gtaa                              34

<210> SEQ ID NO 220
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
agagagtgac tcagcccgag aagctcctct                                   30

<210> SEQ ID NO 221
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
agagcccagt cagtgaccca gcctgac                                      27

<210> SEQ ID NO 222
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
agagcccagt cagtgaccca gcctgac                                      27

<210> SEQ ID NO 223
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
agctgctgga gcagagccct cagtttc                                      27

<210> SEQ ID NO 224
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 224
agtcaacagg gagaagagga tcctcaggcc ttg                                33

<210> SEQ ID NO 225
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
agtggagact cggttaccca gacagaaggc c                                  31

<210> SEQ ID NO 226
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
agtggagcag agtcctccag acctgattct c                                  31

<210> SEQ ID NO 227
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
agtgtggggc tgcatcttcc taccctga                                      28

<210> SEQ ID NO 228
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
atactgaacg tggaacaaag tcctcagtca ctgcatg                            37

<210> SEQ ID NO 229
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
attcagtgac ccagatggaa gggccagtga                                    30

<210> SEQ ID NO 230
<211> LENGTH: 29
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
attgatgcta agaccaccca gcccacctc                                       29

<210> SEQ ID NO 231
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
cagaaggagg tggagcagaa ttctggaccc c                                    31

<210> SEQ ID NO 232
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
cagcaattca gtcaagcaga cgggccaa                                        28

<210> SEQ ID NO 233
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
ccaacaacca gtgcagagtc ctcaagccg                                       29

<210> SEQ ID NO 234
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
cggaaggagg tggagcagga tcctgga                                         27

<210> SEQ ID NO 235
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
ctacatacgc cggagcagag tccttcattc ctgag                                35
```

<210> SEQ ID NO 236
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
ctcaaaccca accaggaatg ttcgtgcagg a                                    31

<210> SEQ ID NO 237
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
cttgctaaga ccacccagcc catctccatg gactc                                35

<210> SEQ ID NO 238
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
gaaaaccagg tggagcacag ccctcatttt ctg                                  33

<210> SEQ ID NO 239
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
gaagacaagg tggtacaaag ccctctatct ctggt                                35

<210> SEQ ID NO 240
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
gaagaccagg tgacgcagag tcccgag                                         27

<210> SEQ ID NO 241
<211> LENGTH: 31
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 241
gaccagcagc aggtgaaaca aagtcctcaa t                                        31

<210> SEQ ID NO 242
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
gagcagagtc ctcagaacct gactgccc                                            28

<210> SEQ ID NO 243
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
gatgaccagc aagttaagca aaattcacca tccct                                    35

<210> SEQ ID NO 244
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
gccaagaact ggagcagagt cctcagtcc                                           29

<210> SEQ ID NO 245
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
gcccagtcgg tgacccagct tgacag                                              26

<210> SEQ ID NO 246
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
gcccagtctg tgagccagca taaccaccac                                          30
```

```
<210> SEQ ID NO 247
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
gcctgttcac ttgccttgta accactccac                                      30

<210> SEQ ID NO 248
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
gctcagtcag tggctcagcc ggaagatcag g                                    31

<210> SEQ ID NO 249
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
ggacaaaaca ttgaccagcc cactgagatg acagc                                35

<210> SEQ ID NO 250
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
ggacaaagcc ttgagcagcc ctctgaagtg ac                                   32

<210> SEQ ID NO 251
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
ggacaacagg taatgcaaat tcctcagtac cagcatg                              37

<210> SEQ ID NO 252
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 252
ggagagaatg tggagcagca tccttcaacc ctg						33

<210> SEQ ID NO 253
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253
ggagaggatg tggagcagag tcttttcctg agtgtc					36

<210> SEQ ID NO 254
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
ggagattcag tggtccagac agaaggccaa gtg						33

<210> SEQ ID NO 255
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
gtctcaacca gagatgtctg tgcaggagg							29

<210> SEQ ID NO 256
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
gtggaacaaa accctctgtt cctgagcatg c						31

<210> SEQ ID NO 257
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
gtggtcaaca gctgaatcag agtcctcaat cta					33

<210> SEQ ID NO 258
<211> LENGTH: 27
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 258
gttccggcag gatccgggga gaagact                                           27

<210> SEQ ID NO 259
<211> LENGTH: 31
<212> TYPE: DNA
<213> ORGANISM: Homo sapiens

<400> SEQUENCE: 259
gcctcctccc agacatctgt atatttctgc g                                      31

<210> SEQ ID NO 260
<211> LENGTH: 30
<212> TYPE: DNA
<213> ORGANISM: Homo sapiens

<400> SEQUENCE: 260
aatttccccc tcactctgga gtcagctacc                                        30

<210> SEQ ID NO 261
<211> LENGTH: 30
<212> TYPE: DNA
<213> ORGANISM: Homo sapiens

<400> SEQUENCE: 261
gatttcctcc tcactctgga gtccgctacc                                        30

<210> SEQ ID NO 262
<211> LENGTH: 31
<212> TYPE: DNA
<213> ORGANISM: Homo sapiens

<400> SEQUENCE: 262
aggctcaaag gagtagactc cactctcaag a                                      31

<210> SEQ ID NO 263
<211> LENGTH: 29
<212> TYPE: DNA
<213> ORGANISM: Homo sapiens

<400> SEQUENCE: 263
caagatccag cctgcaaagc ttgaggact                                         29

<210> SEQ ID NO 264
<211> LENGTH: 30
<212> TYPE: DNA
<213> ORGANISM: Homo sapiens

<400> SEQUENCE: 264
tagactccac tctcaagatc cagcctgcag                                        30

<210> SEQ ID NO 265
<211> LENGTH: 30
<212> TYPE: DNA
<213> ORGANISM: Homo sapiens

<400> SEQUENCE: 265
tggaacccag ggacttgggc ctatatttct                                        30
```

<210> SEQ ID NO 266
<211> LENGTH: 31
<212> TYPE: DNA
<213> ORGANISM: Homo sapiens

<400> SEQUENCE: 266
tcattctcta ctctgaagat ccagcctgca g                                  31

<210> SEQ ID NO 267
<211> LENGTH: 30
<212> TYPE: DNA
<213> ORGANISM: Homo sapiens

<400> SEQUENCE: 267
cattctccac tctgaagatc cagccctcag                                    30

<210> SEQ ID NO 268
<211> LENGTH: 31
<212> TYPE: DNA
<213> ORGANISM: Homo sapiens

<400> SEQUENCE: 268
catcattctc cactctgaag atccagccct c                                  31

<210> SEQ ID NO 269
<211> LENGTH: 30
<212> TYPE: DNA
<213> ORGANISM: Homo sapiens

<400> SEQUENCE: 269
cagcagagat gcctgatgca actttagcca                                    30

<210> SEQ ID NO 270
<211> LENGTH: 29
<212> TYPE: DNA
<213> ORGANISM: Homo sapiens

<400> SEQUENCE: 270
gaactgaaca tgagctcctt ggagctggg                                     29

<210> SEQ ID NO 271
<211> LENGTH: 31
<212> TYPE: DNA
<213> ORGANISM: Homo sapiens

<400> SEQUENCE: 271
ggaggattct ggagtttatt tctgtgccag c                                  31

<210> SEQ ID NO 272
<211> LENGTH: 30
<212> TYPE: DNA
<213> ORGANISM: Homo sapiens

<400> SEQUENCE: 272
ttctgctttc ttgacatccg ctcaccaggc                                    30

<210> SEQ ID NO 273
<211> LENGTH: 31
<212> TYPE: DNA
<213> ORGANISM: Homo sapiens

<400> SEQUENCE: 273
gagatccagg ctacgaagct tgaggattca g                                  31

```
<210> SEQ ID NO 274
<211> LENGTH: 28
<212> TYPE: DNA
<213> ORGANISM: Homo sapiens

<400> SEQUENCE: 274
aacgtcttcc acgctgaaga tccatccc                                28

<210> SEQ ID NO 275
<211> LENGTH: 30
<212> TYPE: DNA
<213> ORGANISM: Homo sapiens

<400> SEQUENCE: 275
aggatccagc aggtagtgcg aggagattcg                              30

<210> SEQ ID NO 276
<211> LENGTH: 30
<212> TYPE: DNA
<213> ORGANISM: Homo sapiens

<400> SEQUENCE: 276
acccgacagc tttctatctc tgtgccagta                              30

<210> SEQ ID NO 277
<211> LENGTH: 30
<212> TYPE: DNA
<213> ORGANISM: Homo sapiens

<400> SEQUENCE: 277
gtgcccatcc tgaagacagc agcttctaca                              30

<210> SEQ ID NO 278
<211> LENGTH: 28
<212> TYPE: DNA
<213> ORGANISM: Homo sapiens

<400> SEQUENCE: 278
cacaaagctg gaggactcag ccatgtac                                28

<210> SEQ ID NO 279
<211> LENGTH: 30
<212> TYPE: DNA
<213> ORGANISM: Homo sapiens

<400> SEQUENCE: 279
tcaggggaca cagcactgta tttctgtgcc                              30

<210> SEQ ID NO 280
<211> LENGTH: 30
<212> TYPE: DNA
<213> ORGANISM: Homo sapiens

<400> SEQUENCE: 280
cacaccagcc aaacagcttt gtacttctgt                              30

<210> SEQ ID NO 281
<211> LENGTH: 28
<212> TYPE: DNA
<213> ORGANISM: Homo sapiens
```

```
<400> SEQUENCE: 281
aatcctgtcc tcagaaccgg gagacacg                                      28

<210> SEQ ID NO 282
<211> LENGTH: 31
<212> TYPE: DNA
<213> ORGANISM: Homo sapiens

<400> SEQUENCE: 282
ccaaccagac agctctttac ttctgtgcca c                                  31

<210> SEQ ID NO 283
<211> LENGTH: 30
<212> TYPE: DNA
<213> ORGANISM: Homo sapiens

<400> SEQUENCE: 283
cacatacctc tcagtacctc tgtgccagca                                    30

<210> SEQ ID NO 284
<211> LENGTH: 32
<212> TYPE: DNA
<213> ORGANISM: Homo sapiens

<400> SEQUENCE: 284
ccaaccagac atctgtgtat ctctatgcca gc                                 32

<210> SEQ ID NO 285
<211> LENGTH: 30
<212> TYPE: DNA
<213> ORGANISM: Homo sapiens

<400> SEQUENCE: 285
accagacctc tctgtacttc tgtgccagca                                    30

<210> SEQ ID NO 286
<211> LENGTH: 30
<212> TYPE: DNA
<213> ORGANISM: Homo sapiens

<400> SEQUENCE: 286
aaccagacat ctatgtacct ctgtgccagc                                    30

<210> SEQ ID NO 287
<211> LENGTH: 32
<212> TYPE: DNA
<213> ORGANISM: Homo sapiens

<400> SEQUENCE: 287
acatgagccc tgaagacagc agcatatatc tc                                 32

<210> SEQ ID NO 288
<211> LENGTH: 30
<212> TYPE: DNA
<213> ORGANISM: Homo sapiens

<400> SEQUENCE: 288
agcttggtga ctctgctgtg tatttctgtg                                    30

<210> SEQ ID NO 289
<211> LENGTH: 30
<212> TYPE: DNA
```

<213> ORGANISM: Homo sapiens

<400> SEQUENCE: 289
cttggtgact ctgctgtgta tttctgtgcc                                30

<210> SEQ ID NO 290
<211> LENGTH: 29
<212> TYPE: DNA
<213> ORGANISM: Homo sapiens

<400> SEQUENCE: 290
cagccagaag actcagccct gtatctctg                                 29

<210> SEQ ID NO 291
<211> LENGTH: 28
<212> TYPE: DNA
<213> ORGANISM: Homo sapiens

<400> SEQUENCE: 291
gccagaagac tcggccctgt atctctgt                                  28

<210> SEQ ID NO 292
<211> LENGTH: 30
<212> TYPE: DNA
<213> ORGANISM: Homo sapiens

<400> SEQUENCE: 292
tattccttca cctacacacc ctgcagccag                                30

<210> SEQ ID NO 293
<211> LENGTH: 27
<212> TYPE: DNA
<213> ORGANISM: Homo sapiens

<400> SEQUENCE: 293
agatgaatgt gagcaccttg gagctgg                                   27

<210> SEQ ID NO 294
<211> LENGTH: 29
<212> TYPE: DNA
<213> ORGANISM: Homo sapiens

<400> SEQUENCE: 294
tactgagtca aacacggagc taggggact                                 29

<210> SEQ ID NO 295
<211> LENGTH: 30
<212> TYPE: DNA
<213> ORGANISM: Homo sapiens

<400> SEQUENCE: 295
gttgctctga gatgaatgtg agtgccttgg                                30

<210> SEQ ID NO 296
<211> LENGTH: 30
<212> TYPE: DNA
<213> ORGANISM: Homo sapiens

<400> SEQUENCE: 296
atagctctga gctgaatgtg aacgccttgg                                30

<210> SEQ ID NO 297
<211> LENGTH: 28

<212> TYPE: DNA
<213> ORGANISM: Homo sapiens

<400> SEQUENCE: 297
gagctgaatg tgaacgcctt gttgctgg                                          28

<210> SEQ ID NO 298
<211> LENGTH: 31
<212> TYPE: DNA
<213> ORGANISM: Homo sapiens

<400> SEQUENCE: 298
aactatagct ctgagctgaa tgtgaacgcc t                                      31

<210> SEQ ID NO 299
<211> LENGTH: 29
<212> TYPE: DNA
<213> ORGANISM: Homo sapiens

<400> SEQUENCE: 299
agctgaatgt gaacgccttg ttgctaggg                                         29

<210> SEQ ID NO 300
<211> LENGTH: 29
<212> TYPE: DNA
<213> ORGANISM: Homo sapiens

<400> SEQUENCE: 300
ctgaatgtga acgccttgga gctggagga                                         29

<210> SEQ ID NO 301
<211> LENGTH: 28
<212> TYPE: DNA
<213> ORGANISM: Homo sapiens

<400> SEQUENCE: 301
gctccctccc agacatctgt gtacttct                                          28

<210> SEQ ID NO 302
<211> LENGTH: 28
<212> TYPE: DNA
<213> ORGANISM: Homo sapiens

<400> SEQUENCE: 302
gctgctccct cccaaacatc tgtgtact                                          28

<210> SEQ ID NO 303
<211> LENGTH: 30
<212> TYPE: DNA
<213> ORGANISM: Homo sapiens

<400> SEQUENCE: 303
gctccctccc aaacatctgt gtacttctgt                                        30

<210> SEQ ID NO 304
<211> LENGTH: 29
<212> TYPE: DNA
<213> ORGANISM: Homo sapiens

<400> SEQUENCE: 304
aacacagatg atttcccct cacgttggc                                          29

<210> SEQ ID NO 305

```
-continued

<211> LENGTH: 29
<212> TYPE: DNA
<213> ORGANISM: Homo sapiens

<400> SEQUENCE: 305
gctgctccct cccagacatc tgtgtactt                                29

<210> SEQ ID NO 306
<211> LENGTH: 27
<212> TYPE: DNA
<213> ORGANISM: Homo sapiens

<400> SEQUENCE: 306
agttggctgc tccctcccag acatctg                                  27

<210> SEQ ID NO 307
<211> LENGTH: 30
<212> TYPE: DNA
<213> ORGANISM: Homo sapiens

<400> SEQUENCE: 307
tcagctgctc cctctcagac ttctgtttac                               30

<210> SEQ ID NO 308
<211> LENGTH: 31
<212> TYPE: DNA
<213> ORGANISM: Homo sapiens

<400> SEQUENCE: 308
taaacacaga ggatttccca ctcaggctgg t                             31

<210> SEQ ID NO 309
<211> LENGTH: 31
<212> TYPE: DNA
<213> ORGANISM: Homo sapiens

<400> SEQUENCE: 309
agtcagctgc tccctcccag acatctgtat a                             31

<210> SEQ ID NO 310
<211> LENGTH: 27
<212> TYPE: DNA
<213> ORGANISM: Homo sapiens

<400> SEQUENCE: 310
cagcaggggg acttggctgt gtatctc                                  27

<210> SEQ ID NO 311
<211> LENGTH: 25
<212> TYPE: DNA
<213> ORGANISM: Homo sapiens

<400> SEQUENCE: 311
gcaggaggac tcggccgtgt atctc                                    25

<210> SEQ ID NO 312
<211> LENGTH: 29
<212> TYPE: DNA
<213> ORGANISM: Homo sapiens

<400> SEQUENCE: 312
tctactctga agatccagcg cacagagcg                                29
```

```
<210> SEQ ID NO 313
<211> LENGTH: 28
<212> TYPE: DNA
<213> ORGANISM: Homo sapiens

<400> SEQUENCE: 313
cacagagcag ggggactcag ctgtgtat                                          28

<210> SEQ ID NO 314
<211> LENGTH: 30
<212> TYPE: DNA
<213> ORGANISM: Homo sapiens

<400> SEQUENCE: 314
atctttctcc acctgaagat ccagcgcaca                                        30

<210> SEQ ID NO 315
<211> LENGTH: 29
<212> TYPE: DNA
<213> ORGANISM: Homo sapiens

<400> SEQUENCE: 315
ttctctgcag agaggcctga gggatccat                                         29

<210> SEQ ID NO 316
<211> LENGTH: 30
<212> TYPE: DNA
<213> ORGANISM: Homo sapiens

<400> SEQUENCE: 316
ctgagggatc cgtctccact ctgaagatcc                                        30

<210> SEQ ID NO 317
<211> LENGTH: 30
<212> TYPE: DNA
<213> ORGANISM: Homo sapiens

<400> SEQUENCE: 317
ggcctaaggg atctttctcc accttggaga                                        30

<210> SEQ ID NO 318
<211> LENGTH: 30
<212> TYPE: DNA
<213> ORGANISM: Homo sapiens

<400> SEQUENCE: 318
ttccctcaac cctggagtct actagcacca                                        30

<210> SEQ ID NO 319
<211> LENGTH: 29
<212> TYPE: DNA
<213> ORGANISM: Homo sapiens

<400> SEQUENCE: 319
ttgagcattt ccccaatcct ggcatccac                                         29

<210> SEQ ID NO 320
<211> LENGTH: 30
<212> TYPE: DNA
<213> ORGANISM: Homo sapiens

<400> SEQUENCE: 320
gggactcagc tttgtatttc tgtgccagca                                        30
```

```
<210> SEQ ID NO 321
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 321
gtgactggag ttcagacgtg tgctcttccg atctgcctcc tcccagacat ctgtatattt    60
ctgcg                                                                 65

<210> SEQ ID NO 322
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 322
gtgactggag ttcagacgtg tgctcttccg atctaatttc cccctcactc tggagtcagc    60
tacc                                                                  64

<210> SEQ ID NO 323
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 323
gtgactggag ttcagacgtg tgctcttccg atctgatttc ctcctcactc tggagtccgc    60
tacc                                                                  64

<210> SEQ ID NO 324
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 324
gtgactggag ttcagacgtg tgctcttccg atctaggctc aaaggagtag actccactct    60
caaga                                                                 65

<210> SEQ ID NO 325
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 325
gtgactggag ttcagacgtg tgctcttccg atctcaagat ccagcctgca aagcttgagg    60
act                                                                   63
```

<210> SEQ ID NO 326
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326
gtgactggag ttcagacgtg tgctcttccg atcttagact ccactctcaa gatccagcct    60
gcag                                                                 64

<210> SEQ ID NO 327
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 327
gtgactggag ttcagacgtg tgctcttccg atcttggaac ccagggactt gggcctatat    60
ttct                                                                 64

<210> SEQ ID NO 328
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 328
gtgactggag ttcagacgtg tgctcttccg atcttcattc tctactctga agatccagcc    60
tgcag                                                                65

<210> SEQ ID NO 329
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 329
gtgactggag ttcagacgtg tgctcttccg atctcattct ccactctgaa gatccagccc    60
tcag                                                                 64

<210> SEQ ID NO 330
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 330
gtgactggag ttcagacgtg tgctcttccg atctcatcat tctccactct gaagatccag    60
ccctc    65

<210> SEQ ID NO 331
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 331
gtgactggag ttcagacgtg tgctcttccg atctcagcag agatgcctga tgcaacttta    60
gcca    64

<210> SEQ ID NO 332
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 332
gtgactggag ttcagacgtg tgctcttccg atctgaactg aacatgagct ccttggagct    60
ggg    63

<210> SEQ ID NO 333
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 333
gtgactggag ttcagacgtg tgctcttccg atctggagga ttctggagtt tatttctgtg    60
ccagc    65

<210> SEQ ID NO 334
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 334
gtgactggag ttcagacgtg tgctcttccg atctttctgc tttcttgaca tccgctcacc    60
aggc    64

<210> SEQ ID NO 335
<211> LENGTH: 65
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 335
gtgactggag ttcagacgtg tgctcttccg atctgagatc caggctacga agcttgagga    60
ttcag                                                                65

<210> SEQ ID NO 336
<211> LENGTH: 62
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 336
gtgactggag ttcagacgtg tgctcttccg atctaacgtc ttccacgctg aagatccatc    60
cc                                                                   62

<210> SEQ ID NO 337
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 337
gtgactggag ttcagacgtg tgctcttccg atctaggatc cagcaggtag tgcgaggaga    60
ttcg                                                                 64

<210> SEQ ID NO 338
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 338
gtgactggag ttcagacgtg tgctcttccg atctacccga cagctttcta tctctgtgcc    60
agta                                                                 64

<210> SEQ ID NO 339
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 339
gtgactggag ttcagacgtg tgctcttccg atctgtgccc atcctgaaga cagcagcttc    60
taca                                                                 64

<210> SEQ ID NO 340
<211> LENGTH: 62
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 340
gtgactggag ttcagacgtg tgctcttccg atctcacaaa gctggaggac tcagccatgt    60
ac                                                                  62

<210> SEQ ID NO 341
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 341
gtgactggag ttcagacgtg tgctcttccg atcttcaggg gacacagcac tgtatttctg    60
tgcc                                                                64

<210> SEQ ID NO 342
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 342
gtgactggag ttcagacgtg tgctcttccg atctcacacc agccaaacag ctttgtactt    60
ctgt                                                                64

<210> SEQ ID NO 343
<211> LENGTH: 62
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 343
gtgactggag ttcagacgtg tgctcttccg atctaatcct gtcctcagaa ccgggagaca    60
cg                                                                  62

<210> SEQ ID NO 344
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 344
gtgactggag ttcagacgtg tgctcttccg atctccaacc agacagctct ttacttctgt    60
gccac                                                               65

<210> SEQ ID NO 345
<211> LENGTH: 64
<212> TYPE: DNA
```

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 345
gtgactggag ttcagacgtg tgctcttccg atctcacata cctctcagta cctctgtgcc    60
agca    64

<210> SEQ ID NO 346
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 346
gtgactggag ttcagacgtg tgctcttccg atctccaacc agacatctgt gtatctctat    60
gccagc    66

<210> SEQ ID NO 347
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 347
gtgactggag ttcagacgtg tgctcttccg atctaccaga cctctctgta cttctgtgcc    60
agca    64

<210> SEQ ID NO 348
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 348
gtgactggag ttcagacgtg tgctcttccg atctaaccag acatctatgt acctctgtgc    60
cagc    64

<210> SEQ ID NO 349
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 349
gtgactggag ttcagacgtg tgctcttccg atctacatga gccctgaaga cagcagcata    60
tatctc    66

<210> SEQ ID NO 350
<211> LENGTH: 64

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 350
gtgactggag ttcagacgtg tgctcttccg atctagcttg gtgactctgc tgtgtatttc    60
tgtg                                                                 64

<210> SEQ ID NO 351
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 351
gtgactggag ttcagacgtg tgctcttccg atctcttggt gactctgctg tgtatttctg    60
tgcc                                                                 64

<210> SEQ ID NO 352
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 352
gtgactggag ttcagacgtg tgctcttccg atctcagcca gaagactcag ccctgtatct    60
ctg                                                                  63

<210> SEQ ID NO 353
<211> LENGTH: 62
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 353
gtgactggag ttcagacgtg tgctcttccg atctgccaga agactcggcc ctgtatctct    60
gt                                                                   62

<210> SEQ ID NO 354
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 354
gtgactggag ttcagacgtg tgctcttccg atcttattcc ttcacctaca caccctgcag    60
ccag                                                                 64

<210> SEQ ID NO 355
```

-continued

```
<211> LENGTH: 61
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 355
gtgactggag ttcagacgtg tgctcttccg atctagatga atgtgagcac cttggagctg    60
g                                                                   61

<210> SEQ ID NO 356
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 356
gtgactggag ttcagacgtg tgctcttccg atcttactga gtcaaacacg gagctagggg    60
act                                                                 63

<210> SEQ ID NO 357
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 357
gtgactggag ttcagacgtg tgctcttccg atctgttgct ctgagatgaa tgtgagtgcc    60
ttgg                                                                64

<210> SEQ ID NO 358
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 358
gtgactggag ttcagacgtg tgctcttccg atctatagct ctgagctgaa tgtgaacgcc    60
ttgg                                                                64

<210> SEQ ID NO 359
<211> LENGTH: 62
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 359
gtgactggag ttcagacgtg tgctcttccg atctgagctg aatgtgaacg ccttgttgct    60
gg                                                                  62
```

```
<210> SEQ ID NO 360
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 360
gtgactggag ttcagacgtg tgctcttccg atctaactat agctctgagc tgaatgtgaa    60
cgcct                                                                65

<210> SEQ ID NO 361
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 361
gtgactggag ttcagacgtg tgctcttccg atctagctga atgtgaacgc cttgttgcta    60
ggg                                                                  63

<210> SEQ ID NO 362
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 362
gtgactggag ttcagacgtg tgctcttccg atctctgaat gtgaacgcct tggagctgga    60
gga                                                                  63

<210> SEQ ID NO 363
<211> LENGTH: 62
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 363
gtgactggag ttcagacgtg tgctcttccg atctgctccc tcccagacat ctgtgtactt    60
ct                                                                   62

<210> SEQ ID NO 364
<211> LENGTH: 62
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 364
gtgactggag ttcagacgtg tgctcttccg atctgctgct ccctcccaaa catctgtgta    60
ct                                                                   62
```

<210> SEQ ID NO 365
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 365
gtgactggag ttcagacgtg tgctcttccg atctgctccc tcccaaacat ctgtgtactt    60
ctgt    64

<210> SEQ ID NO 366
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 366
gtgactggag ttcagacgtg tgctcttccg atctaacaca gatgatttcc ccctcacgtt    60
ggc    63

<210> SEQ ID NO 367
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 367
gtgactggag ttcagacgtg tgctcttccg atctgctgct ccctcccaga catctgtgta    60
ctt    63

<210> SEQ ID NO 368
<211> LENGTH: 61
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 368
gtgactggag ttcagacgtg tgctcttccg atctagttgg ctgctccctc ccagacatct    60
g    61

<210> SEQ ID NO 369
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 369
gtgactggag ttcagacgtg tgctcttccg atcttcagct gctccctctc agacttctgt    60
ttac    64

<210> SEQ ID NO 370
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 370

```
gtgactggag ttcagacgtg tgctcttccg atcttaaaca cagaggattt cccactcagg    60
ctggt                                                                65
```

<210> SEQ ID NO 371
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 371

```
gtgactggag ttcagacgtg tgctcttccg atctagtcag ctgctccctc ccagacatct    60
gtata                                                                65
```

<210> SEQ ID NO 372
<211> LENGTH: 61
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 372

```
gtgactggag ttcagacgtg tgctcttccg atctcagcag ggggacttgg ctgtgtatct    60
c                                                                    61
```

<210> SEQ ID NO 373
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 373

```
gtgactggag ttcagacgtg tgctcttccg atctgcagga ggactcggcc gtgtatctc     59
```

<210> SEQ ID NO 374
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 374

```
gtgactggag ttcagacgtg tgctcttccg atcttctact ctgaagatcc agcgcacaga    60
gcg                                                                  63
```

<210> SEQ ID NO 375
<211> LENGTH: 62
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 375
gtgactggag ttcagacgtg tgctcttccg atctcacaga gcaggggac tcagctgtgt    60 at                                                                  62

<210> SEQ ID NO 376
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 376
gtgactggag ttcagacgtg tgctcttccg atctatcttt ctccacctga agatccagcg    60
caca                                                                64

<210> SEQ ID NO 377
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 377
gtgactggag ttcagacgtg tgctcttccg atctttctct gcagagaggc ctgagggatc    60
cat                                                                 63

<210> SEQ ID NO 378
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 378
gtgactggag ttcagacgtg tgctcttccg atctctgagg gatccgtctc cactctgaag    60
atcc                                                                64

<210> SEQ ID NO 379
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 379
gtgactggag ttcagacgtg tgctcttccg atctggccta agggatcttt ctccaccttg    60
gaga                                                                64

<210> SEQ ID NO 380
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 380
gtgactggag ttcagacgtg tgctcttccg atctttccct caaccctgga gtctactagc    60
acca    64

<210> SEQ ID NO 381
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 381
gtgactggag ttcagacgtg tgctcttccg atctttgagc atttccccaa tcctggcatc    60
cac    63

<210> SEQ ID NO 382
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 382
gtgactggag ttcagacgtg tgctcttccg atctgggact cagctttgta tttctgtgcc    60
agca    64

<210> SEQ ID NO 383
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 383
gctgaaatca cccagagccc aagacacaag    30

<210> SEQ ID NO 384
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 384
cacagagaca ggaaggcagg tgaccttga    29

<210> SEQ ID NO 385

<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 385
gatgctggaa tcacccagag cccaagacac                               30

<210> SEQ ID NO 386
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 386
gccaggctgt ggcttttggg tgtgatccta                               30

<210> SEQ ID NO 387
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 387
ggcagagtgt ggcttttggg tgcaatcct                                29

<210> SEQ ID NO 388
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 388
ggcttttggg tgcaatccta tttctggcca c                             31

<210> SEQ ID NO 389
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 389
gatgctggtg ttatccagtc acccaggcac                               30

<210> SEQ ID NO 390
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 390
gtcacccaag catgaggtga cagaaatggg                                              30

<210> SEQ ID NO 391
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 391
atgctggagt tatccagtca ccccgcc                                                 27

<210> SEQ ID NO 392
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 392
gagttatcca gtcaccccgg cacgaggt                                                28

<210> SEQ ID NO 393
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 393
gctagagtca cccagacacc aaggcaca                                                28

<210> SEQ ID NO 394
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 394
gctgctggag tcatccagtc cccaaga                                                 27

<210> SEQ ID NO 395
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 395
gttactcagt tccccagcca cagcgtaat                                               29

<210> SEQ ID NO 396
<211> LENGTH: 29
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 396
gttacccagt ttggaaagcc agtgaccct                                          29

<210> SEQ ID NO 397
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 397
gaagtcgccc agactccaaa acatcttgtc                                         30

<210> SEQ ID NO 398
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 398
cagacacaag gtcaccaaca tgggacagg                                          29

<210> SEQ ID NO 399
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 399
gtcatgttta ctggtatcgg cagctccca                                          29

<210> SEQ ID NO 400
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 400
atgccatgta ctggtaccga caggaccca                                          29

<210> SEQ ID NO 401
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 401
gtcgtctctc aacatccgag ctgggttat                                          29
```

<210> SEQ ID NO 402
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 402
gaacctgaag tcacccagac tcccagcca                                29

<210> SEQ ID NO 403
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 403
cacggacacc aaggtcaccc agagacct                                 28

<210> SEQ ID NO 404
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 404
agctcactgg ggctggatgg gatgtgac                                 28

<210> SEQ ID NO 405
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 405
gccaaagtca cacagactcc aggacattt                                29

<210> SEQ ID NO 406
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 406
gtatcgacaa gacccaggac tgggcctac                                29

<210> SEQ ID NO 407
<211> LENGTH: 29
<212> TYPE: DNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 407
gctgacatct accagacccc aagatacct                     29

<210> SEQ ID NO 408
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 408
gtatcgacag gacccaggac ttggactga                     29

<210> SEQ ID NO 409
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 409
agcccaagtg acccagaacc caagatac                      28

<210> SEQ ID NO 410
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 410
ctcgtagatg tgaaagtaac ccagagctcg a                  31

<210> SEQ ID NO 411
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 411
gatatctgtc aacgtggaac ctccctgacg                    30

<210> SEQ ID NO 412
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 412
ggtcacacag atgggaaacg acaagtcca                     29

```
<210> SEQ ID NO 413
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 413
ccgtttccca gactccaaaa tacctggtc                                        29

<210> SEQ ID NO 414
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 414
gaagttaccc agacaccaaa acacctggtc                                       30

<210> SEQ ID NO 415
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 415
gagttacgca gacaccaaga cacctggtc                                        29

<210> SEQ ID NO 416
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 416
ggagttacgc agacaccaag acacctgg                                         28

<210> SEQ ID NO 417
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 417
gtgacactga gctgctcccc tatctctgg                                        29

<210> SEQ ID NO 418
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 418
gaatcaccca agctccaaga cacctgatc                                  29

<210> SEQ ID NO 419
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 419
ctggagtcac ccaaagtccc acacacc                                    27

<210> SEQ ID NO 420
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 420
gactggagtc acccaaagtc ccacacac                                   28

<210> SEQ ID NO 421
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 421
gtcccacaca cctgatcaaa acgagagga                                  29

<210> SEQ ID NO 422
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 422
tagtggacgc tggagtcacc caaagtcc                                   28

<210> SEQ ID NO 423
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 423
ctgatcaaaa cgagaggaca gcacgtgac                                  29

<210> SEQ ID NO 424
<211> LENGTH: 29
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 424
gagtcacaca aagtcccaca cacctgatc                                        29

<210> SEQ ID NO 425
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 425
gtgaatgctg gtgtcactca gaccccaaa                                        29

<210> SEQ ID NO 426
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 426
gaatgctggt gtcactcaga ccccaaaat                                        29

<210> SEQ ID NO 427
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 427
gctggtgtca ctcagacccc aaaattccg                                        29

<210> SEQ ID NO 428
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 428
gatcacccag gcaccaacat ctcagatcc                                        29

<210> SEQ ID NO 429
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 429
gctggtgtca ctcagacccc aaaattcca                                        29
```

<210> SEQ ID NO 430
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 430
gctggtgtca ctcagacccc aaaattccg                              29

<210> SEQ ID NO 431
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 431
gaatgctggt gtcactcaga ccccaaaat                              29

<210> SEQ ID NO 432
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 432
gctggtgtca ctcagacccc aaaattcca                              29

<210> SEQ ID NO 433
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 433
gaatgctggt gtcactcaga ccccaaaat                              29

<210> SEQ ID NO 434
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 434
gtgctggagt ctcccagtcc ctgagaca                               28

<210> SEQ ID NO 435
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 435
gtcccccagt aacaaggtca cagagaagg                                29

<210> SEQ ID NO 436
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 436 gaccccagt aacaaggtca cagagaagg                                 29

<210> SEQ ID NO 437
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 437
cagtccccaa ggtacaaagt cgcaaagag                                29

<210> SEQ ID NO 438
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 438
gtctcccagt ccccaaggta cgaagtc                                  27

<210> SEQ ID NO 439
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 439
cacaggtgct ggagtctccc agtctc                                   26

<210> SEQ ID NO 440
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 440
gtgctggagt ctcccagtcc cctagg                                   26

<210> SEQ ID NO 441
<211> LENGTH: 27
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 441
ctggagtctc ccagaacccc agacaca                                            27

<210> SEQ ID NO 442
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 442
gaggcaggga tcagccagat accaagat                                           28

<210> SEQ ID NO 443
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 443
gatgctggga tcacccagat gccaaga                                            27

<210> SEQ ID NO 444
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 444
tggagtcaca caaaccccaa agcacctg                                           28

<210> SEQ ID NO 445
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 445
gaactgtggc tgcaccatct gtcttcatct tcccgccatc tgatgagcag ttgaaatctg        60
gaactgcctc tgttgtgtgc ctgctgaata acttctatcc cagagaggcc aaagtacagt      120

<210> SEQ ID NO 446
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 446
ggaaggtgga taacgccctc caatcgggta actcccagga gagtgtcaca gagcaggaca    60
gcaaggacag cacctacagc ctcagcagca ccctgacgct gagcaaagca gactacgaga   120

<210> SEQ ID NO 447
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 447
ctcgcccgtc acaaagagct tcaacagggg agagtgttag agggagaagt gcccccacct    60
gctcctcagt tccagcctga cccccteccca tcctttggcc tctgacccett tttccacagg   120

<210> SEQ ID NO 448
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 448
ggacctaccc ctattgcggt cctccagctc atctttcacc tcaccccccct cctcctcctt    60 ggctttaatt atgctaatgt tggaggagaa tgaataaata aagtgaatct ttgcacctgt   120

<210> SEQ ID NO 449
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 449
gtcagcccaa ggccaacccc actgtcactc tgttcccgcc ctcctctgag gagctccaag    60
ccaacaaggc cacactagtg tgtctgatca gtgacttcta cccggagct gtgacagtgg    120

<210> SEQ ID NO 450
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 450
gacgcccgag cagtggaagt cccacagaag ctacagctgc caggtcacgc atgaagggag    60
caccgtggag aagacagtgg cccctacaga atgttcatag gttcccaact ctaacccccac   120

<210> SEQ ID NO 451
<211> LENGTH: 120
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic polynucleotide"

<400> SEQUENCE: 451
ccacgggagc ctggagctgc aggatcccag gggaggggtc tctctcccca tcccaagtca    60
tccagccctt ctccctgcac tcatgaaacc ccaataaata tcctcattga caaccagaaa   120

<210> SEQ ID NO 452
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 452
gtcagcccaa ggctgccccc tcggtcactc tgttcccgcc ctcctctgag gagcttcaag    60
ccaacaaggc cacactggtg tgtctcataa gtgacttcta cccgggagcc gtgacagtgg   120

<210> SEQ ID NO 453
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 453
cgcctgagca gtggaagtcc cacagaagct acagctgcca ggtcacgcat gaagggagca    60
ccgtggagaa gacagtggcc cctacagaat gttcataggt tctcaaccct cacccccac    120

<210> SEQ ID NO 454
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 454
cacgggagac tagagctgca ggatcccagg ggaggggtct ctcctcccac cccaaggcat    60
caagcccttc tccctgcact caataaaccc tcaataaata ttctcattgt caatcagaaa   120

<210> SEQ ID NO 455
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 455
gtcagcccaa ggctgccccc tcggtcactc tgttcccacc ctcctctgag gagcttcaag    60
ccaacaaggc cacactggtg tgtctcataa gtgacttcta cccgggagcc gtgacagtgg   120

<210> SEQ ID NO 456
<211> LENGTH: 120
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic polynucleotide"

<400> SEQUENCE: 456
cgcctgagca gtggaagtcc cacaaaagct acagctgcca ggtcacgcat gaagggagca    60
ccgtggagaa gacagtggcc cctacagaat gttcataggt tctcatccct cacccccac    120

<210> SEQ ID NO 457
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 457
cacgggagac tagagctgca ggatcccagg ggagggtct ctcctcccac cccaaggcat    60
caagcccttc tccctgcact caataaaccc tcaataaata ttctcattgt caatcagaaa    120

<210> SEQ ID NO 458
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 458
gtcagcccaa ggctgcccc tcggtcactc tgttcccacc ctcctctgag gagcttcaag    60
ccaacaaggc cacactggtg tgtctcgtaa gtgacttcaa cccgggagcc gtgacagtgg    120

<210> SEQ ID NO 459
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 459
ccagcagcta cctgagcctg acgcccgagc agtggaagtc ccacagaagc tacagctgcc    60
gggtcacgca tgaagggagc accgtggaga agacagtggc ccctgcagaa tgctcttagg    120

<210> SEQ ID NO 460
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 460
cccccgaccc tcaccccacc cacaggggcc tggagctgca ggttcccagg ggagggtct    60 ctgcccccat cccaagtcat ccagcccttc tcaataaata tcctcatcgt caacgagaaa    120

<210> SEQ ID NO 461
<211> LENGTH: 120
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 461
gcatccccga ccagccccaa ggtcttcccg ctgagcctcg acagcacccc ccaagatggg      60
aacgtggtcg tcgcatgcct ggtccagggc ttcttccccc aggagccact cagtgtgacc     120

<210> SEQ ID NO 462
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 462
tggagcgaaa gcggacagaa cgtgaccgcc agaaacttcc cacctagcca ggatgcctcc      60
ggggacctgt acaccacgag cagccagctg accctgccgg ccacacagtg cccagacggc     120

<210> SEQ ID NO 463
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 463
aagtccgtga catgccacgt gaagcactac acgaattcca gccaggatgt gactgtgccc      60
tgccgagttc ccccacctcc cccatgctgc cacccccgac tgtcgctgca ccgaccggcc     120

<210> SEQ ID NO 464
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 464
ctcgaggacc tgctcttagg ttcagaagcg aacctcacgt gcacactgac cggcctgaga      60
gatgcctctg gtgccacctt cacctggacg ccctcaagtg ggaagagcgc tgttcaagga     120

<210> SEQ ID NO 465
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 465
ccacctgagc gtgacctctg tggctgctac agcgtgtcca gtgtcctgcc tggctgtgcc      60
cagccatgga accatgggga gaccttcacc tgcactgctg cccaccccga gttgaagacc     120

<210> SEQ ID NO 466
<211> LENGTH: 120
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 466
ccactaaccg ccaacatcac aaaatccgga aacacattcc ggcccgaggt ccacctgctg     60
ccgccgccgt cggaggagct ggccctgaac gagctggtga cgctgacgtg cctggcacgt    120

<210> SEQ ID NO 467
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 467
ggcttcagcc ccaaggatgt gctggttcgc tggctgcagg ggtcacagga gctgccccgc     60
gagaagtacc tgacttgggc atcccggcag gagcccagcc agggcaccac cacctacgct    120

<210> SEQ ID NO 468
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 468
gtaaccagca tactgcgcgt ggcagctgag gactggaaga aggggagac cttctcctgc     60 atggtgggcc acgaggccct gccgctggcc ttcacacaga agaccatcga ccgcatggcg    120

<210> SEQ ID NO 469
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 469
ggctcttgct gtgttgcaga ttggcagatg ccgcctccct atgtggtgct ggacttgccg     60
caggagaccc tggaggagga gaccccggc gccaacctgt ggcccaccac catcaccttc    120

<210> SEQ ID NO 470
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 470
ctcaccctct tcctgctgag cctgttctat agcacagcac tgaccgtgac cagcgtccgg     60
ggcccatctg gcaagaggga gggcccccag tactgagcgg gagccggcaa ggcacaggga    120

<210> SEQ ID NO 471
```

<210> SEQ ID NO 471
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 471

```
ggaagtgtgg aggaacctct tggagaagcc agctatgctt gccagaactc agcccttTca      60
gacatcaccg acccgccctt actcacgtgg cttccaggtg caataaagtg gccccaagga     120
```

<210> SEQ ID NO 472
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 472

```
gcctccacac agagcccatc cgtcttcccc ttgacccgct gctgcaaaaa cattccctcc      60
aatgccacct ccgtgactct gggctgcctg ccacgggct acttcccgga gccggtgatg     120
```

<210> SEQ ID NO 473
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 473

```
gtgacctggg acacaggctc cctcaacggg acaactatga ccttaccagc caccaccctc      60
acgctctctg gtcactatgc caccatcagc ttgctgaccg tctcgggtgc gtgggccaag     120
```

<210> SEQ ID NO 474
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 474

```
cagatgttca cctgccgtgt ggcacacact ccatcgtcca cagactgggt cgacaacaaa      60
accttcagcg tctgctccag ggacttcacc ccgcccaccg tgaagatctt acagtcgtcc     120
```

<210> SEQ ID NO 475
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 475

```
tgcgacggcg gcgggcactt cccccccgacc atccagctcc tgtgcctcgt ctctgggtac      60
accccaggga ctatcaacat cacctggctg gaggacgggc aggtcatgga cgtggacttg     120
```

```
<210> SEQ ID NO 476
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 476
tccaccgcct ctaccacgca ggagggtgag ctggcctcca cacaaagcga gctcaccctc        60
agccagaagc actggctgtc agaccgcacc tacacctgcc aggtcaccta tcaaggtcac       120

<210> SEQ ID NO 477
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 477
acctttgagg acagcaccaa gaagtgtgca gattccaacc cgagagggt gagcgcctac        60 ctaagccggc ccagcccgtt cgacctgttc atccgcaagt cgcccacgat cacctgtctg      120

<210> SEQ ID NO 478
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 478
tcccgggcca gtgggaagcc tgtgaaccac tccaccagaa aggaggagaa gcagcgcaat       60
ggcacgttaa ccgtcacgtc caccctgccg gtgggcaccc gagactggat cgaggggag       120

<210> SEQ ID NO 479
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 479
acctaccagt gcagggtgac ccaccccccac ctgcccaggg ccctcatgcg gtccacgacc      60
aagaccagcg gcccgcgtgc tgccccggaa gtctatgcgt ttgcgacgcc ggagtggccg      120

<210> SEQ ID NO 480
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 480
gggagccggg acaagcgcac cctcgcctgc ctgatccaga acttcatgcc tgaggacatc       60
tcggtgcagt ggctgcacaa cgaggtgcag ctcccggacg cccggcacag cacgacgcag      120
```

```
<210> SEQ ID NO 481
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 481
ccccgcaaga ccaagggctc cggcttcttc gtcttcagcc gcctggaggt gaccagggcc      60
gaatgggagc agaaagatga gttcatctgc cgtgcagtcc atgaggcagc aagcccctca    120

<210> SEQ ID NO 482
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 482
cagaccgtcc agcgagcggt gtctgtaaat cccgagctgg acgtgtgcgt ggaggaggcc      60
gagggcgagg cgccgtggac gtggaccggc ctctgcatct tcgccgcact cttcctgctc    120

<210> SEQ ID NO 483
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 483
agcgtgagct acagcgccgc catcacgctc ctcatggtgc agcggttcct ctcagccacg      60
cggcagggga ggccccagac ctccctcgac tacaccaacg tcctccagcc ccacgcctag    120

<210> SEQ ID NO 484
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 484
tcctgcctcc ctccctccca gggctccatc cagctgtgca gtggggagga ctggccagac      60
cttctgtcca ctgttgcaat gaccccagga agctaccccc aataaactgt gcctgctcag    120

<210> SEQ ID NO 485
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 485
gcttccacca agggcccatc ggtcttcccc ctggcgccct gctccaggag cacctccgag      60
agcacagccg ccctgggctg cctggtcaag gactacttcc ccgaaccggt gacggtgtcg    120
```

<210> SEQ ID NO 486
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 486

```
tggaactcag gcgccctgac cagcggcgtg cacaccttcc cggctgtcct acagtcctca      60
ggactctact ccctcagcag cgtggtgacc gtgccctcca gcagcttggg cacgaagacc     120
```

<210> SEQ ID NO 487
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 487

```
tacacctgca acgtagatca caagcccagc aacaccaagg tggacaagag agttgagtcc      60
aaatatggtc ccccatgccc atcatgccca gcacctgagt tcctgggggg accatcagtc     120
```

<210> SEQ ID NO 488
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 488

```
ttcctgttcc ccccaaaacc caaggacact ctcatgatct cccggacccc tgaggtcacg      60
tgcgtggtgg tggacgtgag ccaggaagac cccgaggtcc agttcaactg gtacgtggat     120
```

<210> SEQ ID NO 489
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 489

```
ggcgtggagg tgcataatgc caagacaaag ccgcgggagg agcagttcaa cagcacgtac      60
cgtgtggtca gcgtcctcac cgtcctgcac caggactggc tgaacggcaa ggagtacaag     120
```

<210> SEQ ID NO 490
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

```
<400> SEQUENCE: 490
tgcaaggtct ccaacaaagg cctcccgtcc tccatcgaga aaaccatctc caaagccaaa      60
gggcagcccc gagagccaca ggtgtacacc ctgcccccat cccaggagga gatgaccaag     120

<210> SEQ ID NO 491
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 491
aaccaggtca gcctgacctg cctggtcaaa ggcttctacc ccagcgacat cgccgtggag      60
tgggagagca atgggcagcc ggagaacaac tacaagacca cgcctcccgt gctggactcc     120

<210> SEQ ID NO 492
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 492
gacggctcct tcttcctcta cagcaggctc accgtggaca agagcaggtg gcaggagggg      60
aatgtcttct catgctccgt gatgcatgag gctctgcaca accactacac acagaagagc     120

<210> SEQ ID NO 493
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 493
ctctccctgt ctctggagct gcaactggag gagagctgtg cggaggcgca ggacggggag      60
ctggacgggc tgtggacgac catcaccatc ttcatcacac tcttcctgct aagcgtgtgc     120

<210> SEQ ID NO 494
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 494
tacagtgcca ccgtcacctt cttcaaggtg aagtggatct tctcctcagt ggtggacctg      60
aagcagacca tcgtccccga ctacaggaac atgataaggc aggggggccta gggccaccct    120

<210> SEQ ID NO 495
<211> LENGTH: 120
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic polynucleotide"

<400> SEQUENCE: 495 cccctgacc  tcaccgccct  caaccccatg  gctctctggc  ttcgcagtcg  ccctctgagc    60
cctgaaacgc  ccccttcca  gaccctgtgc  atagcaggtc  taccccagac  ctccgctgct   120

<210> SEQ ID NO 496
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 496
tggtgcatgc  agggcgctga  gggccaggtg  tccctcagc   aggacgtccc  tgccctctgg    60
accaccaggt  gctcacacaa  aaggaggtaa  ccggcatccc  aggccccac   tcaggcagga   120

<210> SEQ ID NO 497
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 497
cctcgccctg  gagccaaccc  cgtccacgcc  agcctcctga  acacaggcat  ggtttccaga    60
tggtgagtgg  gagcatcagt  cgccaaggta  gggaagccac  agcaccatca  ggccctgttg   120

<210> SEQ ID NO 498
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 498
gggaggcttc  cgagagctgc  gaaggctcac  tcagacggcc  ttcctcccag  cccgcagcca    60
gccagcctcc  attccgggca  ctcccgtgaa  ctcctgacat  gaggaatgag  gttgttctga   120

<210> SEQ ID NO 499
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 499
tttcaagcaa  agaacgctgc  tctctggctc  ctgggaacag  tctcggtgcc  agcaccaccc    60
cttggctgcc  tgcccacact  gctggattct  cgggtggaac  tggacccgca  gggacagcca   120

<210> SEQ ID NO 500
<211> LENGTH: 120
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic polynucleotide"

<400> SEQUENCE: 500
gccccagagt ccgcactggg gagagaaagg gccaggccca ggacactgcc acctaccac       60 cactccagtc caccgagatc actcggagaa gagcctgggc catgtggccg ctgcaggagc      120

<210> SEQ ID NO 501
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 501
cccacagtgc aagggtgagg atagcccaag gaagggctgg gcatctgccc agacaggcct      60
cccacagaag gctggtgacc aggtcccagg cgggcaagac tcagccttgg tggggcctga     120

<210> SEQ ID NO 502
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 502
ggacagagga ggcccaggag catcggggag agaggtggag ggacaccggg agagccagga      60
gcgtggacac agccagaact catcacagag gctggcgtcc agtcccgggt cacgtgcagc     120

<210> SEQ ID NO 503
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 503
aggaacaagc agccactctg ggggcaccag gtggagaggc aagacgacaa agagggtgcc      60
cgtgttcttg cgaaagcggg gctgctggcc acgagtgctg gacagaggcc cccacgctct     120

<210> SEQ ID NO 504
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 504
gctgccccca tcacaccgtt ccgtgactgt cacgcagaat ccacagacag gaagggaggc      60
tcgagcggga ctgcggccag cgcctgcctc ggccgtcagg gaggactccc gggctcactc     120

<210> SEQ ID NO 505
<211> LENGTH: 120
<212> TYPE: DNA
```

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 505
gaaggaggtg tcaccatttc agctttggct tttcttcttc ttttaaattt tctaaagctc    60
attaattgtc tttgatgttt cttttgtgat gacaataaaa tatccttttt aagtcttgta   120

<210> SEQ ID NO 506
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 506
agcccccgct ccccgggctc tcggggtcgc gcgaggatgc ttggcacgta ccccgtgtac    60
atacttcccg ggcgcccagc atggaaataa agcacccagc gctgccctgg gcccctgcga   120

<210> SEQ ID NO 507
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 507
gcctccacca agggcccatc ggtcttcccc ctggcgccct gctccaggag cacctccgag    60
agcacagcgg ccctgggctg cctggtcaag gactacttcc ccgaaccggt gacggtgtcg   120

<210> SEQ ID NO 508
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 508
tggaactcag cgctctgac cagcggcgtg cacaccttcc cggctgtcct acagtcctca    60
ggactctact ccctcagcag cgtggtgacc gtgccctcca gcaacttcgg cacccagacc   120

<210> SEQ ID NO 509
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 509
tacacctgca acgtagatca caagcccagc aacaccaagg tggacaagac agttgagcgc    60
aaatgttgtg tcgagtgccc accgtgccca gcaccacctg tggcaggacc gtcagtcttc   120

<210> SEQ ID NO 510
<211> LENGTH: 120

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 510
ctcttccccc caaaacccaa ggacaccctc atgatctccc ggacccctga ggtcacgtgc    60
gtggtggtgg acgtgagcca cgaagacccc gaggtccagt tcaactggta cgtggacggc   120

<210> SEQ ID NO 511
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 511
gtggaggtgc ataatgccaa gacaaagcca cgggaggagc agttcaacag cacgttccgt    60
gtggtcagcg tcctcaccgt cgtgcaccag gactggctga acggcaagga gtacaagtgc   120

<210> SEQ ID NO 512
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 512
aaggtctcca caaaggcct cccagccccc atcgagaaaa ccatctccaa aaccaaaggg     60
cagccccgag aaccacaggt gtacaccctg cccccatccc gggaggagat gaccaagaac   120

<210> SEQ ID NO 513
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 513
caggtcagcc tgacctgcct ggtcaaaggc ttctacccca gcgacatctc cgtggagtgg    60
gagagcaatg ggcagccgga gaacaactac aagaccacac ctcccatgct ggactccgac   120

<210> SEQ ID NO 514
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 514
ggctccttct tcctctacag caagctcacc gtggacaaga gcaggtggca gcaggggaac    60
gtcttctcat gctccgtgat gcatgaggct ctgcacaacc actacacaca gaagagcctc   120

<210> SEQ ID NO 515

```
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 515
tccctgtctc cggagctgca actggaggag agctgtgcgg aggcgcagga cggggagctg      60
gacgggctgt ggaccaccat caccatcttc atcacactct tcctgctaag cgtgtgctac     120

<210> SEQ ID NO 516
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 516
agtgccacca tcaccttctt caaggtgaag tggatcttct cctcagtggt ggacctgaag      60
cagaccatcg tccccgacta caggaacatg atcaggcagg gggcctaggg ccaccctctg     120

<210> SEQ ID NO 517
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 517
cccccgacct caccgccctc aaccccatgg ctctctggcc tcgcagtcgc cctctgaccc      60
tgacacgccc cccttccaga ccctgtgcat agcaggtcta ccccagacct ccgctgcttg     120

<210> SEQ ID NO 518
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 518
gtgcatgcag ggcgctgggg gccaagtgtc ccctcagcag gacgtccctg ccctccggcc      60
cgccaggtgc tcacacaaaa ggaggtagtg accagcatcc caggccccca ctcaggcagg     120

<210> SEQ ID NO 519
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 519
acctcgccct ggagccaacc ctgtccacgc cagcctcctg aacacaggcg tggtttccag      60
atggtgagtg ggagcatcag tcgccaaggt agggaagtca cagcaccatc aggccctgtt     120
```

```
<210> SEQ ID NO 520
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 520
ggggaggctt ccgagagctg cgaaggctca ctcagacggc cttcctccca gcccgcagcc      60
agccagcctc cattccaggc actcccgtga actcctgaca tgaggaatga ggttgttctg     120

<210> SEQ ID NO 521
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 521
atttcaagca aagaacgctg ctctctggct cctgggaaca gtctcagtgc cagcaccacc      60
ccttggctgc ctgcccacac tgctggattc tcgggtggaa ctcgaccgc agggacagcc     120

<210> SEQ ID NO 522
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 522
agccccagag tccgcactgg ggagagaagg ggccaggccc aggacactgc cacctaccac      60
ccactccagt ccaccgagat cactcggaga agagcctggg ccatgtggcc gctgcaggag     120

<210> SEQ ID NO 523
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 523
ccccacggtg caagggtgag gatagcccaa ggaagggctg ggcatctgcc cagacaggcc      60
tcccagagaa ggctggtgac caggtcccag gcgggcaaga ctcagccttg gtggggcctg     120

<210> SEQ ID NO 524
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 524
aggacagagg aggcccagga gcatcgggga gagaggtgga gggacaccgg gagagccagg      60
agcgtggaca cagccagaac tcatcacaga ggctggcgtc cagcccgggg tcacgtgcag     120
```

<210> SEQ ID NO 525
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 525
caggaacaag cagccactct gggggcacca ggtggagagg caagacgaca aagagggtgc    60
ccgtgttctt gtgaaagcgg ggctgctggc cacgagtgct ggacagaggc ccccacgctc   120

<210> SEQ ID NO 526
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 526
tgctgccccc atcacgccgt tccgtgactg tcacgcagaa tccgcagaca gggagactcg    60
agcgggagtg cggccagcgc ctgcctcagc tgtcagggag gactcccggg ctcactcgaa   120

<210> SEQ ID NO 527
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 527
ggaggtgcca ccatttcagc tttggtagct tttcttcttc ttttaaattt tctaaagctc    60
attaattgtc tttgatgttt cttttgtgat gacaataaaa tatccttttt aagtcttgta   120

<210> SEQ ID NO 528
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 528
agcccccgct ccccaggctc tcggggtcgc gcgaggatgc ttggcacgta ccccgtctac    60
atacttcccg ggcacccagc atggaaataa agcacccagc gctgccctgg gccctgcga   120

<210> SEQ ID NO 529
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 529
gcatccccga ccagccccaa ggtcttcccg ctgagcctct gcagcaccca gccagatggg    60
aacgtggtca tcgcctgcct ggtccagggc ttcttccccc aggagccact cagtgtgacc   120

<210> SEQ ID NO 530
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 530
tggagcgaaa gcggacaggg cgtgaccgcc agaaacttcc cacccagcca ggatgcctcc      60
ggggacctgt acaccacgag cagccagctg accctgccgg ccacacagtg cctagccggc     120

<210> SEQ ID NO 531
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 531
aagtccgtga catgccacgt gaagcactac acgaatccca gccaggatgt gactgtgccc      60
tgcccagttc cctcaactcc acctacccca tctccctcaa ctccacctac cccatctccc     120

<210> SEQ ID NO 532
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 532
tcatgctgcc accccgact gtcactgcac cgaccggccc tcgaggacct gctcttaggt       60
tcagaagcga acctcacgtg cacactgacc ggcctgagag atgcctcagg tgtcaccttc     120

<210> SEQ ID NO 533
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 533
acctggacgc cctcaagtgg gaagagcgct gttcaaggac cacctgagcg tgacctctgt      60
ggctgctaca gcgtgtccag tgtcctgccg ggctgtgccg agccatggaa ccatgggaag     120

<210> SEQ ID NO 534
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

```
<400> SEQUENCE: 534
ggaggagctg gccctgaacg agctggtgac gctgacgtgc ctggcacgcg gcttcagccc    60
caaggatgtg ctggttcgct ggctgcaggg gtcacaggag ctgccccgcg agaagtacct   120

<210> SEQ ID NO 535
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 535
gacttgggca tcccggcagg agcccagcca gggcaccacc accttcgctg tgaccagcat    60
actgcgcgtg gcagccgagg actggaagaa gggggacacc ttctcctgca tggtgggcca   120

<210> SEQ ID NO 536
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 536
cgaggccctg ccgctggcct tcacacagaa gaccatcgac cgcttggcgg attggcagat    60
gccgcctccc tatgtggtgc tggacttgcc gcaggagacc ctggaggagg agaccccgg   120

<210> SEQ ID NO 537
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 537
cgccaacctg tggcccacca ccatcacctt cctcaccctc ttcctgctga gcctgttcta    60
tagcacagca ctgaccgtga ccagcgtccg gggcccatct ggcaacaggg agggccccca   120

<210> SEQ ID NO 538
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 538
gtactgagca ggagccggca aggcacaggg aggaagtgtg gaggaacctc ttggagaagc    60
cagctatgct tgccagaact cagcccttc agacatcacc gacccgccct tactcacatg   120

<210> SEQ ID NO 539
<211> LENGTH: 120
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic polynucleotide"

<400> SEQUENCE: 539
cttggcgggt aaacccaccc atgtcaatgt gtctgttgtc atggcggagg tggacggcac      60
ctgctactga gccgcccgcc tgtccccacc cctgaataaa ctccatgctc ccccaagcag     120

<210> SEQ ID NO 540
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 540
gcctccacca agggcccatc ggtcttcccc ctggcaccct cctccaagag cacctctggg      60
ggcacagcag ccctgggctg cctggtcaag gactacttcc ccgaaccggt gacggtgtcg     120

<210> SEQ ID NO 541
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 541
tggaactcag gcgccctgac cagcggcgtg cacaccttcc cggctgtcct acagtcctca      60
ggactctact ccctcagcag cgtggtgacc gtgccctcca gcagcttggg cacccagacc     120

<210> SEQ ID NO 542
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 542
tacatctgca acgtgaatca caagcccagc aacaccaagg tggacaagaa agttgagccc      60
aaatcttgtg acaaaactca cacatgccca ccgtgcccag cacctgaact cctgggggga    120

<210> SEQ ID NO 543
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 543
ccgtcagtct tcctcttccc cccaaaaccc aaggacaccc tcatgatctc ccggacccct      60
gaggtcacat gcgtggtggt ggacgtgagc cacgaagacc ctgaggtcaa gttcaactgg    120

<210> SEQ ID NO 544
<211> LENGTH: 120
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic polynucleotide"

<400> SEQUENCE: 544
tacgtggacg gcgtggaggt gcataatgcc aagacaaagc cgcgggagga gcagtacaac    60
agcacgtacc gtgtggtcag cgtcctcacc gtcctgcacc aggactggct gaatggcaag    120

<210> SEQ ID NO 545
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 545
gagtacaagt gcaaggtctc caacaaagcc ctcccagccc ccatcgagaa aaccatctcc    60
aaagccaaag ggcagccccg agaaccacag gtgtacaccc tgcccccatc ccgggatgag    120

<210> SEQ ID NO 546
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 546
ctgaccaaga accaggtcag cctgacctgc ctggtcaaag gcttctatcc cagcgacatc    60
gccgtggagt gggagagcaa tgggcagccg gagaacaact acaagaccac gcctcccgtg    120

<210> SEQ ID NO 547
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 547
ctggactccg acggctcctt cttcctctac agcaagctca ccgtggacaa gagcaggtgg    60
cagcagggga acgtcttctc atgctccgtg atgcatgagg ctctgcacaa ccactacaca    120

<210> SEQ ID NO 548
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 548
cagaagagcc tctccctgtc tccggagctg caactggagg agagctgtgc ggaggcgcag    60
gacggggagc tggacgggct gtggacgacc atcaccatct tcatcacact cttcctgtta    120

<210> SEQ ID NO 549
<211> LENGTH: 120
<212> TYPE: DNA

-continued

```
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 549
agcgtgtgct acagtgccac cgtcaccttc ttcaaggtga agtggatctt ctcctcggtg      60
gtggacctga agcagaccat catccccgac tacaggaaca tgatcggaca gggggcctag    120

<210> SEQ ID NO 550
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 550
cgccctcaac cccatgactc tctggcctcg cagttgccct ctgaccctga cacacctgac      60 acgccccct tccagaccct gtgcatagca ggtctacccc agacctccgc tgcttggtgc     120

<210> SEQ ID NO 551
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 551
atgcagggca ctgggggcca ggtgtcccct cagcaggacg tccttgccct ccggaccaca      60
aggtgctcac acaaaaggag gcagtgaccg gtatcccagg cccccaccca ggcaggacct    120

<210> SEQ ID NO 552
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 552
cgccctggag ccaaccccgt ccacgccagc ctcctgaaca caggcgtggt ttccagatgg      60
tgagtgggag cgtcagccgc caaggtaggg aagccacagc accatcaggc cctgttgggg    120

<210> SEQ ID NO 553
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 553
aggcttccga gagctgcgaa ggctcactca gacggccttc ctcccagccc gcagccagcc      60
agcctccatt ccgggcactc ccgtgaactc ctgacatgag gaatgaggtt gttctgattt    120

<210> SEQ ID NO 554
<211> LENGTH: 120
```

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 554
caagcaaaga acgctgctct ctggctcctg ggaacagtct cagtgccagc accacccctt    60
ggctgcctgc ccacactgct ggattctcgg gtggaactgg acccgcaggg acagccagcc   120

<210> SEQ ID NO 555
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 555
ccagagtccg cactggggag agaaggggcc aggcccagga cactgccacc tcccacccac    60
tccagtccac cgagatcact cagagaagag cctgggccat gtggccgctg caggagcccc   120

<210> SEQ ID NO 556
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 556
acagtgcaag ggtgaggata gcccaaggaa gggctgggca tctgcccaga caggcctccc    60
agagaaggct ggtgaccagg tcccaggcgg gcaagactca gccttggtgg ggcctgagga   120

<210> SEQ ID NO 557
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 557
cagaggaggc ccaggagcat cggggagaga ggtggaggga caccgggaga gccaggagcg    60
tggacacagc cagaactcat cacagaggct ggcgtccagc cccgggtcac gtgcagcagg   120

<210> SEQ ID NO 558
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 558
aacaagcagc cactctgggg gcaccaggtg gagaggcaag acgacaaaga gggtgcccgt    60
gttcttgcga aagcagggct gctggccacg agtgctggac agaggccccc acgctctgct   120

<210> SEQ ID NO 559

```
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 559
gcccccatca cgccgttccg tgactgtcac gcagaatctg cagacaggaa gggagactcg     60
agcgggagtg cggccagcgc ctgcctcggc cgtcagggag gactcctggg ctcactcgaa    120

<210> SEQ ID NO 560
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 560
ggaggtgcca ccatttcagc tttggtagct tttcttcttc ttttaaattt tctaaagctc     60
attaattgtc tttgatgttt cttttgtgat gacaataaaa tatccttttt aagtcttgta    120

<210> SEQ ID NO 561
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 561
aagcccccgc tccccaggct ctcggggtcg cgcgaggatg cttggcacgt accccgtgta     60
catacttccc aggcacccag catggaaata aagcacccag cgcttccctg ggcccctgcg    120

<210> SEQ ID NO 562
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 562
cttccaccaa gggcccatcg gtcttccccc tggcgccctg ctccaggagc acctctgggg     60
gcacagcggc cctgggctgc ctggtcaagg actacttccc agaaccggtg acggtgtcgt    120

<210> SEQ ID NO 563
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 563
ggaactcagg cgccctgacc agcggcgtgc acaccttccc ggctgtccta cagtcctcag     60
gactctactc cctcagcagc gtggtgaccg tgccctccag cagcttgggc acccagacct    120
```

```
<210> SEQ ID NO 564
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 564
acacctgcaa cgtgaatcac aagcccagca acaccaaggt ggacaagaga gttgagctca    60 aaacccact tggtgacaca actcacacat gcccacggtg cccagagccc aaatcttgtg   120

<210> SEQ ID NO 565
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 565
acacacctcc cccgtgccca cggtgcccag agcccaaatc ttgtgacaca cctcccccat    60
gcccacggtg cccagagccc aaatcttgtg acacacctcc cccgtgccca aggtgcccag   120

<210> SEQ ID NO 566
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 566
cacctgaact cctgggagga ccgtcagtct tcctcttccc cccaaaaccc aaggataccc    60
ttatgatttc ccggaccccct gaggtcacgt gcgtggtggt ggacgtgagc cacgaagacc   120

<210> SEQ ID NO 567
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 567
ccgaggtcca gttcaagtgg tacgtggacg gcgtggaggt gcataatgcc aagacaaagc    60
cgcgggagga gcagtacaac agcacgttcc gtgtggtcag cgtcctcacc gtcctgcacc   120

<210> SEQ ID NO 568
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 568
aggactggct gaacggcaag gagtacaagt gcaaggtctc caacaaagcc ctcccagccc    60
ccatcgagaa aaccatctcc aaaaccaaag gacagccccg agaaccacag gtgtacaccc   120
```

<210> SEQ ID NO 569
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 569
tgcccccatc ccgggaggag atgaccaaga accaggtcag cctgacctgc ctggtcaaag     60
gcttctaccc cagcgacatc gccgtggagt gggagagcag cgggcagccg gagaacaact    120

<210> SEQ ID NO 570
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 570
acaacaccac gcctcccatg ctggactccg acggctcctt cttcctctac agcaagctca     60
ccgtggacaa gagcaggtgg cagcagggga acatcttctc atgctccgtg atgcatgagg    120

<210> SEQ ID NO 571
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 571
ctctgcacaa ccgcttcacg cagaagagcc tctccctgtc tccggagctg caactggagg     60
agagctgtgc ggaggcgcag gacggggagc tggacgggct gtggacgacc atcaccatct    120

<210> SEQ ID NO 572
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 572
tcatcacact cttcctgtta agcgtgtgct acagtgccac cgtcaccttc ttcaaggtga     60
agtggatctt ctcctcggtg gtggacctga agcagaccat catccccgac tataggaaca    120

<210> SEQ ID NO 573
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 573
gacctcaccg ccctcaaccc catggctctc tgtctttgca gtcgccctct gagccctgac     60
acgcccccct tccagaccct gtgcatagca ggtctacccc agacctccgc tgcttggtgc    120

<210> SEQ ID NO 574
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 574
atgcagggag ctggggacca ggtgtcccct cagcaggatg tccctgccct ccagaccgcc     60
agatgctcac acaaaaggag gcagtgacca gcatccgagg cccccaccca ggcaggagct    120

<210> SEQ ID NO 575
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 575
ggccctggag ccaaccccgt ccacgccagc ctcctgaaca caggcgtggt ttccagatgg     60
tgagtgggag catcagccgc caaggtaggg aagccacagc accatcaggc cctgttgggg    120

<210> SEQ ID NO 576
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 576
aggcttccga gagctgcgaa ggctcactca gacggccttc ctcccagccc gcagccagcc     60
agcctccatt ccgggcactc ccgtgaactc ctgacatgag gaatgaggtt gttctgattt    120

<210> SEQ ID NO 577
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 577
caagcaaaga acgctgctct ctggctcctg ggaacagtct cggtgccagc accacccctt     60
ggctgcctgc ctacactgct ggattctcgg gtggaactgg acccgcaggg acagccagcc    120

<210> SEQ ID NO 578
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

```
<400> SEQUENCE: 578
ccagagtccg cactggggag agaaggggcc aggcccagga cactgccacc tcccacccac    60
tccagtccac cgagatcact cagagaagag cctgggccat gtggccactg caggagcccc   120

<210> SEQ ID NO 579
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 579
acagtgcaag agtgaggata gcccaaggaa gggctgggca tctgcccaga caggcctccc    60
agagaaggct ggtgaccagg tcccaggcgg gcaagactca gccttggtgg ggcctgagga   120

<210> SEQ ID NO 580
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 580
cagaggaggc ccaggagcat cggggagaga ggtggaggga caccgggaga gccaggagcg    60
tggacacagc cagaactcat cacagaggct ggcgtccagc cccgggtcac gtgcagcagg   120

<210> SEQ ID NO 581
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 581
aacaagcagc cactctgggg gcaccaggtg gagaggcaag atgccaaaga gggtgcccgt    60
gttcttgcga aagcggggct gctggccacg agtgctggac agaggccccc acgctctgct   120

<210> SEQ ID NO 582
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 582
gcccccatca cgccgttccg tgactgtcac gcagaatccg cagacaggaa gggaggctcg    60
agcgggactg cggccagcgc ctgcctcggc cgtcagggag gactcccggg ctcactcgaa   120

<210> SEQ ID NO 583
<211> LENGTH: 120
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic polynucleotide"

<400> SEQUENCE: 583
ggaggtgcca ccatttcagc tttggtagct tttcttcttc ttttaaattt tctaaagctc    60
attaattgtc tttgatgttt cttttgtgat gacaataaaa tatccttttt aagtcttgta   120

<210> SEQ ID NO 584
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 584
agcccccgct ccccgggctc tcggggtcgc gcgaggatgc ttggcacgta ccccgtgtac    60
atacttcccg ggcacccagc atggaaataa agcacccagc gctgccctgg gccctgcga   120

<210> SEQ ID NO 585
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 585
cacccaccaa ggctccggat gtgttcccca tcatatcagg gtgcagacac ccaaaggata    60
acagccctgt ggtcctggca tgcttgataa ctgggtacca cccaacgtcc gtgactgtca   120

<210> SEQ ID NO 586
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 586
cctggtacat ggggacacag agccagcccc agagaacctt ccctgagata caaagacggg    60
acagctacta catgacaagc agccagctct ccaccccct ccagcagtgg cgccaaggcg    120

<210> SEQ ID NO 587
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 587
agtacaaatg cgtggtccag cacaccgcca gcaagagtaa gaaggagatc ttccgctggc    60
cagagtctcc aaaggcacag gcctcctcag tgcccactgc acaacccccaa gcagagggca   120

<210> SEQ ID NO 588
<211> LENGTH: 120
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic polynucleotide"

<400> SEQUENCE: 588
gcctcgccaa ggcaaccaca gccccagcca ccacccgtaa cacaggaaga ggaggagaag      60
agaagaagaa ggagaaggag aaagaggaac aagaagagag agagacaaag acaccagagt     120

<210> SEQ ID NO 589
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 589
gtccgagcca cacccagcct cttggcgtct acctgctaac ccctgcagtg caggacctgt      60
ggctccggga caaagccacc ttcacctgct tcgtggtggg cagtgacctg aaggatgctc     120

<210> SEQ ID NO 590
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 590
acctgacctg ggaggtggct gggaaggtcc ccacaggggg cgtggaggaa gggctgctgg      60
agcggcacag caacggctcc cagagccagc acagccgtct gaccctgccc aggtccttgt     120

<210> SEQ ID NO 591
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 591
ggcctcgtct gaccctcccg aggcggcctc gtggctcctg tgtgaggtgt ctggcttctc      60
gccccccaac atcctcctga tgtggctgga ggaccagcgt gaggtgaaca cttctgggtt     120

<210> SEQ ID NO 592
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 592 tgccccgca cgccccctc cacagcccag gagcaccacg ttctgggcct ggagtgtgct      60
gcgtgtccca gccccgccca gccctcagcc agccacctac acgtgtgtgg tcagccacga     120

<210> SEQ ID NO 593
<211> LENGTH: 120
<212> TYPE: DNA
```

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 593
ggactcccgg actctgctca acgccagccg agcctagaa gtcagctacc tggccatgac      60 cccctgatc cctcagagca aggatgagaa cagcgatgac tacacgacct ttgatgatgt     120

<210> SEQ ID NO 594
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 594
gggcagcctg tggaccaccc tgtccacgtt tgtggccctc ttcatcctca ccctcctcta      60
cagcggcatt gtcactttca tcaaggtgaa gtagccccag aagagcagga cgccctgtac    120

<210> SEQ ID NO 595
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 595
ctgcagagaa gggaagcagc ctctgtacct catctgtggc taccagagag cagaaaggac      60
ccaccctgga ctcttctgtg tgcaggaaga tgcgccagcc cctgccccg gctcccctct     120

<210> SEQ ID NO 596
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 596
gtccgccaca gaacccagtc ttctagacca gggggacggg cacccatcac tccgcaggcg      60
aatcagagcc cccctgcccc ggccctaacc cctgtgcctc cttcccatgc ttccccgaga    120

<210> SEQ ID NO 597
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 597
gccagctaca cccctgcccc ggccctaacc cccatgcctc cttcctgtgc ttcccccaga      60
gccagctagt cccacctgca gcccgctggc ctccccataa acacactttg gttcatttca    120

<210> SEQ ID NO 598
<211> LENGTH: 120

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 598
gggagtgcat ccgccccaac ccttttcccc ctcgtctcct gtgagaattc cccgtcggat      60
acgagcagcg tggccgttgg ctgcctcgca caggacttcc ttcccgactc catcactttc     120

<210> SEQ ID NO 599
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 599
tcctggaaat acaagaacaa ctctgacatc agcagcaccc ggggcttccc atcagtcctg      60
agagggggca agtacgcagc cacctcacag gtgctgctgc cttccaagga cgtcatgcag     120

<210> SEQ ID NO 600
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 600
ggcacagacg aacacgtggt gtgcaaagtc cagcacccca acggcaacaa agaaaagaac      60
gtgcctcttc cagtgattgc tgagctgcct cccaaagtga gcgtcttcgt cccacccgc      120

<210> SEQ ID NO 601
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 601
gacggcttct tcggcaaccc ccgcaagtcc aagctcatct gccaggccac gggtttcagt      60
ccccggcaga ttcaggtgtc ctggctgcgc gaggggaagc aggtggggtc tggcgtcacc     120

<210> SEQ ID NO 602
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 602
acggaccagg tgcaggctga ggccaaagag tctgggccca cgacctacaa ggtgaccagc      60
acactgacca tcaaagagag cgactggctc ggccagagca tgttcacctg ccgcgtggat     120

<210> SEQ ID NO 603
```

```
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 603
cacaggggcc tgaccttcca gcagaatgcg tcctccatgt gtgtccccga tcaagacaca      60
gccatccggg tcttcgccat cccccccatcc tttgccagca tcttcctcac caagtccacc   120

<210> SEQ ID NO 604
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 604
aagttgacct gcctggtcac agacctgacc acctatgaca gcgtgaccat ctcctggacc      60
cgccagaatg gcgaagctgt gaaaacccac accaacatct ccgagagcca ccccaatgcc    120

<210> SEQ ID NO 605
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 605
agcgccgtgg gtgaggccag catctgcgag gatgactgga attccgggga gaggttcacg      60
tgcaccgtga cccacacaga cctgccctcg ccactgaagc agaccatctc ccggcccaag    120

<210> SEQ ID NO 606
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 606
ggggtggccc tgcacaggcc cgatgtctac ttgctgccac cagcccggga gcagctgaac      60
ctgcgggagt cggccaccat cacgtgcctg gtgacgggct tctctcccgc ggacgtcttc    120

<210> SEQ ID NO 607
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 607
gtgcagtgga tgcagagggg gcagcccttg tccccggaga agtatgtgac cagcgcccca      60
atgcctgagc cccaggcccc aggccggtac ttcgcccaca gcatcctgac cgtgtccgaa    120
```

```
<210> SEQ ID NO 608
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 608
gaggaatgga acacggggga gacctacacc tgcgtggtgg cccatgaggc cctgcccaac      60
agggtcaccg agaggaccgt ggacaagtcc accgaggggg aggtgagcgc cgacgaggag     120

<210> SEQ ID NO 609
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 609
ggctttgaga acctgtgggc caccgcctcc accttcatcg tcctcttcct cctgagcctc      60
ttctacagta ccaccgtcac cttgttcaag gtgaaatgat cccaacagaa gaacatcgga     120

<210> SEQ ID NO 610
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 610
gaccagagag aggaactcaa aggggcgctg cctccgggtc tggggtcctg gcctgcgtgg      60
cctgttggca cgtgtttctc ttccccgccc ggcctccagt tgtgtgctct cacacaggct     120

<210> SEQ ID NO 611
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 611
tccttctcga ccggcagggg ctggctggct tgcaggccac gaggtgggct ctaccccaca      60
ctgctttgct gtgtatacgc ttgttgccct gaaataaata tgcacatttt atccatgaaa     120

<210> SEQ ID NO 612
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 612
tgctggcctg cccacaggct cggggcggct ggccgctctg tgtgtgcatg caaactaacc      60
gtgtcaacgg ggtgagatgt tgcatcttat aaaattagaa ataaaaagat ccattcaaaa     120
```

<210> SEQ ID NO 613
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 613

```
gccacccct tggtcactct gttcccgccc tcctctgagg agctccaagc caacaaggcc      60
atgctggtgt gtctcataaa tgacttctac ccaggagcca tagaaggaaa atggcaccct    120
```

<210> SEQ ID NO 614
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 614

```
atgcggccag cagctacctg agcctgacgc ccgagcagtg gaagtcccac agaagctaca      60
gctgccaggt cacgcacaaa gaaagtacca tggagaagac aatggcccat gcagaatgtt    120
```

<210> SEQ ID NO 615
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 615

```
acaaggccac actggtgtgt ctcatgagtg acttctaccc gagagccatg acagtggcct      60
ggaagataga tggcatcacc atcacccagg gtgtggagac caccacaccc tccaaacaga    120
```

<210> SEQ ID NO 616
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 616

```
tatgcggcca gcagctacct aagactggca cccgacagtg gaagtcccac aacctctaca      60
gctgccaggt cacgcatgaa aggaacactg tggagaagac agtggcccct gcagaatgtt    120
```

<210> SEQ ID NO 617
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 617

```
gtcagcccaa ggctgcccca tcggtcactc tgttcccgcc ctcctctgag gagcttcaag      60
ccaacaaggc cacactggtg tgcctgatca gtgacttcta cccgggagct gtgaaagtgg    120
```

<210> SEQ ID NO 618
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 618
gcggccagca gctagctacc tgagcctgac gcctgagcag tggaagtccc acagaagcta    60
cagttgccag gtcacgcatg aagggagcac cgtggagaag acagtggccc ctgcagaatg   120

<210> SEQ ID NO 619
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 619
aggacctgaa caaggtgttc ccacccgagg tcgctgtgtt tgagccatca gaagcagaga    60
tctcccacac ccaaaaggcc acactggtgt gcctggccac aggcttcttc cctgaccacg   120

<210> SEQ ID NO 620
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 620
tggagctgag ctggtgggtg aatgggaagg aggtgcacag tggggtcagc acggacccgc    60
agcccctcaa ggagcagccc gccctcaatg actccagata ctgcctgagc agccgcctga   120

<210> SEQ ID NO 621
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 621
gggtctcggc caccttctgg cagaaccccc gcaaccactt ccgctgtcaa gtccagttct    60
acgggctctc ggagaatgac gagtggaccc aggatagggc caaacccgtc acccagatcg   120

<210> SEQ ID NO 622
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 622
ctcggtgtcc taccagcaag gggtcctgtc tgccaccatc ctctatgaga tcctgctagg     60
gaaggccacc ctgtatgctg tgctggtcag cgcccttgtg ttgatggcca tggtcaagag    120

<210> SEQ ID NO 623
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 623
aaaggatttc tgaaggcagc cctggaagtg gagttaggag cttctaaccc gtcatggttt     60
caatacacat tcttcttttg ccagcgcttc tgaagagctg ctctcacctc tctgcatccc    120

<210> SEQ ID NO 624
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 624
aatagatatc cccctatgtg catgcacacc tgcacactca cggctgaaat ctccctaacc     60 caggggggacc ttagcatgcc taagtgacta aaccaataaa aatgttctgg tctggcctga   120

<210> SEQ ID NO 625
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 625
aggacctgaa aaacgtgttc ccacccaagg tcgctgtgtt tgagccatca gaagcagaga     60
tctcccacac ccaaaaggcc acactggtgt gcctggccac aggcttctac cccgaccacg    120

<210> SEQ ID NO 626
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 626
tggagctgag ctggtgggtg aatgggaagg aggtgcacag tggggtcagc acagacccgc     60
agcccctcaa ggagcagccc gccctcaatg actccagata ctgcctgagc agccgcctga   120

<210> SEQ ID NO 627
<211> LENGTH: 120
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic polynucleotide"

<400> SEQUENCE: 627
gggtctcggc caccttctgg cagaaccccc gcaaccactt ccgctgtcaa gtccagttct    60
acgggctctc ggagaatgac gagtggaccc aggatagggc caaacctgtc acccagatcg   120

<210> SEQ ID NO 628
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 628
acctccgagt cttaccagca aggggtcctg tctgccacca tcctctatga gatcttgcta    60
gggaaggcca ccttgtatgc cgtgctggtc agtgccctcg tgctgatggc catggtcaag   120

<210> SEQ ID NO 629
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 629
agaaaggatt ccagaggcta gctccaaaac catcccaggt cattcttcat cctcacccag    60
gattctcctg tacctgctcc caatctgtgt tcctaaaagt gattctcact ctgcttctca   120

<210> SEQ ID NO 630
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 630
tctcctactt acatgaatac ttctctcttt tttctgtttc cctgaagatt gagctcccaa    60
cccccaagta cgaaataggc taaaccaata aaaaattgtg tgttgggcct ggttgcattt   120

<210> SEQ ID NO 631
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 631
atatccagaa ccctgaccct gccgtgtacc agctgagaga ctctaaatcc agtgacaagt    60
ctgtctgcct attcaccgat tttgattctc aaacaaatgt gtcacaaagt aaggattctg   120

<210> SEQ ID NO 632
<211> LENGTH: 120
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic polynucleotide"

<400> SEQUENCE: 632
atgtgtatat cacagacaaa actgtgctag acatgaggtc tatggacttc aagagcaaca     60
gtgctgtggc ctggagcaac aaatctgact ttgcatgtgc aaacgccttc aacaacagca    120

<210> SEQ ID NO 633
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 633
ttattccaga agacaccttc ttccccagcc cagaaagttc ctgtgatgtc aagctggtcg     60
agaaaagctt tgaaacagat acgaacctaa actttcaaaa cctgtcagtg attgggttcc    120

<210> SEQ ID NO 634
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 634
gaatcctcct cctgaaagtg gccgggttta atctgctcat gacgctgcgg ctgtggtcca     60
gctgagatct gcaagattgt aagacagcct gtgctccctc gctccttcct ctgcattgcc    120

<210> SEQ ID NO 635
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 635
acagagggaa ctctcctacc cccaaggagg tgaaagctgc taccacctct gtgccccccc     60
ggcaatgcca ccaactggat cctacccgaa tttatgatta agattgctga agagctgcca    120

<210> SEQ ID NO 636
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 636
aacactgctg ccacccctc tgttcccta ttgctgcttg tcactgcctg acattcacgg      60
cagaggcaag gctgctgcag cctcccctgg ctgtgcacat tccctcctgc tccccagaga   120

<210> SEQ ID NO 637
<211> LENGTH: 120
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 637
ctgcctccgc catcccacag atgatggatc ttcagtgggt tctcttgggc tctaggtcct      60
gcagaatgtt gtgaggggtt tattttttt  taatagtgtt cataaagaaa tacatagtat    120

<210> SEQ ID NO 638
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 638
tcttcttctc aagacgtggg gggaaattat ctcattatcg aggccctgct atgctgtgta     60
tctgggcgtg ttgtatgtcc tgctgccgat gccttcatta aaatgatttg aagagcaga    120

<210> SEQ ID NO 639
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (23)..(50)
<223> OTHER INFORMATION: a, c, t, g, unknown or other
<220> FEATURE:
<221> NAME/KEY: modified_base
<222> LOCATION: (82)..(82)
<223> OTHER INFORMATION: a, c, t, g, unknown or other

<400> SEQUENCE: 639
ctacacgacg ctcttccgat ctnnnnnnnn nnnnnnnnnn nnnnnnnnnn tttttttttt     60
tttttttttt tttttttttt vn                                              82

<210> SEQ ID NO 640
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 640
cccatgtact ctgcgttgat accactgctt                                      30
```

SPATIAL TRANSCRIPTOMICS FOR ANTIGEN-RECEPTORS

CROSS-REFERENCE TO RELATED APPLICATIONS

Pursuant to 35 U.S.C. § 119(e), this application is a continuation of International Patent Application No. PCT/US2021/035242 with an international filing date of Jun. 1, 2021, which claims priority to U.S. Provisional Patent Application Ser. No. 63/033,568, filed on Jun. 2, 2020, the contents of each of which are incorporated herein by reference in its entirety.

SEQUENCE LISTING

A computer readable form (CRF) sequence listing text file having the file name 0208001_SequenceListing.txt and file size of 173 KB is being submitted herewith. The sequence information contained in this sequence listing is limited to the sequence information in the application as originally filed, and does not include any new matter

BACKGROUND

Cells within a tissue have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, signaling, and cross-talk with other cells in the tissue.

Spatial heterogeneity has been previously studied using techniques that typically provide data for a handful of analytes in the context of intact tissue or a portion of a tissue (e.g., tissue section), or provide significant analyte data from individual, single cells, but fails to provide information regarding the position of the single cells from the originating biological sample (e.g., tissue).

Understanding spatial heterogeneity in the context of immune cell clonotypes (e.g., T-cell receptor, B-cell receptor) within an intact biological sample, or a portion thereof, can give insight into which cells or cell-types specific T-cell or B-cell clonotypes may be interacting. Single-cell methods can identify clonotype populations, but fail to link the spatial organization of immune cell clonotypes within a biological sample.

SUMMARY

A fundamental understanding of spatial heterogeneity with respect to T-cell receptor (TCR) and B-cell receptor (BCR) clonotypes within a biological sample is needed to understand which cells a TCR or BCR may interacting with, the identity of TCR and/or BCR clonotypes in a given biological sample, or the identity of TCR and/or BCR clonotypes that are autoreactive in different autoimmune disorders. Numerous single-cell sequencing approaches can identify TCR and BCR clonotypes from a biological sample, however, at present methods are needed to link TCR and BCR sequences to spatial locations within a biological sample. Additionally, identifying the clonal regions, that is, regions defined by the places where variable (V), diverse (D), and joining (J) segments join to form the complementarity determining regions, including CDR1, CDR2, and CDR3, which provide specificity to the TCRs and/or BCRs, is important in understanding the TCR and BCR biological interactions. By coupling clonal information to spatial information it is possible to understand which T-cell and B-cell clonotypes may be specifically interacting with given cell types within a biological sample.

Provided herein are methods for determining the presence and/or abundance of an immune cell clonotype at a location in a biological sample. Some embodiments of any of the methods described herein include capturing transcripts to identify an immune cell clonotype. Some embodiments of any of the methods herein include generating a nucleic acid library from captured transcripts. Some embodiments of any of the methods described herein include enriching analytes of interest in the nucleic acid library, including analytes to identify an immune cell clonotype.

Provided herein are methods for determining the presence and/or abundance of an immune cell receptor at a location in a biological sample. Some embodiments of any of the methods described herein include capturing analytes to identify an immune cell receptor. Some embodiments of any of the methods described herein include generating a nucleic acid library from captured analytes. Some embodiments of any of the methods described here include enriching analytes of interest in the nucleic acid library, including analytes to identify an immune cell receptor.

Thus provided herein are methods for determining the presence and/or abundance of an immune cell clonotype at a location in a biological sample, the method including: (a) contacting a biological sample with an array including a plurality of capture probes, where a capture probe of the plurality of capture probes includes (i) a spatial barcode and (ii) a capture domain that binds to a nucleic acid encoding an immune cell receptor of the immune cell clonotype; and (b) determining (i) all or a portion of the sequence of the spatial barcode or a complement thereof, and (ii) all or a portion of the sequence of the nucleic acid encoding the immune cell receptor or a complement thereof, and using the determined sequences of (i) and (ii) to determine the presence and/or abundance of the immune cell clonotype at a location in the biological sample.

In some embodiments, the immune cell clonotype is a T cell clonotype. In some embodiments, the T cell clonotype is a T cell receptor alpha chain. In some embodiments, the capture domain binds to a nucleic acid sequence encoding a constant region of the T cell receptor alpha chain. In some embodiments, step (b) includes determining a sequence encoding CDR3 of the T cell receptor alpha chain. In some embodiments, step (b) includes determining a sequence encoding one or both of CDR1 and CDR2 of the T cell receptor alpha chain. In some embodiments, step (b) includes determining a sequence encoding a full-length variable domain of the T cell receptor alpha chain.

In some embodiments, the immune cell receptor is a T cell receptor beta chain. In some embodiments, the capture domain binds specifically to a nucleic acid sequence encoding a constant region of the T cell receptor beta chain. In some embodiments, step (b) includes determining a sequence encoding CDR3 of the T cell receptor beta chain. In some embodiments, step (b) includes determining a sequence encoding one or both of CDR1 and CDR2 of the T cell receptor beta chain. In some embodiments, step (b) includes determining a sequence encoding a full-length variable domain of the T cell receptor beta chain.

In some embodiments, the immune cell clonotype is a B cell clonotype. In some embodiments, the B cell clonotype is an immunoglobulin kappa light chain. In some embodiments, the capture domain binds specifically to a nucleic acid sequence encoding a constant region of the immunoglobulin kappa light chain. In some embodiments, step (b) includes determining a sequence encoding CDR3 of the immunoglobulin kappa light chain.

In some embodiments, step (b) includes determining a sequence encoding one or both of CDR1 and CDR2 of the immunoglobulin kappa light chain. In some embodiments, step (b) includes determining a sequence encoding a full-length variable domain of the immunoglobulin kappa light chain. In some embodiments, the B cell clonotype is an immunoglobulin lambda light chain. In some embodiments, the capture domain binds specifically to a nucleic acid sequence encoding a constant region of the immunoglobulin lambda light chain. In some embodiments, step (b) includes determining a sequence encoding CDR3 of the immunoglobulin lambda light chain. In some embodiments, step (b) includes determining a sequence encoding one or both of CDR1 and CDR2 of the immunoglobulin lambda light chain. In some embodiments, step (b) includes determining a sequence encoding a full-length variable domain of the immunoglobulin lambda light chain. In some embodiments, the B cell clonotype is an immunoglobulin heavy chain. In some embodiments, the capture domain binds specifically to a nucleic acid sequence encoding a constant region of the immunoglobulin heavy chain. In some embodiments, step (b) includes determining a sequence encoding CDR3 of the immunoglobulin heavy chain. In some embodiments, step (b) includes determining a sequence encoding one or both of CDR1 and CDR2 of the immunoglobulin heavy chain. In some embodiments, step (b) includes determining a sequence encoding a full-length variable domain of the immunoglobulin heavy chain.

In some embodiments, the capture domain binds a poly (A) sequence of a nucleic acid encoding an immune cell clonotype. In some embodiments, the capture domain binds to a nucleic acid sequence encoding a T cell clonotype. In some embodiments, the T cell clonotype is a T cell receptor alpha chain, a T cell receptor beta chain, and combinations thereof. In some embodiments, step (b) includes determining: a sequence encoding CDR3 of the T cell receptor alpha chain, a sequence encoding CDR3 of the T cell receptor beta chain, and combinations thereof. In some embodiments, step (b) includes determining: a sequence encoding one or both of CDR1 and CDR2 of the T cell receptor alpha chain, a sequence encoding one or both of CDR1 and CDR2 of the T cell receptor beta chain, and combinations thereof. In some embodiments, step (b) includes determining: a sequence encoding a full-length variable domain of the T cell receptor alpha chain, a sequence encoding a full-length variable domain of the T cell receptor beta chain, and combinations thereof.

In some embodiments, the capture domain binds to a nucleic acid encoding a B cell clonotype. In some embodiments, the B cell clonotype is an immunoglobulin kappa light chain, an immunoglobulin lambda light chain, an immunoglobulin heavy chain, and combinations thereof. In some embodiments, step (b) includes determining: a sequence encoding CDR3 of the immunoglobulin kappa light chain, a sequence encoding CDR3 of immunoglobulin lambda light chain, a sequence encoding CDR3 of the immunoglobulin heavy chain, and combinations thereof. In some embodiments, step (b) includes determining: a sequence encoding one or both of CDR1 and CDR2 of the immunoglobulin kappa light chain, a sequence encoding one or both of CDR1 and CDR2 of the immunoglobulin lambda light chain, a sequence encoding one or both of CDR1 and CDR2 of the immunoglobulin heavy chain, and combinations thereof. In some embodiments, step (b) includes determining: a sequence encoding a full-length variable domain of the immunoglobulin kappa light chain, a sequence encoding a full-length variable domain of the immunoglobulin lambda light chain, a sequence encoding a full-length variable domain of the immunoglobulin heavy chain, and combinations thereof.

In some embodiments, step (b) includes the capture probe using the nucleic acid encoding the immune cell receptor as a template, thereby generating an extended capture probe. In some embodiments, step (b) includes extending a 3' end of the capture probe.

In some embodiments, step (b) includes generating a second strand of nucleic acid that includes (i) a sequence that is complementary to all or a portion of the spatial barcode, and (ii) a sequence that corresponds to all or a portion of the sequence of the nucleic acid encoding the immune cell receptor.

In some embodiments, the capture probe includes a cleavage domain, a functional domain, a unique molecular identifier, or any combination thereof. In some embodiments, the capture probe includes a functional domain.

In some embodiments, step (b) includes generating a second strand of nucleic acid that includes (i) a sequence that is complementary to all or a portion of the functional domain, (ii) a sequence that is complementary to all or a portion of the spatial barcode, and (iii) a sequence that corresponds to all or a portion of the sequence of the nucleic acid encoding the immune cell receptor.

In some embodiments, the method includes enriching the nucleic acid encoding the immune cell receptor of the immune cell clonotype.

In some embodiments, enriching includes hybridizing a plurality of hybridization probes to the nucleic acid encoding the immune cell receptor of the immune cell clonotype, where a hybridization probe includes (i) a sequence complementary to a portion of the nucleic acid encoding the immune cell receptor and (ii) a binding moiety that interacts with a capture moiety.

In some embodiments, the binding moiety includes biotin and the capture moiety includes streptavidin.

In some embodiments, enriching the nucleic acid encoding the immune cell receptor of the immune cell clonotype includes one or more blocking probes. In some embodiments, the one or more blocking probes includes a sequence having at least 80% identity to SEQ ID NO: 639. In some embodiments, the one or more blocking probes includes a sequence having at least 80% identity to SEQ ID NO: 640.

In some embodiments, the method includes amplifying the nucleic acid encoding the immune cell receptor of the immune cell clonotype, or a complement thereof, using (i) a first primer including all or a portion of the functional domain, where the functional domain is 5' to the spatial barcode, and (ii) a second primer including a sequence that is substantially complementary to a portion of a sequence encoding a variable region of the immune cell receptor.

In some embodiments, the method includes amplifying the nucleic acid encoding the immune cell receptor of the immune cell clonotype, or a complement thereof, using (i) the first primer including all or a portion of the functional domain, where the functional domain is 5' to the spatial barcode, and (ii) a third primer including a sequence that is substantially complementary to a portion of the nucleic acid sequence encoding a variable region of the immune cell receptor, where the third primer is 5' to the second primer.

In some embodiments, the biological sample includes a tissue sample. In some embodiments, the tissue sample is a tissue section. In some embodiments, the tissue section is a fixed tissue section. In some embodiments, the fixed tissue section is a formalin-fixed paraffin-embedded tissue section. In some embodiments, the tissue section includes a tumor region.

In some embodiments, the nucleic acid encoding the immune cell receptor includes RNA. In some embodiments, the RNA is mRNA. In some embodiments, the nucleic acid encoding the immune cell receptor includes DNA. In some embodiments, the DNA is genomic DNA.

In some embodiments, the method includes imaging the biological sample.

In some embodiments, the determining in step (b) includes sequencing (i) all or a portion of the sequence of the spatial barcode or a complement thereof, and (ii) all or a portion of the sequence of the nucleic acid encoding the immune cell receptor or a complement thereof.

In some embodiments, step (b) includes determining the presence of the immune cell clonotype at a location in the biological sample. In some embodiments, step (b) includes determining the abundance of the immune cell clonotype at a location in the biological sample. In some embodiments, step (b) includes determining the presence and abundance of the immune cell clonotype at a location in the biological sample. In some embodiments, step (b) includes determining the presence of two or more immune cell clonotypes at a location in the biological sample. In some embodiments, step (b) includes determining the abundance of two or more immune cell clonotypes at a location in the biological sample. In some embodiments, step (b) includes determining the presence and abundance of two or more immune cell clonotypes at a location in the biological sample. In some embodiments, the method includes comparing the two or more immune cell clonotypes. In some embodiments, the two or more immune cell clonotypes are each a B cell clonotype.

In some embodiments, the two or more immune cell clonotypes are each a T cell clonotype. In some embodiments, the two or more immune cell clonotypes comprise at least one T cell clonotype and at least one B cell clonotype.

Also provided herein are methods for determining the presence and/or abundance of an immune cell receptor at a location in a biological sample, the method including: (a) contacting a biological sample with an array including a plurality of capture probes, where a capture probe of the plurality of capture probes includes (i) a spatial barcode and (ii) a capture domain that specifically binds to a nucleic acid encoding an immune cell receptor; and (b) determining (i) all or a portion of the sequence of the spatial barcode or a complement thereof, and (ii) all or a portion of the sequence of the nucleic acid encoding the immune cell receptor or a complement thereof, and using the determined sequences of (i) and (ii) to determine the presence and/or abundance of the immune cell receptor at a location in the biological sample.

In some embodiments, the immune cell receptor is a T cell receptor alpha chain. In some embodiments, the capture domain binds specifically to a nucleic acid sequence encoding a constant region of the T cell receptor alpha chain. In some embodiments, step (b) includes determining a sequence encoding CDR3 of the T cell receptor alpha chain. In some embodiments, step (b) includes determining a sequence encoding one or both of CDR1 and CDR2 of the T cell receptor alpha chain. In some embodiments, step (b) includes determining a sequence encoding a full-length variable domain of the T cell receptor alpha chain. In some embodiments, the immune cell receptor is a T cell receptor beta chain. In some embodiments, the capture domain binds specifically to a nucleic acid sequence encoding a constant region of the T cell receptor beta chain. In some embodiments, step (b) includes determining a sequence encoding CDR3 of the T cell receptor beta chain. In some embodiments, step (b) includes determining a sequence encoding one or both of CDR1 and CDR2 of the T cell receptor beta chain. In some embodiments, step (b) includes determining a full-length variable domain of the T cell receptor beta chain. In some embodiments, the immune cell receptor is an immunoglobulin kappa light chain. In some embodiments, the capture domain binds specifically to a nucleic acid sequence encoding a constant region of the immunoglobulin kappa light chain. In some embodiments, step (b) includes determining a sequence encoding CDR3 of the immunoglobulin kappa light chain. In some embodiments, step (b) includes determining a sequence encoding one or both of CDR1 and CDR2 of the immunoglobulin kappa light chain. In some embodiments, step (b) includes determining a sequence encoding a full-length variable domain of the immunoglobulin kappa light chain. In some embodiments, the immune cell receptor is an immunoglobulin lambda light chain. In some embodiments, the capture domain binds specifically to a nucleic acid sequence encoding a constant region of the immunoglobulin lambda light chain. In some embodiments, step (b) includes determining a sequence encoding CDR3 of the immunoglobulin lambda light chain. In some embodiments, step (b) includes determining a sequence encoding one or both of CDR1 and CDR2 of the immunoglobulin lambda light chain. In some embodiments, step (b) includes determining a sequence encoding a full-length variable domain of the immunoglobulin lambda light chain. In some embodiments, the immune cell receptor is an immunoglobulin heavy chain. In some embodiments, the capture domain binds specifically to a nucleic acid sequence encoding a constant region of the immunoglobulin heavy chain. In some embodiments, step (b) includes determining a sequence encoding CDR3 of the immunoglobulin heavy chain. In some embodiments, step (b) includes determining a sequence encoding one or both of CDR1 and CDR2 of the immunoglobulin heavy chain. In some embodiments, step (b) includes determining a sequence encoding a full-length variable domain of the immunoglobulin heavy chain.

In some embodiments, the capture domain binds a poly (A) sequence of a nucleic acid encoding an immune cell receptor. In some embodiments, the immune cell receptor is a T cell receptor alpha chain, a T cell receptor beta chain, and combinations thereof. In some embodiments, step (b) includes determining: a sequence encoding CDR3 of the T cell receptor alpha chain, a sequence encoding CDR3 of the T cell receptor beta chain, and combinations thereof. In some embodiments, step (b) includes determining: a sequence encoding one or both of CDR1 and CDR2 of the T cell receptor alpha chain, a sequence encoding one or both of CDR1 and CDR2 of the T cell receptor beta chain, and combinations thereof. In some embodiments, step (b) includes determining: a sequence encoding a full-length variable domain of the T cell receptor alpha chain, a sequence encoding a full-length variable domain of the T cell receptor beta chain, and combinations thereof.

In some embodiments, the immune cell receptor is a B cell receptor an immunoglobulin kappa light chain, an immunoglobulin lambda light chain, an immunoglobulin heavy chain, and combinations thereof. In some embodiments, step (b) includes determining: a sequence encoding CDR3 of the immunoglobulin kappa light chain, a sequence encoding CDR3 of immunoglobulin lambda light chain, a sequence encoding CDR3 of the immunoglobulin heavy chain, and combinations thereof. In some embodiments, step (b) includes determining: a sequence encoding one or both of CDR1 and CDR2 of the immunoglobulin kappa light chain, a sequence encoding one or both of CDR1 and CDR2 of the immunoglobulin lambda light chain, a sequence encoding one or both of CDR1 and CDR2 of the immunoglobulin heavy chain, and combinations thereof. In some embodiments, step (b) includes determining: a sequence encoding a full-length variable domain of the immunoglobulin kappa light chain, a sequence encoding a full-length variable domain of the immunoglobulin lambda light chain, a sequence encoding a full-length variable domain of the immunoglobulin heavy chain, and combinations thereof.

In some embodiments, step (b) includes extending an end of the capture probe using the nucleic acid encoding the immune cell receptor as a template, thereby generating an extended capture probe. In some embodiments, step (b) includes extending a 3' end of the capture probe.

In some embodiments, step (b) includes generating a second strand of nucleic acid that includes (i) a sequence that is complementary to all or a portion of the spatial barcode, and (ii) a sequence that corresponds to all or a portion of the sequence of the nucleic acid encoding the immune cell receptor.

In some embodiments, the capture probe includes a cleavage domain, a functional domain, a unique molecular identifier, or any combination thereof. In some embodiments, the capture probe includes a functional domain.

In some embodiments, step (b) includes generating a second strand of nucleic acid that includes (i) a sequence that is complementary to all or a portion of the functional domain, (ii) a sequence that is complementary to all or a portion of the spatial barcode, and (iii) a sequence that corresponds to all or a portion of the sequence of the nucleic acid encoding the immune cell receptor.

In some embodiments, the method includes enriching the nucleic acid encoding the immune cell receptor. In some embodiments, enriching includes hybridizing a plurality of hybridization probes to the nucleic acid encoding the immune cell receptor, where a hybridization probe includes (i) a sequence complementary to a portion of the nucleic acid encoding the immune cell receptor and (ii) a binding moiety that interacts with a capture moiety. In some embodiments, the binding moiety includes biotin and the capture moiety includes streptavidin. In some embodiments, enriching the nucleic acid encoding the immune cell receptor of the immune cell receptor includes one or more blocking probes. In some embodiments, the one or more blocking probes includes a sequence having at least 80% identity to SEQ ID NO: 639. In some embodiments, the one or more blocking probes includes a sequence having at least 80% identity to SEQ ID NO: 640.

In some embodiments, the method includes amplifying the nucleic acid encoding an immune cell receptor, or a complement thereof, using (i) a first primer including all or a portion of the functional domain, where the functional domain is 5' to the spatial barcode in the second strand of nucleic acid, and (ii) a second primer including a sequence that is substantially complementary to a portion of a sequence encoding a variable region of the immune cell receptor.

In some embodiments, the method includes amplifying the nucleic acid encoding the immune cell receptor, or a complement thereof, using (i) the first primer including all or a portion of the functional domain, where the functional domain is 5' to the spatial barcode, and (ii) a third primer including a sequence that is substantially complementary to a portion of the nucleic acid sequence encoding a variable region of the immune cell receptor, where the third primer is 5' to the second primer.

In some embodiments, the biological sample includes a tissue sample. In some embodiments, the tissue sample is a tissue section. In some embodiments, the tissue section is a fixed tissue section. In some embodiments, the fixed tissue section is a formalin-fixed paraffin-embedded tissue section. In some embodiments, the tissue section includes a tumor region.

In some embodiments, the nucleic acid encoding the immune cell receptor includes RNA. In some embodiments, the RNA is mRNA. In some embodiments, the nucleic acid encoding the immune cell receptor includes DNA. In some embodiments, the DNA is genomic DNA.

In some embodiments, the method includes, prior to step (b), contacting the biological sample with ribosomal RNA depletion probes and mitochondrial RNA depletion probes.

In some embodiments, the method includes imaging the biological sample.

In some embodiments, the determining in step (b) includes sequencing (i) all or a portion of the sequence of the spatial barcode or a complement thereof, and (ii) all or a portion of the sequence of the nucleic acid encoding the immune cell receptor or a complement thereof.

In some embodiments, step (b) includes determining the presence of the immune cell receptor at a location in the biological sample. In some embodiments, step (b) includes determining the abundance of the immune cell receptor at a location in the biological sample. In some embodiments, step (b) includes determining the presence and abundance of the immune cell receptor at a location in the biological sample. In some embodiments, step (b) includes determining the presence of two or more immune cell receptors at a location in the biological sample. In some embodiments, step (b) includes determining the abundance of two or more immune cell receptors at a location in the biological sample. In some embodiments, step (b) includes determining the presence and abundance of two or more immune cell receptors at a location in the biological sample. In some embodiments, the method includes comparing the two or more immune cell receptors. In some embodiments, the two or more immune cell clonotypes are each an immune cell receptor of a B cell. In some embodiments, the two or more immune cell clonotypes are each an immune cell receptor of a T cell. In some embodiments, the two or more immune cell clonotypes comprise at least one immune cell receptor of a T cell and at least one immune cell receptor from a B cell.

Also provided herein are arrays including a plurality of capture probes, where a capture probe of the plurality of capture probes includes (i) a spatial barcode and (ii) a capture domain that binds to a nucleic acid encoding an immune cell receptor of an immune cell clonotype.

In some embodiments, the immune cell clonotype is a T cell clonotype. In some embodiments, the immune cell receptor is a T cell receptor alpha chain. In some embodiments, the capture domain binds specifically to a nucleic acid sequence encoding a constant region of the T cell receptor alpha chain. In some embodiments, the immune cell receptor is a T cell receptor beta chain. In some embodiments, the capture domain binds specifically to a nucleic acid sequence encoding a constant region of the T cell receptor beta chain.

In some embodiments, the immune cell clonotype is a B cell clonotype. In some embodiments, the immune cell receptor is an immunoglobulin kappa light chain. In some embodiments, the capture domain binds specifically to a nucleic acid sequence encoding a constant region of the immunoglobulin kappa light chain. In some embodiments, the immune cell receptor is an immunoglobulin lambda light chain. In some embodiments, the capture domain binds specifically to a nucleic acid sequence encoding a constant region of the immunoglobulin lambda light chain. In some embodiments, the immune cell receptor is an immunoglobulin heavy chain. In some embodiments, the capture domain binds specifically to a nucleic acid sequence encoding a constant region of the immunoglobulin heavy chain.

In some embodiments, the capture probe includes a cleavage domain, a functional domain, a unique molecular identifier, or any combination thereof.

Also provided herein are kits any one of the arrays described herein; one or more hybridization probes, where a hybridization probe includes (i) a sequence substantially complementary to a nucleic acid encoding an immune cell receptor and (ii) a binding moiety that interacts with a capturing moiety; and one or more blocking probes.

All publications, patents, and patent applications mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

FIG. 3A shows an exemplary capture probe with a capture sequence complementary to a constant region of an analyte.

FIG. 3B shows an exemplary capture probe with a poly (dT) capture domain.

FIG. 11 shows single-cell clustering analysis of the T-cell receptor and B-cell receptor clonotypes present in a breast tumor sample.

FIG. 18D shows detected IG clone expression (IGHM) in single B-cell follicles in tonsil tissue in replicate experiments.

FIG. 18E shows detected IG clone expression (IGHA) expression outside B-cell follicles in tonsil tissue in replicate experiments.

FIG. 18F shows a representative T-cell clone expression (TRB) distributed outside of B-cell follicles in tonsil tissue in replicate experiments.

FIG. 18G shows a representative T-cell clone expression (TRA) distributed outside of B-cell follicles in tonsil tissue in replicate experiments.

DETAILED DESCRIPTION

Figure 1:
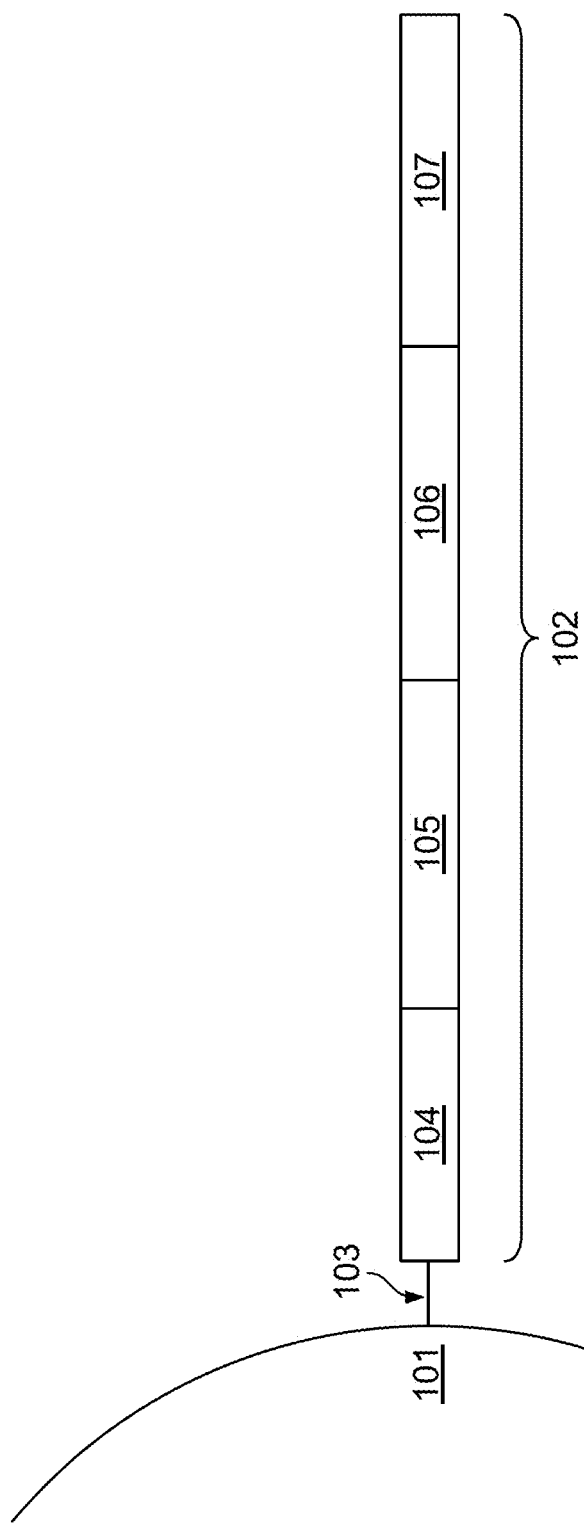
FIG. 1 is a schematic diagram showing an example of a barcoded capture probe, as described herein.

A fundamental understanding of spatial heterogeneity with respect to T-cell receptor (TCR) and B-cell receptor (BCR) clonotypes within a biological sample is needed to understand which cells a TCR or BCR may be interacting with, the identity of TCR and/or BCR clonotypes in a given biological sample, or the identity of TCR and/or BCR clonotypes that are autoreactive in different autoimmune disorders. Numerous single-cell sequencing approaches can identify TCR and BCR clonotypes from a biological sample, however, at present methods are need to link TCR and BCR sequences to spatial locations within a biological sample. Additionally, identifying the clonal regions, that is, regions defined by the places where variable (V), diverse (D), and joining (J) segments join to from the complementarity determining regions, including CDR1, CDR2, and CDR3, which provide specificity to the TCRs and/or BCRs, is needed to help determine biological interactions. By coupling clonal information to spatial information it is possible to understand which T-cell and B-cell clonotypes may be specifically interacting with given cell types within a biological sample.

Provided herein are methods for determining the presence and/or abundance of an immune cell clonotype at a location in a biological sample. Some embodiments of any of the methods described herein include capturing transcripts to identify an immune cell clonotype. Some embodiments of any of the methods herein include generating a nucleic acid library from captured transcripts. Some embodiments of any of the methods described herein include enriching analytes of interest in the nucleic acid library, including analytes to identify an immune cell clonotype.

Provided herein are methods for determining the presence and/or abundance of an immune cell receptor at a location in a biological sample. Some embodiments of any of the methods described herein include capturing analytes to identify an immune cell receptor. Some embodiments of any of the methods described herein include generating a nucleic acid library from captured analytes. Some embodiments of any of the methods described here include enriching analytes of interest in the nucleic acid library, including analytes to identify an immune cell receptor.

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample. Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodrigues et al., Science 363(6434):1463-1467, 2019; Lee et al., Nat. Protoc. 10(3):442-458, 2015; Trejo et al., PLoS ONE 14(2):e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics® Support Documentation website, and can be used herein in any combination. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

In some embodiments, the analyte is an immune cell receptor. In some embodiments, the immune cell receptor is a B cell receptor. In some embodiments, the B cell receptor is an immunoglobulin kappa light chain. In some embodiments, the variable region of the analyte includes a CDR3 region of the immunoglobulin kappa light chain. In some embodiments, the variable region of the analyte includes one or both of CDR1 and CDR2 of the immunoglobulin kappa light chain. In some embodiments, the variable region of the analyte includes a full-length variable domain of the immunoglobulin kappa light chain.

In some embodiments, the B cell receptor is an immunoglobulin lambda light chain. In some embodiments, the variable region of the analyte includes a CDR3 of the immunoglobulin lambda light chain. In some embodiments, the variable region of the analyte includes one or both of CDR1 and CDR2 of the immunoglobulin lambda light chain. In some embodiments, the variable region of the analyte includes a full-length variable domain of the immunoglobulin lambda light chain.

In some embodiments, the B cell receptor is an immunoglobulin heavy chain. In some embodiments, the variable region of the analyte includes a CDR3 of the immunoglobulin heavy chain. In some embodiments, the variable region of the analyte includes one or both of CDR1 and CDR2 of the immunoglobulin heavy chain. In some embodiments, the variable region of the analyte includes a full-length variable domain of the immunoglobulin heavy chain.

In some embodiments, the immune cell receptor is a T cell receptor. In some embodiments, the T cell receptor is a T cell receptor alpha chain. In some embodiments, the variable region of the analyte includes a CDR3 of the T cell receptor alpha chain. In some embodiments, the variable region of the analyte includes one or both of CDR1 and CDR2 of the T cell receptor alpha chain. In some embodiments, the variable region of the analyte includes a full-length variable domain of the T cell receptor alpha chain.

In some embodiments, the T cell receptor is a T cell receptor beta chain. In some embodiments, the variable region of the analyte includes a CDR3 of the T cell receptor beta chain. In some embodiments, the variable region of the analyte includes one or both of CDR1 and CDR2 of the T cell receptor beta chain. In some embodiments, the variable region of the analyte further includes a full-length variable domain of the T cell receptor beta chain.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)). See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof (ii) analyte binding moiety barcode; and (iii) an analyte capture sequence. As used herein, the term "analyte binding moiety barcode" refers to a barcode that is associated with or otherwise identifies the analyte binding moiety. As used herein, the term "analyte capture sequence" refers to a region or moiety configured to hybridize to, bind to, couple to, or otherwise interact with a capture domain of a capture probe. In some cases, an analyte binding moiety barcode (or portion thereof) may be able to be removed (e.g., cleaved) from the analyte capture agent. Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/ or into or onto the biological sample.

FIG. 1 is a schematic diagram showing an exemplary capture probe, as described herein. As shown, the capture probe 102 is optionally coupled to a feature 101 by a cleavage domain 103, such as a disulfide linker. The capture probe can include a functional sequence 104 that are useful for subsequent processing. The functional sequence 104 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 105. The capture probe can also include a unique molecular identifier (UMI) sequence 106. While FIG. 1 shows the spatial barcode 105 as being located upstream (5') of UMI sequence 106, it is to be understood that capture probes wherein UMI sequence 106 is located upstream (5') of the spatial barcode 105 is also suitable for use in any of the methods described herein. The capture probe can also include a capture domain 107 to facilitate capture of a target analyte. In some embodiments, the capture probe comprises one or more additional functional sequences that can be located, for example between the spatial barcode 105 and the UMI sequence 106, between the UMI sequence 106 and the capture domain 107, or following the capture domain 107. The capture domain can have a sequence complementary to a sequence of a nucleic acid analyte. The capture domain can have a sequence complementary to a connected probe described herein. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence of a nucleic acid analyte, a sequence complementary to a portion of a connected probe described herein, and/or a capture handle sequence described herein.

The functional sequences can generally be selected for compatibility with any of a variety of different sequencing systems, e.g., Ion Torrent Proton or PGM, ILLUMINA® (sequencing technology) sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, ILLUMINA® (sequencing technology) sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 105 and functional sequences 104 is common to all of the probes attached to a given feature. In some embodiments, the UMI sequence 106 of a capture probe attached to a given feature is different from the UMI sequence of a different capture probe attached to the given feature.

In some cases, capture probes may be configured to prime, replicate, and consequently yield optionally barcoded extension products from a template (e.g., a DNA or RNA template, such as an analyte or an intermediate agent (e.g., a ligation product or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form ligation products with a template (e.g., a DNA or RNA template, such as an analyte or an intermediate agent, or portion thereof), thereby creating ligations products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

Spatial Transcriptomics for Antigen Receptors

A fundamental understanding of spatial heterogeneity with respect to T-cell receptor (TCR) and B-cell receptor (BCR) clonotypes within a biological sample is needed to understand multiple facets of their functionality, including, for example, which cells a particular TCR or BCR may be interacting with within the biological sample, the identity of TCR and/or BCR clonotypes in a given biological sample, and/or the identity of TCR and/or BCR clonotypes that are autoreactive in different autoimmune disorders. Numerous single-cell sequencing approaches can identify TCR and BCR clonotypes from a biological sample, however, at present methods are needed to link TCR and BCR sequences to spatial locations within a biological sample. Additionally, identifying the clonal regions, that is, regions defined by the places where variable (V), diverse (D), and joining (J) segments join to form the complementarity determining regions, including CDR1, CDR2, and CDR3, which provide specificity to the TCRs and/or BCRs, would greatly benefit the scientific arts. By coupling clonal information to spatial information it is possible to understand which T-cell and B-cell clonotypes may be specifically interacting with given cell types within a biological sample.

However, capturing analytes encoding immune cell receptors can provide unique challenges. For example, spatially capturing the TCR and BCR gene components with sufficient efficiency to profile the majority of clonotypes in a given tissue is difficult. Capturing analytes encoding immune cell receptors with conventional short-read sequencing methods can result in a loss of sequenced regions that are more than about 1 kb away from the point where sequencing starts. Linking separate TCR or BCR gene components that together form a complete receptor using sequencing data from spots containing multiple different cells are challenges addressed by the methods described herein.

Methods described herein are utilized to analyze the various sequences of TCRs and BCRs from immune cells, for example, various clonotypes. In some embodiments, the methods are used to analyze the sequence of a TCR alpha chain, a TCR beta chain, a TCR delta chain, a TCR gamma chain, or any fragment thereof (e.g., variable regions including V(D)J or VJ regions, constant regions, transmembrane regions, fragments thereof, combinations thereof, and combinations of fragments thereof). In some embodiments, the methods described herein can be used to analyze the sequence of a B cell receptor heavy chain, B cell receptor light chain, or any fragment thereof (e.g., variable regions including V(D)J or VJ regions, constant regions, transmembrane regions, fragments thereof, combinations thereof, and combinations of fragments thereof).

Analytes

The analyte sequences present in the nucleic acid library (e.g., nucleic acid library generated from single-cells or from a biological sample on an array) can be captured from a biological sample (e.g., any of the biological samples described herein). In some embodiments, the biological sample is a tissue sample. In some embodiments, the tissue sample is a tissue section. In some embodiments, the tissue section is a fixed tissue section. In some embodiments, the fixed tissue section is formalin-fixed paraffin-embedded tissue section. In some embodiments, the tissue section is a fresh, frozen tissue section.

The analytes to be detected can be any of the analytes described herein. Analytes can include a nucleic acid molecule with a nucleic acid sequence encoding at least a portion of a V(D)J sequence of an immune cell receptor (e.g., a TCR or BCR). In some embodiments, the analyte is RNA. In some embodiments, the RNA is mRNA. In some embodiments, the analyte is DNA. In some embodiments, the DNA is genomic DNA. In some embodiments, the analytes are analytes encoding immune cell receptors. In some embodiments, analytes encoding immune cell receptors identify clonotype populations from a biological sample.

In some embodiments, analytes include a constant region, such as a constant region present in analytes encoding immune cell receptors. In some embodiments, analytes include a variable region, such as analytes encoding immune cell receptors. In some embodiments, analytes encoding immune cell receptors identify clonotype populations present in a biological sample.

In some embodiments, the analyte is an immune cell receptor. In some embodiments, the immune cell receptor is a B cell receptor. In some embodiments, the B cell receptor is an immunoglobulin kappa light chain. In some embodiments, the variable region of the analyte includes a CDR3 region of the immunoglobulin kappa light chain. In some embodiments, the variable region of the analyte includes one or both of CDR1 and CDR2 of the immunoglobulin kappa light chain. In some embodiments, the variable region of the analyte includes a full-length variable domain of the immunoglobulin kappa light chain. In some embodiments, the B cell receptor is an immunoglobulin lambda light chain.

In some embodiments, the variable region of the analyte includes a CDR3 of the immunoglobulin lambda light chain. In some embodiments, the variable region of the analyte includes one or both of CDR1 and CDR2 of the immunoglobulin lambda light chain. In some embodiments, the variable region of the analyte includes a full-length variable domain of the immunoglobulin lambda light chain.

In some embodiments, the B cell receptor is an immunoglobulin heavy chain. In some embodiments, the variable region of the analyte includes a CDR3 of the immunoglobulin heavy chain. In some embodiments, the variable region of the analyte includes one or both of CDR1 and CDR2 of the immunoglobulin heavy chain. In some embodiments, the variable region of the analyte includes a full-length variable domain of the immunoglobulin heavy chain.

In some embodiments, the immune cell receptor is a T cell receptor. In some embodiments, the T cell receptor is a T cell receptor alpha chain. In some embodiments, the variable region of the analyte includes a CDR3 of the T cell receptor alpha chain. In some embodiments, the variable region of the analyte includes one or both of CDR1 and CDR2 of the T cell receptor alpha chain. In some embodiments, the variable region of the analyte includes a full-length variable domain of the T cell receptor alpha chain.

In some embodiments, the T cell receptor is a T cell receptor beta chain. In some embodiments, the variable region of the analyte includes a CDR3 of the T cell receptor beta chain. In some embodiments, the variable region of the analyte includes one or both of CDR1 and CDR2 of the T cell receptor beta chain. In some embodiments, the variable region of the analyte further includes a full-length variable domain of the T cell receptor beta chain.

Capturing Analytes Encoding Immune Cell Receptors

Provided herein are methods for determining the presence and/or abundance of an immune cell clonotype at a location in a biological sample, the method including (a) contacting a biological sample with an array including a plurality of capture probes, wherein a capture probe of the plurality of capture probes includes (i) a spatial barcode and (ii) a capture domain that specifically binds to a nucleic acid encoding an immune cell receptor of the immune cell clonotype, and, (b) determining (i) all or a portion of the sequence of the spatial barcode or a complement thereof, and (ii) all or a portion of the sequence of the nucleic acid encoding the immune cell receptor or a complement thereof, and using the determined sequences of (i) and (ii) to determine the presence and/or abundance of the immune cell clonotype at a location in the biological sample.

Also provided herein are methods for determining the presence and/or abundance of an immune cell receptor at a location in a biological sample, the method including (a) contacting a biological sample with an array including a plurality of capture probes, wherein a capture probe of the plurality of capture probes includes (i) a spatial barcode and (ii) a capture domain that specifically binds to a nucleic acid encoding an immune cell receptor; and (b) determining (i) all or a portion of the sequence of the spatial barcode or a complement thereof, and (ii) all or a portion of the sequence of the nucleic acid encoding the immune cell receptor or a complement thereof, and using the determined sequences of (i) and (ii) to determine the presence and/or abundance of the immune cell receptor at a location in the biological sample.

Also provided herein are methods for determining the presence and/or abundance of an immune cell clonotype at a location in a biological sample, the method including (a) contacting a biological sample with an array including a plurality of capture probes, wherein a capture probe of the plurality of capture probes includes (i) a spatial barcode and (ii) a capture domain that binds to a nucleic acid encoding an immune cell receptor of the immune cell clonotype; (b) determining (i) all or a portion of the sequence of the spatial barcode or a complement thereof, and (ii) all or a portion of the sequence of the nucleic acid encoding the immune cell receptor or a complement thereof, and using the determined sequences of (i) and (ii) to determine the presence and/or abundance of the immune cell clonotype at a location in the biological sample.

Also provided herein are methods for determining the presence and/or abundance of an immune cell receptor at a location in a biological sample, the method including (a) contacting a biological sample with an array including a plurality of capture probes, wherein a capture probe of the plurality of capture probes includes (i) a spatial barcode and (ii) a capture domain that binds to a nucleic acid encoding an immune cell receptor and (b) determining (i) all or a portion of the sequence of the spatial barcode or a complement thereof, and (ii) all or a portion of the sequence of the nucleic acid encoding the immune cell receptor or a complement thereof, and using the determined sequences of (i) and (ii) to determine the presence and/or abundance of the immune cell receptor at a location in the biological sample.

In some embodiments of determining the presence and/or abundance of an immune cell clonotype or an immune cell receptor at a location in a biological sample, step (b) includes extending an end of the capture probe using the nucleic acid encoding the immune cell receptor as a template, thereby generating an extended capture probe. In some embodiments, extending an end of the capture probe includes using a reverse transcriptase (e.g., any of the reverse transcriptases described herein). In some embodiments, step (b) includes extending a 3' end of the capture probe. In some embodiments, step (b) includes generating a second strand of nucleic acid that includes (i) a sequence that is complementary to all or a portion of the spatial barcode, and (ii) a sequence that corresponds to all or a portion of the sequence of the nucleic acid encoding the immune cell receptor.

In some embodiments of determining the presence and/or abundance of an immune cell clonotype or an immune cell receptor at a location in a biological sample, the capture probe includes a cleavage domain, a functional domain, a unique molecular identifier, or any combination thereof. In some embodiments, the capture probe includes a functional domain. In some embodiments, the capture domain includes a poly(T) sequence. In some embodiments, the capture domain binds specifically to a nucleic acid sequence encoding a constant region of the T cell receptor alpha chain. In some embodiments, the capture domain binds specifically to a nucleic acid sequence encoding a constant region of the T cell receptor beta chain. In some embodiments, the capture domain binds specifically to a nucleic acid sequence encoding a constant region of the immunoglobulin kappa light chain. In some embodiments, the capture domain binds specifically to a nucleic acid sequence encoding a constant region of the immunoglobulin lambda light chain. In some embodiments, the capture probe binds specifically to a nucleic acid sequence encoding a constant region of the immunoglobulin heavy chain.

Variable Region Primer Enrichment

As demonstrated in the Examples, analytes encoding immune cell receptors were captured and identified with capture domains designed to specifically bind a constant region of a particular immune cell receptor from a biological sample. However, such a strategy does not capture analytes other than analytes encoding immune cell receptors. An additional and alternative approach can include using one or more variable region (V-region) specific primer sets to amplify analytes encoding immune cell receptors (e.g., TCRs and/or BCRs) from nucleic acid libraries generated from poly(T) captured total cDNA libraries, thus allowing sequencing into CDR regions (e.g., CDR3 region) from the 5' end of an amplicon. An advantage of this approach would be the simultaneous detection of lymphocyte clonality alongside global spatial gene expression. An additional consideration is capturing full IGH complexity (e.g., IGH isotypes, e.g., IGHA1-2, IGHG1-4, IGHM, IGHD, and IGHE) without paired end sequencing reads through the CDR3 region. Additional receptor diversity is added to the BCR throughout development and may be difficult to distinguish from sequencing errors with only a single CDR3 read. Additionally, some analytes encoding immune cell receptors are known to be in low abundance (See e.g., Tu, A. A., et al., TCR sequencing paired with massively parallel 3' RNAseq reveals clonotypic T cell signatures, *Nature Immunology*, 20, 1692-1699 (2019); Singh M., et al., High-throughput long-read single cell sequencing reveals the clonal and transcriptional landscape of lymphocytes. *Nature Communications*, 10, 3120 (2019), both of which are incorporated herein by reference in their entireties). Thus, for example, variable region primer enrichment can provide an alternate method to enrich for analytes encoding immune cell receptors from arrays with capture probes including a poly(T) capture domain, followed by one or more amplification reactions (e.g., PCR).

In some embodiments of any of the spatial methods described herein, step (b) further includes generating a second strand of nucleic acid that includes (i) a sequence that is complementary to all or a portion of the functional domain, (ii) a sequence that is complementary to all or a portion of the spatial barcode, and (iii) a sequence that corresponds to all or a portion of the sequence of the nucleic acid encoding the immune cell receptor. In some embodiments, step (b) further includes amplifying the second strand of the nucleic acid using (i) a first primer including all or a portion of the functional domain, wherein the functional domain is 5' to the spatial barcode in the second strand of nucleic acid, and (ii) a second primer including a sequence that is substantially complementary to a portion of a sequence encoding a variable region of the immune cell receptor.

In some embodiments, more than one second primer including a sequence substantially complementary to a portion of the sequence encoding the variable region of the immune cell receptor is used. For example, a nested PCR strategy can be used where a first amplification product is generated with a variable region primer and a primer substantially complementary to the functional domain 5' to the spatial barcode, followed by a second, a third, or a fourth round of amplification using a second, a third, or a fourth variable region primer internal to the first region variable region primer (e.g., 5' to the first variable region primer)(for example, see FIG. 22). It will be understood to a person of ordinary skill in the art that additional rounds of amplification require an internal (e.g., 5') located variable region primer in subsequent amplification rounds.

Hybridization Probes and Blocking Probes

In some embodiments, targeted enrichment of cDNAs of interest are enriched from cDNA derived libraries generated from captured analytes (e.g., immune cell analytes). For example, a pool of hybridization probes to an analyte of interest, or a complement thereof, can be designed. In some embodiments, about 10 to about 500 hybridization probes, about 25 to about 450 hybridization probes, about 50 to about 400 hybridization probes, about 75 to about 350 hybridization probes, or about 100 to 300 hybridization probes can be designed for hybridizing to an analyte of interest, or a complement thereof. In some embodiments, the hybridization probes can include an additional moiety, such as a binding moiety, (e.g., biotin) capable of binding another moiety, such as a capture moiety, (e.g., streptavidin). Thus, in some embodiments, one or more hybridization probes (e.g., including an additional moiety, such as biotin) hybridize to the analyte of interest, or complement thereof, in the cDNA library and the total cDNA library is processed on streptavidin beads, for example. The biotin moieties of the hybridization probes specifically bind the streptavidin molecules, thereby enriching for the analytes of interest, or complements thereof. Hybridization probes can be designed to be complementary to any analyte or its complementary sequence, including, for example, analytes encoding immune cell analytes.

In some embodiments, enriching analytes of interest includes the use of blocking probes. Blocking probes can be added to the cDNA library before, after, or concurrently with hybridization probes. In some embodiments, blocking probes reduce background (e.g., non-specific binding events) when enriching for targets within the cDNA library. In some embodiments, blocking probes can be about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, or about 150 nucleotides long. In some embodiments, blocking probes are designed specifically to domains present in one or more members of the cDNA library. In some embodiments, one blocking probe is added to the cDNA library. In some embodiments, two or more blocking probes (e.g., different blocking probes). In some embodiments, 3, 4, 5 or more different blocking probes are added to the cDNA library (e.g., blocking probes having a different sequence). In some embodiments, the blocking probe comprises SEQ ID NO: 639. In some embodiments, the blocking probe comprises SEQ ID NO: 640. In some embodiments, the blocking probe comprises at least 80%, at least 85%, at least 90%, at least 95%, at least 96%, at least 97%, at least 98%, or at least 99% identity to SEQ ID NO: 639. In some embodiments, the blocking probe comprises at least 80%, at least 85%, at least 90%, at least 95%, at least 96%, at least 97%, at least 98%, or at least 99% identity to SEQ ID NO: 640.

Identifying Immune Cell Receptors

In some embodiments of determining the presence and/or abundance of an immune cell clonotype at a location in a biological sample, determining in step (b) includes sequencing (i) all or a portion of the sequence of the spatial barcode or a complement thereof, and (ii) all or a portion of the sequence of the nucleic acid encoding the immune cell receptor or a complement thereof. Any of the sequencing methods described herein can be used. In some embodiments, step (b) includes determining the presence of the immune cell clonotype at a location in the biological sample. In some embodiments, step (b) includes determining the abundance of the immune cell clonotype at a location in the biological sample. In some embodiments, step (b) includes determining the presence and abundance of the immune cell clonotype at a location in the biological sample. In some embodiments, step (b) includes determining the presence of two or more immune cell clonotypes at a location in the biological sample. In some embodiments, step (b) includes determining the abundance of two or more immune cell clonotypes at a location in the biological sample. In some embodiments, step (b) includes determining the presence and abundance of two or more immune cell clonotypes at a location in the biological sample. In some embodiments, the method includes comparing the two or more immune cell clonotypes. In some embodiments, the two or more immune cell clonotypes are each a B cell clonotype. In some embodiments, the two or more immune cell clonotypes are each a T cell clonotype. In some embodiments, the two or more immune cell clonotypes include at least one T cell clonotype and at least one B cell clonotype.

In some embodiments of determining the presence and/or abundance of an immune cell receptor at a location in a biological sample, the determining in step (b) includes sequencing (i) all or a portion of the sequence of the spatial barcode or a complement thereof, and (ii) all or a portion of the sequence of the nucleic acid encoding the immune cell receptor or a complement thereof. In some embodiments, step (b) includes determining the presence of the immune cell receptor at a location in the biological sample. In some embodiments, step (b) includes determining the abundance of the immune cell receptor at a location in the biological sample. In some embodiments, step (b) includes determining the presence and abundance of the immune cell receptor at a location in the biological sample. In some embodiments, step (b) includes determining the presence of two or more immune cell receptors at a location in the biological sample. In some embodiments, step (b) includes determining the abundance of two or more immune cell receptors at a location in the biological sample. In some embodiments, step (b) includes determining the presence and abundance of two or more immune cell receptors at a location in the biological sample. In some embodiments, the method includes comparing the two or more immune cell receptors. In some embodiments, the two or more immune cell clonotypes are each an immune cell receptor of a B cell. In some embodiments, two or more immune cell clonotypes are each an immune cell receptor of a T cell. In some embodiments, two or more immune cell clonotypes include at least one immune cell receptor of a T cell and at least one immune cell receptor from a B cell.

In some embodiments of determining the presence and/or abundance of an immune cell clonotype or an immune cell receptor at a location in a biological sample, includes prior to step (b), contacting the biological sample with ribosomal RNA depletion probes and/or mitochondrial RNA depletion probes. In some embodiments, the biological sample is imaged. In some embodiments, the biological sample is stained.

Arrays and Kits

Provided herein are arrays including a plurality of capture probes, where a capture probe of the plurality of capture probes includes (i) a spatial barcode and (ii) a capture domain that specifically binds to a nucleic acid encoding an immune cell receptor of an immune cell clonotype. In some arrays, the immune cell clonotype is a T cell clonotype. In some arrays, the immune cell receptor is a T cell receptor alpha chain. In some arrays, the capture domain binds specifically to a nucleic acid sequence encoding a constant region of the T cell receptor alpha chain. In some arrays, the immune cell receptor is a T cell receptor beta chain. In some arrays, the capture domain binds specifically to a nucleic acid sequence encoding a constant region of the T cell receptor beta chain. In some arrays, the immune cell clonotype is a B cell clonotype. In some arrays, the immune cell receptor is an immunoglobulin kappa light chain. In some arrays, the capture domain binds specifically to a nucleic acid sequence encoding a constant region of the immunoglobulin kappa light chain. In some arrays, the immune cell receptor is an immunoglobulin lambda light chain. In some arrays, the capture domain binds specifically to a nucleic acid sequence encoding a constant region of the immunoglobulin lambda light chain. In some arrays, the immune cell receptor is an immunoglobulin heavy chain. In some arrays, the capture domain binds specifically to a nucleic acid sequence encoding a constant region of the immunoglobulin heavy chain. In some arrays, the capture probe includes a cleavage domain, a functional domain, a unique molecular identifier, or any combination thereof.

Also provided herein are kits including an array (e.g., any of the arrays described herein) and one or more hybridization probes, wherein a hybridization probe includes (i) a sequence substantially complementary to a nucleic acid encoding an immune cell receptor and (ii) a binding moiety that interacts with a capturing moiety and one or more blocking probes.

Also provided herein are kits, including an array of any of the arrays described herein and one or both of ribosomal RNA depletion probes and mitochondrial RNA depletion probes.

Targeted RNA depletion allows for depletion or removal of one or more species of undesirable RNA molecules (e.g., ribosomal RNA and/or mitochondrial RNA), thereby reducing the pool and concentration of undesirable RNA molecules in the sample which could interfere with desired target detection (e.g., detection of mRNA). To achieve depletion, one or more probes are designed that hybridize to one or more undesirable RNA molecules. For example, in one embodiment, probes can be administered to a biological sample that selectively hybridize to ribosomal RNA (rRNA), thereby reducing the pool and concentration of rRNA in the sample. In one embodiment, probes can be administered to a biological sample that selectively hybridize to mitochondria RNA (mtRNA), thereby reducing the pool and concentration of mtRNA in the sample. Subsequent application of capture probes to the sample can result in improved capture of other types of RNA due to a reduction in undesirable RNA (e.g., down-selected RNA) present in the sample.

Upon depletion of the undesirable RNA, the sample will contain an enriched population of the RNA target of interest (e.g., an mRNA target). In some embodiments, the undesirable RNA comprises less than 20%, 19%, 18%, 17%, 16% 15%, 14%, 13%, 12%, 11% 10%, 9%, 8%, 7%, 6%, 5%, 4%, 3%, 2%, or 1%, or any range therein, of the total RNA in the sample after depletion of the undesirable RNA (i.e., less than 20%, 19%, 18%, 17%, 16% 15%, 14%, 13%, 12%, 11% 10%, 9%, 8%, 7%, 6%, 5%, 4%, 3%, 2%, or 1%, or any range therein compared to a sample that undergoes no depletion step). Consequently, the enriched population of the RNA target of interest may comprise at least 99%, 98%, 97%, 96%, 95%, 94%, 93%, 92%, 91%, 90%, 89%, 88%, 87%, 86%, 85%, 84%, 83%, 82%, 81%, or 80%, or any range therein, of the total RNA in the sample.

As used herein, the term "undesirable RNA molecule", or "undesirable RNA", refers to an undesired RNA that is the target for depletion from the biological sample. In some embodiments, examples of the undesirable RNA include, but are not limited to, messenger RNA (mRNA), ribosomal RNA (rRNA), mitochondrial RNA (mtRNA), transfer RNA (tRNA), microRNA (miRNA), and viral RNA. In some embodiments, the undesirable RNA can be a transcript (e.g., present in a tissue section). The undesirable RNA can be small (e.g., less than 200 nucleic acid bases in length) or large (e.g., RNA greater than 200 nucleic acid bases in length).

In some embodiments, the undesirable RNA molecule includes 5.8S ribosomal RNA (rRNA), 5S rRNA, transfer RNA (tRNA), microRNA (miRNA), a small nucleolar RNA (snoRNAs), Piwi-interacting RNA (piRNA), tRNA-derived small RNA (tsRNA), and small rDNA-derived RNA (srRNA), or mitochondrial RNA (mtRNA). In some embodiments, the undesirable RNA molecule includes an RNA molecule that is added (e.g., transfected) into a sample (e.g., a small interfering RNA (siRNA)). The undesirable RNA can be double-stranded RNA or single-stranded RNA. In embodiments where the undesirable RNA is double-stranded it is processed as a single-stranded RNA prior to depletion. In some embodiments, the undesirable RNA can be circular RNA. In some embodiments, the undesirable RNA can be a bacterial rRNA (e.g., 16s rRNA or 23s rRNA). In some embodiments, the undesirable RNA is from E. coli.

In some embodiments, the undesirable RNA molecule is rRNA. In some embodiments, the rRNA is eukaryotic rRNA. In some embodiments, the rRNA is cytoplasmic rRNA. In some embodiments, the rRNA is mitochondrial rRNA. Cytoplasmic rRNAs include, for example, 28S, 5.8S, 5S and 18S rRNAs. Mitochondrial rRNAs include, for example, 12S and 16S rRNAs. The rRNA may also be prokaryotic rRNA, which includes, for example, 5S, 16S, and 23S rRNA. The sequences for rRNAs are well known to those skilled in the art and can be readily found in sequence databases such as GenBank or may be found in the literature. For example, the sequence for the human 18S rRNA can be found in GenBank as Accession No. M10098 and the human 28S rRNA as Accession No. M11167.

In some embodiments, the undesirable RNA molecule is mitochondrial RNA. Mitochondrial RNAs include, for example, 12S rRNA (encoded by MT-RNR1), and 16S rRNA (encoded by MT-RNR2), RNAs encoding electron transport chain proteins (e.g., NADH dehydrogenase, coenzyme Q-cytochrome c reductase/cytochrome b, cytochrome c oxidase, ATP synthase, or humanin), and tRNAs (encoded by MT-TA, MT-TR, MT-TN, MT-TD, MT-TC, MT-TE, MT-TQ, MT-TG, MT-TH, MT-TI, MT-TL1, MT-TL2, MT-TK, MT-TM, MT-TF, MT-TP, MT-TS1, MT-TS2, MT-TT, MT-TW, MT-TY, or MT-TV).

In some embodiments, the one or more undesirable RNA depletion probes is a DNA probe. In some embodiments, the DNA probe includes a single-stranded DNA oligonucleotide having a sequence partially or completely complementary to an undesirable RNA and specifically hybridizes to the undesirable RNA. In some embodiments, the one or more undesirable RNA depletion probes are at least 70%, at least 75%, at least 80%, at least 85%, at least 90%, at least 91%, at least 92%, at least 93%, at least 94%, at least 95%, at least 96%, at least 97%, at least 98%, or at least 99% complementary to one or more undesirable RNA molecules. In some embodiments, the one or more undesirable RNA depletion probes is 100% (i.e., completely) complementary to one or more undesirable RNA molecules.

In some embodiments, probes used herein have been described in Morlan et al., PLoS One. 2012; 7(8):e42882, which is incorporated by reference in its entirety. In some embodiments, probes used herein have been described in U.S. Appl. Publ. No. 2011/0111409, which is incorporated by reference in its entirety. In some embodiments, probes used herein have been described in Adiconis et al., Nat Methods. 2013 July; 10(7):623-9, which is incorporated by reference in its entirety.

The DNA probe can be produced by techniques known in the art. For example, in some embodiments, a DNA probe is produced by chemical synthesis, by in vitro expression from recombinant nucleic acid molecules, or by in vivo expression from recombinant nucleic acid molecules. The undesirable RNA depletion probe may also be produced by amplification of the undesirable RNA, e.g., RT-PCR, asymmetric PCR, or rolling circle amplification.

EXAMPLES

Example 1: Analyte Capture and Enrichment Strategies

FIGS. 3A and 3B show two different capture probes with different exemplary capture strategies to capture analytes encoding immune cell receptors in a biological sample. FIG. 3A shows "targeted" capture where the capture domain is substantially complementary to the constant region of the analyte encoding an immune cell receptor to be detected. Targeted capture increases the likelihood that the portion of interest in the variable domain, CDR3, is retained during library preparation. Alternatively, FIG. 3B shows poly(A) capture with a poly(T) capture domain. A poly(T) capture domain can capture other analytes, including analytes encoding immune cell receptors within the biological sample.

Figure 4:
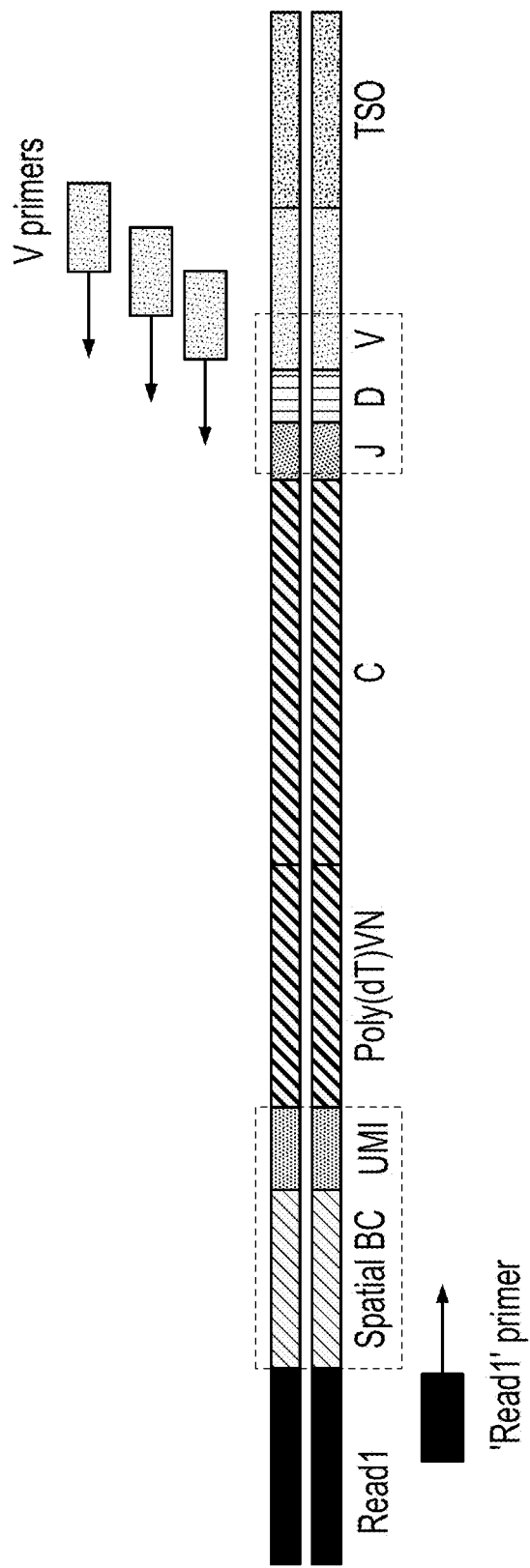
FIG. 4 shows an exemplary enrichment strategy with a Read1 primer and a primer(s) complementary to a variable region of an analyte.

FIG. 4 shows an exemplary analyte enrichment strategy following analyte capture on the array. The portion of the immune cell analyte of interest includes the sequence of the V(D)J region. The CDR sequences are also important because these sequences define the immune cell receptor's binding specificity. As described herein, a poly(T) capture probe captures an analyte encoding an immune cell receptor, an extended capture probe is generated by a reverse transcription reaction, and a second strand is generated. The resulting nucleic acid library can be enriched by the exemplary scheme shown in FIG. 4, where an amplification reaction including a Read 1 primer complementary to the Read 1 sequence of the capture probe and a primer complementary to a portion of the variable region of the immune cell analyte, can enrich the library via PCR. The enriched library can be further enriched by nested primers complementary to a portion of the variable region internal (e.g., 5') to the initial variable region primer for practicing nested PCR.

Figure 5:
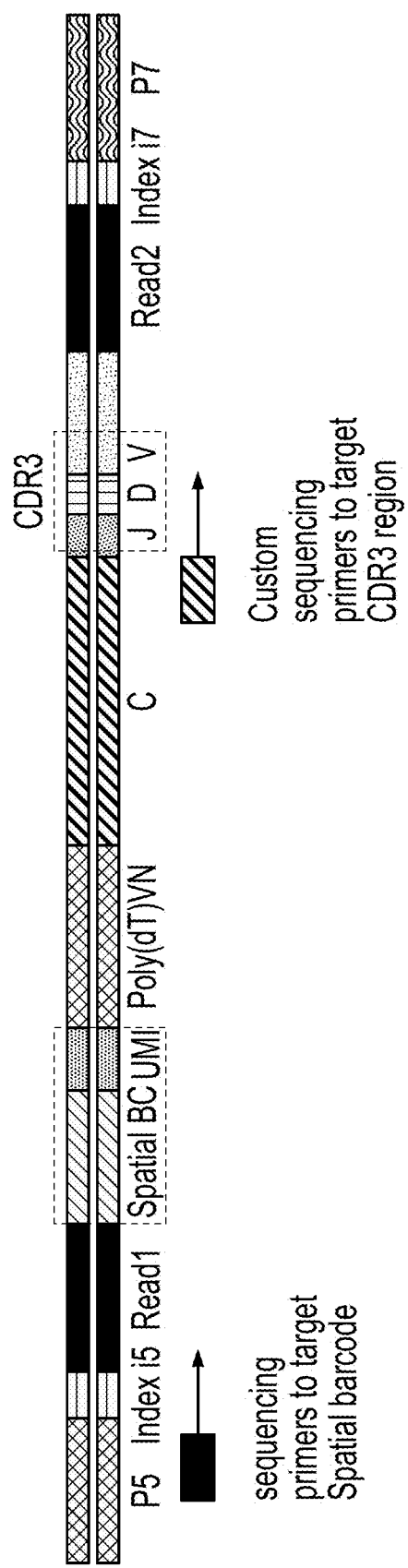
FIG. 5 shows an exemplary sequencing strategy with a ligated sequencing handle (P5) and a custom sequencing primer complementary to a portion of the constant region of an analyte.

FIG. 5 shows a sequencing strategy with a primer specific complementary to the sequencing flow cell attachment sequence (e.g., P5) and a custom sequencing primer complementary to a portion of the constant region of the analyte. This sequencing strategy targets the constant region to obtain the sequence of the CDR regions, including CDR3, while concurrently or sequentially sequencing the spatial barcode (BC) and/or unique molecular identifier (UMI) of the capture probe. By capturing the sequence of a spatial barcode, UMI and a V(D)J region the receptor is not only determined, but its spatial location and abundance within a cell or tissue is also identified.

Example 2—Capture of Analytes Encoding Immune Cell Receptors

Figure 6:
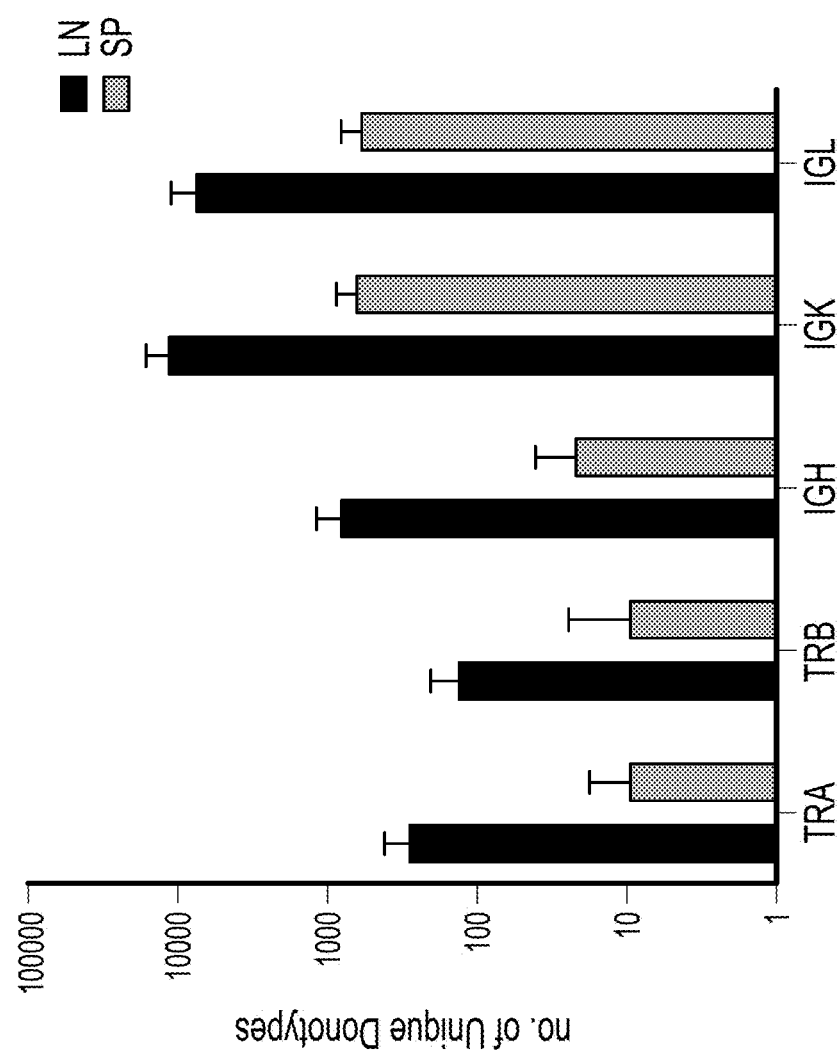
FIG. 6 shows a graph showing the number of unique clonotypes detected from lymph node (LN) and spleen (SP) tissues.

FIG. 6 shows the number of unique clonotypes detected for TRA, TRB, IGH, IGK, and IGL on an array for both lymph node tissue (LN, black) and spleen tissue (SP, gray). It is contemplated that the lack of detected clonotypes found may be the result of inefficient or decreased TRAC/TRBC/IGH transcript capture or decreased sequencing of the variable region (e.g., CDR3 region) due to its distance from the sequencing domain (e.g. Read 1 sequencing domain). A greater abundance of unique clonotypes were detected for IGK and IGL, which may be due in part to the shorter constant regions present in these clonotypes relative to the constant regions present in TRAC, TRAB, and IGH transcripts.

Figure 7B:
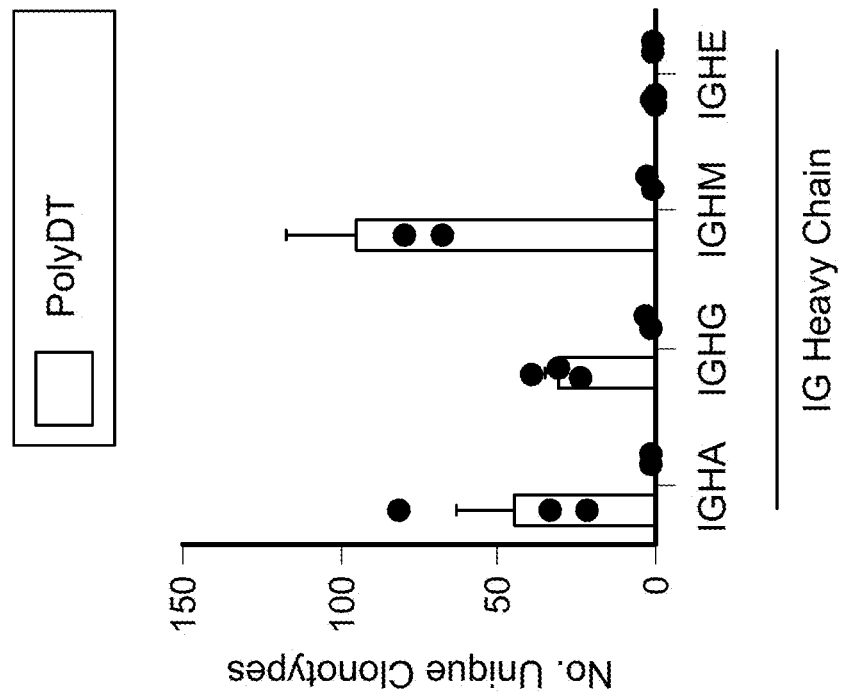
FIG. 7B shows an exemplary graph of the number of unique IG heavy chain clonotypes (e.g., A, G, M and E clonotypes) detected with a targeted capture probe compared with a poly(dT) capture probe.
Figure 7A:
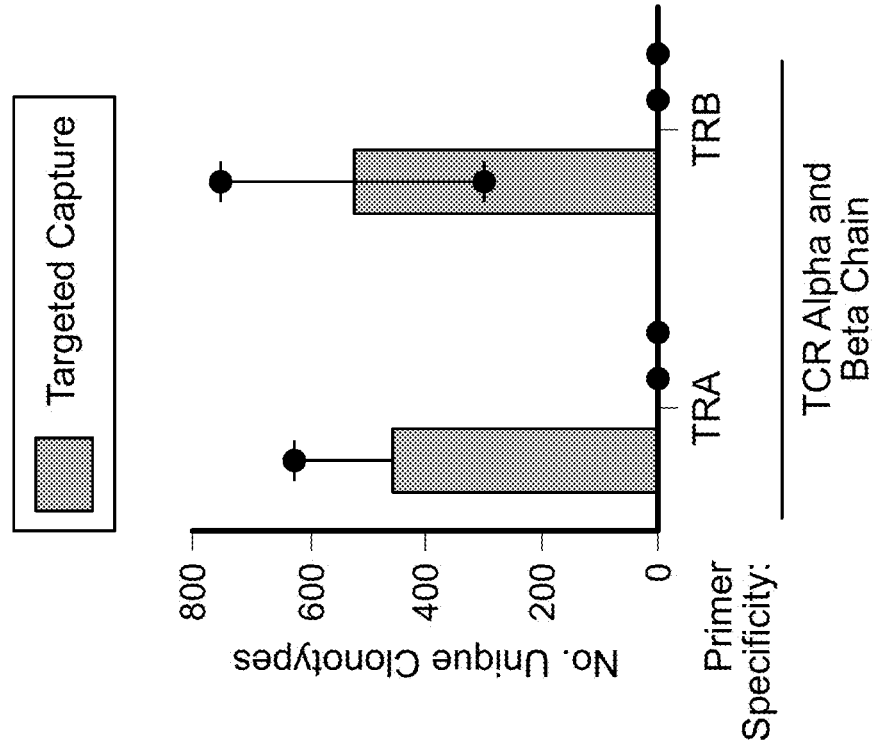
FIG. 7A shows an exemplary graph of the number of unique T-cell receptor A (TRA) and T-cell receptor B (TRB) clonotypes detected with a targeted capture probe compared with a poly(dT) capture probe.

FIGS. 7A-B show the number of unique clonotypes detected for TRA and TRB (FIG. 7A) and the number of unique clonotypes detected for IGA, IGHG, IGHM, and IGHE (FIG. 7B). The data show that targeted capture (gray bars) yields a higher number of TRA and TRB clonotypes (FIG. 7A) than poly(T) capture as demonstrated by the lack of clonotypes detected. Similarly, targeted capture of IGHA, IGHG, and IGHM yielded a higher number of unique clonotypes detected than poly(T) capture, as demonstrated by the lack of clonotypes detected. Thus the data demonstrate that targeted capture of analytes encoding immune cell receptors is possible for some analytes, but may not be sufficient for other analytes encoding immune cell receptors (e.g., IGHE).

As discussed, undetectable levels of T-cell receptor and B-cell receptor transcripts were captured with poly(T) capture domains as shown in FIGS. 7A-B. Targeted capture, however, requires custom capture domains for each analyte encoding an immune cell receptor and does not allow for the simultaneous capture of analytes other than targeted analytes encoding immune cell receptors.

A strategy to detect whether analytes encoding immune cell receptors were captured was investigated and includes using poly(T) capture sequences in combination with PCR amplification performed on full length cDNA from several different sources, including lymph node tissue and tonsil tissue (Table 1).

TABLE 1

| Lymph Node (LN) spatial library | n = 6 |
| Tonsil spatial library | n = 2 |
| Tonsil SmartSeq2 (SS2) (single-cell) RNAseq (positive control) | n = 1 |

The tonsil SS2 sample was derived from the same tonsil as the tonsil spatial libraries and adapted from Picelli et al., Full-length RNA-seq from single cells using Smart-seq2, 9, 171-181, *Nature* (2014), and used as a positive control and without PCR enrichment.

To begin, 0.5 ng of each library in Table 1 as input material was run in triplicate for each sample and PCR reaction (TRB, IGHG, and IGHM), except for one LN (#9) and the Tonsil SS2 bulk sample, which were run in duplicate and once, respectively. The PCR primers targeted: a) the constant region of either TRB, IGHG, or IGHM (Table 2), and b) the variable segments for TRB (Balazs, A. B., et al., Isolation of unknown rearranged T-cell receptors from single cells WO 2011/008502, which is incorporated herein by reference in its entirety) and IGH (Vazquez, B., et al., High-Quality Library Preparation for NGS-Based Immunoglobulin Germline Gene Inference and Repertoire Expression Analysis, *Frontiers Immunol*, 10, 660 (2019), which is incorporated herein by reference in its entirety). The constant primers were selected based on their proximity to the CDR3 region and testing of various primers for each target was performed in PCR optimization experiments. Both the 5 forward and reverse primers were tagged with partial P5 and P7 domains that allowed subsequent Truseq indexing for ILLUMINA® (sequencing technology) sequencing. PCR was performed using the KAPA HiFi Hotstart ready mix according to the manufacturer's instructions with 30 amplification cycles.

TABLE 2

Constant Primer Sequence

| | | |
|---|---|---|
| TRB | SEQ ID NO: 1 | TCTGATGGCTCAAACACAGC |
| IGHG | SEQ ID NO: 2 | GCCAGGGGAAGACCGATGGG |
| IGHM | SEQ ID NO: 3 | CACGCTGCTCGTATCCGA |

TABLE 3

| Variable Region Primer | Sequence | |
|---|---|---|
| TCRa V inner pool | | |
| TCRaV17 | SEQ ID NO: 4 | CAACAGGGAGAAGAGGATCCTCAGGCC |
| TCRaV1-2 | SEQ ID NO: 5 | GGACAAAACATTGACCAGCCCACTGAGAT |
| TCRaV10 | SEQ ID NO: 6 | AAAAACCAAGTGGAGCAGAGTCCTCAGTCC |
| TCRaV12-1 | SEQ ID NO: 7 | CAACGGAAGGAGGTGGAGCAGGATC |
| TCRaV12-2 | SEQ ID NO: 8 | CAACAGAAGGAGGTGGAGCAGAATTCTGG |
| TCRaV12-3 | SEQ ID NO: 9 | CAACAGAAGGAGGTGGAGCAGGATCCT |
| TCRaV13-1 | SEQ ID NO: 10 | GAGAATGTGGAGCAGCATCCTTCAACC |
| TCRaV13-2 | SEQ ID NO: 11 | GAGAGTGTGGGGCTGCATCTTCCTACC |
| TCRaV14D4 | SEQ ID NO: 12 | CAGAAGATAACTCAAACCCAACCAGGAATGTTC |
| TCRav16 | SEQ ID NO: 13 | CAGAGAGTGACTCAGCCCGAGAAGCTC |
| TCRaV18 | SEQ ID NO: 14 | GACTCGGTTACCCAGACAGAAGGCCC |
| TCRaV19 | SEQ ID NO: 15 | CAGAAGGTAACTCAAGCGCAGACTGAAATTTCT |
| TCRaV2 | SEQ ID NO: 16 | AAGGACCAAGTGTTTCAGCCTTCCACAGTG |
| TCRaV20 | SEQ ID NO: 17 | GAAGACCAGGTGACGCAGAGTCCCG |
| TCRaV21 | SEQ ID NO: 18 | AAACAGGAGGTGACGCAGATTCCTGC |
| TCRaV22 | SEQ ID NO: 19 | ATACAAGTGGAGCAGAGTCCTCCAGACCTGA |
| TCRaV23DV6 | SEQ ID NO: 20 | CAACAGAAGGAGAAAAGTGACCAGCAGCA |
| TCRaV24 | SEQ ID NO: 21 | ATACTGAACGTGGAACAAAGTCCTCAGTCACTG |
| TCRaV25 | SEQ ID NO: 22 | CAACAGGTAATGCAAATTCCTCAGTACCAGC |
| TCRaV26-1 | SEQ ID NO: 23 | AAGACCACCCAGCCCCCCTCC |
| TCRaV26-2 | SEQ ID NO: 24 | AAGACCACACAGCCAAATTCAATGGAGAGTAAC |
| TCRaV27 | SEQ ID NO: 25 | CAGCTGCTGGAGCAGAGCCCTCAGT |
| TCRaV29DV5 | SEQ ID NO: 26 | CAACAGAAGAATGATGACCAGCAAGTTAAGCAA |
| TCRaV3 | SEQ ID NO: 27 | CAGTCAGTGGCTCAGCCGGAAGATC |
| TCRaV30 | SEQ ID NO: 28 | CAACAACCAGTGCAGAGTCCTCAAGCC |
| TCRaV34 | SEQ ID NO: 29 | CAAGAACTGGAGCAGAGTCCTCAGTCCTTG |
| TCRaV35 | SEQ ID NO: 30 | CAACAGCTGAATCAGAGTCCTCAATCTATGTTTATC |
| TCRaV36DV7 | SEQ ID NO: 31 | GAAGACAAGGTGGTACAAAGCCCTCTATCTCTG |
| TCRaV38-2DV8 | SEQ ID NO: 32 | CAGACAGTCACTCAGTCTCAACCAGAGATGCT |
| TCRaV39 | SEQ ID NO: 33 | GAGCTGAAAGTGGAACAAAACCCCTCTGTTC |
| TCRaV4 | SEQ ID NO: 34 | AAGACCACCCAGCCCATCTCCATG |
| TCRaV40 | SEQ ID NO: 35 | AATTCAGTCAAGCAGACGGGCCAAATAAC |
| TCRaV41 | SEQ ID NO: 36 | GCCAAAAATGAAGTGGAGCAGAGTCCTC |
| TCRaV5 | SEQ ID NO: 37 | GAGGATGTGGAGCAGAGTCTTTTCCTGAGTG |
| TCRaV6 | SEQ ID NO: 38 | CAAAAGATAGAACAGAATTCCGAGGCCCTG |
| TCRaV7 | SEQ ID NO: 39 | GAAAACCAGGTGGAGCACAGCCCTC |
| TCRaV8-1 | SEQ ID NO: 40 | CAGTCTGTGAGCCAGCATAACCACCAC |
| TCRaV8-2 | SEQ ID NO: 41 | CAGTCGGTGACCCAGCTTGACAGC |
| TCRaV8-3 | SEQ ID NO: 42 | CAGTCAGTGACCCAGCCTGACATCCAC |
| TCRaV8-4 | SEQ ID NO: 43 | CAGTCGGTGACCCAGCTTGGCAG |
| TCRaV8-6 | SEQ ID NO: 44 | CAGTCTGTGACCCAGCTTGACAGCCA |
| TCRaV8-7 | SEQ ID NO: 45 | CAGTCGGTGACCCAGCTTGATGGC |
| TCRaV9-1 | SEQ ID NO: 46 | GATTCAGTGGTCCAGACAGAAGGCCAAGT |
| TCRaV9-2 | SEQ ID NO: 47 | AATTCAGTGACCCAGATGGAAGGGCC |
| TCRb V Inner Pool | | |
| TCRb_JM_V2 | SEQ ID NO: 48 | GAACCTGAAGTCACCCAGACTCCCAGC |
| TCRb_JM_V3-1 | SEQ ID NO: 49 | GCTGTTTCCCAGACTCCAAAATACCTGGTC |
| TCRb_JM_V4-1 | SEQ ID NO: 50 | GAAGTTACCCAGACACCAAAACACCTGGTC |
| TCRb_JM_V5-1 | SEQ ID NO: 51 | GGAGTCACTCAAACTCCAAGATATCTGATCAAAAC |
| TCRb_JM_V6-1 | SEQ ID NO: 52 | GGTGTCACTCAGACCCCAAAATTCCAG |
| TCRb_JM_V7-1 | SEQ ID NO: 53 | GGAGTCTCCCAGTCCCTGAGACAAGG |
| TCRb_JM_V4-2 | SEQ ID NO: 54 | GGAGTTACGCAGACACCAAGACACCTGG |
| TCRb_JM_V6-2 | SEQ ID NO: 55 | GGTGTCACTCAGACCCCAAAATTCCG |
| TCRb_JM_V7-2 | SEQ ID NO: 56 | GGAGTCTCCCAGTCCCCCAGTAACAAG |
| TCRb_JM_V6-4 | SEQ ID NO: 57 | GGGATCACCCAGGCACCAACATCTC |
| TCRb_JM_V7-3 | SEQ ID NO: 58 | GGAGTCTCCCAGACCCCCAGTAACAAG |

TABLE 3-continued

| Variable Region Primer | Sequence |
| --- | --- |
| TCRb_JM_V5-3 | SEQ ID NO: 59 GGAGTCACCCAAAGTCCCACACACCT |
| TCRb_JM_V9 | SEQ ID NO: 60 GGAGTCACACAAACCCCAAAGCACCT |
| TCRb_JM_V10-1 | SEQ ID NO: 61 GAAATCACCCAGAGCCCAAGACACAAGA |
| TCRb_JM_V11-1 | SEQ ID NO: 62 GAAGTTGCCCAGTCCCCCAGATATAAGATTA |
| TCRb_JM_V10-2 | SEQ ID NO: 63 GGAATCACCCAGAGCCCAAGATACAAGAT |
| TCRb_JM_V11-2 | SEQ ID NO: 64 GGAGTTGCCCAGTCTCCCAGATATAAGATTATAGAG |
| TCRb_JM_V7-4 | SEQ ID NO: 65 GGAGTCTCCCAGTCCCCAAGGTACAAAG |
| TCRb_JM_V7-5 | SEQ ID NO: 66 GGAGTCTCCCAGTCCCCAAGGTACGA |
| TCRb_JM_V6-7 | SEQ ID NO: 67 GGTGTCACTCAGACCCCAAAATTCCAC |
| TCRb_JM_V7-6 | SEQ ID NO: 68 GGAGTCTCCCAGTCTCCCAGGTACAAAGTC |
| TCRb_JM_V6-8 | SEQ ID NO: 69 GGTGTCACTCAGACCCCAAAATTCCACAT |
| TCRb_JM_V7-8 | SEQ ID NO: 70 GGAGTCTCCCAGTCCCCTAGGTACAAAGTC |
| TCRb_JM_V5-8 | SEQ ID NO: 71 GGAGTCACACAAAGTCCCACACACCTGA |
| TCRb_JM_V7-9 | SEQ ID NO: 72 GGAGTCTCCCAGAACCCCAGACACAAG |
| TCRb_JM_V13 | SEQ ID NO: 73 GGAGTCATCCAGTCCCCAAGACATCTGAT |
| TCRb_JM_V12-3 | SEQ ID NO: 74 GGAGTTATCCAGTCACCCCGCCATG |
| TCRb_JM_V12-4 | SEQ ID NO: 75 GGAGTTATCCAGTCACCCCGGCAC |
| TCRb_JM_V12-5 | SEQ ID NO: 76 AGAGTCACCCAGACACCAAGGCACAAG |
| TCRb_JM_V14 | SEQ ID NO: 77 GGAGTTACTCAGTTCCCCAGCCACAGC |
| TCRb_JM_V15 | SEQ ID NO: 78 ATGGTCATCCAGAACCCAAGATACCAGGTT |
| TCRb_JM_V17 | SEQ ID NO: 79 GAGCCTGGAGTCAGCCAGACCCC |
| TCRb_JM_V18 | SEQ ID NO: 80 GGCGTCATGCAGAACCCAAGACAC |
| TCRb_JM_V19 | SEQ ID NO: 81 GGAATCACTCAGTCCCCAAAGTACCTGTTCA |
| TCRb_JM_V20-1 | SEQ ID NO: 82 GCTGTCGTCTCTCAACATCCGAGCTG |
| TCRb_JM_V22 | SEQ ID NO: 83 ATTCCAGCTCACTGGGGCTGGATG |
| TCRb_JM_V23-1 | SEQ ID NO: 84 AAAGTCACACAGACTCCAGGACATTTGGTCA |
| TCRb_JM_V24-1 | SEQ ID NO: 85 GATGTTACCCAGACCCCAAGGAATAGGATC |
| TCRb_JM_V25-1 | SEQ ID NO: 86 GACATCTACCAGACCCCAAGATACCTTGTTATAGG |
| TCRb_JM_V26 | SEQ ID NO: 87 GTAGTTACACAATTCCCAAGACACAGAATCATTGG |
| TCRb_JM_V27 | SEQ ID NO: 88 CAAGTGACCCAGAACCCAAGATACCTCATC |
| IGH V pool | |
| IGH_MTPX_1 | SEQ ID NO: 89 GGTGGCAGCAGTCACAGATGCCTACTC |
| IGH_MTPX_2 | SEQ ID NO: 90 GGTGGCAGCAGCCACAGGTGCCCACTC |
| IGH_MTPX_3 | SEQ ID NO: 91 GGTGGCAGCAGCTACAGGTGTCCAGTC |
| IGH_MTPX_4 | SEQ ID NO: 92 GGTGGSAGCAGCAACARGWGCCCACTC |
| IGH_MTPX_5 | SEQ ID NO: 93 GCTGGCTGTAGCTCCAGGTGCTCACTC |
| IGH_MTPX_6 | SEQ ID NO: 94 CCTGCTGCTGACCAYCCCTTCMTGGGTCTTGTC |
| IGH_MTPX_7 | SEQ ID NO: 95 CCTGCTACTGACTGTCCCGTCCTGGGTCTTATC |
| IGH_MTPX_8 | SEQ ID NO: 96 GGGTTTTCCTCGTTGCTCTTTTAAGAGGTGTCCAGTG |
| IGH_MTPX_9 | SEQ ID NO: 97 GGGTTTTCCTTGTTGCTATTTTAAAAGGTGTCCARTG |
| IGH_MTPX_10 | SEQ ID NO: 98 GGATTTTCCTTGCTGCTATTTTAAAAGGTGTCCAGTG |
| IGH_MTPX_11 | SEQ ID NO: 99 GGGTTTTCCTTKTKGCTATWTTAGAAGGTGTCCAGTG |
| IGH_MTPX_12 | SEQ ID NO: 100 GGTGGCRGCTCCCAGATGGGTCCTGTC |
| IGH_MTPX_13 | SEQ ID NO: 101 CTGGCTGTTCTCCAAGGAGTCTGTG |
| IGH_MTPX_14 | SEQ ID NO: 102 GGCCTCCCATGGGGTGTCCTGTC |
| IGH_MTPX_15 | SEQ ID NO: 103 GGTGGCAGCAGCAACAGGTGCCCACT |
| IGH_MTPX_16 | SEQ ID NO: 104 ATGGAACTGGGGCTCCGCTGGGTTTTCC |
| IGH_MTPX_17 | SEQ ID NO: 105 ATGGACTGCACCTGGAGGATCCTCCTC |
| IGH_MTPX_18 | SEQ ID NO: 106 TGGCTGAGCTGGGTTTYCCTTGTTGC |
| IGH_MTPX_19 | SEQ ID NO: 107 GGAGTTKGGGCTGMGCTGGGTTTTCC |
| IGH_MTPX_20 | SEQ ID NO: 108 GCACCTGTGGTTTTTCCTCCTGCTGGTG |
| IGH_MTPX_21 | SEQ ID NO: 109 CACCTGTGGTTCTTCCTCCTSCTGG |
| IGH_MTPX_22 | SEQ ID NO: 110 CCAGGATGGGTCAACCGCCATCCTC |
| IGH_MTPX_23 | SEQ ID NO: 111 CAGAGGACTCACCATGGAGTTTGGGCTGAG |
| IGH_MTPX_24 | SEQ ID NO: 112 GGACTCACCATGGAGTTGGGACTGAGC |
| IGH_MTPX_25 | SEQ ID NO: 113 GGGCTGAGCTGGCTTTTTCTTGTGGC |
| TSO Sequence | SEQ ID NO: 114 AAGCAGTGGTATCAACGCAGAGTACATGGG |
| TSO Sequence Portion | SEQ ID NO: 115 TCTGCGTTGATACCACT |
| CDR3 | |
| TRAV1-2 | SEQ ID NO: 116 gaaggagctccagatgaaagactctgcctc |
| TRAV2 | SEQ ID NO: 117 gttctcttcatcgctgctcatcctccaggt |
| TRAV3 | SEQ ID NO: 118 cttgtgagcgactccgctttgtacttctgt |
| TRAV4 | SEQ ID NO: 119 ttatccctgccgacagaaagtccagcactc |
| TRAV5 | SEQ ID NO: 120 aaggataaacatctgtctctgcgcattgcag |
| TRAV6 | SEQ ID NO: 121 ttgtttcatatcacagcctcccagcctgca |
| TRAV7 | SEQ ID NO: 122 tacattacagccgtgcagcctgaagattcag |
| TRAV8-1 | SEQ ID NO: 123 aatctgcaggaaaacccctctgtgcagttggagt |
| TRAV8-2 | SEQ ID NO: 124 gaaacctcctccacctgacgaaaccctca |
| TRAV8-3 | SEQ ID NO: 125 caatctgaggaaaacccctctgtgcattggag |
| TRAV8-4 | SEQ ID NO: 126 cacctgacgaaaccctcagcccatatgagc |
| TRAV8-6 | SEQ ID NO: 127 ggaaaccctcagtccatataagcgacacgg |
| TRAV8-7 | SEQ ID NO: 128 gaggaaaccatcaacccatgtgagtgatgc |

TABLE 3-continued

| Variable Region Primer | Sequence |
|---|---|
| TRAV9-1 | SEQ ID NO: 129 ggaaggaacaaaggttttgaagccatgtaccg |
| TRAV9-2 | SEQ ID NO: 130 tccacttggagaaaggctcagttcaagtgt |
| TRAV10 | SEQ ID NO: 131 gcagacacaaagcaaagctctctgcacatc |
| TRAV12-1 | SEQ ID NO: 132 gccagccagtatatttccctgctcatcaga |
| TRAV12-2 | SEQ ID NO: 133 gccagccagtatgtttctctgctcatcaga |
| TRAV12-3 | SEQ ID NO: 134 ggtttacagcacaggtcgataaatccagca |
| TRAV13-1 | SEQ ID NO: 135 gccaaacatttctccctgcacatcacagag |
| TRAV13-2 | SEQ ID NO: 136 tctgcaaattgcagctactcaacctggaga |
| TRAV14D4 | SEQ ID NO: 137 gccaaccttgtcatctccgcttcacaactg |
| TRAV16 | SEQ ID NO: 138 gaccttaacaaaggcgagacatcttccacc |
| TRAV17 | SEQ ID NO: 139 gtcacgcttgacacttccaagaaaagcagt |
| TRAV18 | SEQ ID NO: 140 cctatcaagagtgacagttccttccacctg |
| TRAV19 | SEQ ID NO: 141 ggaacttccagaaatccaccagttccttca |
| TRAV20 | SEQ ID NO: 142 agaaggaaagcttttctgcacatcacagcc |
| TRAV21 | SEQ ID NO: 143 caagtggaagacttaatgcctcgctggata |
| TRAV22 | SEQ ID NO: 144 gactgtcgctacggaacgctacagcttatt |
| TRAV23DV6 | SEQ ID NO: 145 tgccaagcagttctcatcgcatatcatgga |
| TRAV24 | SEQ ID NO: 146 gccactcttaataccaaggaggggttacagc |
| TRAV25 | SEQ ID NO: 147 cacatcacagccacccagactacagatgta |
| TRAV26-1 | SEQ ID NO: 148 tcatcacagaagacagaaagtccagcacct |
| TRAV26-2 | SEQ ID NO: 149 agaaagtccagtaccttgatcctgcaccgt |
| TRAV27 | SEQ ID NO: 150 gttctctccacatcactgcagcccagactg |
| TRAV29DV5 | SEQ ID NO: 151 aaagtgccaagcacctctctctgcacattg |
| TRAV30 | SEQ ID NO: 152 ctgtacccttacggcctcccagctcagttac |
| TRAV34 | SEQ ID NO: 153 gccaagttggatgagaaaaagcagcaaagt |
| TRAV35 | SEQ ID NO: 154 gacctcaaatggaagactgactgctcagtt |
| TRAV36DV7 | SEQ ID NO: 155 tttcagcatcctgaacatcacagccaccca |
| TRAV38-2DV8 | SEQ ID NO: 156 cctttcagtctcaagatctcagactcacagc |
| TRAV39 | SEQ ID NO: 157 aatggcctcacttgataccaaagcccgtc |
| TRAV40 | SEQ ID NO: 158 ctcccccattgtgaaatattcagtccaggt |
| TRAV41 | SEQ ID NO: 159 catacaggaaaagcacagctccctgcacat |
| TRAV11 | SEQ ID NO: 160 atatcgcagcctctcatctgggagattcagc |
| TRAV1-1 | SEQ ID NO: 161 caggagctccagatgaaagactctgcctctt |
| TRAV8-5 | SEQ ID NO: 162 acttccttccacttgaggaaaccctcagtcca |
| Inner TRAV Primers | |
| TRAV-Handle 1 | SEQ ID NO: 163 gtgactggagttcagacgtgtgctcttccgatctgaaggagctccagatgaaagactctgcctc |
| TRAV-Handle 2 | SEQ ID NO: 164 gtgactggagttcagacgtgtgctcttccgatctgttctcttcatcgctgctcatcctccaggt |
| TRAV-Handle 3 | SEQ ID NO: 165 gtgactggagttcagacgtgtgctcttccgatctcttgtgagcgactccgctttgtacttctgt |
| TRAV-Handle 4 | SEQ ID NO: 166 gtgactggagttcagacgtgtgctcttccgatctttatccctgccgacagaaagtccagcactc |
| TRAV-Handle 5 | SEQ ID NO: 167 gtgactggagttcagacgtgtgctcttccgatctaaggataaacatctgtctctgcgcattgcag |
| TRAV-Handle 6 | SEQ ID NO: 168 gtgactggagttcagacgtgtgctcttccgatctttgtttcatatcacagcctcccagcctgca |
| TRAV-Handle 7 | SEQ ID NO: 169 gtgactggagttcagacgtgtgctcttccgatcttacattacagccgtgcagcctgaagattcag |
| TRAV-Handle 8 | SEQ ID NO: 170 gtgactggagttcagacgtgtgctcttccgatctaatctgaggaaaccctctgtgcagtggagt |
| TRAV-Handle 9 | SEQ ID NO: 171 gtgactggagttcagacgtgtgctcttccgatctgaaacctccttccacctgacgaaaccctca |
| TRAV-Handle 10 | SEQ ID NO: 172 gtgactggagttcagacgtgtgctcttccgatctcaatctgaggaaaccctctgtgcattggag |
| TRAV-Handle 11 | SEQ ID NO: 173 gtgactggagttcagacgtgtgctcttccgatctcacctgacgaaaccctcagcccatatgagc |
| TRAV-Handle 12 | SEQ ID NO: 174 gtgactggagttcagacgtgtgctcttccgatctggaaaccctcagtccatataagcgacacgg |
| TRAV-Handle 13 | SEQ ID NO: 175 gtgactggagttcagacgtgtgctcttccgatctgaggaaaccatccaacccatgtgagtgatgc |
| TRAV-Handle 14 | SEQ ID NO: 176 gtgactggagttcagacgtgtgctcttccgatctggaaggaacaaaggttttgaagccatgtaccg |
| TRAV-Handle 15 | SEQ ID NO: 177 gtgactggagttcagacgtgtgctcttccgatcttccacttggagaaaggctcagttcaagtgt |
| TRAV-Handle 16 | SEQ ID NO: 178 gtgactggagttcagacgtgtgctcttccgatctgcagacacaaagcaaagctctctgcacatc |
| TRAV-Handle 17 | SEQ ID NO: 179 gtgactggagttcagacgtgtgctcttccgatctgccagccagtatatttccctgctcatcaga |
| TRAV-Handle 18 | SEQ ID NO: 180 gtgactggagttcagacgtgtgctcttccgatctgccagccagtatgtttctctgctcatcaga |
| TRAV-Handle 19 | SEQ ID NO: 181 gtgactggagttcagacgtgtgctcttccgatctggtttacagcacaggtcgataaatccagca |
| TRAV-Handle 20 | SEQ ID NO: 182 gtgactggagttcagacgtgtgctcttccgatctgccaaacatttctccctgcacatcacagag |
| TRAV-Handle 21 | SEQ ID NO: 183 gtgactggagttcagacgtgtgctcttccgatctctgcaaattgcagctactcaacctggaga |
| TRAV-Handle 22 | SEQ ID NO: 184 gtgactggagttcagacgtgtgctcttccgatctgccaaccttgtcatctccgcttcacaactg |
| TRAV-Handle 23 | SEQ ID NO: 185 gtgactggagttcagacgtgtgctcttccgatctgaccttaacaaaggcgagacatcttccacc |
| TRAV-Handle 24 | SEQ ID NO: 186 gtgactggagttcagacgtgtgctcttccgatctgtcacgcttgacacttccaagaaaagcagt |
| TRAV-Handle 25 | SEQ ID NO: 187 gtgactggagttcagacgtgtgctcttccgatctcctatcaagagtgacagttccttccacctg |
| TRAV-Handle 26 | SEQ ID NO: 188 gtgactggagttcagacgtgtgctcttccgatctggaacttccagaaatccaccagttccttca |
| TRAV-Handle 27 | SEQ ID NO: 189 gtgactggagttcagacgtgtgctcttccgatctagaaggaaagcttttctgcacatcacagcc |
| TRAV-Handle 28 | SEQ ID NO: 190 gtgactggagttcagacgtgtgctcttccgatctcaagtggaagacttaatgcctcgctggata |
| TRAV-Handle 29 | SEQ ID NO: 191 gtgactggagttcagacgtgtgctcttccgatctgactgtcgctacggaacgctacagcttatt |
| TRAV-Handle 30 | SEQ ID NO: 192 gtgactggagttcagacgtgtgctcttccgatctgccaagcagttctcatcgcatatcatgga |
| TRAV-Handle 31 | SEQ ID NO: 193 gtgactggagttcagacgtgtgctcttccgatctgccactcttaataccaaggaggggttacagc |
| TRAV-Handle 32 | SEQ ID NO: 194 gtgactggagttcagacgtgtgctcttccgatctcacatcacagccacccagactacagatgta |
| TRAV-Handle 33 | SEQ ID NO: 195 gtgactggagttcagacgtgtgctcttccgatcttcatcacagaagacagaaagtccagcacct |
| TRAV-Handle 34 | SEQ ID NO: 196 gtgactggagttcagacgtgtgctcttccgatctagaaagtccagtaccttgatcctgcaccgt |
| TRAV-Handle 35 | SEQ ID NO: 197 gtgactggagttcagacgtgtgctcttccgatctgttctctccacatcactgcagcccagactg |
| TRAV-Handle 36 | SEQ ID NO: 198 gtgactggagttcagacgtgtgctcttccgatctaaagtgccaagcacctctctctgcacattg |
| TRAV-Handle 37 | SEQ ID NO: 199 gtgactggagttcagacgtgtgctcttccgatctctgtacccttacggcctcccagctcagttac |
| TRAV-Handle 38 | SEQ ID NO: 200 gtgactggagttcagacgtgtgctcttccgatctgccaagttggatgagaaaaagcagcaaagt |
| TRAV-Handle 39 | SEQ ID NO: 201 gtgactggagttcagacgtgtgctcttccgatctgacctcaaatggaagactgactgctcagtt |
| TRAV-Handle 40 | SEQ ID NO: 202 gtgactggagttcagacgtgtgctcttccgatcttttcagcatcctgaacatcacagccaccca |

TABLE 3-continued

| Variable Region Primer | Sequence |
|---|---|
| TRAV-Handle 41 | SEQ ID NO: 203 gtgactggagttcagacgtgtgctcttccgatctccttcagtctcaagatctcagactcacagc |
| TRAV-Handle 42 | SEQ ID NO: 204 gtgactggagttcagacgtgtgctcttccgatctaatggcctcacttgataccaaagcccgtc |
| TRAV-Handle 43 | SEQ ID NO: 205 gtgactggagttcagacgtgtgctcttccgatctctcccccattgtgaaatattcagtccaggt |
| TRAV-Handle 44 | SEQ ID NO: 206 gtgactggagttcagacgtgtgctcttccgatctcatacaggaaaagcacagctccctgcacat |
| TRAV-Handle 45 | SEQ ID NO: 207 gtgactggagttcagacgtgtgctcttccgatctatatcgcagcctctcatctgggagattcagc |
| TRAV-Handle 46 | SEQ ID NO: 208 gtgactggagttcagacgtgtgctcttccgatctcaggagctccagatgaaagactctgcctctt |
| TRAV-Handle 47 | SEQ ID NO: 209 gtgactggagttcagacgtgtgctcttccgatctacttccttccacttgaggaaaccctcagtcca |
| 5' Sequence Handle LN2 | SEQ ID NO: 210 gtgactggagttcagacgtgtgctcttccgatct |

Outer TRAV Primers

| | |
|---|---|
| TRAV10*01_outer | SEQ ID NO: 211 aaaaaccaagtggagcagagtcctcagtccctg |
| TRAV21*01_outer | SEQ ID NO: 212 aaacaggaggtgacgcagattcctgcagctc |
| TRAV2*01_outer | SEQ ID NO: 213 aaggaccaagtgtttcagccttccacagtggc |
| TRAV8-6*02_outer | SEQ ID NO: 214 acccagcttgacagccaagtccctgtct |
| TRAV8-7*02_outer | SEQ ID NO: 215 acccagcttgatggccacatcactgtctct |
| TRAV8-4*01_outer | SEQ ID NO: 216 acccagcttggcagccacgtctctg |
| TRAV19*01_outer | SEQ ID NO: 217 actcaagcgcagactgaaatttctgtggtgg |
| TRAV12-3*01_outer | SEQ ID NO: 218 agaaggaggtggagcaggatcctggacca |
| TRAV6*01_outer | SEQ ID NO: 219 agaattccgaggctctgaacattcaggagggtaa |
| TRAV16*01_outer | SEQ ID NO: 220 agagagtgactcagcccgagaagctcctct |
| TRAV8-3*01_outer | SEQ ID NO: 221 agagcccagtcagtgacccagcctgac |
| TRAV8-5*01_outer | SEQ ID NO: 222 agagcccagtcagtgacccagcctgac |
| TRAV27*01_outer | SEQ ID NO: 223 agctgctggagcagagccctcagtttc |
| TRAV17*01_outer | SEQ ID NO: 224 agtcaacagggagaagaggatcctcaggccttg |
| TRAV18*01_outer | SEQ ID NO: 225 agtggagactcggttacccagacagaaggcc |
| TRAV22*01_outer | SEQ ID NO: 226 agtggagcagagtcctccagacctgattctc |
| TRAV13-2*01_outer | SEQ ID NO: 227 agtgtggggctgcatcttcctaccctga |
| TRAV24*01_outer | SEQ ID NO: 228 atactgaacgtggaacaaagtcctcagtcactgcatg |
| TRAV9-2*01_outer | SEQ ID NO: 229 attcagtgacccagatggaagggccagtga |
| TRAV26-1*01_outer | SEQ ID NO: 230 attgatgctaagaccacccagcccacctc |
| TRAV12-2*01_outer | SEQ ID NO: 231 cagaaggaggtggagcagaattctggaccccc |
| TRAV40*01_outer | SEQ ID NO: 232 cagcaattcagtcaagcagacgggccaa |
| TRAV30*01_outer | SEQ ID NO: 233 ccaacaaccagtgcagagtcctcaagccg |
| TRAV12-1*01_outer | SEQ ID NO: 234 cggaaggaggtggagcaggatcctgga |
| TRAV11-1*01_outer | SEQ ID NO: 235 ctacatacgccggagcagagtccttcattcctgag |
| TRAV14/DV4*02_outer | SEQ ID NO: 236 ctcaaacccaaccaggaatgttcgtgcagga |
| TRAV4*01_outer | SEQ ID NO: 237 cttgctaagaccacccagcccatctccatggactc |
| TRAV7*01_outer | SEQ ID NO: 238 gaaaaccaggtggagcacagcccccattttctg |
| TRAV36/DV7*01_outer | SEQ ID NO: 239 gaagacaaggtggtacaaaagccctctatctctggt |
| TRAV20*01_outer | SEQ ID NO: 240 gaagaccaggtgacgcagagtcccgag |
| TRAV23/DV6*01_outer | SEQ ID NO: 241 gaccagcacaggtgaaacaaagtcctcaat |
| TRAV41*01_outer | SEQ ID NO: 242 gagcagagtcctcagaacctgactgccc |
| TRAV29/DV5*01_outer | SEQ ID NO: 243 gatgaccagcaagttaagcaaaattcaccatccct |
| TRAV34*01_outer | SEQ ID NO: 244 gccaagaactggagcagagtcctcagtcc |
| TRAV8-2*01_outer | SEQ ID NO: 245 gcccagtcggtgacccagcttgacag |
| TRAV8-1*01_outer | SEQ ID NO: 246 gcccagtctgtgagccagcataaccaccac |
| TRAV26-2*01_outer | SEQ ID NO: 247 gcctgttcacttgccttgtaaccactccac |
| TRAV3*01_outer | SEQ ID NO: 248 gctcagtcagtggctcagccggaagatcagg |
| TRAV1-2*01_outer | SEQ ID NO: 249 ggacaaaacattgaccagcccactgagatgacagc |
| TRAV1-1*01_outer | SEQ ID NO: 250 ggacaaagccttgagcagccctctgaagtgac |
| TRAV25*01_outer | SEQ ID NO: 251 ggacaacaggtaatgcaaattcctcagtaccagcatg |
| TRAV13-1*01_outer | SEQ ID NO: 252 ggagagaatgtggagcagcatccttcaaccctg |
| TRAV5*01_outer | SEQ ID NO: 253 ggagaggatgtggagcagagtcttttcctgagtgtc |
| TRAV9-1*01_outer | SEQ ID NO: 254 ggagattcagtggtccagacagaaggccaagtg |
| TRAV38-2/DV8*01_outer | SEQ ID NO: 255 gtctcaaccagagatgtctgtgcaggagg |
| TRAV39*01_outer | SEQ ID NO: 256 gtggaacaaaaccctctgttcctgagcatgc |
| TRAV35*01_outer | SEQ ID NO: 257 gtggtcaacagctgaatcagagtcctcaatcta |
| TRAV11*01_outer | SEQ ID NO: 258 gttccggcaggatccggggagaagact |

CDR3

| | |
|---|---|
| TRBV10-1 | SEQ ID NO: 259 gcctcctcccagacatctgtatatttctgcg |
| TRBV10-2 | SEQ ID NO: 260 aatttcccccctcactctggagtcagctacc |
| TRBV10-3 | SEQ ID NO: 261 gatttcctcctcactctggagtccgctacc |
| TRBV11-1 | SEQ ID NO: 262 aggctcaaaggagtagactccactctcaaga |
| TRBV11-2 | SEQ ID NO: 263 caagatcagcctgcaaagcttgaggact |
| TRBV11-3 | SEQ ID NO: 264 tagactccactctcaagatccagcctgcag |
| TRBV12-1 | SEQ ID NO: 265 tggaacccagggacttgggcctatatttct |
| TRBV12-2 | SEQ ID NO: 266 tcattctctactctgaagatccagcctgca |
| TRBV12-3 | SEQ ID NO: 267 cattctctactctgaagatccagccctcag |
| TRBV12-4 | SEQ ID NO: 268 catcattctccactctgaagatccagccctc |
| TRBV12-5 | SEQ ID NO: 269 cagcagagatgcctgatgcaactttagcca |
| TRBV13 | SEQ ID NO: 270 gaactgaacatgagctccttggagctggg |
| TRBV14 | SEQ ID NO: 271 ggaggattctggagtttatttctgtgccagc |
| TRBV15 | SEQ ID NO: 272 ttctgctttcttgacatccgctcaccaggc |

TABLE 3-continued

| Variable Region Primer | Sequence |
|---|---|
| TRBV16 | SEQ ID NO: 273 gagatccaggctacgaagcttgaggattcag |
| TRBV17 | SEQ ID NO: 274 aacgtcttccacgctgaagatccatccc |
| TRBV18 | SEQ ID NO: 275 aggatccagcaggtagtgcgaggagattcg |
| TRBV19 | SEQ ID NO: 276 acccgacagctttctatctctgtgccagta |
| TRBV20-1 | SEQ ID NO: 277 gtgcccatcctgaagacagcagcttctaca |
| TRBV2 | SEQ ID NO: 278 cacaaagctggaggactcagccatgtac |
| TRBV21-1 | SEQ ID NO: 279 tcaggggacacagcactgtatttctgtgcc |
| TRBV22-1 | SEQ ID NO: 280 cacaccagccaaacagctttgtacttctgt |
| TRBV23-1 | SEQ ID NO: 281 aatcctgtcctcagaaccgggagacacg |
| TRBV24-1 | SEQ ID NO: 282 ccaaccagacagctctttacttctgtgccac |
| TRBV25-1 | SEQ ID NO: 283 cacatacctctcagtacctctgtgccagca |
| TRBV26 | SEQ ID NO: 284 ccaaccagacatctgtgtatctctatgccagc |
| TRBV27 | SEQ ID NO: 285 accagacctctctgtacttctgtgccagca |
| TRBV28 | SEQ ID NO: 286 aaccagacatctatgtacctctgtgccagc |
| TRBV29-1 | SEQ ID NO: 287 acatgagccctgaagacagcagcatatatctc |
| TRBV3-1 | SEQ ID NO: 288 agcttggtgactctgctgtgtatttctgtg |
| TRBV3-2 | SEQ ID NO: 289 cttggtgactctgctgtgtatttctgtgcc |
| TRBV4-1 | SEQ ID NO: 290 cagccagaagactcagccctgtatctctg |
| TRBV4-2 | SEQ ID NO: 291 gccagaagactcggccctgtatctctgt |
| TRBV4-3 | SEQ ID NO: 292 tattccttcacctacacaccctgcagccag |
| TRBV5-1 | SEQ ID NO: 293 agatgaatgtgagcaccttggagctgg |
| TRBV5-2 | SEQ ID NO: 294 tactgagtcaaacacggagctagggact |
| TRBV5-3 | SEQ ID NO: 295 gttgctctgagatgaatgtgagtgccttgg |
| TRBV5-4 | SEQ ID NO: 296 atagctctgagctgaatgtgaacgccttgg |
| TRBV5-5 | SEQ ID NO: 297 gagctgaatgtgaacgccttgttgctgg |
| TRBV5-6 | SEQ ID NO: 298 aactatagctctgagctgaatgtgaacgcct |
| TRBV5-7 | SEQ ID NO: 299 agctgaatgtgaacgccttgttgctaggg |
| TRBV5-8 | SEQ ID NO: 300 ctgaatgtgaacgccttggagctggagga |
| TRBV6-1 | SEQ ID NO: 301 gctccctcccagacatctgtgtacttct |
| TRBV6-2 | SEQ ID NO: 302 gctgctccctcccaaacatctgtgtact |
| TRBV6-3 | SEQ ID NO: 303 gctccctcccaaacatctgtgtactctgt |
| TRBV6-4 | SEQ ID NO: 304 aacacagatgatttcccccctcacgttggc |
| TRBV6-5 | SEQ ID NO: 305 gctgctccctcccagacatctgtgtactt |
| TRBV6-6 | SEQ ID NO: 306 agttggctgctccctcccagacatctg |
| TRBV6-7 | SEQ ID NO: 307 tcagctgtccctctcagacttctgtttac |
| TRBV6-8 | SEQ ID NO: 308 taaacacagaggatttcccactcaggctggt |
| TRBV6-9 | SEQ ID NO: 309 agtcagctgctccctcccagacatctgtata |
| TRBV7-1 | SEQ ID NO: 310 cagcagggggacttggctgtgtatctc |
| TRBV7-2 | SEQ ID NO: 311 gcaggaggactcggccgtgtatctc |
| TRBV7-3 | SEQ ID NO: 312 tctactctgaagatccagcgcacagagcg |
| TRBV7-4 | SEQ ID NO: 313 cacagagcaggggggactcagctgtgtat |
| TRBV7-5 | SEQ ID NO: 314 atctttctccacctgaagatccagcgcaca |
| TRBV7-6 | SEQ ID NO: 315 ttctctcagagaggcctgagggatccat |
| TRBV7-7 | SEQ ID NO: 316 ctgagggatccgtctccactctgaagatcc |
| TRBV7-8 | SEQ ID NO: 317 ggcctaagggatctttctccaccttggaga |
| TRBV8-1 | SEQ ID NO: 318 ttccctcaaccaggagtctactagcacca |
| TRBV8-2 | SEQ ID NO: 319 ttgagcatttcccaatcctggcatccac |
| TRBV9 | SEQ ID NO: 320 gggactcagctttgtatttctgtgccagca |

Inner TRBV Primers

| | |
|---|---|
| TRBV-Handle 1 | SEQ ID NO: 321 gtgactggagttcagacgtgtgctcttccgatctgcctcctcccagacatctgtatatttctgcg |
| TRBV-Handle 2 | SEQ ID NO: 322 gtgactggagttcagacgtgtgctcttccgatctaatttcccccctcactctggagtcagctacc |
| TRBV-Handle 3 | SEQ ID NO: 323 gtgactggagttcagacgtgtgctcttccgatctgatttcctcctcactctggagtccgctacc |
| TRBV-Handle 4 | SEQ ID NO: 324 gtgactggagttcagacgtgtgctcttccgatctaggctcaaaggagtagactccactctcaaga |
| TRBV-Handle 5 | SEQ ID NO: 325 gtgactggagttcagacgtgtgctcttccgatctcaagatccagcctgcaaagcttgaggact |
| TRBV-Handle 6 | SEQ ID NO: 326 gtgactggagttcagacgtgtgctcttccgatcttagactccactctcaagatccagcctgcag |
| TRBV-Handle 7 | SEQ ID NO: 327 gtgactggagttcagacgtgtgctcttccgatcttggaaccagggacttgggcctatatttct |
| TRBV-Handle 8 | SEQ ID NO: 328 gtgactggagttcagacgtgtgctcttccgatcttcattctctactctgaagatccagcctgcag |
| TRBV-Handle 9 | SEQ ID NO: 329 gtgactggagttcagacgtgtgctcttccgatctcattctccactctgaagatccagcctcag |
| TRBV-Handle 10 | SEQ ID NO: 330 gtgactggagttcagacgtgtgctcttccgatctcatcattctccactctgaagatccagccctc |
| TRBV-Handle 11 | SEQ ID NO: 331 gtgactggagttcagacgtgtgctcttccgatctcagcagagatgcctgatgcaactttagcca |
| TRBV-Handle 12 | SEQ ID NO: 332 gtgactggagttcagacgtgtgctcttccgatctgaactgaacatgagctccttggagctggg |
| TRBV-Handle 13 | SEQ ID NO: 333 gtgactggagttcagacgtgtgctcttccgatctggagattctggagtttatttctgtgccagc |
| TRBV-Handle 14 | SEQ ID NO: 334 gtgactggagttcagacgtgtgctcttccgatctttctgctttcttgacatccgctcaccaggc |
| TRBV-Handle 15 | SEQ ID NO: 335 gtgactggagttcagacgtgtgctcttccgatctgagatccaggctacgaagcttgaggattcag |
| TRBV-Handle 16 | SEQ ID NO: 336 gtgactggagttcagacgtgtgctcttccgatctaacgtcttccacgctgaagatccatccc |
| TRBV-Handle 17 | SEQ ID NO: 337 gtgactggagttcagacgtgtgctcttccgatctaggatccagcaggtagtgcgaggagattcg |
| TRBV-Handle 18 | SEQ ID NO: 338 gtgactggagttcagacgtgtgctcttccgatctacccgacagctttctatctctgtgccagta |
| TRBV-Handle 19 | SEQ ID NO: 339 gtgactggagttcagacgtgtgctcttccgatctgtgcccatcctgaagacagcagcttctaca |
| TRBV-Handle 20 | SEQ ID NO: 340 gtgactggagttcagacgtgtgctcttccgatctcacaaagctggaggactcagccatgtac |
| TRBV-Handle 21 | SEQ ID NO: 341 gtgactggagttcagacgtgtgctcttccgatcttcaggggacacagcactgtatttctgtgcc |
| TRBV-Handle 22 | SEQ ID NO: 342 gtgactggagttcagacgtgtgctcttccgatctcacaccagccaaacagctttgtacttctgt |
| TRBV-Handle 23 | SEQ ID NO: 343 gtgactggagttcagacgtgtgctcttccgatctaatcctgtcctcagaaccgggagacacg |
| TRBV-Handle 24 | SEQ ID NO: 344 gtgactggagttcagacgtgtgctcttccgatctccaaccagacagctctttacttctgtgccac |
| TRBV-Handle 25 | SEQ ID NO: 345 gtgactggagttcagacgtgtgctcttccgatctcacatacctctcagtacctctgtgccagca |
| TRBV-Handle 26 | SEQ ID NO: 346 gtgactggagttcagacgtgtgctcttccgatctccaaccagacatctgtgtatctctatgccagc |

TABLE 3-continued

| Variable Region Primer | Sequence |
|---|---|
| TRBV-Handle 27 | SEQ ID NO: 347 gtgactggagttcagacgtgtgctcttccgatctaccagacctctctgtacttctgtgccagca |
| TRBV-Handle 28 | SEQ ID NO: 348 gtgactggagttcagacgtgtgctcttccgatctaaccagacatctatgtacctctgtgccagc |
| TRBV-Handle 29 | SEQ ID NO: 349 gtgactggagttcagacgtgtgctcttccgatctacatgagccctgaagacagcagcatatatctc |
| TRBV-Handle 30 | SEQ ID NO: 350 gtgactggagttcagacgtgtgctcttccgatctagcttggtgactctgctgtgtatttctgtg |
| TRBV-Handle 31 | SEQ ID NO: 351 gtgactggagttcagacgtgtgctcttccgatctcttggtgactctgctgtgtatttctgtgcc |
| TRBV-Handle 32 | SEQ ID NO: 352 gtgactggagttcagacgtgtgctcttccgatctcagccagaagactcagccctgtatctctg |
| TRBV-Handle 33 | SEQ ID NO: 353 gtgactggagttcagacgtgtgctcttccgatctgccagaagactcggccctgtatctctgt |
| TRBV-Handle 34 | SEQ ID NO: 354 gtgactggagttcagacgtgtgctcttccgatcttattccttcacctacacaccctgcagccag |
| TRBV-Handle 35 | SEQ ID NO: 355 gtgactggagttcagacgtgtgctcttccgatctagatgaatgtgagcaccttggagctgg |
| TRBV-Handle 36 | SEQ ID NO: 356 gtgactggagttcagacgtgtgctcttccgatcttactgagtcaaacacggagctaggggact |
| TRBV-Handle 37 | SEQ ID NO: 357 gtgactggagttcagacgtgtgctcttccgatctgttgctctgagatgaatgtgagtgccttgg |
| TRBV-Handle 38 | SEQ ID NO: 358 gtgactggagttcagacgtgtgctcttccgatctatagctctgagctgaatgtgaacgccttgg |
| TRBV-Handle 39 | SEQ ID NO: 359 gtgactggagttcagacgtgtgctcttccgatctgagctgaatgtgaacgccttgttgctgg |
| TRBV-Handle 40 | SEQ ID NO: 360 gtgactggagttcagacgtgtgctcttccgatctaactatagctctgagctgaatgtgaacgcct |
| TRBV-Handle 41 | SEQ ID NO: 361 gtgactggagttcagacgtgtgctcttccgatctagctgaatgtgaacgccttgttgctaggg |
| TRBV-Handle 42 | SEQ ID NO: 362 gtgactggagttcagacgtgtgctcttccgatctctgaatgtgaacgccttggagctggagga |
| TRBV-Handle 43 | SEQ ID NO: 363 gtgactggagttcagacgtgtgctcttccgatctgctccctcccagacatctgtgtacttct |
| TRBV-Handle 44 | SEQ ID NO: 364 gtgactggagttcagacgtgtgctcttccgatctgctgcctcccaaacatctgtgtact |
| TRBV-Handle 45 | SEQ ID NO: 365 gtgactggagttcagacgtgtgctcttccgatctgctccctcccaaacatctgtgtacttctgt |
| TRBV-Handle 46 | SEQ ID NO: 366 gtgactggagttcagacgtgtgctcttccgatctaacacagatgatttcccctcacgttggc |
| TRBV-Handle 47 | SEQ ID NO: 367 gtgactggagttcagacgtgtgctcttccgatctgctgctccctcccagacatctgtgtactt |
| TRBV-Handle 48 | SEQ ID NO: 368 gtgactggagttcagacgtgtgctcttccgatctagttggctgctccctcccagacatct |
| TRBV-Handle 49 | SEQ ID NO: 369 gtgactggagttcagacgtgtgctcttccgatcttcagctgctccctctcagacttctgtttac |
| TRBV-Handle 50 | SEQ ID NO: 370 gtgactggagttcagacgtgtgctcttccgatcttaaacacagaggatttcccactcaggctggt |
| TRBV-Handle 51 | SEQ ID NO: 371 gtgactggagttcagacgtgtgctcttccgatctagtcagctgctccctcccagacatctgtata |
| TRBV-Handle 52 | SEQ ID NO: 372 gtgactggagttcagacgtgtgctcttccgatctcagcaggggggacttggctgtgtatctc |
| TRBV-Handle 53 | SEQ ID NO: 373 gtgactggagttcagacgtgtgctcttccgatctgcaggaggactcggccgtgtatctc |
| TRBV-Handle 54 | SEQ ID NO: 374 gtgactggagttcagacgtgtgctcttccgatcttctactctgaagatccagcgcacagagcg |
| TRBV-Handle 55 | SEQ ID NO: 375 gtgactggagttcagacgtgtgctcttccgatctcacagagcaggggggactcagctgtgtat |
| TRBV-Handle 56 | SEQ ID NO: 376 gtgactggagttcagacgtgtgctcttccgatctatctttctccacctgaagatccagcgcaca |
| TRBV-Handle 57 | SEQ ID NO: 377 gtgactggagttcagacgtgtgctcttccgatctttctctgcagagaggcctgagggatccat |
| TRBV-Handle 58 | SEQ ID NO: 378 gtgactggagttcagacgtgtgctcttccgatctctgagggatccgtctccactctgaagatcc |
| TRBV-Handle 59 | SEQ ID NO: 379 gtgactggagttcagacgtgtgctcttccgatctggcctaagggatctttctccaccttggaga |
| TRBV-Handle 60 | SEQ ID NO: 380 gtgactggagttcagacgtgtgctcttccgatcttttccctcaacccgggagtctactagcacca |
| TRBV-Handle 61 | SEQ ID NO: 381 gtgactggagttcagacgtgtgctcttccgatctttgagcatttccccaatcctggcatccac |
| TRBV-Handle 62 | SEQ ID NO: 382 gtgactggagttcagacgtgtgctcttccgatctgggactcagctttgtatttctgtgccagca |
| Outer TRBV Primers | |
| TRBV10-1_outer | SEQ ID NO: 383 gctgaaatcacccagagcccaagacacaag |
| TRBV10-2_outer | SEQ ID NO: 384 cacagagacaggaaggcaggtgaccttga |
| TRBV10-3_outer | SEQ ID NO: 385 gatgctggaatcacccagagcccaagacac |
| TRBV11-1_outer | SEQ ID NO: 386 gccaggctgtggcttttttggtgtgatccta |
| TRBV11-2_outer | SEQ ID NO: 387 ggcagagtgtggcttttttggtgcaatcct |
| TRBV11-3_outer | SEQ ID NO: 388 ggcttttttggtgcaatcctatttctggccac |
| TRBV12-1_outer | SEQ ID NO: 389 gatgctggtgttatccagtcacccaggcac |
| TRBV12-2_outer | SEQ ID NO: 390 gtcacccaagcatgaggtgacagataggg |
| TRBV12-3_outer | SEQ ID NO: 391 atgctggagttatccagtcaccccgcc |
| TRBV12-4_outer | SEQ ID NO: 392 gagttatccagtcaccccggcacgaggt |
| TRBV12-5_outer | SEQ ID NO: 393 gctagagtcacccagacaccaaggcaca |
| TRBV13_outer | SEQ ID NO: 394 gctgctgtcatccagtccccaaga |
| TRBV14_outer | SEQ ID NO: 395 gttactcagttccccagccacagcgtaat |
| TRBV15_outer | SEQ ID NO: 396 gttacccagtttggaaagccagtgaccct |
| TRBV16_outer | SEQ ID NO: 397 gaagtcgcccagactccaaaacatcttgtc |
| TRBV17_outer | SEQ ID NO: 398 cagacacaaggtcaccaacatgggacagg |
| TRBV18_outer | SEQ ID NO: 399 gtcatgtttactggtatcggcagctccca |
| TRBV19_outer | SEQ ID NO: 400 atgccatgtactggtaccgacaggaccca |
| TRBV20-1_outer | SEQ ID NO: 401 gtcgtctctcaacatccgagctgggttat |
| TRBV2_outer | SEQ ID NO: 402 gaacctgaagtcacccagactcccagcca |
| TRBV21-1_outer | SEQ ID NO: 403 cacggacaccaaggtcacccagagacct |
| TRBV22-1_outer | SEQ ID NO: 404 agctcactggggctggatgggatgtgac |
| TRBV23-1_outer | SEQ ID NO: 405 gccaaagtcacacagactccaggacattt |
| TRBV24-1_outer | SEQ ID NO: 406 gtatcgacaagacccaggactgggcctac |
| TRBV25-1_outer | SEQ ID NO: 407 gctgacatctaccagaccccaagatacct |
| TRBV26_outer | SEQ ID NO: 408 gtatcgacaggacccaggacttggactga |
| TRBV27_outer | SEQ ID NO: 409 agcccaagtgacccagaacccaagatac |
| TRBV28_outer | SEQ ID NO: 410 ctcgtagatgtgaaagtaacccagagctcga |
| TRBV29-1_outer | SEQ ID NO: 411 gatatctgtcaacgtggaacctccctgacg |
| TRBV3-1_outer | SEQ ID NO: 412 ggtcacacagatgggaaacgacaagtcca |
| TRBV3-2_outer | SEQ ID NO: 413 ccgtttcccagactccaaaatacctggtc |
| TRBV4-1_outer | SEQ ID NO: 414 gaagttacccagacaccaaaaacctggtc |
| TRBV4-2_outer | SEQ ID NO: 415 gagttacgcagacaccaagacacctggtc |
| TRBV4-3_outer | SEQ ID NO: 416 ggagttacgcagacaccaagacacctgg |
| TRBV5-1_outer | SEQ ID NO: 417 gtgacactgagctgctccctatctctgg |
| TRBV5-2_outer | SEQ ID NO: 418 gaatcacccaagctccaagacacctgatc |
| TRBV5-3_outer | SEQ ID NO: 419 ctggagtcacccaaagtcccacacacc |
| TRBV5-4_outer | SEQ ID NO: 420 gactggagtcacccaaagtcccacacac |

TABLE 3-continued

| Variable Region Primer | Sequence |
|---|---|
| TRBV5-5_outer | SEQ ID NO: 421 gtcccacacacctgatcaaaacgagagga |
| TRBV5-6_outer | SEQ ID NO: 422 tagtggacgctggagtcacccaaagtcc |
| TRBV5-7_outer | SEQ ID NO: 423 ctgatcaaaacgagaggacagcacgtgac |
| TRBV5-8_outer | SEQ ID NO: 424 gagtcacacaaagtcccacacacctgatc |
| TRBV6-1_outer | SEQ ID NO: 425 gtgaatgctggtgtcactcagaccccaaa |
| TRBV6-2_outer | SEQ ID NO: 426 gaatgctggtgtcactcagaccccaaaat |
| TRBV6-3_outer | SEQ ID NO: 427 gctggtgtcactcagaccccaaaattccg |
| TRBV6-4_outer | SEQ ID NO: 428 gatcacccaggcaccaacatctcagatcc |
| TRBV6-5_outer | SEQ ID NO: 429 gctggtgtcactcagaccccaaaattcca |
| TRBV6-6_outer | SEQ ID NO: 430 gctggtgtcactcagaccccaaaattccg |
| TRBV6-7_outer | SEQ ID NO: 431 gaatgctggtgtcactcagaccccaaaat |
| TRBV6-8_outer | SEQ ID NO: 432 gctggtgtcactcagaccccaaaattcca |
| TRBV6-9_outer | SEQ ID NO: 433 gaatgctggtgtcactcagaccccaaaat |
| TRBV7-1_outer | SEQ ID NO: 434 gtgctggagtctcccagtccctgagaca |
| TRBV7-2_outer | SEQ ID NO: 435 gtcccccagtaacaaggtcacagagaagg |
| TRBV7-3_outer | SEQ ID NO: 436 gaccccagtaacaaggtcacagagaagg |
| TRBV7-4_outer | SEQ ID NO: 437 cagtcccccaaggtacaaagtcgcaaagag |
| TRBV7-5_outer | SEQ ID NO: 438 gtctccccagtcccccaaggtacgaagtc |
| TRBV7-6_outer | SEQ ID NO: 439 cacaggtgctggagtctcccagtctc |
| TRBV7-8_outer | SEQ ID NO: 440 gtgctggagtctcccagtccctagg |
| TRBV7-9_outer | SEQ ID NO: 441 ctggagtctcccagaaccccagacaca |
| TRBV8-1_outer | SEQ ID NO: 442 gaggcagggatcagccagataccaagat |
| TRBV8-2_outer | SEQ ID NO: 443 gatgctgggatcacccagatgccaaga |
| TRBV9_outer | SEQ ID NO: 444 tggagtcacacaaaccccaaagcacctg |
| Hybridization Probe Pool | |
| Ig1 | SEQ ID NO: 445 GAACTGTGGCTGCACCATCTGTCTTCATCTTCCCGCCATCTGATGAGCAGTTGAAATCTGGAACT GCCTCTGTTGTGTGCCTGCTGAATAACTTCTATCCCAGAGAGGCCAAAGTACAGT |
| Ig2 | SEQ ID NO: 446 GGAAGGTGGATAACGCCCTCCAATCGGGTAACTCCCAGGAGAGTGTCACAGAGCAGGACAGCAAG GACAGCACCTACAGCCTCAGCAGCACCCTGACGCTGAGCAAAGCAGACTACGAGA |
| Ig3 | SEQ ID NO: 447 CTCGCCCGTCACAAAGAGCTTCAACAGGGGAGAGTGTTAGAGGGAGAAGTGCCCCCACCTGCTCC TCAGTTCCAGCCTGACCCCCTCCCATCCTTTGGCCTCTGACCTTTTTCCACAGG |
| Ig4 | SEQ ID NO: 448 GGACCTACCCCTATTGCGGTCCTCCAGCTCATCTTTCACCTCACCCCCCTCCTCCTCCTTGGCTT TAATTATGCTAATGTTGGAGGAGAATGAATAAATAAAGTGAATCTTTGCACCTGT |
| Ig5 | SEQ ID NO: 449 GTCAGCCCAAGGCAACCCCACTGTCACTCTGTTCCCGCCCTCCTCTGAGGAGCTCCAAGCCAAC AAGGCCACACTAGTGTGTCTGATCAGTGACTTCTACCCGGGAGCTGTGACAGTGG |
| Ig6 | SEQ ID NO: 450 GACGCCCGAGCAGTGGAAGTCCCACAGAAGCTACAGCTGCCAGGTCACGCATGAAGGGAGCACCG TGGAGAAGACAGTGGCCCCTACAGAATGTTCATAGGTTCCCAACTCTAACCCCAC |
| Ig7 | SEQ ID NO: 451 CCACGGGAGCCTGGAGCTGCAGGATCCCAGGGGAGGGGTCTCTCTCCCCATCCCAAGTCATCCAG CCCTTCTCCCTGCACTCATGAAACCCAATAAATATCCTCATTGACAACCAGAAA |
| Ig8 | SEQ ID NO: 452 GTCAGCCCAAGGCTGCCCCCTCGGTCACTCTGTTCCCGCCCTCCTCTGAGGAGCTTCAAGCCAAC AAGGCCACACTGGTGTGTCTCATAAGTGACTTCTACCCGGGAGCCGTGACAGTGG |
| Ig9 | SEQ ID NO: 453 CGCCTGAGCAGTGGAAGTCCCACAGAAGCTACAGCTGCCAGGTCACGCATGAAGGGAGCACCGTG GAGAAGACAGTGGCCCCTACAGAATGTTCATAGGTTCTCAACCCTCACCCCCCAC |
| Ig10 | SEQ ID NO: 454 CACGGGAGACTAGAGCTGCAGGATCCCAGGGGAGGGGTCTCTCCTCCCACCCCAAGGCATCAAGC CCTTCTCCCTGCACTCAATAAACCCTCAATAAATATTCTCATTGTCAATCAGAAA |
| Ig11 | SEQ ID NO: 455 GTCAGCCCAAGGCTGCCCCCTCGGTCACTCTGTTCCCACCCTCCTCTGAGGAGCTTCAAGCCAAC AAGGCCACACTGGTGTGTCTCATAAGTGACTTCTACCCGGGAGCCGTGACAGTGG |
| Ig12 | SEQ ID NO: 456 CGCCTGAGCAGTGGAAGTCCCACAAAAGCTACAGCTGCCAGGTCACGCATGAAGGGAGCACCGTG GAGAAGACAGTGGCCCCTACAGAATGTTCATAGGTTCTCATCCCTCACCCCCCAC |
| Ig13 | SEQ ID NO: 457 CACGGGAGACTAGAGCTGCAGGATCCCAGGGGAGGGGTCTCTCCTCCCACCCCAAGGCATCAAGC CCTTCTCCCTGCACTCAATAAACCCTCAATAAATATTCTCATTGTCAATCAGAAA |
| Ig14 | SEQ ID NO: 458 GTCAGCCCAAGGCTGCCCCCTCGGTCACTCTGTTCCCACCCTCCTCTGAGGAGCTTCAAGCCAAC AAGGCCACACTGGTGTGTCTCGTAAGTGACTTCAACCCGGGAGCCGTGACAGTGG |
| Ig15 | SEQ ID NO: 459 CCAGCAGCTACCTGAGCCTGACGCCCGAGCAGTGGAAGTCCCACAGAAGCTACAGCTGCCGGGTC ACGCATGAAGGGAGCACCGTGGAGAAGACAGTGGCCCCTGCAGAATGCTCTTAGG |
| Ig16 | SEQ ID NO: 460 CCCCCGACCCTCACCCCACCCACAGGGGCCTGGAGCTGCAGGTTCCCAGGGGAGGGGTCTCTGCC CCCATCCCAAGTCATCCAGCCCTTCTCAATAAATATCCTCATCGTCAACGAGAAA |
| Ig17 | SEQ ID NO: 461 GCATCCCCGACCAGCCCCAAGGTCTTCCCGCTGAGCCTCGACAGCACCCCCCAAGATGGGAACGT GGTCGTCGCATGCCTGGTCCAGGGCTTCTTCCCCCAGGAGCCACTCAGTGTGACC |
| Ig18 | SEQ ID NO: 462 TGGAGCGAAAGCGGACAGAACGTGACCGCCAGAAACTTCCCACCTAGCCAGGATGCCTCCGGGGA CCTGTACACCACGAGCAGCCAGCTGACCCTGCCGGCCACACAGTGCCCAGACGGC |
| Ig19 | SEQ ID NO: 463 AAGTCCGTGACATGCCACGTGAAGCACTACACGAATTCCAGCCAGGATGTGACTGTGCCCTGCCG AGTTCCCCACCTCCCCCATGCTGCCACCCCCGACTGTCGCTGCACCGACCGGCC |
| Ig20 | SEQ ID NO: 464 CTCGAGGACCTGCTCTTAGGTTCAGAAGCGAACCTCACGTGCACACTGACCGGCCTGAGAGATGC CTCTGGTGCCACCTTCACCTGGACGCCCTCAAGTGGGAAGAGCGCTGTTCAAGGA |
| Ig21 | SEQ ID NO: 465 CCACCTGAGCGTGACCTCTGTGGCTGCTACAGCGTGTCCAGTGTCCTGCCTGGCTGTGCCCAGCC ATGGAACCATGGGGAGACCTTCACCTGCACTGCTGCCCACCCCGAGTTGAAGACT |
| Ig22 | SEQ ID NO: 466 CCACTAACCGCCAACATCACAAAATCCGGAAACACATTCCGGCCCGAGGTCCACCTGCTGCCGCC GCCGTCGGAGGAGCTGGCCCTGAACGAGCTGGTGACGCTGACGTGCCTGGCACGT |
| Ig23 | SEQ ID NO: 467 GGCTTCAGCCCCAAGGATGTGCTGGTTCGCTGGCTGCAGGGGTCACAGGAGCTGCCCCGCGAGAA GTACCTGACTTGGGCATCCCGGCAGGAGCCCAGCCAGGGCACCACCACCTACGCT |
| Ig24 | SEQ ID NO: 468 GTAACCAGCATACTGCGCGTGGCAGCTGAGGACTGGAAGAAGGGGGAGACCTTCTCCTGCATGGT GGGCCACGAGGCCCTGCCGCTGGCCTTCACACAGAAGACCATCGACCGCATGGCG |

TABLE 3-continued

| Variable Region Primer | Sequence |
|---|---|
| Ig25 | SEQ ID NO: 469 GGCTCTTGCTGTGTTGCAGATTGGCAGATGCCGCCTCCCTATGTGGTGCTGGACTTGCCGCAGGA GACCCTGGAGGAGGAGACCCCCGGCGCCAACCTGTGGCCCACCACCATCACCTTC |
| Ig26 | SEQ ID NO: 470 CTCACCCTCTTCCTGCTGAGCCTGTTCTATAGCACAGCACTGACCGTGACCAGCGTCCGGGGCCC ATCTGGCAAGAGGGAGGGCCCCCAGTACTGAGCGGGAGCCGGCAAGGCACAGGGA |
| Ig27 | SEQ ID NO: 471 GGAAGTGTGGAGGAACCTCTTGGAGAAGCCAGCTATGCTTGCCAGAACTCAGCCCTTTCAGACAT CACCGACCCGCCCTTACTCACGTGGCTTCCAGGTGCAATAAAGTGGCCCCAAGGA |
| Ig28 | SEQ ID NO: 472 GCCTCCACACAGAGCCCATCCGTCTTCCCCTTGACCCGCTGCTGCAAAAACATTCCCTCCAATGC CACCTCCGTGACTCTGGGCTGCCTGGCCACGGGCTACTTCCCGGAGCCGGTGATG |
| Ig29 | SEQ ID NO: 473 GTGACCTGGGACACAGGCTCCCTCAACGGGACAACTATGACCTTACCAGCCACCACCCTCACGCT CTCTGGTCACTATGCCACCATCAGCTTGCTGACCGTCTCGGGTGCGTGGGCCAAG |
| Ig30 | SEQ ID NO: 474 CAGATGTTCACCTGCCGTGTGGCACACACTCCATCGTCCACAGACTGGGTCGACAACAAAACCTT CAGCGTCTGCTCCAGGGACTTCACCCCGCCCACCGTGAAGATCTTACAGTCGTCC |
| Ig31 | SEQ ID NO: 475 TGCGACGGCGGCGGGCACTTCCCCCCGACCATCCAGCTCCTGTGCCTCGTCTCTGGGTACACCCC AGGGACTATCAACATCACCTGGCTGGAGGACGGGCAGGTCATGGACGTGGACTTG |
| Ig32 | SEQ ID NO: 476 TCCACCGCCTCTACCACGCAGGAGGGTGAGCTGGCCTCCACACAAAGCGAGCTCACCCTCAGCCA GAAGCACTGGCTGTCAGACCGCACCTACACCTGCCAGGTCACCTATCAAGGTCAC |
| Ig33 | SEQ ID NO: 477 ACCTTTGAGGACAGCACCAAGAAGTGTGCAGATTCCAACCCGAGAGGGGTGAGCGCCTACCTAAG CCGGCCCAGCCCGTTCGACCTGTTCATCCGCAAGTCGCCCACGATCACCTGTCTG |
| Ig34 | SEQ ID NO: 478 TCCCGGGCCAGTGGGAAGCCTGTGAACACTCCACCAGAAAGGAGGAGAAGCAGCGCAATGGCAC GTTAACCGTCACGTCCACCCTGCCGGTGGGCACCCGAGACTGGATCGAGGGGGAG |
| Ig35 | SEQ ID NO: 479 ACCTACCAGTGCAGGGTGACCCACCCCCACCTGCCCAGGGCCCTCATGCGGTCCACGACCAAGAC CAGCGGACCCGCGTGCTGCCCCGGAAGTCTATGCGTTTGCGACGCCGGAGTGGCCG |
| Ig36 | SEQ ID NO: 480 GGGAGCCGGGACAAGCGCACCCTCGCTGCCTGATCCAGAACTTCATGCCTGAGGACATCTCGGT GCAGTGGCTGCACAACGAGGTGCAGCTCCCGGACGCCCGGCACAGCACGACGCAG |
| Ig37 | SEQ ID NO: 481 CCCCGCAAGACCAAGGGCTCCGGCTTCTTCGTCTTCAGCCGCCTGGAGGTGACCAGGGCCGAATG GGAGCAGAAAGATGAGTTCATCTGCCGTGCAGTCATGAGGCAGCAAGCCCCTCA |
| Ig38 | SEQ ID NO: 482 CAGACCGTCCAGCGAGCGGTGTCTGTAAATCCCGAGCTGGACGTGTGCGTGGAGGAGGCCGAGGG CGAGGCGCCGTGGACGTGGACCGGCCTCTGCATCTTCGCCGCACTCTTCCTGCTC |
| Ig39 | SEQ ID NO: 483 AGCGTGAGCTACAGCGCCGCCATCACGCTCCTCATGGTGCAGCGGTTCCTCTCAGCCACGCGGCA GGGGAGGCCCCAGACCTCCCTCGACTACACCAACGTCCTCCAGCCCCACGCCTAG |
| Ig40 | SEQ ID NO: 484 TCCTGCCTCCCTCCCTCCCAGGGTCCATCCAGCTGTGCAGTGGGAGGACTGGCCAGACCTTCT GTCCACTGTTGCAATGACCCCAGGAAGCTACCCCCAATAAACTGTGCCTGCTCAG |
| Ig41 | SEQ ID NO: 485 GCTTCCACCAAGGGCCCATCGGTCTTCCCCCTGGCGCCCTGCTCCAGGAGCACCTCCGAGAGCAC AGCCGCCCTGGGCTGCCTGGTCAAGGACTACTTCCCCGAACCGGTGACGGTGTCG |
| Ig42 | SEQ ID NO: 486 TGGAACTCAGGCGCCTGACCAGCGGCGTGCACACCTTCCCGGCTGTCCTACAGTCCTCAGGACT CTACTCCCTCAGCAGCGTGGTGACCGTGCCCTCCAGCAGCTTGGGCACGAAGACC |
| Ig43 | SEQ ID NO: 487 TACACCTGCAACGTAGATCACAAGCCCAGCAACACCAAGGTGGACAAGAGAGTTGAGTCCAAATA TGGTCCCCCATGCCCATCATGCCCAGCACCTGAGTTCCTGGGGGGACCATCAGTC |
| Ig44 | SEQ ID NO: 488 TTCCTGTTCCCCCCAAAACCCAAGGACACTCTCATGATCTCCCGGACCCCTGAGGTCACGTGCGT GGTGGTGGACGTGAGCCAGGAAGACCCCGAGGTCCAGTTCAACTGGTACGTGGAT |
| Ig45 | SEQ ID NO: 489 GGCGTGGAGGTGCATAATGCCAAGACAAAGCCGCGGGAGGAGCAGTTCAACAGCACGTACCGTGT GGTCAGCGTCCTCACCGTCCTGCACCAGGACTGGCTGAACGGCAAGGAGTACAAG |
| Ig46 | SEQ ID NO: 490 TGCAAGGTCTCCAACAAAGGCCTCCCGTCCTCCATCGAGAAAACCATCTCCAAAGCCAAAGGGCA GCCCCGAGAGCCACAGGTGTACACCCTGCCCCCATCCCAGGAGGAGATGACCAAG |
| Ig47 | SEQ ID NO: 491 AACCAGGTCAGCCTGACCTGCCTGGTCAAAGGCTTCTACCCCAGCGACATCGCCGTGGAGTGGGA GAGCAATGGGCAGCCGGAGAACAACTACAAGACCACGCCTCCCGTGCTGGACTCC |
| Ig48 | SEQ ID NO: 492 GACGGCTCCTTCTTCCTCTACAGCAGGCTCACCGTGGACAAGAGCAGGTGGCAGGAGGGGAATGT CTTCTCATGCTCCGTGATGCATGAGGCTCTGCACAACCACTACACACAGAAGAGC |
| Ig49 | SEQ ID NO: 493 CTCTCCCTGTCTCTGGAGCTGCAACTGGAGGAGAGCTGTGCGGAGGCGCAGGACGGGGAGCTGGA CGGGCTGTGGACGACCATCACCATCTTCATCACACTCTTCCTGCTAAGCGTGTGC |
| Ig50 | SEQ ID NO: 494 TACAGTGCCACCGTCACCTTCTTCAAGGTGAAGTGGATCTTCTCCTCAGTGGTGGACCTGAAGCA GACCATCGTCCCCGACTACAGGAACATGATAAGGCAGGGGCCTAGGGCCACCCT |
| Ig51 | SEQ ID NO: 495 CCCCCTGACCTCACCGCCCTCAACCCCATGGCTCTCTGGCTTCGCAGTCGCCCTCTGAGCCCTGA AACGCCCCCTTCCAGACCCTGTGCATAGCAGGTCTACCCCAGACCTCCGCTGCT |
| Ig52 | SEQ ID NO: 496 TGGTGCATGCAGGGCGCTGAGGGCCAGGTGTCCCCTCAGCAGGACGTCCCTGCCCTCTGGACCAC CAGGTGCTCACACAAAAGGAGGTAACCGGCATCCCAGGCCCCCACTCAGGCAGGA |
| Ig53 | SEQ ID NO: 497 CCTCGCCCTGGAGCCAACCCCGTCCACGCCAGCCTCCTGAACACAGGCATGGTTTCCAGATGGTG AGTGGGAGCATCAGTCGCCAAGGTAGGGAAGCCACAGCACCATCAGGCCCTGTTG |
| Ig54 | SEQ ID NO: 498 GGGAGGCTTCCGAGAGCTGCGAAGGCTCACTCAGACGGCCTTCCTCCCAGCCCGCAGCCAGCCAG CCTCCATTCCGGGCACTCCCGTGAACTCCTGACATGAGGAATGAGGTTGTTCTGA |
| Ig55 | SEQ ID NO: 499 TTTCAAGCAAAGAACGCTGCTCTCTGGCTCCTGGGAACAGTCTCGGTGCCAGCACCACCCCTTGG CTGCCTGCCCACACTGCTGGATTCTCGGGTGGAACTGGACCCGCAGGGACAGCCA |
| Ig56 | SEQ ID NO: 500 GCCCCAGAGTCCGCACTGGGGAGAGAAAGGGCCAGGCCCAGGACACTGCCACCTACCACCCACTC CAGTCCACCGAGATCACTCGGAGAAGAGCCTGGCCATGTGGCCGCTGCAGGAGC |
| Ig57 | SEQ ID NO: 501 CCCACAGTGCAAGGGTGAGGATAGCCAAGGAAGGGCTGGGCATCTGCCCAGACAGGCCTCCCAC AGAAGGCTGGTGACCAGGTCCCAGGCGGGCAAGACTCAGCCTTGGTGGGGCCTGA |
| Ig58 | SEQ ID NO: 502 GGACAGAGGAGGCCCAGGAGCATCGGGGAGAGAGGTGGAGGGACACCGGGAGAGCCAGGAGCGTG GACACAGCCAGAACTCATCACAGAGGCTGCCGTCCAGTCCCGGGTCACGTGCAGC |
| Ig59 | SEQ ID NO: 503 AGGAACAAGCAGCCACTCTGGGGCACCAGGTGGAGAGGCAAGACGACAAAGAGGGTGCCCGTGT TCTTGCGAAAGCGGGGCTGCTGGCCACGAGTGCTGGACAGAGGCCCCACGCTCT |
| Ig60 | SEQ ID NO: 504 GCTGCCCCCATCACACCGTTCCGTGACTGTCACGCAGAATCCACAGACAGGAAGGGAGGCTCGAG CGGGACTGCGGCCAGCGCCTGCCTCGGCCGTCAGGGAGGACTCCCGGGCTCACTC |
| Ig61 | SEQ ID NO: 505 GAAGGAGGTGTCACCATTTCAGCTTTGGCTTTTCTTCTTCTTTTAAATTTTCTAAAGCTCATTAA TTGTCTTTGATGTTTCTTTTGTGATGACAATAAAATATCCTTTTTAAGTCTTGTA |
| Ig62 | SEQ ID NO: 506 AGCCCCCGCTCCCCGGGCTCTCGGGGTCGCGCGAGGATGCTTGGCACGTACCCCGTGTACATACT TCCCGGGCGCCCAGCATGGAAATAAAGCACCCAGCGCTGCCCTGGGCCCCTGCGA |

TABLE 3-continued

| Variable Region Primer | Sequence |
|---|---|
| Ig63 | SEQ ID NO: 507 GCCTCCACCAAGGGCCCATCGGTCTTCCCCCTGGCGCCCTGCTCCAGGAGCACCTCCGAGAGCAC AGCGGCCCTGGGCTGCCTGGTCAAGGACTACTTCCCCGAACCGGTGACGGTGTCG |
| Ig64 | SEQ ID NO: 508 TGGAACTCAGGCGCTCTGACCAGCGGCGTGCACACCTTCCCGGCTGTCCTACAGTCCTCAGGACT CTACTCCCTCAGCAGCGTGGTGACCGTGCCCTCCAGCAACTTCGGCACCCAGACC |
| Ig65 | SEQ ID NO: 509 TACACCTGCAACGTAGATCACAAGCCCAGCAACACCAAGGTGGACAAGACAGTTGAGCGCAAATG TTGTGTCGAGTGCCCACCGTGCCCAGCACCACCTGTGGCAGGACCGTCAGTCTTC |
| Ig66 | SEQ ID NO: 510 CTCTTCCCCCCAAAACCCAAGGACACCCTCATGATCTCCCGGACCCCTGAGGTCACGTGCGTGGT GGTGGACGTGAGCCACGAAGACCCCGAGGTCCAGTTCAACTGGTACGTGGACGGC |
| Ig67 | SEQ ID NO: 511 GTGGAGGTGCATAATGCCAAGACAAAGCCACGGGAGGAGCAGTTCAACAGCACGTTCCGTGTGGT CAGCGTCCTCACCGTCGTGCACCAGGACTGGCTGAACGGCAAGGAGTACAAGTGC |
| Ig68 | SEQ ID NO: 512 AAGGTCTCCAACAAAGGCCTCCCAGCCCCCATCGAGAAAACCATCTCCAAAACCAAAGGGCAGCC CCGAGAACCACAGGTGTACACCCTGCCCCCATCCCGGGAGGAGATGACCAAGAAC |
| Ig69 | SEQ ID NO: 513 CAGGTCAGCCTGACCTGCCTGGTCAAAGGCTTCTACCCCAGCGACATCTCCGTGGAGTGGGAGAG CAATGGGCAGCCGGAGAACAACTACAAGACCACACCTCCCATGCTGGACTCCGAC |
| Ig70 | SEQ ID NO: 514 GGCTCCTTCTTCCTCTACAGCAAGCTCACCGTGGACAAGAGCAGGTGGCAGCAGGGGAACGTCTT CTCATGCTCCGTGATGCATGAGGCTCTGCACAACCACTACACACAGAAGAGCCTC |
| Ig71 | SEQ ID NO: 515 TCCCTGTCTCCGGGAGCTGCAACTGGAGGAGAGCTGTGCGGAGGCGCAGGACGGGGAGCTGGACGG GCTGTGGACCACCATCTTCATCACACTCTTCCTGCTAAGCGTGTGCTAC |
| Ig72 | SEQ ID NO: 516 AGTGCCACCATCACCTTCTTCAAGGTGAAGTGGATCTTCTCCTCAGTGGTGGACCTGAAGCAGAC CATCGTCCCCGACTACAGGAACATGATCAGGCAGGGGGCCTAGGGCCACCCTCTG |
| Ig73 | SEQ ID NO: 517 CCCCCGACCTCACCGCCCTCAACCCCATGGCTCTCTGGCCTCGCAGTCGCCCTCTGACCCTGACA CGCCCCCCTTCCAGACCCTGTGCATAGCAGGTCTACCCCAGACCTCCGCTGCTTG |
| Ig74 | SEQ ID NO: 518 GTGCATGCAGGGCGCTGGGGGCCAAGTGTCCCCTCAGCAGGACGTCCCTGCCCTCCGGCCCGCCA GGTGCTCACACAAAAGGAGGTAGTGACCAGCATCCCAGGCCCCCACTCAGGCAGG |
| Ig75 | SEQ ID NO: 519 ACCTCGCCCTGGAGCCAACCCTGTCCACGCCAGCCTCCTGAACACAGGCGTGGTTTCCAGATGGT GAGTGGGAGCATCGCCAAGGTAGGGAAGTCACAGCACCATCAGGCCCTGTT |
| Ig76 | SEQ ID NO: 520 GGGGAGGCTTCCGAGAGCTGCGAAGGCTCACTCAGACGGCCTTCCTCCCAGCCCGCAGCCAGCCA GCCTCCATTCCAGGCACTCCCGTGAACTCCTGACATGAGGAATGAGGTTGTTCTG |
| Ig77 | SEQ ID NO: 521 ATTTCAAGCAAAGAACGCTGCTCTCTGGCTCCTGGGAACAGTCTCAGTGCCAGCACCACCCCTTG GCTGCCTGCCCACACTGCTGGATTCTGGGTGGAACTCGACCCGCAGGGACAGCC |
| Ig78 | SEQ ID NO: 522 AGCCCCAGAGTCCGCACTGGGGAGAGAAGGGGCCAGGCCCAGGACACTGCCACCTACCACCCACT CCAGTCCACCGAGATCACTCGGAGAAGAGCCTGGGCCATGTGGCCGCTGCAGGAG |
| Ig79 | SEQ ID NO: 523 CCCCACGGTGCAAGGGTGAGGATAGCCCAAGGAAGGGCTGGGCATCTGCCCAGACAGGCCTCCCA GAGAAGGCTGGTGACCAGGTCCCAGGCGGGCAAGACTCAGCCTTGGTGGGGCCTG |
| Ig80 | SEQ ID NO: 524 AGGACAGAGGAGGCCCAGGAGCATCGGGGAGAGAGGTGGAGGGACACCGGAGAGCCAGGAGCGT GGACACAGCCAGAACTCATCACAGAGGCTGGCGTCCAGCCCGGGTCACGTGCAG |
| Ig81 | SEQ ID NO: 525 CAGGAACAAGCAGCCACTCTGGGGGCACCAGGTGGAGAGGCAAGACGACAAAGAGGGTGCCCGTG TTCTTGTGAAAGCGGGGCTGCTGGCCACGAGTGCTGGACAGAGGCCCCCACGCTC |
| Ig82 | SEQ ID NO: 526 TGCTGCCCCCATCACGCCGTTCCGTGACTGTCACGCAGAATCCGCAGACAGGGAGACTCGAGCGG GAGTGCGGCCAGCGCCTGCCTCAGCTGTCAGGGAGGACTCCCGGGCTCACTCGAA |
| Ig83 | SEQ ID NO: 527 GGAGGTGCCACCATTTCAGCTTTGGTAGCTTTTCTTCTTCTTTTAAATTTTCTAAAGCTCATTAA TTGTCTTTGATGTTTCTTTTGTGATGACAATAAAATATCCTTTTTAAGTCTTGTA |
| Ig84 | SEQ ID NO: 528 AGCCCCCGCTCCCCAGGCTCTCGGGGTTCGCGCGAGGATGCTTGGCACGTACCCCGTCTACATACT TCCCGGGCACCCAGCATGGAAATAAAGCACCCAGCGCTGCCCTGGGCCCCTGCGA |
| Ig85 | SEQ ID NO: 529 GCATCCCCGACCAGCCCCAAGGTCTTCCCGCTGAGCCTCTGCAGCACCCAGCCAGATGGGAACGT GGTCATCGCCTGCCTGGTCCAGGGCTTCTTCCCCCAGGAGCCACTCAGTGTGACC |
| Ig86 | SEQ ID NO: 530 TGGAGCGAAAGCGGACAGGGCGTGACCGCCAGAAACTTCCCACCCAGCCAGGATGCCTCCGGGGA CCTGTACACCACGAGCAGCCAGCTGACCCTGCCGGCCACACAGTGCCTAGCCGGC |
| Ig87 | SEQ ID NO: 531 AAGTCCGTGACATGCCACGTGAAGCACTACACGAATCCCAGCCAGGATGTGACTGTGCCCTGCCC AGTTCCCTCAACTCCACCTACCCCATCTCCCTCAACTCCACCTACCCCATCTCCC |
| Ig88 | SEQ ID NO: 532 TCATGCTGCCACCCCGACTGTCACTGCACCGACCGGCCTCGAGGACCTGCTCTTAGGTTCAGA AGCGAACCTCACGTGCACACTGACCGGCTGTGAGAGATGCCTCAGGTGTCACCTTC |
| Ig89 | SEQ ID NO: 533 ACCTGGACGCCCTCAAGTGGGAAGAGCGCTGTTCAAGGACCACCTGAGCGTGACCTCTGTGGCTG CTACAGCGTGTCCAGTGTCCTGCCGGGCTGTGCCGAGCCATGGAACCATGGGAAG |
| Ig90 | SEQ ID NO: 534 GGAGGAGCTGGCCCTGAACGAGCTGGTGACGCTGACGTGCCTGGCACGCGGCTTCAGCCCCAAGG ATGTGCTGGTTCGCTGGCTGCAGGGGTCACAGGAGCTGCCCCGCGAGAAGTACCT |
| Ig91 | SEQ ID NO: 535 GACTTGGGCATCCCGGCAGGAGCCCAGCCAGGGCACCACCACCTTCGCTGTGACCAGCATACTGC GCGTGGCAGCCGAGGACTGGAAGAAGGGGGACACCTTCTCCTGCATGGTGGGCCA |
| Ig92 | SEQ ID NO: 536 CGAGGCCCTGCCGCTGGCCTTCACACAGAAGACCATCGACCGCTTGGCGGATTGGCAGATGCCGC CTCCCTATGTGGTGACTTGCCGCAGGAGACCCTGGAGGAGGAGACCCCCGTG |
| Ig93 | SEQ ID NO: 537 CGCCAACCTGTGCCCACCACCATCACCTTCCTCACCCTCTTCCTGCTGAGCCTGTTCTATAGCA CAGCACTGACCGTGACCAGCGTCGGGGCCCATCTGGCAACAGGGAGGGCCCCCA |
| Ig94 | SEQ ID NO: 538 GTACTGAGCAGGAGCCGGCAAGGCACAGGGAGGAAGTGTGGAGGAACCTCTTGGAGAAGCCAGCT ATGCTTGCCAGAACTCAGCCCTTTCAGACATCACCGACCCGCCCTTACTCACATG |
| Ig95 | SEQ ID NO: 539 CTTGGCGGGTAAACCCACCCATGTCAATGTGTCTGTTGTCATGGCGGAGGTGGACGGCACCTGCT ACTGAGCGCCCGCCTGTCCCCACCCCTGAATAAACTCCATGCTCCCCAAGCAG |
| Ig96 | SEQ ID NO: 540 GCCTCCACCAAGGGCCCATCGGTCTTCCCCCTGGCACCCTCCTCCAAGAGCACCTCTGGGGGCAC AGCAGCCCTGGGCTGCCTGGTCAAGGACTACTTCCCCGAACCGGTGACGGTGTCG |
| Ig97 | SEQ ID NO: 541 TGGAACTCAGGCGCCCTGACCAGCGGCGTGCACACCTTCCCGGCTGTCCTACAGTCCTCAGGACT CTACTCCCTCAGCAGCGTGGTGACCGTGCCCTCCAGCAGCTTGGGCACCCAGACC |
| Ig98 | SEQ ID NO: 542 TACATCTGCAACGTGAATCACAAGCCCAGCAACACCAAGGTGGACAAGAAAGTTGAGCCCAAATC TTGTGACAAAACTCACACATGCCCACCGTGCCCAGCACCTGAACTCCTGGGGGGA |
| Ig99 | SEQ ID NO: 543 CCGTCAGTCTTCCTCTTCCCCCCAAAACCCAAGGACACCCTCATGATCTCCCGGACCCCTGAGGT CACATGCGTGGTGGTGGACGTGAGCCACGAAGACCCTGAGGTCAAGTTCAACTGG |
| Ig100 | SEQ ID NO: 544 TACGTGGACGGCGTGGAGGTGCATAATGCCAAGACAAAGCCGCGGGAGGAGCAGTACAACAGCAC GTACCGTGTGGTCAGCGTCCTCACCGTCCTGCACCAGGACTGGCTGAATGGCAAG |

TABLE 3-continued

| Variable Region Primer | Sequence |
|---|---|
| Ig101 | SEQ ID NO: 545 GAGTACAAGTGCAAGGTCTCCAACAAAGCCCTCCCAGCCCCCATCGAGAAAACCATCTCCAAAGC CAAAGGGCAGCCCCGAGAACCACAGGTGTACACCCTGCCCCCATCCCGGGATGAG |
| Ig102 | SEQ ID NO: 546 CTGACCAAGAACCAGGTCAGCCTGACCTGCCTGGTCAAAGGCTTCTATCCCAGCGACATCGCCGT GGAGTGGGAGAGCAATGGGCAGCCGGAGAACAACTACAAGACCACGCCTCCCGTG |
| Ig103 | SEQ ID NO: 547 CTGGACTCCGACGGCTCCTTCTTCCTCTACAGCAAGCTCACCGTGGACAAGAGCAGGTGGCAGCA GGGGAACGTCTTCTCATGCTCCGTGATGCATGAGGCTCTGCACAACCACTACACA |
| Ig104 | SEQ ID NO: 548 CAGAAGAGCCTCTCCCTGTCTCCGGAGCTGCAACTGGAGGAGAGCTGTGCGGAGGCGCAGGACGG GGAGCTGGACGGGCTGTGGACGACCATCACCATCTTCATCACACTCTTCCTGTTA |
| Ig105 | SEQ ID NO: 549 AGCGTGTGCTACAGTGCCACCGTCACCTTCTTCAAGGTGAAGTGGATCTTCTCCTCGGTGGTGGA CCTGAAGCAGACCATCATCCCCGACTACAGGAACATGATCGGACAGGGGGCCTAG |
| Ig106 | SEQ ID NO: 550 CGCCCTCAACCCCATGACTCTCTGGCCTCGCAGTTGCCCTCTGACCCTGACACACCTGACACGCC CCCCTTCCAGACCCTGTGCATAGCAGGTCTACCCCAGACCTCCGCTGCTTGGTGC |
| Ig107 | SEQ ID NO: 551 ATGCAGGGCACTGGGGGCCAGGTGTCCCCTCAGCAGGACGTCCTTGCCCTCCGGACCACAAGGTG CTCACACAAAAGGAGGCAGTGACCGGTATCCCAGGCCCCCACCCAGGCAGGACCT |
| Ig108 | SEQ ID NO: 552 CGCCCTGGAGCCAACCCCGTCCACGCCAGCCTCCTGAACACAGGCGTGGTTTCCAGATGGTGAGT GGGAGCGTCAGCCGCCAAGGTAGGGAAGCCACAGCACCATCAGGCCCTGTTGGGG |
| Ig109 | SEQ ID NO: 553 AGGCTTCCGAGAGCTGCGAAGGCTCACTCAGACGGCCTTCCTCCCAGCCCGCAGCCAGCCAGCCT CCATTCCGGGCACTCCCGTGAACTCCTGACATGAGGAATGAGGTTGTTCTGATTT |
| Ig110 | SEQ ID NO: 554 CAAGCAAAGAACGCTGCTCTCTGGCTCCTGGGAACAGTCTCAGTGCCAGCACCACCCCTTGGCTG CCTGCCCACACTGCTGGATTCTCGGGTGGAACTGGACCCGCAGGGACAGCCAGCC |
| Ig111 | SEQ ID NO: 555 CCAGAGTCCGCACTGGGGAGAGAAGGGGCCAGGCCCAGGACACTGCCACCTCCCACCCACTCCAG TCCACCGAGATCACTCAGAGAAGAGCCTGGGCCATGTGGCCGCTGCAGGAGCCCC |
| Ig112 | SEQ ID NO: 556 ACAGTGCAAGGGTGAGGATAGCCCAAGGAAGGGCTGGGCATCTGCCCAGACAGGCCTCCCAGAGA AGGCTGGTGACCAGGTCCCAGGCGGGCAAGACTCAGCCTTGGTGGGGCCTGAGGA |
| Ig113 | SEQ ID NO: 557 CAGAGGAGGCCCAGGAGCATCGGGGAGAGAGGTGGAGGGACACCGGGAGAGCCAGGAGCGTGGAC ACAGCCAGAACTCATCACAGAGGCTGGCGTCCAGCCCCGGGTCACGTGCAGCAGG |
| Ig114 | SEQ ID NO: 558 AACAAGCAGCCACTCTGGGGGCACCAGGTGGAGAGGCAAGACGACAAAGAGGGTGCCCGTGTTCT TGCGAAAGCAGGGCTGCTGGCCACGAGTGCTGGACAGAGGCCCCCACGCTCTGCT |
| Ig115 | SEQ ID NO: 559 GCCCCCATCACGCCGTTCCGTGACTGTCACGCAGAATCTGCAGACAGGAAGGGAGACTCGAGCGG GAGTGCGGCCAGCGCCTGCCTCGGCCGTCAGGGAGGACTCCTGGGCTCACTCGAA |
| Ig116 | SEQ ID NO: 560 GGAGGTGCCACCATTTCAGCTTTGGTAGCTTTTCTTCTTCTTTTAAATTTTCTAAAGCTCATTAA TTGTCTTTGATGTTTCTTTTGTGATGACAATAAAATATCCTTTTTAAGTCTTGTA |
| Ig117 | SEQ ID NO: 561 AAGCCCCCGCTCCCCAGGCTCTCGGGGTCGCGCGAGGATGCTTGGCACGTACCCCGTGTACATAC TTCCCAGGCACCCAGCATGGAAATAAAGCACCCAGCGCTTCCTGGGCCCCTGCG |
| Ig118 | SEQ ID NO: 562 CTTCCACCAAGGGCCCATCGGTCTTCCCCCTGGCGCCCTGCTCCAGGAGCACCTCTGGGGGCACA GCGGCCCTGGGCTGCCTGGTCAAGGACTACTTCCCCAGAACCGGTGACGGTGTCGT |
| Ig119 | SEQ ID NO: 563 GGAACTCAGGCGCCCTGACCAGCGGCGTGCACACCTTCCCGGCTGTCCTACAGTCCTCAGGACTC TACTCCCTCAGCAGCGTGGTGACCGTGCCCTCCAGCAGCTTGGGCACCCAGACCT |
| Ig120 | SEQ ID NO: 564 ACACCTGCAACGTGAATCACAAGCCCAGCAACACCAAGGTGGACAAGAGAGTTGAGCTCAAAACC CCACTTGGTGACACAACTCACACATGCCCACGGTGCCCAGAGCCCAAATCTTGTG |
| Ig121 | SEQ ID NO: 565 ACACACCTCCCCCGTGCCCACGGTGCCCAGAGCCCAAATCTTGTGACACACCTCCCCCATGCCCA CGGTGCCCAGAGCCCAAATCTTGTGACACACCTCCCCGTGCCCAAGGTGCCCAG |
| Ig122 | SEQ ID NO: 566 CACCTGAACTCCTGGGAGGACCGTCAGTCTTCCTCTTCCCCCCAAAACCCAAGGATACCCTTATG ATTTCCCGGACCCCTGAGGTCACGTGCGTGGTGGTGGACGTGAGCCACGAAGACC |
| Ig123 | SEQ ID NO: 567 CCGAGGTCCAGTTCAAGTGGTACGTGGACGGCGTGGAGGTGCATAATGCCAAGACAAAGCCGCGG GAGGAGCAGTACAACAGCACGTTCCGTGTGGTCAGCGTCCTCACCGTCCTGCACC |
| Ig124 | SEQ ID NO: 568 AGGACTGGCTGAACGGCAAGGAGTACAAGTGCAAGGTCTCCAACAAAGCCCTCCCAGCCCCCATC GAGAAAACCATCTCCAAAACCAAAGGACAGCCCCGAGAACCACAGGTGTACACCC |
| Ig125 | SEQ ID NO: 569 TGCCCCCATCCCGGGAGGAGATGACCAAGAACCAGGTCAGCCTGACCTGCCTGGTCAAAGGCTTC TACCCCAGCGACATCGCCGTGGAGTGGGAGAGCAGCGGGCAGCCGGAGAACAACT |
| Ig126 | SEQ ID NO: 570 ACAACACCACGCCTCCCATGCTGGACTCCGACGGCTCCTTCTTCCTCTACAGCAAGCTCACCGTG GACAAGAGCAGGTGGCAGCAGGGGAACATCTTCTCATGCTCCGTGATGCATGAGG |
| Ig127 | SEQ ID NO: 571 CTCTGCACAACCGCTTCACGCAGAAGAGCCTCTCCCTGTCTCCGGAGCTGCAACTGGAGGAGAGC TGTGCGGAGGCGCAGGACGGGGAGCTGGACGGGCTGTGGACGACCATCACCATCT |
| Ig128 | SEQ ID NO: 572 TCATCACACTCTTCCTGTTAAGCGTGTGCTACAGTGCCACCGTCACCTTCTTCAAGGTGAAGTGG ATCTTCTCCTCGGTGGTGGACCTGAAGCAGACCATCATCCCCGACTATAGGAACA |
| Ig129 | SEQ ID NO: 573 GACCTCACCGCCCTCAACCCCATGGCTCTCTGTCTTTGCAGTCGCCCTCTGAGCCCTGACACGCC CCCCTTCCAGACCCTGTGCATAGCAGGTCTACCCCAGACCTCCGCTGCTTGGTGC |
| Ig130 | SEQ ID NO: 574 ATGCAGGGAGCTGGGGACCAGGTGTCCCCTCAGCAGGATGTCCCTGCCCTCCAGACCGCCAGATG CTCACACAAAAGGAGGCAGTGACCAGCATCCGAGGCCCCCACCCAGGCAGGAGCT |
| Ig131 | SEQ ID NO: 575 GGCCCTGGAGCCAACCCCGTCCACGCCAGCCTCCTGAACACAGGCGTGGTTTCCAGATGGTGAGT GGGAGCATCAGCCGCCAAGGTAGGGAAGCCACAGCACCATCAGGCCCTGTTGGGG |
| Ig132 | SEQ ID NO: 576 AGGCTTCCGAGAGCTGCGAAGGCTCACTCAGACGGCCTTCCTCCCAGCCCGCAGCCAGCCAGCCT CCATTCCGGGCACTCCCGTGAACTCCTGACATGAGGAATGAGGTTGTTCTGATTT |
| Ig133 | SEQ ID NO: 577 CAAGCAAAGAACGCTGCTCTCTGGCTCCTGGGAACACTCGGTGCCAGCACCACCCCTTGGCTG CCTGCCTACACTGCTGGATTCTCGGGTGGAACTGGACCCGCAGGGACAGCCAGCC |
| Ig134 | SEQ ID NO: 578 CCAGAGTCCGCACTGGGGAGAGAAGGGGCCAGGCCCAGGACACTGCCACCTCCCACCCACTCCAG TCCACCGAGATCACTCAGAGAAGAGCCTGGGCCATGTGGCCACTGCAGGAGCCCC |
| Ig135 | SEQ ID NO: 579 ACAGTGCAAGAGTGAGGATAGCCCAAGGAAGGGCTGGGCATCTGCCCAGACAGGCCTCCCAGAGA AGGCTGGTGACCAGGTCCCAGGCGGGCAAGACTCAGCCTTGGTGGGGCCTGAGGA |
| Ig136 | SEQ ID NO: 580 CAGAGGAGGCCCAGGAGCATCGGGGAGAGAGGTGGAGGGACACCGGGAGAGCCAGGAGCGTGGAC ACAGCCAGAACTCATCACAGAGGCTGGCGTCCAGCCCCGGGTCACGTGCAGCAGG |
| Ig137 | SEQ ID NO: 581 AACAAGCAGCCACTCTGGGGGCACCAGGTGGAGAGGCAAGATGCCAAAGAGGGTGCCCGTGTTCT TGCGAAAGCGGGGCTGCTGGCCACGAGTGCTGGACAGAGGCCCCCACGCTCTGCT |
| Ig138 | SEQ ID NO: 582 GCCCCCATCACGCCGTTCCGTGACTGTCACGCAGAATCGCAGACAGGAAGGGAGGCTCGAGCGG GACTGCGGCCAGCGCCTGCCTCGGCCGTCAGGGAGGACTCCCGGGCTCACTCGAA |

TABLE 3-continued

| Variable Region Primer | Sequence |
|---|---|
| Ig139 | SEQ ID NO: 583 GGAGGTGCCACCATTTCAGCTTTGGTAGCTTTTCTTCTTCTTTTAAATTTTCTAAAGCTCATTAA TTGTCTTTGATGTTTCTTTTGTGATGACAATAAAATATCCTTTTTAAGTCTTGTA |
| Ig140 | SEQ ID NO: 584 AGCCCCCGCTCCCCGGGCTCTCGGGGTCGCGCGAGGATGCTTGGCACGTACCCCGTGTACATACT TCCCGGGCACCCAGCATGGAAATAAAGCACCCAGCGCTGCCCTGGGCCCCTGCGA |
| Ig141 | SEQ ID NO: 585 CACCCATCCAAGGCTCCGGATGTGTTCCCCATCATATCAGGGTGCAGACACCCAAAGGATAACAGC CCTGTGGTCCTGGCATGCTTGATAACTGGGTACCACCCAACGTCCGTGACTGTCA |
| Ig142 | SEQ ID NO: 586 CCTGGTACATGGGGACACAGAGCCAGCCCCAGAGAACCTTCCCTGAGATACAAAGACGGGACAGC TACTACATGACAAGCAGCCAGCTCTCCACCCCCCTCCAGCAGTGGCGCCAAGGCG |
| Ig143 | SEQ ID NO: 587 AGTACAAATGCGTGGTCCAGCACACCGCCAGCAAGAGTAAGAAGGAGATCTTCCGCTGGCCAGAG TCTCCAAAGGCACAGGCCTTCCTCAGTGCCCACTGCACAACCCCAAGCAGAGGGCA |
| Ig144 | SEQ ID NO: 588 GCCTCGCCAAGGCAACCACAGCCCCAGCCACCACCCGTAACACAGGAAGAGGAGGAGAAGAGAAG AAGAAGGAGAAGGAGAAAGAGGAACAAGAAGAGAGAGAGACAAAGACACCAGAGT |
| Ig145 | SEQ ID NO: 589 GTCCGAGCCACACCCAGCCTCTTGGCGTCTACCTGCTAACCCCTGCAGTGCAGGACCTGTGGCTC CGGGACAAAGCCACCTTCACCTGCTTCGTGGTGGGCAGTGACCTGAAGGATGCTC |
| Ig146 | SEQ ID NO: 590 ACCTGACCTGGGAGGTGGCTGGGAAGGTCCCCACAGGGGGCGTGGAGGAAGGGCTGCTGGAGCGG CACAGCAACGGCTCCCAGAGCCAGCACAGCCGTCTGACCCTGCCCAGGTCCTTGT |
| Ig147 | SEQ ID NO: 591 GGCCTCGTCTGACCCTCCCGAGGCGGCCTCGTGGCTCCTGTGTGAGGTGTCTGGCTTCTCGCCCC CCAACATCCTCCTGATGTGGCTGGAGGACCAGCGTGAGGTGAACACTTCTGGGTT |
| Ig148 | SEQ ID NO: 592 TGCCCCCGCACGCCCCCCTCCACAGCCCAGGAGCACCACGTTCTGGGCCTGGAGTGTGCTGCGTG TCCCAGCCCCGCCCAGCCCTCAGCCAGCCACCTACACGTGTGTGGTCAGCCACGA |
| Ig149 | SEQ ID NO: 593 GGACTCCCGGACTCTGCTCAACGCCAGCCGGAGCCTAGAAGTCAGCTACCTGGCCATGACCCCCC TGATCCCTCAGAGCAAGGATGAGAACAGCGATGACTACACGACCTTTGATGATGT |
| Ig150 | SEQ ID NO: 594 GGGCAGCCTGTGGACCACCCTGTCCACGTTTGTGGCCCTCTTCATCCTCACCCTCCTCTACAGCG GCATTGTCACTTTCATCAAGGTGAAGTAGCCCCAGAAGAGCAGGACGCCCTGTAC |
| Ig151 | SEQ ID NO: 595 CTGCAGAGAAGGGAAGCAGCCTCTGTACCTCATCTGTGGCTACCAGAGAGCAGAAAGGACCCACC CTGGACTCTTCTGTGTGCAGGAAGATGCGCCAGCCCCTGCCCCCGGCTCCCCTCT |
| Ig152 | SEQ ID NO: 596 GTCCGCCACAGAACCCAGTCTTCTAGACCAGGGGGACGGGCACCCATCACTCCGCAGGCGAATCA GAGCCCCCCTGCCCCGGCCCTAACCCCTGTGCCTCCTTCCCATGCTTCCCCGAGA |
| Ig153 | SEQ ID NO: 597 GCCAGCTACACCCCTGCCCCGGCCCTAACCCCCATGCCTCCTTCCTGTGCTTCCCCCAGAGCCAG CTAGTCCCACCTGCCACCCGCTGGCCTCCCCATAAACACACTTTGGTTCATTTCA |
| Ig154 | SEQ ID NO: 598 GGGGAGTGCATCCGCCCCAACCCTTTTCCCCCTCGTCTCCTGTGAGAATTCCCCGTCGGATACGAG CAGCGTGGCCGTTGGCTGCCTCGCACAGGACTTCCTTCCCGACTCCATCACTTTC |
| Ig155 | SEQ ID NO: 599 TCCTGGAAATACAAGAACAACTCTGACATCAGCAGCACCCGGGGCTTCCCATCAGTCCTGAGAGG GGGCAAGTACGCAGCCACCTCACAGGTGCTGCTGCCTTCCAAGGACGTCATGCAG |
| Ig156 | SEQ ID NO: 600 GGCACAGACGAACACGGTGGTGCAAAGTCCAGCACCCCAACGGCAACAAAGAAAAGAACGTGCC TCTTCCAGTGATTGCTGAGCTGCCTCCCAAAGTGAGCGTCTTCGTCCCACCCCGC |
| Ig157 | SEQ ID NO: 601 GACGGCTTCTTCCGGCAACCCCCGCAAGTCCAAGCTCATCTGCCAGGCCACGGGTTTCAGTCCCG GCAGATTCAGGTGTCCTGGCTGCGCGAGGGGAAGCAGGTGGGGTCTGGCGTCACC |
| Ig158 | SEQ ID NO: 602 ACGGACCAGGTGCAGGCTGAGGCCAAAGAGTCTGGGCCCACGACCTACAAGGTGACCAGCACACT GACCATCAAAGAGAGCGACTGGCTCGGCCAGAGCATGTTCACCTGCCGCGTGGAT |
| Ig159 | SEQ ID NO: 603 CACAGGGGCCTGACCTTCCAGCAGAATGCGTCCTCCATGTGTGTCCCCGATCAAGACACAGCCAT CCGGGTCTTCGCCATCCCCCCATCCTTTGCCAGCATCTTCCTCACCAAGTCCACC |
| Ig160 | SEQ ID NO: 604 AAGTTGACCTGCCTGGTCACAGACCTGACCACCTATGACAGCGTGACCATCTCCTGGACCCGCCA GAATGGCGAAGCTGTGAAAACCCACACCAACATCTCCGAGAGCCACCCCAATGCC |
| Ig161 | SEQ ID NO: 605 AGCGCCGTGGGTGAGGCCAGCATCTGCGAGGATGACTGGAATTCCGGGGAGAGGTTCACGTGCAC CGTGACCCACACAGACCTGCCCTCGCCACTGAAGCAGACCATCTCCCGGCCCAAG |
| Ig162 | SEQ ID NO: 606 GGGGTGGCCTGCACAGGCCCGATGTCTACTTGCTGCCACCAGCCCGGGAGCAGCTGAACCTGCG GGAGTCGGCCACCATCACGTGCCTGGTGACGGGCTTCTCTCCCGCGGACGTCTTC |
| Ig163 | SEQ ID NO: 607 GTGCAGTGGATGCAGAGGGGGCAGCCTTGTCCCCGGAGAAGTATGTGACCAGCGCCCCAATGCC TGAGCCCCAGGCCCCAGGCCGGTACTTCGCCCACAGCATCCTGACCGTGTCCGAA |
| Ig164 | SEQ ID NO: 608 GAGGAATGGAACACGGGGAGACCTACACCTGCGTGGTGGCCCATGAGGCCCTGCCCAACAGGGT CACCGAGAGGACCGTGGACAAGTCCACCGAGGGGGAGGTGAGCGCCGACGAGGAG |
| Ig165 | SEQ ID NO: 609 GGCTTTGAGAACCTGTGGGCCACCGCCTCCACCTTCATCGTCCTCTTCCTCCTGAGCCTCTTCTA CAGTACCACCGTCACCTTGTTCAAGGTGAAATGATCCCAACAGAAGAACATCGGA |
| Ig166 | SEQ ID NO: 610 GACCAGAGAGAGGAACTCAAAGGGCGCTGCCTCCGGGTCTGGGGTCCTGGCCTGCGTGGCCTGT TGGCACGTGTTTCTCTTCCCCGCCCGGCCTCCAGTTGTGTGCTCTCACACAGGCT |
| Ig167 | SEQ ID NO: 611 TCCTTCTCGACCGGCAGGGCTGGCTGGCTTGCAGGCCACGAGGTGGGCTCTACCCCACACTGCT TTGCTGTGTATACGCTTGTTGCCCTGAAATAAATATGCACATTTTATCCATGAAA |
| Ig168 | SEQ ID NO: 612 TGCTGGCCTGCCCACAGGCTCGGGCGGCTGGCCGCTCTGTGTGTGCATGCAAACTAACCGTGTC AACGGGGTGAGATGTTGCATCTTATAAAATTAGAAATAAAAAGATCCATTCAAAA |
| Ig169 | SEQ ID NO: 613 GCCACCCCCTTGGTCACTCTGTTCCCGCCCTCCTCTGAGGAGCTCAAGCCAACAAGGCCATGCT GGTGTGTCTCATAAATGACTTCTACCCAGGAGCCATAGAAGGAAAATGGCACCCT |
| Ig170 | SEQ ID NO: 614 ATGCGGCCAGCAGCTACCTGAGCCTGACGCCCGAGCAGTGGAAGTCCCACAGAAGCTACAGCTGC CAGGTCACGCACAAAGAAAGTACCATGGAGAAGACAATGGCCCATGCAGAATGTT |
| Ig171 | SEQ ID NO: 615 ACAAGGCCACACTGGTGTGTCTCATAAGTGACTTCTACCCGAGAGCCATGACAGTGGCCTGGAAG ATAGATGGCATCACCATCACCCAGGGTGTGGAGACCACCACACCCTCCAAACAGA |
| Ig172 | SEQ ID NO: 616 TATGCGGCCAGCAGCTACCTAAGACTGGCACCCGACAGTGGAAGTCCCACAACCTCTACAGCTGC CAGGTCACGCATGAAAGGAACACTGTGGAGAAGACAGTGGCCCCTGCAGAATGTT |
| Ig173 | SEQ ID NO: 617 GTCAGCCCAAGGCTGCCCCATCGGTCACTCTGTTCCCGCCCTCCTCTGAGGAGCTTCAAGCCAAC AAGGCCACACTGGTGTGCCTGATCAGTGACTTCTACCCGGGAGCTGTGAAAGTGG |
| Ig174 | SEQ ID NO: 618 GCGGCCAGCAGCTAGTACCTGAGCCTGACGCCTGAGCAGTGGAAGTCCCACAGAAGCTACAGTT GCCAGGTCACGCATGAAGGGAGCACCGTGGAGAAGACAGTGGCCCCTGCAGAATG |
| TCR1 | SEQ ID NO: 619 AGGACCTGAACAAGGTGTTCCCACCCGAGGTCGCTGTGTTTGAGCCATCAGAAGCAGAGATCTCC CACACCCAAAAGGCCACACTGGTGTGCCTGGCCACAGGCTTCTTCCCTGACCACG |
| TCR2 | SEQ ID NO: 620 TGGAGCTGAGCTGGTGGGTGAATGGGAAGGAGGTGCACAGTGGGGTCAGCACGGACCCGCAGCCCC CTCAAGGAGCAGCCCGCCCTCAATGACTCCAGATACTGCCTGAGCAGCCGCCTGA |

TABLE 3-continued

| Variable Region Primer | Sequence |
| --- | --- |
| TCR3 | SEQ ID NO: 621 GGGTCTCGGCCACCTTCTGGCAGAACCCCCGCAACCACTTCCGCTGTCAAGTCCAGTTCTACGGG CTCTCGGAGAATGACGAGTGGACCCAGGATAGGGCCAAACCCGTCACCCAGATCG |
| TCR4 | SEQ ID NO: 622 CTCGGTGTCCTACCAGCAAGGGGTCCTGTCTGCCACCATCCTCTATGAGATCCTGCTAGGGAAGG CCACCCTGTATGCTGTGCTGGTCAGCGCCCTTGTGTTGATGGCCATGGTCAAGAG |
| TCR5 | SEQ ID NO: 623 AAAGGATTTCTGAAGGCAGCCCTGGAAGTGGAGTTAGGAGCTTCTAACCCGTCATGGTTTCAATA CACATTCTTCTTTTGCCAGCGCTTCTGAAGAGCTGCTCTCACCTCTCTGCATCCC |
| TCR6 | SEQ ID NO: 624 AATAGATATCCCCCTATGTGCATGCACACCTGCACACTCACGGCTGAAATCTCCCTAACCCAGGG GGACCTTAGCATGCCTAAGTGACTAAACCAATAAAAATGTTCTGGTCTGGCCTGA |
| TCR7 | SEQ ID NO: 625 AGGACCTGAAAAACGTGTTCCCACCCAAGGTCGCTGTGTTTGAGCCATCAGAAGCAGAGATCTCC CACACCCAAAAGGCCACACTGGTGTGCCTGGCCACAGGCTTCTACCCCGACCACG |
| TCR8 | SEQ ID NO: 626 TGGAGCTGAGCTGGTGGGTGAATGGGAAGGAGGTGCACAGTGGGGTCAGCACAGACCCGCAGCCC CTCAAGGAGCAGCCCGCCCTCAATGACTCCAGATACTGCCTGAGCAGCCGCCTGA |
| TCR9 | SEQ ID NO: 627 GGGTCTCGGCCACCTTCTGGCAGAACCCCCGCAACCACTTCCGCTGTCAAGTCCAGTTCTACGGG CTCTCGGAGAATGACGAGTGGACCCAGGATAGGGCCAAACCTGTCACCCAGATCG |
| TCR10 | SEQ ID NO: 628 ACCTCCGAGTCTTACCAGCAAGGGGTCCTGTCTGCCACCATCCTCTATGAGATCTTGCTAGGGAA GGCCACCTTGTATGCCGTGCTGGTCAGTGCCCTCGTGCTGATGGCCATGGTCAAG |
| TCR11 | SEQ ID NO: 629 AGAAAGGATTCCAGAGGCTAGCTCCAAAACCATCCCAGGTCATTCTTCATCCTCACCCAGGATTC TCCTGTACCTGCTCCCAATCTGTGTTCCTAAAAGTGATTCTCACTCTGCTTCTCA |
| TCR12 | SEQ ID NO: 630 TCTCCTACTTACATGAATACTTCTCTCTTTTTTCTGTTTCCCTGAAGATTGAGCTCCCAACCCCC AAGTACGAAATAGGCTAAACCAATAAAAAATTGTGTGTTGGGCCTGGTTGCATTT |
| TCR13 | SEQ ID NO: 631 ATATCCAGAACCCTGACCCTGCCGTGTACCAGCTGAGAGACTCTAAATCCAGTGACAAGTCTGTC TGCCTATTCACCGATTTTGATTCTCAAACAAATGTGTCACAAAGTAAGGATTCTG |
| TCR14 | SEQ ID NO: 632 ATGTGTATATCACAGACAAAACTGTGCTAGACATGAGGTCTATGGACTTCAAGAGCAACAGTGCT GTGGCCTGGAGCAACAAATCTGACTTTGCATGTGCAAACGCCTTCAACAACAGCA |
| TCR15 | SEQ ID NO: 633 TTATTCCAGAAGACACCTTCTTCCCCAGCCCAGAAAGTTCCTGTGATGTCAAGCTGGTCGAGAAA AGCTTTGAAACAGATACGAACCTAAACTTTCAAAACCTGTCAGTGATTGGGTTCC |
| TCR16 | SEQ ID NO: 634 GAATCCTCCTCCTGAAAGTGGCCGGGTTTAATCTGCTCATGACGCTGCGGCTGTGGTCCAGCTGA GATCTGCAAGATTGTAAGACAGCCTGTGCTCCCTCGCTCCTTCCTCTGCATTGCC |
| TCR17 | SEQ ID NO: 635 ACAGAGGGAACTCTCCTACCCCCAAGGAGGTGAAAGCTGCTACCACCTCTGTGCCCCCCCGGCAA TGCCACCAACTGGATCCTACCCGAATTTATGATTAAGATTGCTGAAGAGCTGCCA |
| TCR18 | SEQ ID NO: 636 AACACTGCTGCCACCCCCTCTGTTCCCTTATTGCTGCTTGTCACTGCCTGACATTCACGGCAGAG GCAAGGCTGCTGCAGCCTCCCCTGGCTGTGCACATTCCCTCCTGCTCCCCAGAGA |
| TCR19 | SEQ ID NO: 637 CTGCCTCCGCCATCCCACAGATGATGGATCTTCAGTGGGTTCTCTTGGGCTCTAGGTCCTGCAGA ATGTTGTGAGGGGTTTATTTTTTTTAATAGTGTTCATAAAGAAATACATAGTAT |
| TCR20 | SEQ ID NO: 638 TCTTCTTCTCAAGACGTGGGGGGAAATTATCTCATTATCGAGGCCCTGCTATGCTGTGTATCTGG GCGTGTTGTATGTCCTGCTGCCGATGCCTTCATTAAAATGATTTGGAAGAGCAGA |
| Blocking Oligonucleotides | |
| Read1 and poly(T) | SEQ ID NO: 639 CTACACGACGCTCTTCCGATCTNNNNNNNNNNNNNNNNNNNNNNNNNNNNNTTTTTTTTTTTTTT TTTTTTTTTTTTTTVN |
| Blocking Template Switching Oligonucleotide | SEQ ID NO: 640 CCCATGTACTCTGCGTTGATACCACTGCTT |

Variable Region Primer

After PCR enrichment, the PCR product was purified before the PCR indexing reaction. Quant-iT (ThermoFisher Scientific) analysis measured the DNA concentration of each sample, which was also normalized to the input material in the PCR indexing reaction (1.25 ng/reaction). Indexing PCR was performed as previously described (Stahl, P. L., et al., Visualization and analysis of gene expression in tissue sections by spatial transcriptomics, *Science*, 353(6294), 78-82, (2016)). In total, 24 unique indexes were used, with each cDNA library receiving a unique index (TRB, IGHG, and IGHM products from the same cDNA library received the same indexing since the TCR and BCR clonotypes can be distinguished from each other bioinformatically using the constant primer sequence). After purification, PCR reactions were pooled. The pooled PCR library was run on a gel and a large band at around 500 bp excised was gel-purified and sequenced (NovaSeq, 2×150 bp). The resulting data were de-multiplexed and the FastQ files were analyzed using MiXCR (Bolotin, D. A., et al., MiXCR: software for comprehensive adaptive immune profiling, *Nature Methods*, 12, 380-381 (2015), which is incorporated herein by reference in its entirety).

After PCR variable region primer enrichment, a number of TRB and IGH clonotypes in all prepared libraries were detected. For TRB, about 10,000 unique clonotypes were detected in spatial libraries prepared from tonsil tissue (data not shown) and between about 12,000 and about 25,000 unique clonotypes were detected in spatial libraries prepared from lymph node (data not shown). The positive control (SmartSeq2 RNAseq after PCR enrichment) yielded about 35,000 unique clonotypes. Variable region primer enrichment of the Smartseq2 library increased the TRB unique clonotype count over 35-fold, however, the SmartSeq2 library contained RNA extracted from two tonsil sections, whereas only a single tissue section was used for the spatial samples.

Figure 8:
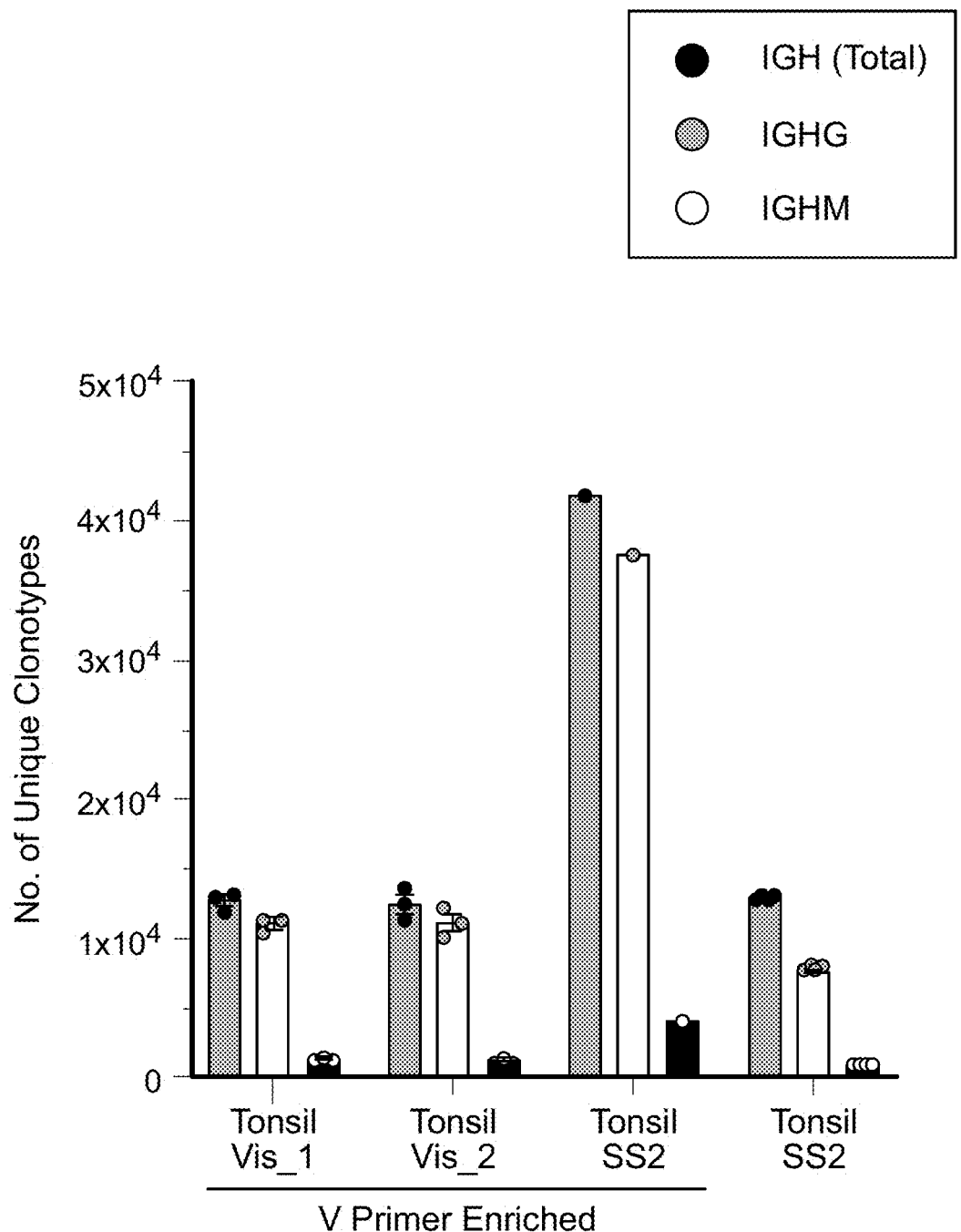
FIG. 8 shows an exemplary graph of the number of unique IG clonotypes detected in tonsil tissue on a spatial array (Vis) compared with single cell (SS2) analysis, with or without an enrichment strategy.
Figure 9:
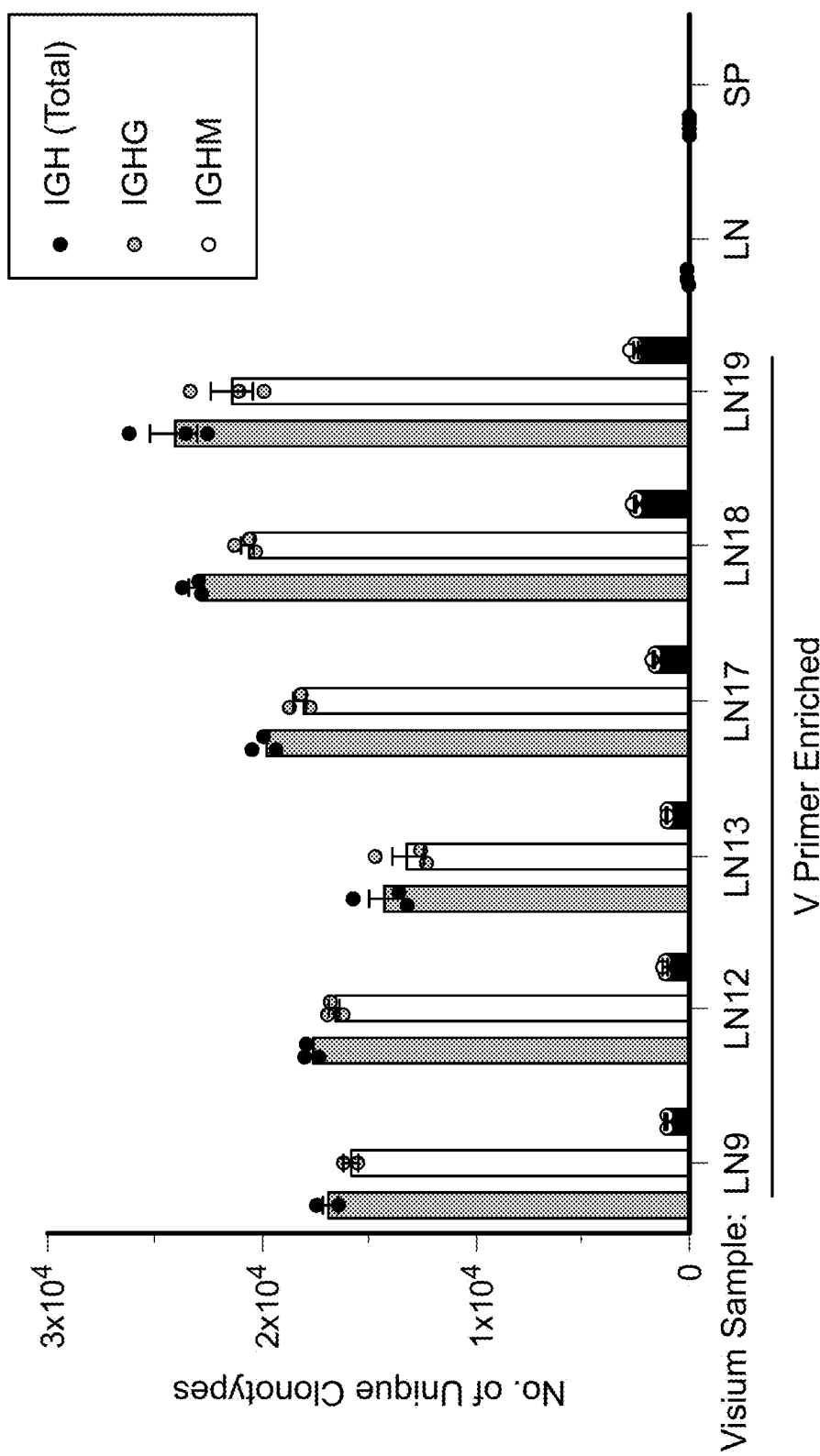
FIG. 9 shows an exemplary graph of the number of unique IG clonotypes detected in lymph node (LN) tissue on a spatial array with and without an enrichment strategy. Lymph node and spleen (SP) non-enrichment samples serve as controls.

Similar results were observed for IGH detection with about 10,000 unique clonotypes detected from spatial libraries prepared from tonsil (FIG. 8) and between about 12,000 and about 25,000 unique clonotypes detected from spatial libraries prepared from the lymph node (FIG. 9). FIGS. 8 and 9 also shows the number of unique clonotypes found in non-enriched samples (far right) and the data show the number of unique clonotypes found is less than the V primer enriched samples. Approximately 10-fold higher IGHG clonotypes were detected relative to IGHM clonotypes similar to previous results for the SmartSeq2 RNAseq libraries (data not shown).

Variable region primer enrichment also resulted in a 4-fold increase in detected clonotypes for single-cell Smart-Seq2 libraries. The clonotype increase observed after PCR variable primer enrichment of TRB relative to IGH is consistent with a known lower abundance of TRB transcripts in the cDNA library. For example, it is known that TRA/TRB transcript expression per T-cell is less relative to IGH/IGK/IGL expression per B-cell, and in particular, for plasma cells. Substantial, but not complete overlap, of IGH clonotypes between technical replicates detected in spatial libraries from tonsil tissue was observed. Similarly, substantial, but not complete, overlap of TRB clonotypes between technical replicates detected in spatial libraries from tonsil tissue was also observed. The data show that approximately half the clonotypes from a given technical replicate were detected in at least one or more of the other two technical replicates, which suggests many clonotypes were detected in a given technical replicate, but not all clonotypes were detected in each sample (data not shown). Approximately 10-20 fold increase in clonotype counts were detected with a poly(T) capture domain combined with PCR variable region primer enrichment relative to targeted capture, without variable region primer enrichment.

Collectively, these data show that PCR primer enrichment of analytes encoding immune cell receptors captured by poly(A) capture domains is possible. The use of a poly(A) capture domain allows for the simultaneous capture of analytes that do not encode for immune cell receptors and also does not require a custom array with targeted capture domains.

Figure 10B:
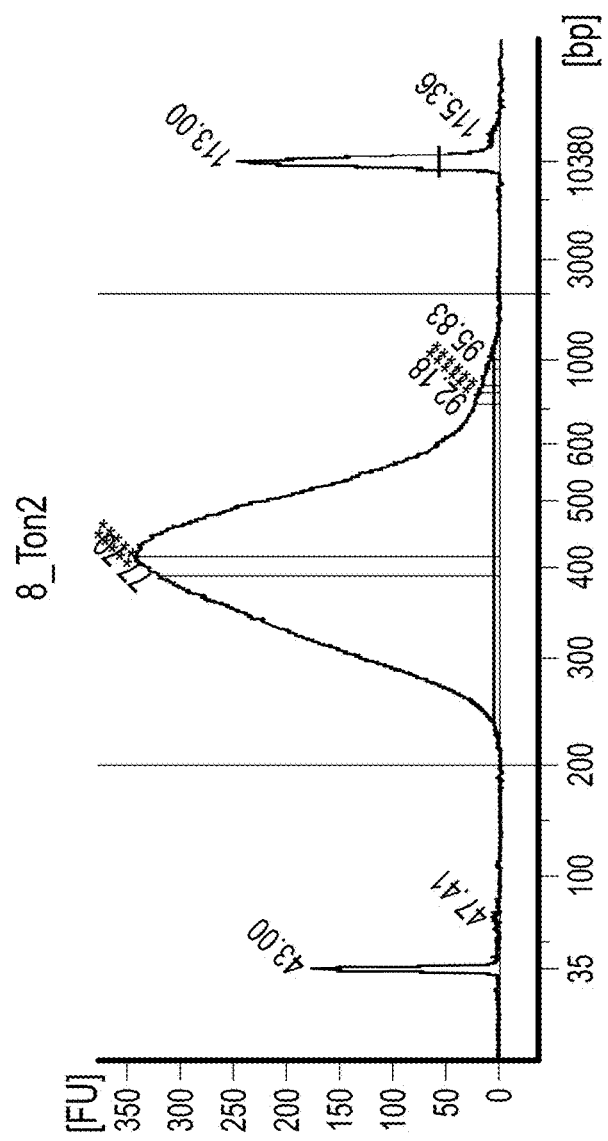
FIG. 10B shows a gene expression library generated from the tonsil tissue in FIG. 10A.
Figure 10A:
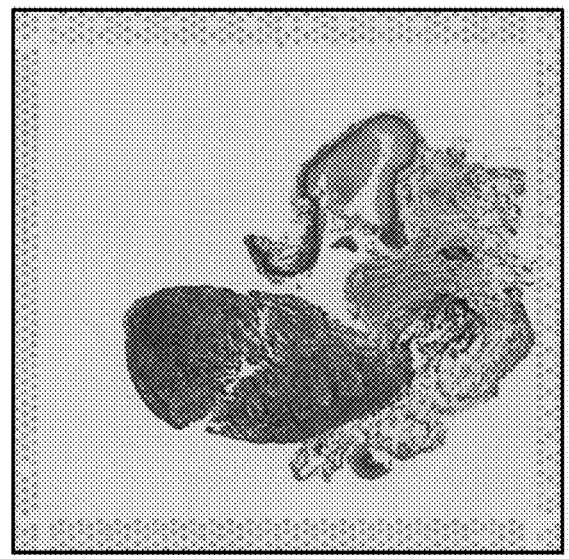
FIG. 10A shows H&E stained tonsil tissue.

FIG. 10A shows H&E stained tonsil tissue on a spatial array and FIG. 10B shows the size distribution of spatial libraries prepared from tonsil tissue. The data shown in FIGS. 10A-B show the stained tonsil tissue and size distribution of the spatial libraries of the data included in this Example. Similar H&E staining was performed on breast tumor tissue on a spatial array and size distribution of spatial libraries were also prepared from breast tumor tissue (data not shown). FIG. 11 shows clustering of B-cells and T-cells from the single-cell analysis performed in this Example. FIG. 11 shows that while identifying populations of cells that include immune cell receptors, there is no connection to the spatial location of those cells within a biological sample. FIG. 11 shows a single-cell analysis which is not designed to be a spatial representation of immune cells within a biological sample.

Example 3—Enrichment of Analytes Encoding Immune Cell Receptors

Figure 2:
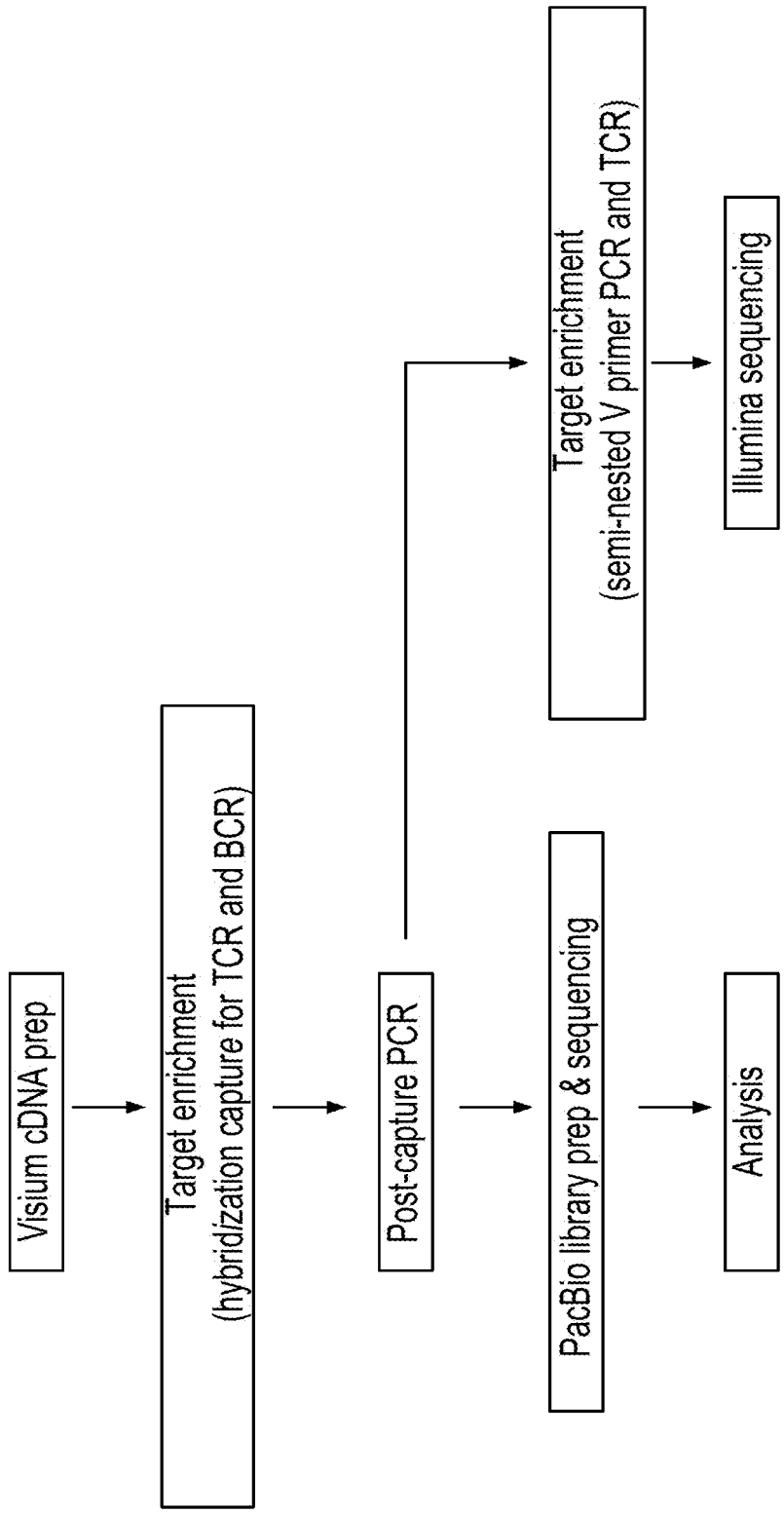
FIG. 2 shows an exemplary workflow for spatial transcriptomics for antigen-receptors.

FIG. 2 shows an exemplary workflow for the enrichment of T-cell receptor (TCR) analytes and B-cell receptor (BCR) analytes after capture on a spatial array. After capture of analytes (e.g., TCR and BCR analytes) cDNA is synthesized, followed by target enrichment and either library preparation and sequencing or further target enrichment via a semi-nested PCR for TCR analytes followed by ILLUMINA® (sequencing technology) sequencing and finally analysis.

Preparation of Visium Spatial Gene Expression Libraries

Sections of fresh-frozen breast tumor and tonsil tissue were sliced to 10 μm thickness and mounted onto slides from the Visium Spatial Gene Expression Slide & Reagent kit (10×Genomics®). Sequencing libraries were prepared following the manufacturer's protocol (Document number CG000239 Rev A, 10× Genomics®). Prior to imaging, coverslips were mounted on the slides according to the protocol's optional step "Coverslip Application & Removal". Tissue images were taken at 20× magnification using a Metafer Slide Scanning platform (MetaSystems) and raw images were stitched with VSlide software (MetaSystems). Adaptions of the protocol were made in that the Hematoxylin and Eosin (H&E) staining time was reduced to 4 minutes and tissue permeabilization was performed for 12 minutes.

Sequencing and data processing of Visium Spatial Gene Expression Libraries

Final sequencing libraries were sequenced on NextSeg™ 2000 (sequencer) (ILLUMINA® (sequencing technology)) with a 28-10-10-150 setup (tonsil), or NovaSeq6000 (ILLUMINA® (sequencing technology)) with a 28-10-10-120 setup (breast tumor). 172M and 93M raw read pairs were obtained from tonsil-1 and tonsil-2, respectively, and 215M and 244M from breast tumor 1 and breast tumor 2, respectively.

Following demultiplexing of the bcl files, read 2 fastq files were trimmed using Cutadapt (Martin, M., Cutadapt removes adapter sequences from high-throughput sequencing reads, *EMBnet Journal*, 17(1) (2011)) to remove full-length or truncated template switch oligo (TSO) sequences from the 5' end (e.g., beginning of Read 2) and poly(A) homopolymers from the 3' end (e.g., end of read 2). The TSO sequence (SEQ ID NO: 114) (AAGCAGTGGTAT-CAACGCAGAGTACATGGG) was used as a non-internal 5' adapter with a minimum overlap of 5, meaning that partial matches (up to 5 base pairs) or intact TSO sequences were removed from the 5' end. The error tolerance was set to 0.1 for the TSO trimming to allow for a maximum of 3 errors. For the 3' end homopolymer trimming, a sequence of 10 As was used as a regular 3' adapter to remove potential polyA tail products regardless of its position in the read, also with a minimum overlap of 5 base pairs. The trimmed data was processed with the SpaceRanger pipeline (10× Genomics®), version 1.2.1 (tonsil) and version 1.0.0 (BC) and mapped to the GRCH38 v93 genome assembly.

Target Enrichment with Hybridization Capture

TCR and BCR target enrichment was performed using IDT xGen Hybridization and Wash Kit (#1080584) with one enrichment probe pool (IDT) each for BCR and TCR transcripts (IG and TCR pool, Table 3). Custom blocking oligos (IDT, Table 3) were designed to hybridize to adaptor sequences of the cDNA library and to prevent off-target fragments from binding to BCR/TCR transcripts and contaminating the enriched library. The IG and TCR enrichment probe pools were mixed at ratio 1:3 and 1:12, respectively and each sample was enriched using both settings.

The "xGen hybridization capture of DNA libraries", version 4 (IDT) protocol was followed with an input of 10 μl Visium cDNA per reaction, corresponding to between about 45-130 ng and the hybridization enrichment reaction was performed overnight. The enriched and purified libraries were amplified twice with an AMPure bead wash after each PCR reaction, using 25 μl 2×KAPA mix, 7.5 μl cDNA primers (10× Genomics®) and 17.5 μl sample in MQ water. The following settings were used for the PCRs: 1. 98° C. 3 min; 2. 98° C. 15 sec; 3. 63° C. 30 sec; 4. 72° C. 2 min; 5. Repeat steps 2-5 6× for a total of 7 cycles (1st PCR) and 4× for a total of 5 cycles (2nd PCR); 6. 72° C. 1 min Library Preparation and Sequencing The resulting product from the hybridization enrichment capture method was used as input into the SMRTbell library preparation protocol (PacBio). The DNA was concentrated by AMPure Bead Purification (0.8×), eluting in 6 μl of Elution Buffer, using 1 μl for Qubit measurements. At least 1 μg of input was used for each library and multiplexed 8 samples in total per sequencing run. PacBio Barcoded Overhand Adapters was used for multiplexing and followed the manufacturer's instructions for the library preparations. The pooled library had a concentration of 11.4 ng/μl (50 μl total eluted volume). A SMRT Enzyme clean up kit was used to remove linear and single stranded DNA. The final libraries were sequenced at 2.7 million long read sequences (168-422K reads/sample) on a Sequel II at the National Genomics Infrastructure (NGI)/Uppsala Genome Center.

Sequencing Data Analysis

The input for the analysis was de-multiplexed consensus reads obtained from PacBio sequencing and performed with Python programming language. The fastq files were parsed into a dataframe with readID, sequence and quality columns. Data was searched for the Truseq adapter sequence and the TSO sequence to anchor the ends of each of the reads, and reads that lacked these sequences were discarded. A portion of the Truseq adapter starting in the first seven bases of either the read or its reverse complement was identified. If any of the positions matched the sequence with hamming distance 1 or less they were tagged. The same was performed for a portion of the TSO sequence. The sequences were reverse complemented as needed so that all the reads had the Truseq adapter (SEQ ID NO: 115) at the beginning and the TSO (SEQ ID NO: 114) at the end. The spatial barcode and the UMI were identified. The first 16 bases were obtained following the TruSeq adapter to determine the spatial barcode and subsequent bases determined the unique molecular identifier (UMI). Additionally, following the sequence of the UMI at least 4 bases were identified as all thymines (e.g., the poly(dT) capture domain) and filtered out of the reads that had any other bases within that interval. Any read with a UMI identified as a poly(dT) sequence was removed. The end of poly(dT) region is defined as the first matching position for the pattern '[^T]T{0,2}[^T]T{0,2}[^T]'.

Clonality Analysis and Visualization

To run MIXCR (version 3.0.3), poly(dT) and TSO sequences were trimmed and the reads were written to a new fastq file. The reads were analyzed with MIXCR and the following command:

'mixcr analyze shotgun-s hsa—alignOsaveOriginalReads=true—starting-material rna<TrimmedFastq><SampleName>'

The following MIXCR command was performed to report alignments for each read:

'mixcr exportAlignments-f-cloneIdWithMappingType-cloneId-readIds-descrsR1<SampleName>.clna <ReportFile>'

The resulting tabular file was used to assign reads to the clonotypes in MIXCR output. Any reads that did not map to any clone were filtered out (cloneID=-1), then the reads were grouped in a table by the spatial barcode and UMI and counted how many reads were present and how many clones were associated with each UMI. UMIs that were assigned to more than one clonotype were filtered out, since they are likely due to PCR or sequencing errors.

The resulting clonotype count matrices were subsequently loaded into R (R Core Team, A language and environment for statistical computing, *R Foundation for Statistical Computing*, (2017)). Tissue images, spatial coordinates and total gene expression counts obtained through the Visium platform and SpaceRanger pipeline were also loaded, and one Seurat object (Stuart et al. Comprehensive Integration of Single-Cell Data, *Cell,* 177(7) (2019)) per sample type (tonsil and breast tumor tumor) was created using the STutility package (Bergenståhle et al., Seamless integration of image and molecular analysis for spatial transcriptomics workflows, *BMC Genomics,* 21(1), (2020)). The clonotype count matrix was extended by adding any missing spatial barcodes that were present in the total gene expression count matrix, and filled with zero counts for all added barcodes. The new, extended matrix was loaded as a new assay into the Seurat object, where genes and clonotypes were visualized on the tissue images using built-in functions of the STUtility package.

Cell Processing for Single-Cell RNA Sequencing

Single cell suspensions from five breast tumor regions (Tumor A-E) were prepared by enzymatic tissue dissociation using the human Tumor Dissociation Kit (Miltenyi Biotec, 130-095-929) and gentleMACS dissociator (Miltenyi Biotec). Cell suspensions were stained with the Zombie Aqua Fixable viability dye (Biolegend, 423101) at room temperature for 20 minutes, then washed with Phosphate Buffered Saline (PBS). The cells were incubated with Human TruStain Fc block (Biolegend, 422302) for 10 minutes to limit non-specific antibody binding, then stained for 20 minutes with anti-EPCAM (1:40, Biolegend, 324206) and anti-CD45 (1:40, Biolegend, 304021) in FACS buffer (PBS+0.5% Bovine Serum Albumin). The cells were subsequently washed and resuspended in FACS buffer. Fluorescence-activated cell sorting (FACS) using an influx flow cytometer (BD Biosciences) was performed to sort live EPCAM+ CD45+ single cells an Eppendorf tube for 10× Genomics® Chromium Single Cell gene expression analysis. Single stain controls (e.g., cells and beads) and fluorescence minus one controls (FMO), containing all the fluorochromes in the panel except the one being measured, were used to set voltages and to define the proper gating strategy.

10× Genomics® Chromium Single-Cell Library Preparation and Sequencing

Single-cell gene expression and VDJ clonotype libraries were generated from EPCAM-CD45+ cells using the 10× Genomics® Chromium Single Cell 5' assay following the manufacturer's instructions. Libraries were profiled and quantified using a Bioanalyzer High Sensitivity DNA kit (Agilent Technologies) and Qubit High sensitivity kit (Thermo Fischer Scientific). Final single-cell gene expression libraries were sequenced (aiming for at least 30,000 reads per cell) on a NovaSeq 6000 SP flowcell (ILLUMINA® (sequencing technology) 150-8-8-150 read set-up) by the National Genomics Infrastructure, SciLifeLab.

Single-Cell Gene Expression and VDJ Data Processing

Sequencing outputs were processed by Cell Ranger (version 5.0, 10×Genomics®). Gene-barcode count matrices were analyzed with the Seurat package (version 4.0, Satija Lab). Two steps of filtering were introduced here. First, raw gene expression matrices were subset by the barcode list in VDJ output, including T cell subsets and B cell subsets. Based on the UMI count, gene count, and mitochondrial percentage of raw gene expression matrices and their subsets, each threshold was selected to keep the maximum count of high-quality cells and avoid losing T and B cells which have VDJ sequencing outputs. Second, doublets in each sample were detected and filtered out by HTODemux() function in Seurat. All samples were integrated and scaled into one count matrix by Seurat. Dimension reduction, UMAP generation, and clustering, were performed on the merged dataset by Seurat. The merged dataset was clustered by a gradient of the resolution, from 0.2 to 2. The final resolution was determined by the significance of top-listed differentially expressed genes in each cluster. Cell types were annotated by differentially expressed genes and their marker genes expression level. All dimension reduction and annotation results, along with the VDJ output files were imported into Loupe Browser (version 5.0, 10× Genomics®) and Loupe VDJ Browser (version 4.0, 10× Genomics®) for interactive analysis.

Semi-Nested PCR

After hybridization capture and post-capture PCR amplification (14 cycles), semi-nested PCR reactions were performed with the following primers: V primers targeting either the TRAV or TRBV genes, 5' of the CDR3 region (i.e. 'Outer' TRAV or TRBV primers, see Table 3 for sequences) and a primer ('partRead1', see Table 3) targeting the universal partial read 1 sequence present on the transcripts in Visium cDNA libraries. PartRead1 is also compatible with TruSeq indexes to allow multiplexing of samples for sequencing. For the semi-nested PCR experiments, the Visium cDNA was further pre-amplified prior to hybridization capture to generate more input needed for testing. The Outer V primer PCR input was 1-5 ng of hybridization captured cDNA from two breast tumor tissue Visium libraries (replicate, adjacent sections) and the reaction was run with KAPA HiFi HotStart ReadyMix (2×) (KAPA Biosystems). All primers were diluted 40× for a final concentration of 2.5 µM (Integrated DNA Technologies). The PCR was run for 15 cycles under the following conditions: 1. 98° C. 5 min; 2. 98° C. 20 sec; 3. 65° C. 30 sec; 4. 72° C. 1:30 min; 5. Repeat steps 2-5 14× for a total of 15 cycles; and 6. 72° C. 7 min.

Quantitative real-time PCR (qPCR) was performed to determine the appropriate number of cycles (to avoid exponential amplification). The Outer V primer PCR product was purified using AMPure beads (0.6×), followed by two 80% EtOH washes. The Outer V primer PCR product was eluted in EB buffer after incubation at 15 min at 37° C. The cleaned up PCR product was quantified using Qubit and BioAnalyzer (Agilent). 3-5 ng of each PCR product was used as input to the subsequent Inner V primer PCR.

The Inner V primer PCR was performed with the following primers: V primers targeting either the TRAV or the TRBV gene, close/adjacent to the CDR3 region (e.g., 'Inner' V primers) and the same universal partial read 1 primer as described for the Outer V primer PCR ('partRead1'). These Inner V primers have a handle compatible with TruSeq indexing. The primer concentrations and reagents were as described for the OUTER V primer PCR. qPCR was used to determine the optimal number of cycles (7). The following conditions were used for the PCR reaction: 7. 98° C. 5 min; 8. 98° C. 20 sec; 9. 72° C. 30 sec; 10. 72° C. 1:30 min; 11. Repeat steps 2-5 14× for a total of 15 cycles; 12. 72° C. 7 min.

The same AMPure bead-clean up and ethanol washes were performed as described above. The final eluted PCR product was quantified using Qubit and BioAnalyzer (Agilent). The samples were PCR indexed using TruSeq Indexes (5 cycles) and sequenced on a Novaseq sequencing instrument using a short read 1 and a longer read 2 to capture the entire CDR3 region and part of the constant region from the 5' end.

Target Enrichment with Hybridization Capture for TCR and BCR Sequences

Figure 12:
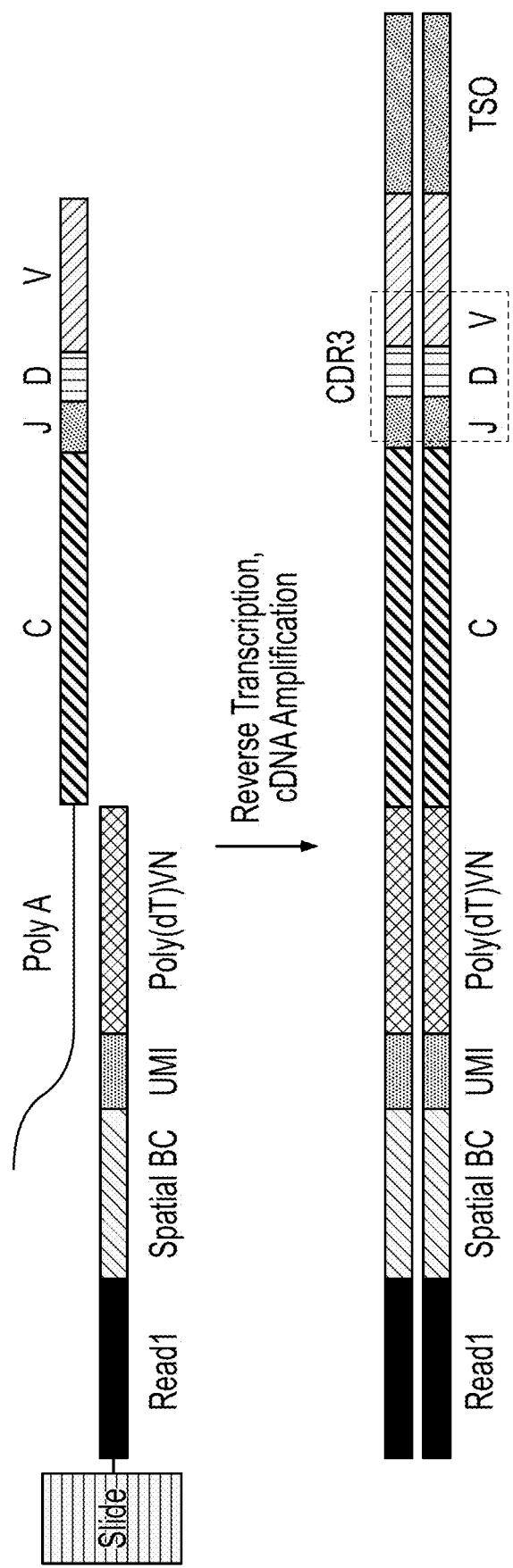
FIG. 12 shows an exemplary capture probe with a poly (dT) capture domain (top) followed by reverse transcription to generate cDNA of an analyte.
Figure 13:
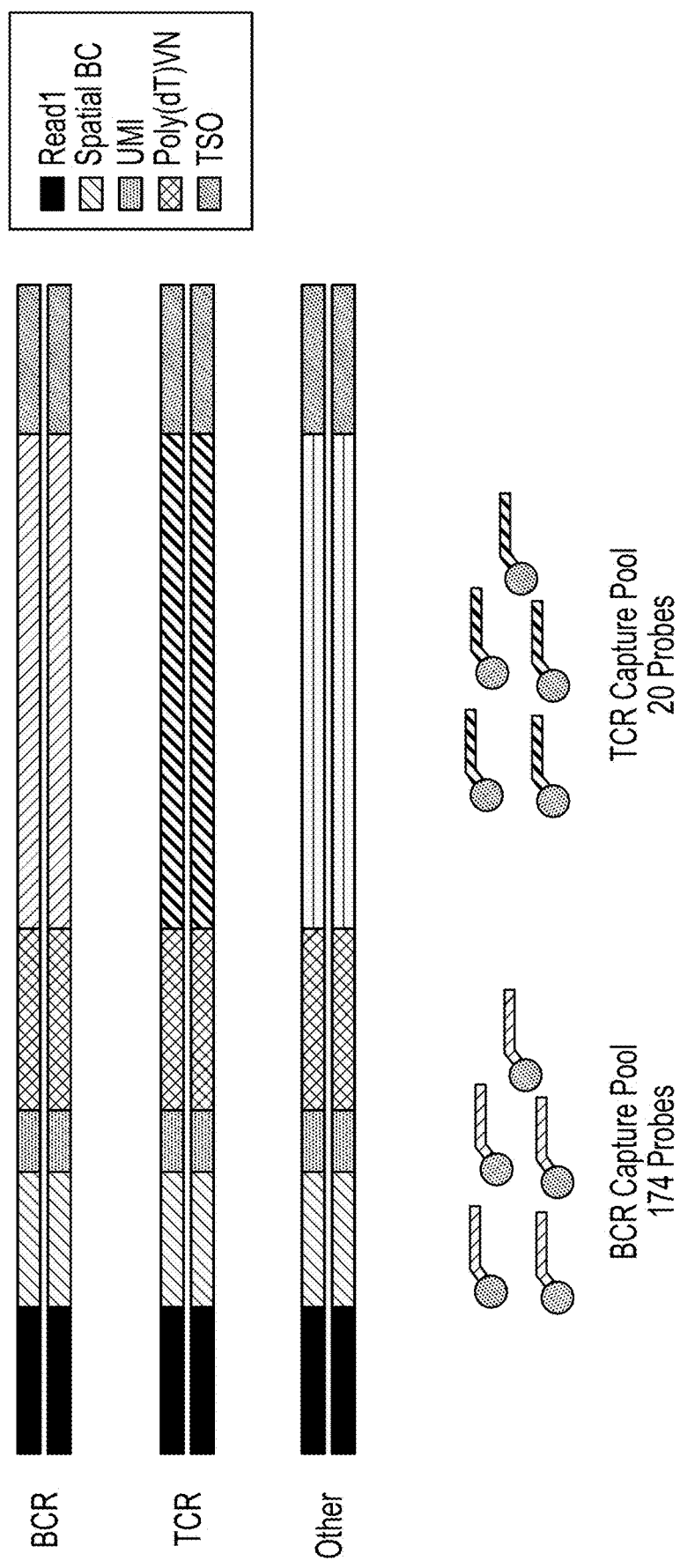
FIG. 13 shows cDNA libraries for either B-cell receptors (BCR), T-cell receptors (TCR), or other analytes and pools of BCR and TCR with enrichment hybridization probes.
Figure 14:
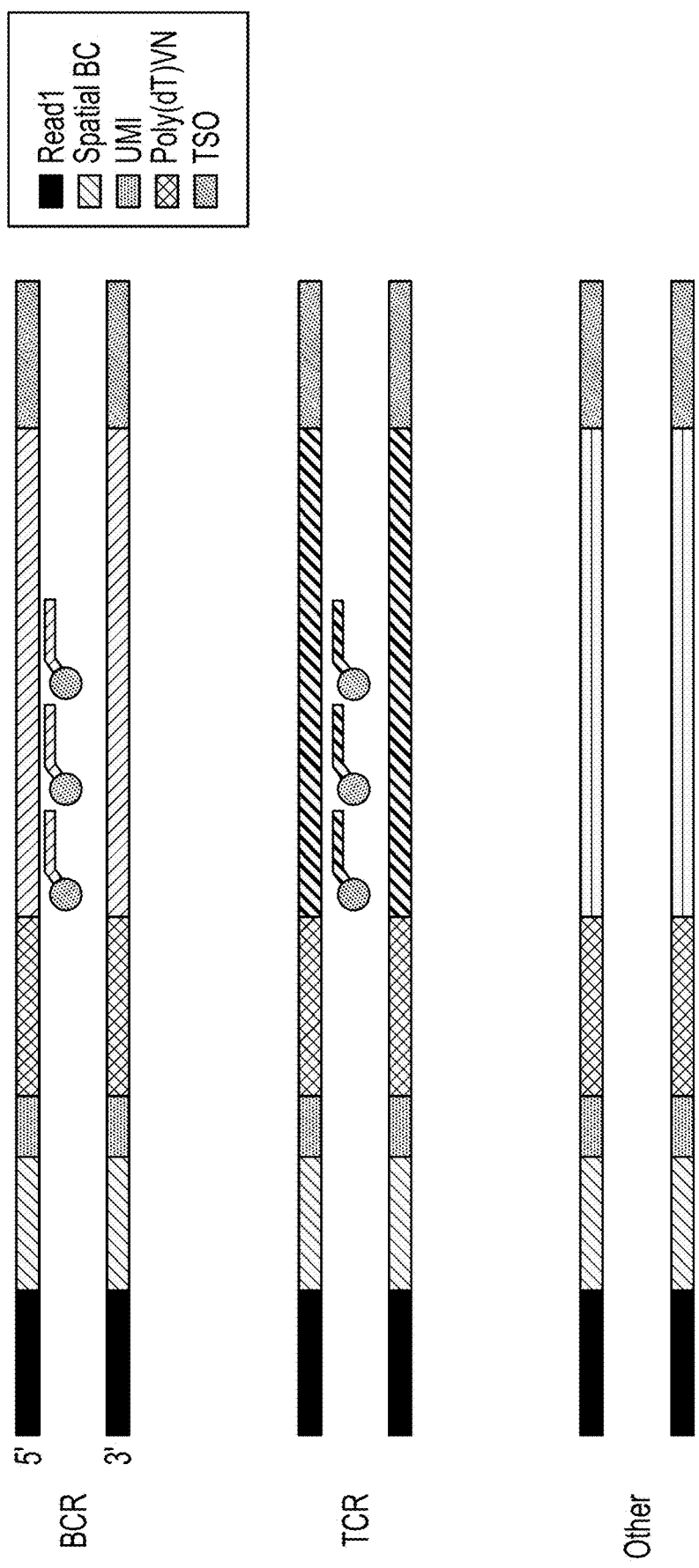
FIG. 14 shows hybridization of the BCR and TCR specific enrichment hybridization probes to their respective targets in the cDNA library.
Figure 15:
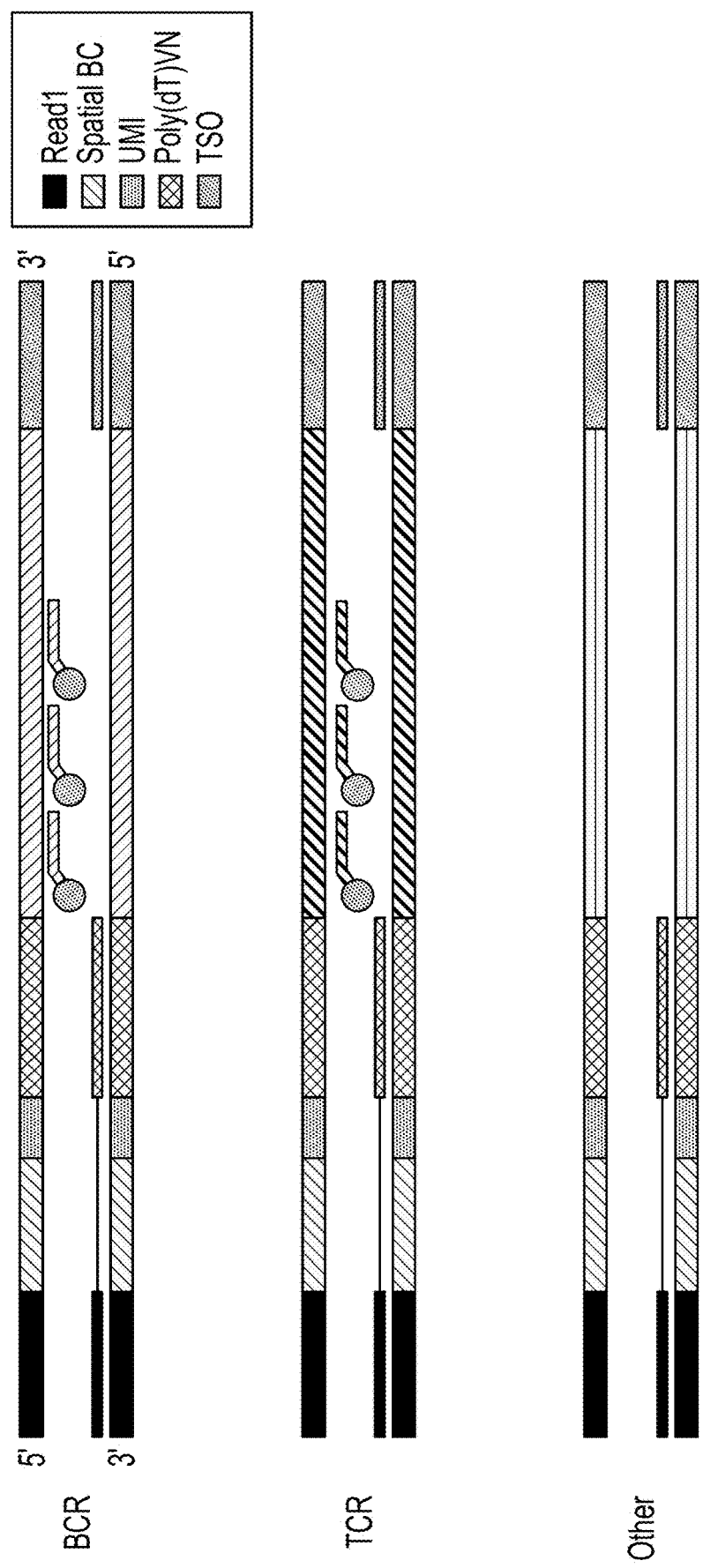
FIG. 15 shows hybridization of blocking oligonucleotides targeting various domains present in the cDNA library.

As discussed above BCR (IGH, IGK, IGL) and TCR (TRA, TRB) clones can be amplified using PCR from poly(dT) captured cDNA libraries, e.g., Visium (10×Genomics®). In some instances, the obtained amplicons lacked the spatial barcode. Therefore, to enrich for TCR and BCR sequences while preserving the spatial barcode and the CDR3 clonal information, a target enrichment strategy with hybridization probes (IDT technologies) was tested. Manufacturer's instructions were followed with some minor adaptations according to the methods described above. Visium cDNA from two tonsil sections (e.g., from the same tonsil, spaced 150 µM apart) were used as input material. FIG. 12 shows poly(A) capture with a poly(T) capture domain. A poly(T) capture domain can capture other mRNA analytes from a tissue, including mRNA analytes encoding immune cell receptors, however, immune cell analytes were enriched using a hybridization enrichment probe strategy. BCR hybridization probes (n=174) were designed to span all BCR constant genes (e.g., IGH, IGL, IGK), see Table 3. Similarly, TCR hybridization probes (n=20) were designed to target the TCR constant genes (e.g., TRA, TRB), see Table 3. FIG. 13 shows an exemplary cDNA library that would include BCR, TCR, other analytes and a pool of hybridization probes specific for BCR and TCR analytes. The Visium cDNA samples were hybridized with the hybridization enrichment capture probes and the hybridization reaction was performed overnight (FIG. 14), in the presence of blocking oligos as shown in FIG. 15 targeting Read 1, Poly(dT)VN, and TSO sequences present on the transcripts in the cDNA library. After a series of washes, a post-capture PCR reaction was performed, which amplifies all, or a portion of, the captured analyte pool. Indexed PacBio libraries were prepared for long read sequencing from the eluted PCR products. To avoid unnecessary PCR cycles, which can introduce artifacts, errors, and chimeric fragments, barcoded overhang adapter ligation was performed to add unique sample indexes to each sample. The enriched libraries were then sequenced, de-multiplexed, and analyzed.

Figure 16A:
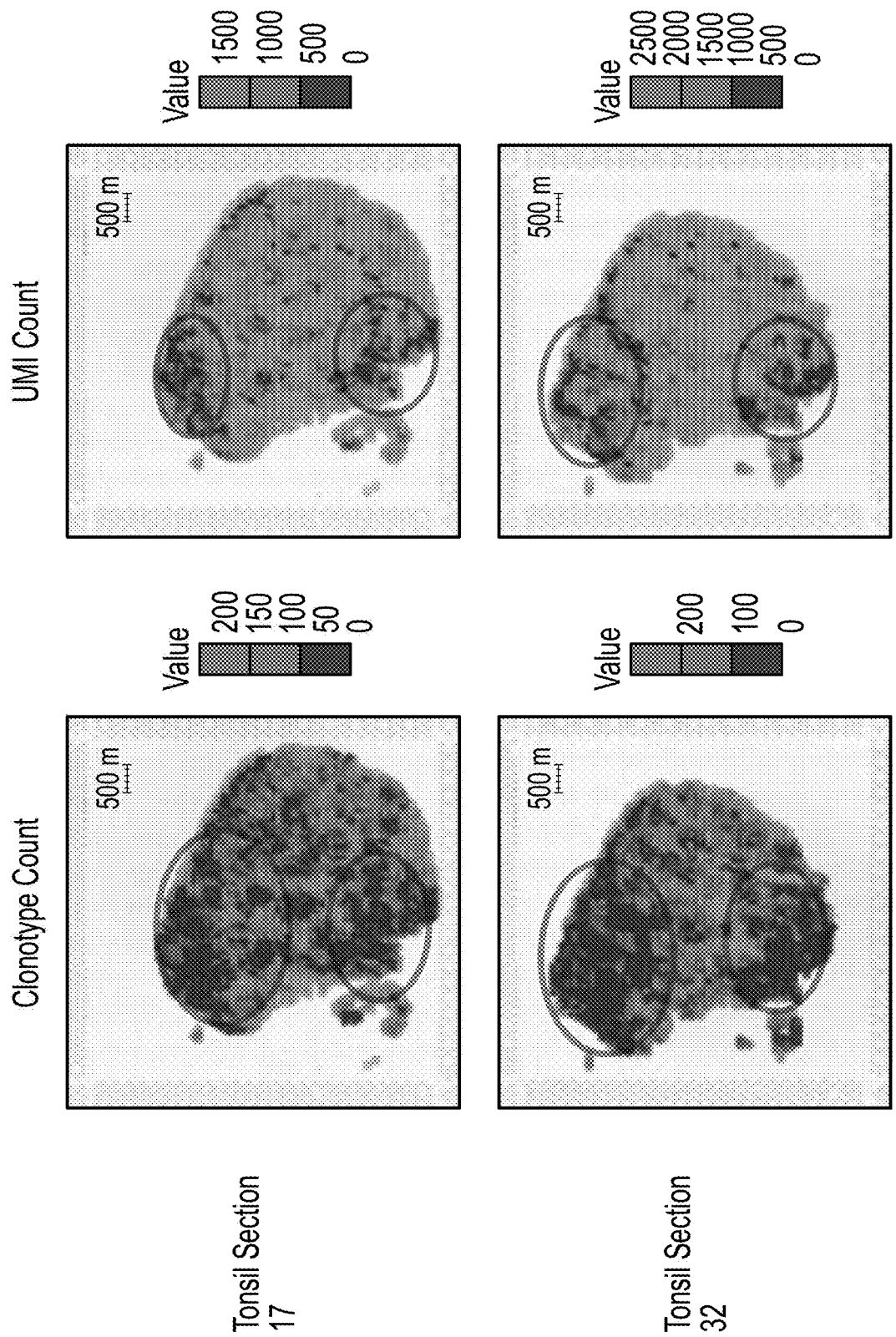
FIG. 16A shows replicate tonsil sections (top and bottom) and detection of BCR and TCR clonotype count (left) and BCR and TCR unique molecular identifier count (right).
Figure 16B:
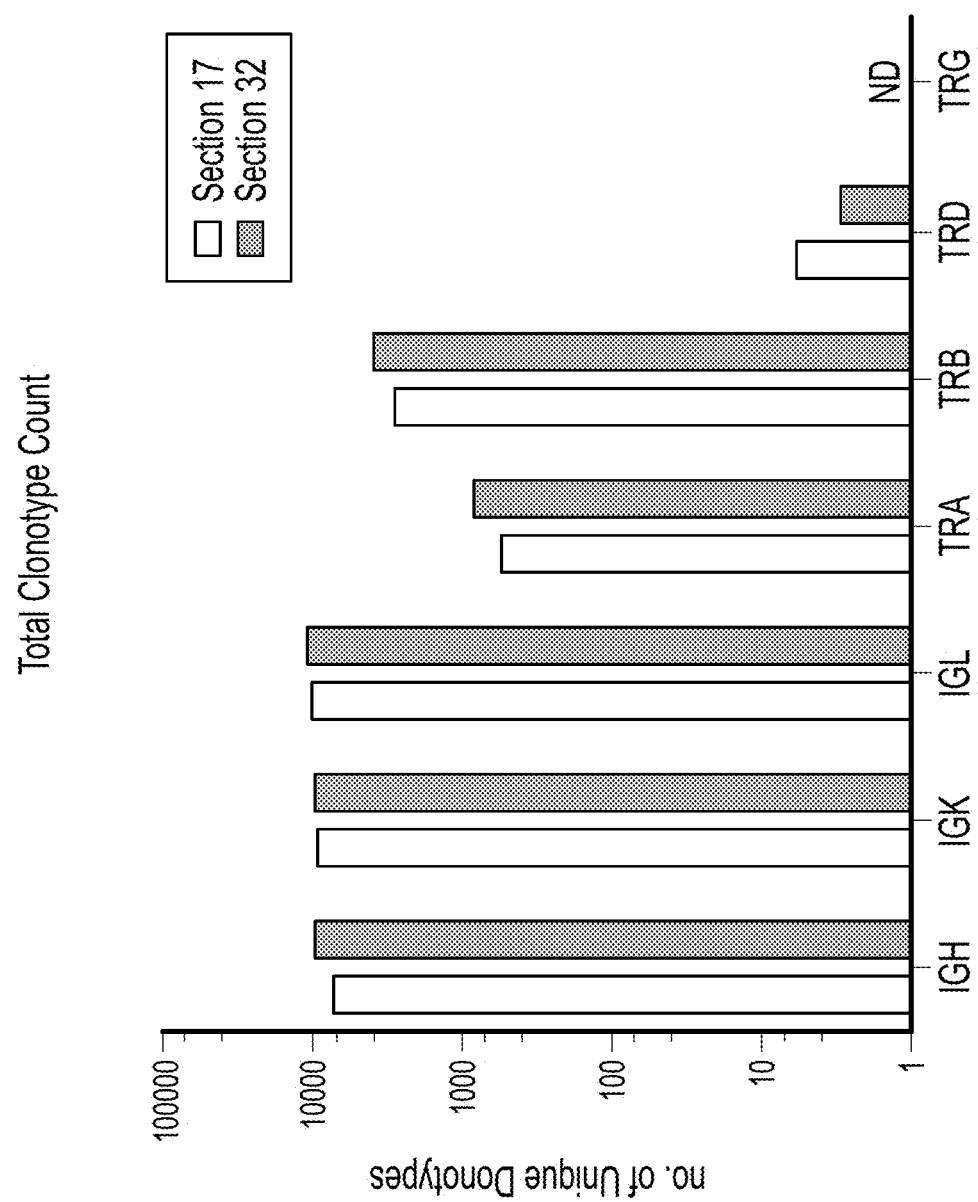
FIG. 16B shows a graph showing the total number of unique clonotypes found in the replicate tonsil sections from FIG. 16A.
Figure 16C:
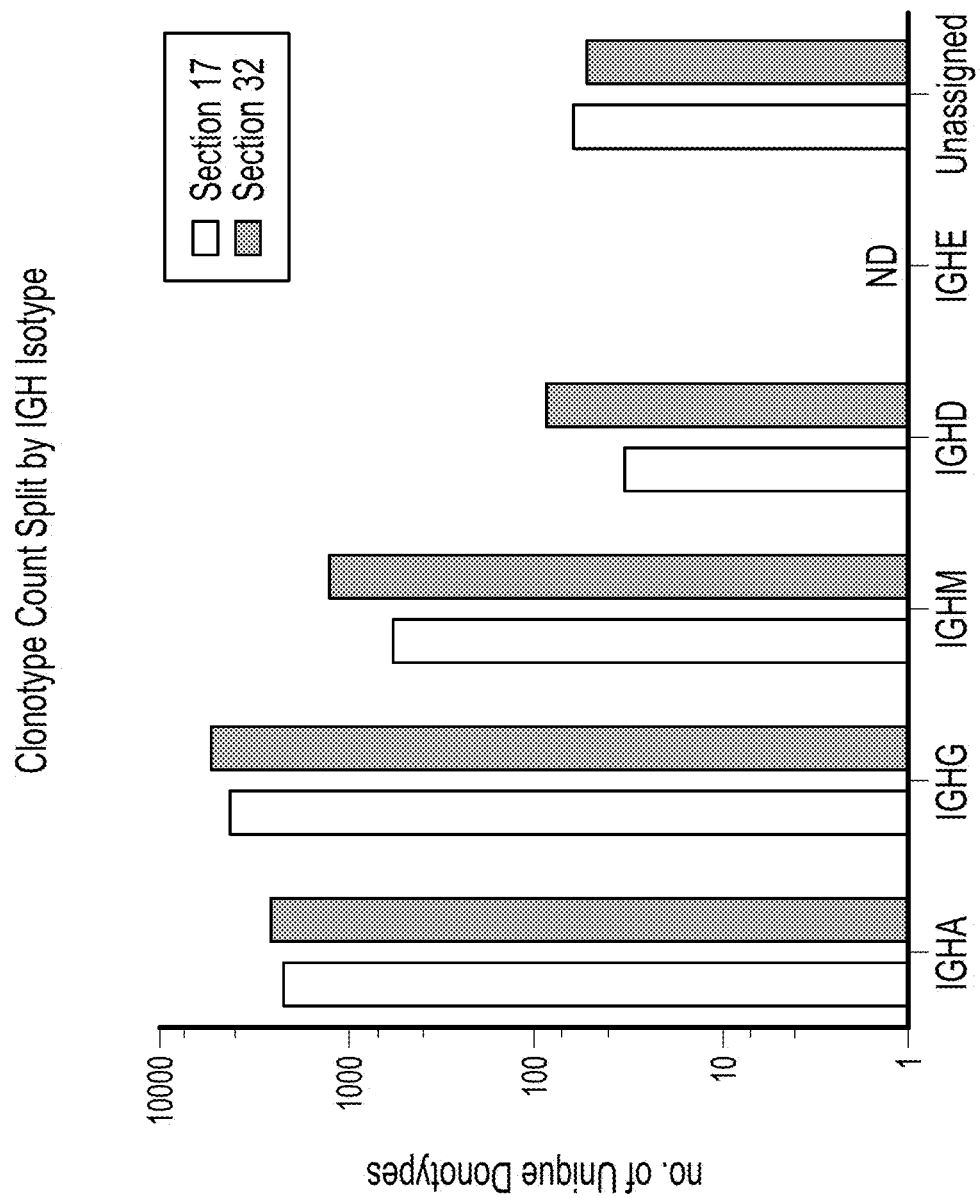
FIG. 16C shows a graph showing the clonotype count split by IGH isotype found in the replicate tonsil sections from FIG. 16A.

Clonotype Numbers cDNA prepared from captured immune cell mRNA analytes were enriched via a hybridization capture approach as described above and combined with PacBio long read sequencing. The resulting data successfully identified spatially barcoded BCR and TCR clones from tonsil Visium libraries (FIGS. 16A-C). A clone was defined as a single-chain with a unique combination of VDJ gene segments and a CDR3 region, based on MIXCR analysis (previously described) (Bolotin et al., (2015)). FIG. 16A shows the distribution of the clonotype (left) and UMI (right) count for two tonsil sections, spaced 150 µm apart, from the same tonsil. The number of clonotypes per spot ranged between 0 and 300. For each tonsil sample, approximately 10,000 IGH, IGK and IGL clones (BCR) were identified (FIG. 16B). For TCRs, 3,437 TRB clonotypes and 687 TRA clonotypes were captured on average. The approximately five-fold lower capture of TRA clones was likely due to the lower expression of TRAC on a per cell basis consistent with previous results. The date demonstrate more successful capture of BCR clones (relative to TCR clones), which, without wishing to be bound by theory may be due to several reasons, including a higher receptor expression by B cell lineage cells (particularly plasma cells) and a higher number of cells per B cell clone. Furthermore, all IGH isotypes were found, except for IGHE, which is expressed by very rare IgE positive B cell lineage cells (FIG. 16C). A small number of IGH clones were not assigned a constant gene. As expected, IGHG and IGHA-expressing cells dominate, followed by IGHM. The BCR light chains (IGK and IGL) were expressed at comparable numbers.

Collectively, the data demonstrate that target enrichment with hybridization probes from Visium cDNA mRNA libraries successfully enrich BCR and TCR clones from lymphocyte rich tissue.

B and T cell Spatial Segregation in the Tonsil

Figure 17A:
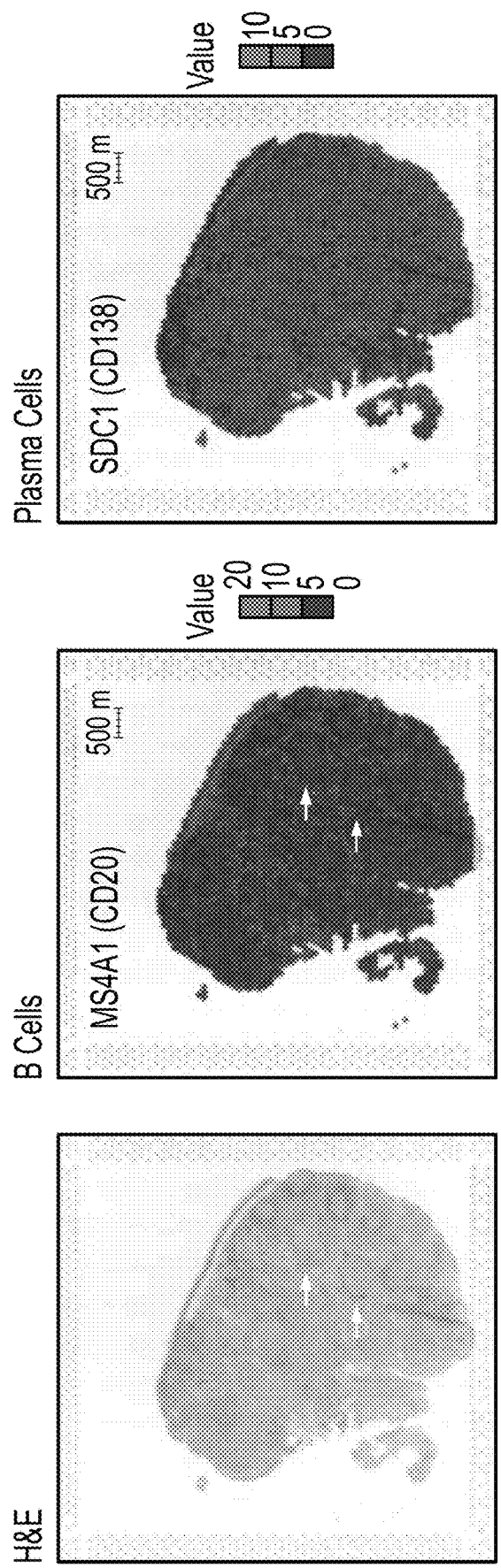
FIG. 17A shows H&E stained tonsil tissue (left), CD20 spatial expression (middle), and CD138 expression (control).
Figure 17B:
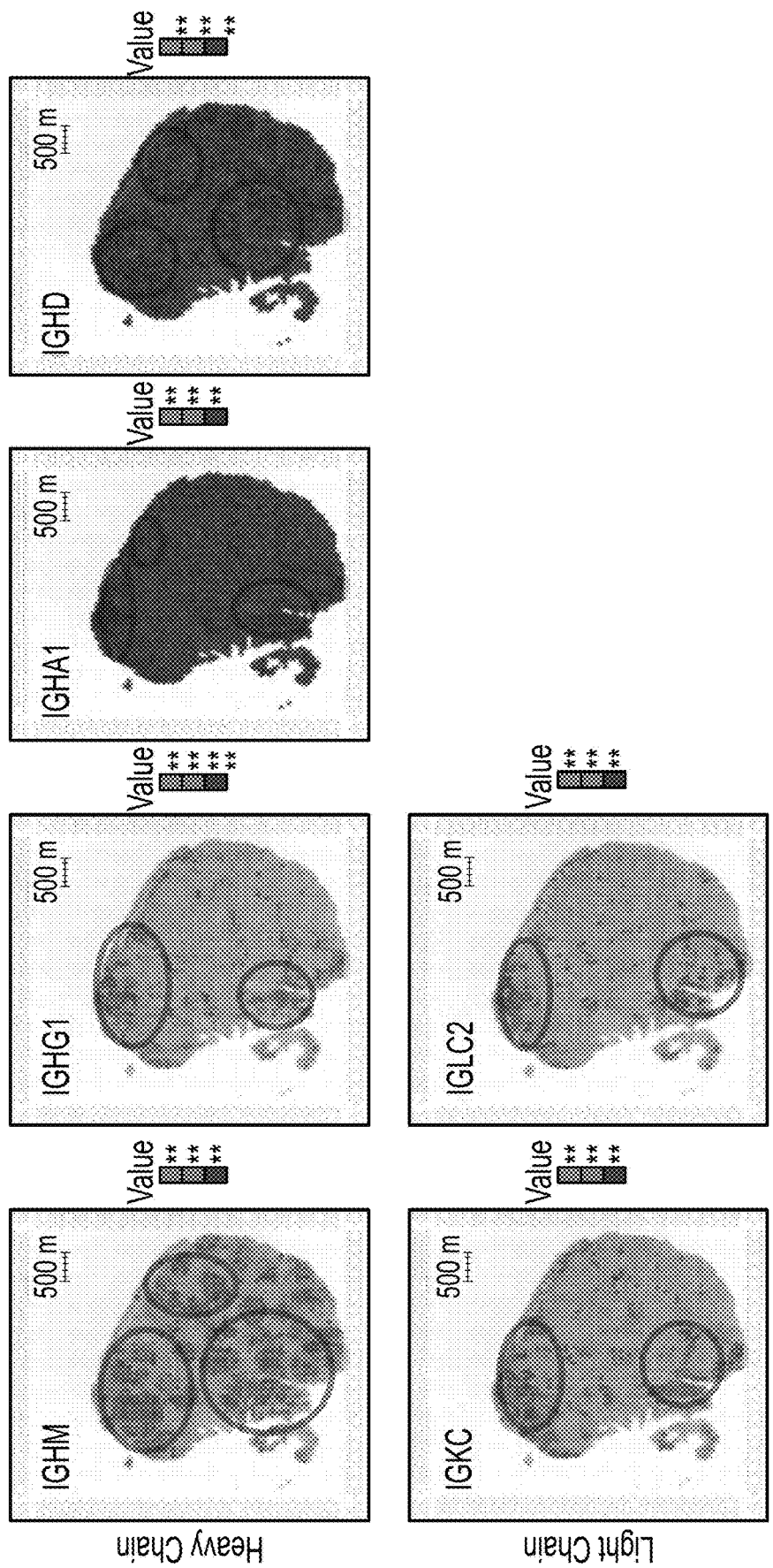
FIG. 17B shows spatial expression in tonsil tissue of the heavy chain IGH constant gene (top) including IGHM, IGHG1, IGHA1, and IGHD and the light chain (bottom) including IGKC and IGLC2.
Figure 17C:
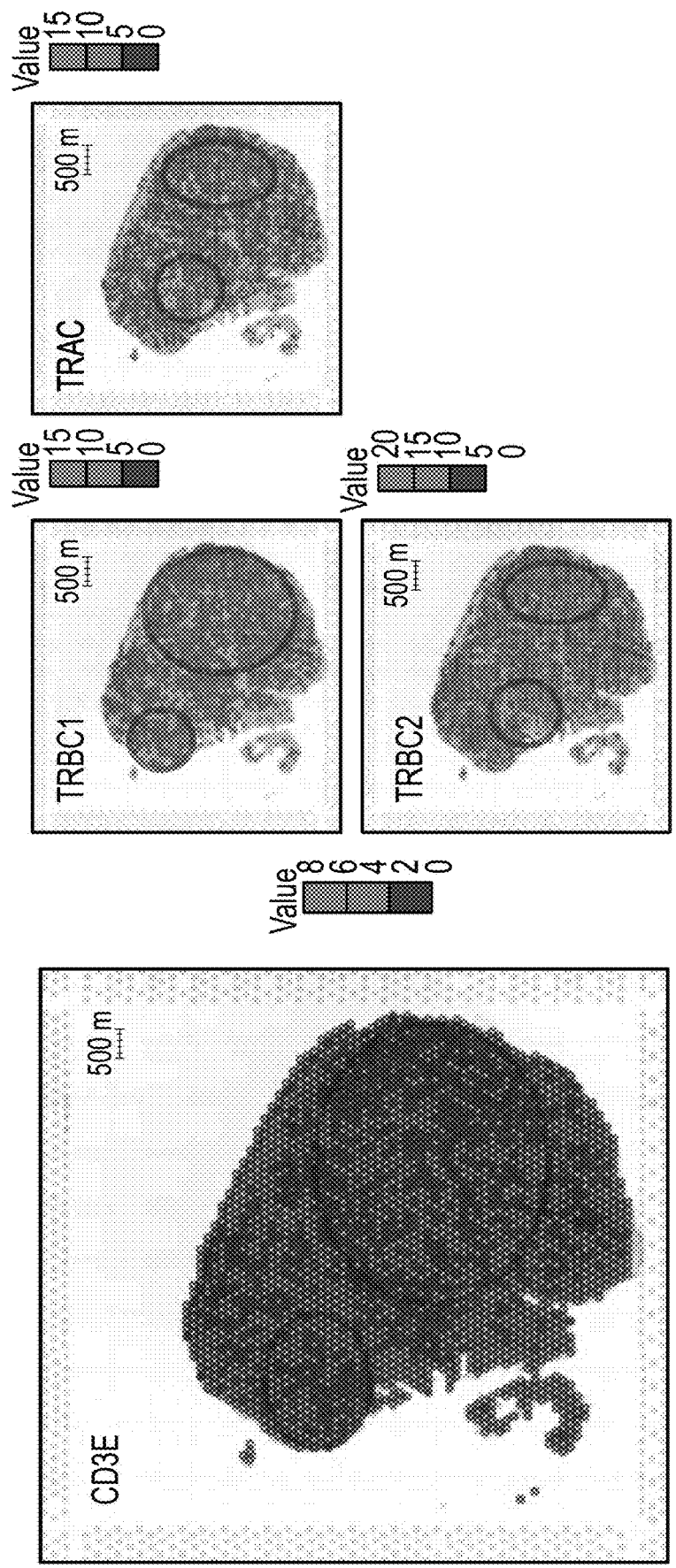
FIG. 17C shows T-cell specific spatial expression for CD3E, TRBC1, TRABC2, and TRAC in tonsil tissue.

It was expected that with tonsil and similar tissues, e.g., lymph node, B cell clones would segregate mainly in follicles or germinal centers, in which B cell clonal selection and expansion occurs. In the Visium gene expression data, MS4A1, which encodes CD20 a B cell specific gene, was expressed in a cluster-like pattern that corresponded with increased cell density as visualized by the H&E staining, suggestive of B cell follicles ("B cell follicles") (FIG. 17A, arrows). In contrast, SDC1, which encodes CD138 and is considered a reliable plasma cell enriched gene, was expressed mainly at the borders of the tissue and around B cell follicles, as expected from plasma cells (FIG. 17A). This cell type distribution was also supported by the spatial expression of the IGH constant gene (FIG. 17B, top), IGHM, which is expressed by B cells prior to class switching into other isotypes and was mostly enriched in the same B cell follicle-like areas as MS4A1. Similarly, IGHD, though more sparsely expressed, was also enriched in the B cell follicular areas. For other IGH isotypes (FIG. 17A, top) and the light chain (FIG. 17B, bottom), the highest gene expression was mainly outside B cell follicles, suggestive of increased expression by plasma cells. Based on CD3E and TCR constant gene (e.g., TRAC, TRBC1, TRBC2) expression, T cells were likely situated outside or around B cell follicles, which corresponds well with the presence of known, so-called "T cell zones" in lymphoid tissues (FIG. 17C).

Clonotype Distribution in the Tonsil

Figure 18A:
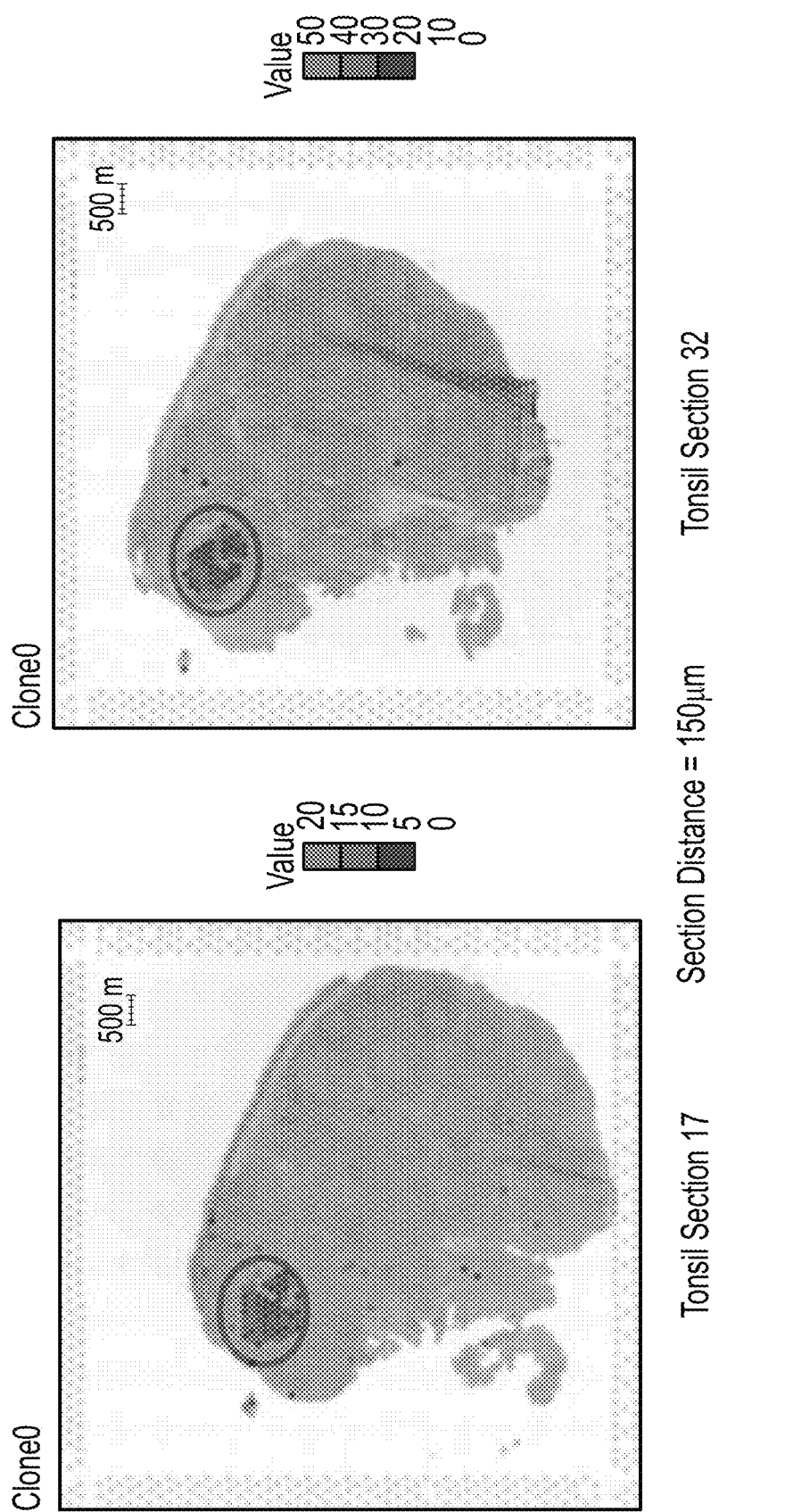
FIG. 18A shows a detected IG clone expression (IGKC) restricted to about one B-cell follicle of in tonsil tissue in replicate experiments.
Figure 18B:
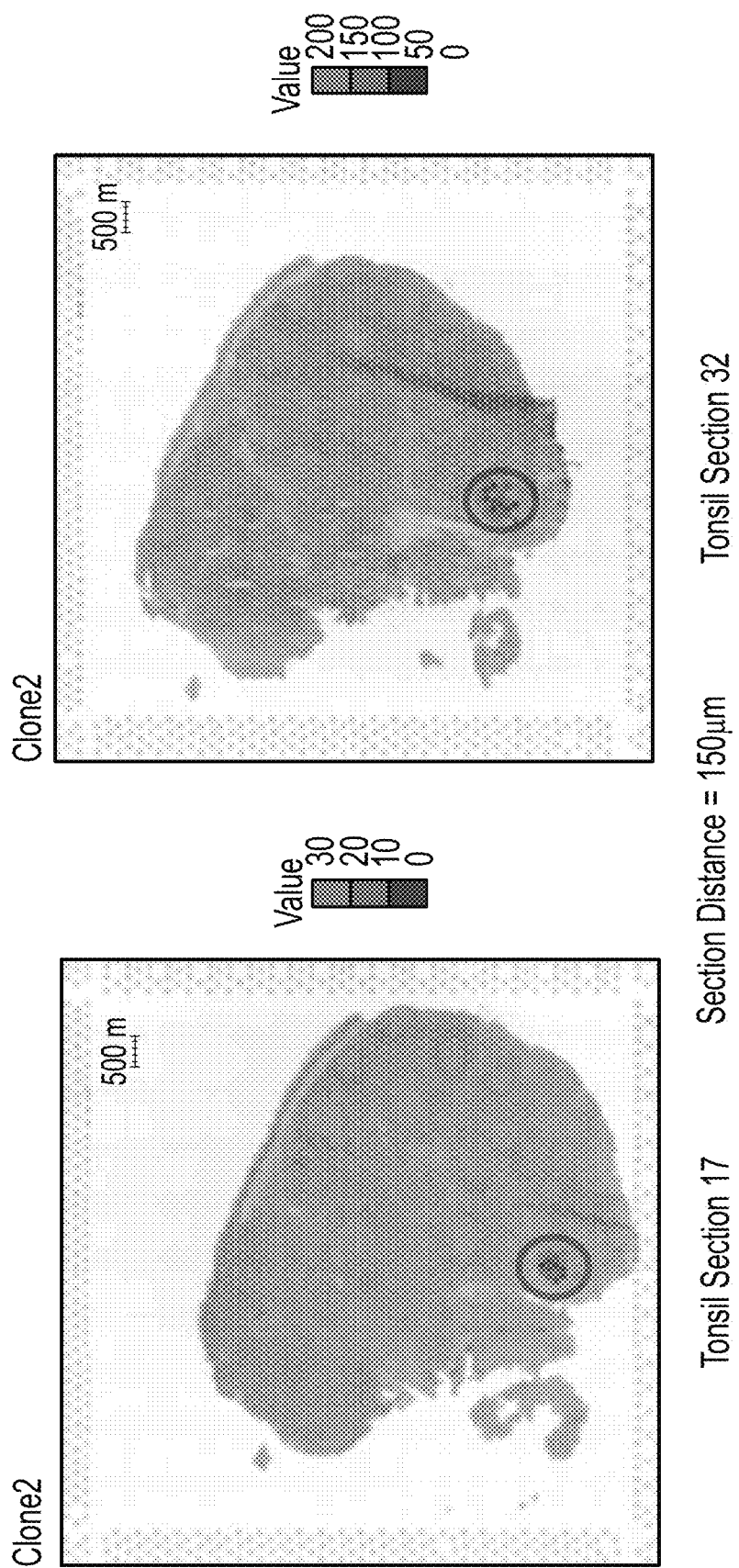
FIG. 18B shows a detected IG clone expression (IGLC) restricted to a B-cell follicle in tonsil tissue in replicate experiments.
Figure 18C:
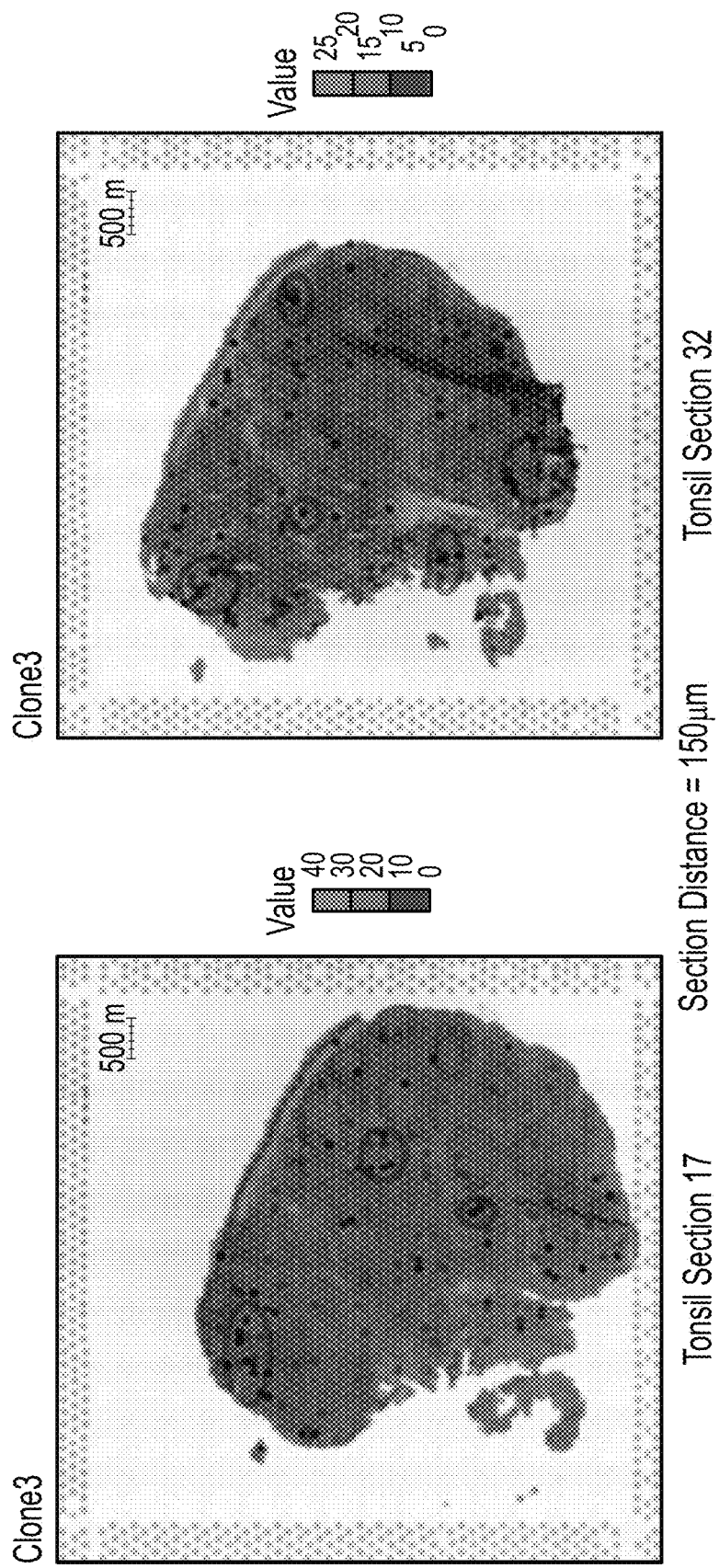
FIG. 18C shows detected IG clone expression (IGLV3-1, IGLJ2, IGLC2/IGLC3) with expression not restricted to B-cell follicles in tonsil tissue in replicate experiments.

The data determined whether captured clones spatially segregate in tonsil tissue relative to the observed B and T cell segregation (FIGS. 17A-C and FIGS. 18A-G). The most abundant clone, IGKC, was highly expressed almost exclusively in a single B cell follicle, as captured by the two tonsil sections spaced 150 μM apart (FIG. 18A). Similar expression patterns were also observed for many clones; e.g., in FIG. 18B, a second representative clone, IGLC, was restricted to another B cell follicle. Without wishing to be bound by theory, these light chains may be expressed by B cells under-going selection and therefore are present in higher concentrations. Large clones, whose expression was not restricted to B cell follicles, were also found (see, e.g., FIG. 18C). These results indicate that clones can be captured with distinct spatial segregation within a tissue section. In accordance with IGHM gene expression, IGHM clones were also found in single follicles (see, e.g., FIG. 18D for a representative example). In contrast, IGHA-expressing clones, tended to be expressed along the border of the tonsil tissue (FIG. 18E), consistent with the spatial IGHA gene expression (FIG. 18B). TCR clones tended to locate at the border of B cell follicles (see, e.g., FIG. 18F and FIG. 18G for representative examples of TRB and TRA clones, respectively). TCR clones also tended to have lower UMI counts per clone on average compared to the BCR clones, again, confirming that TCR transcripts are less abundant in tonsil Visium cDNA libraries and subsequently in the enriched libraries.

Target Enrichment of Lymphocyte Receptors in Breast Tumor Tissue

Figure 19A:
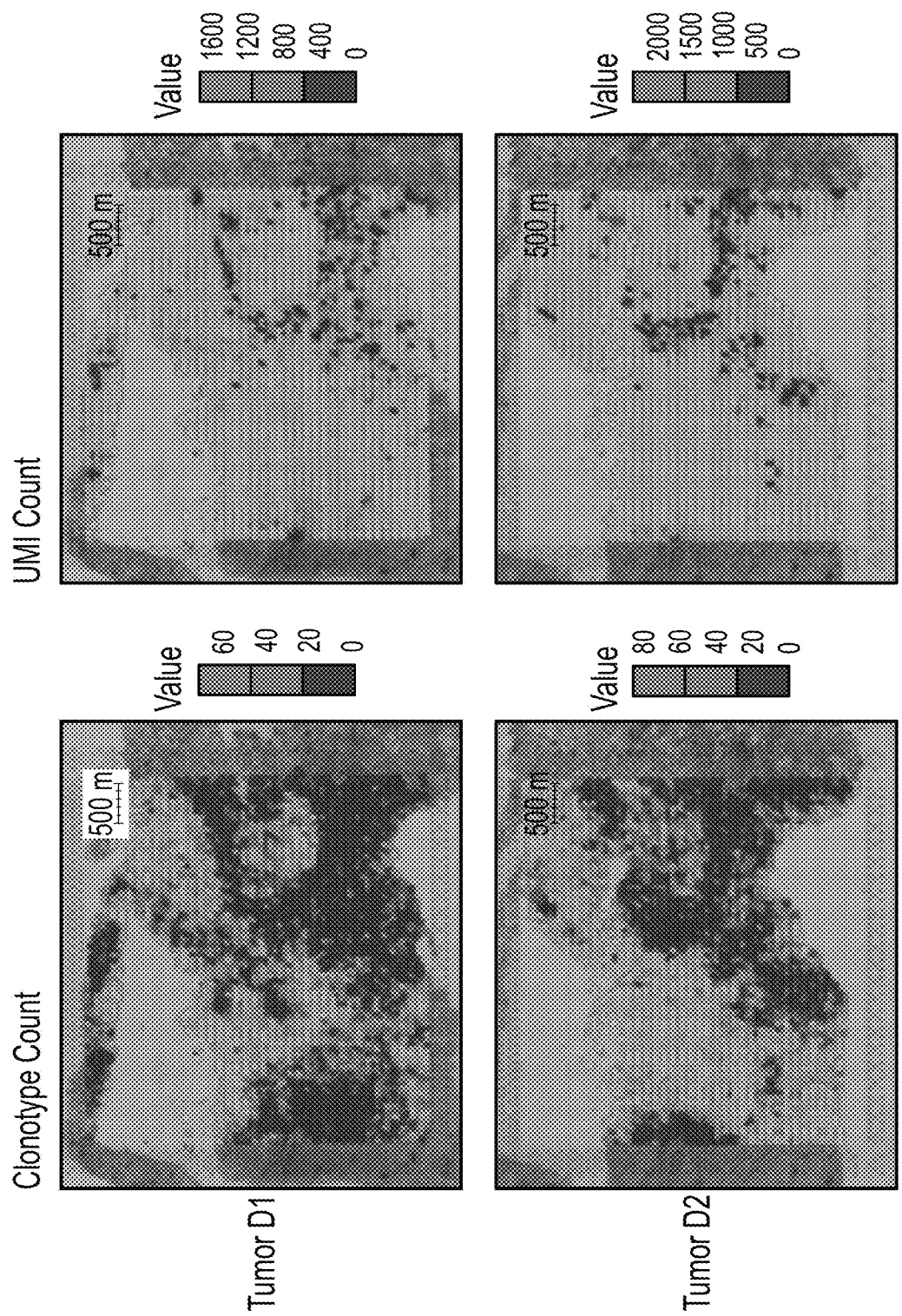
FIG. 19A shows clonotype distribution in replicate breast tumor samples (Tumor D1, Tumor D2) and clonotype count (left) and UMI count (right).
Figure 19B:
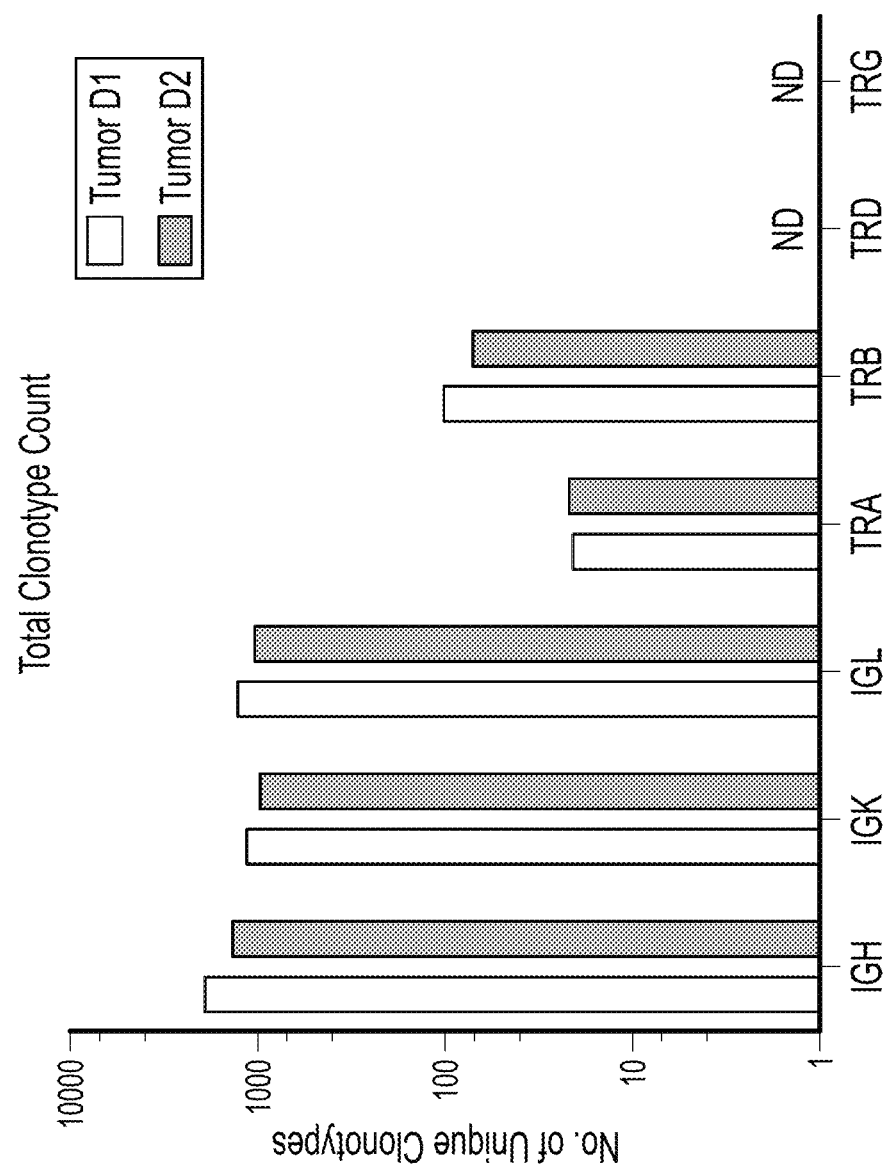
FIG. 19B is a graph showing total clonotype count of the replicate breast tumor samples shown in FIG. 19A.
Figure 19C:
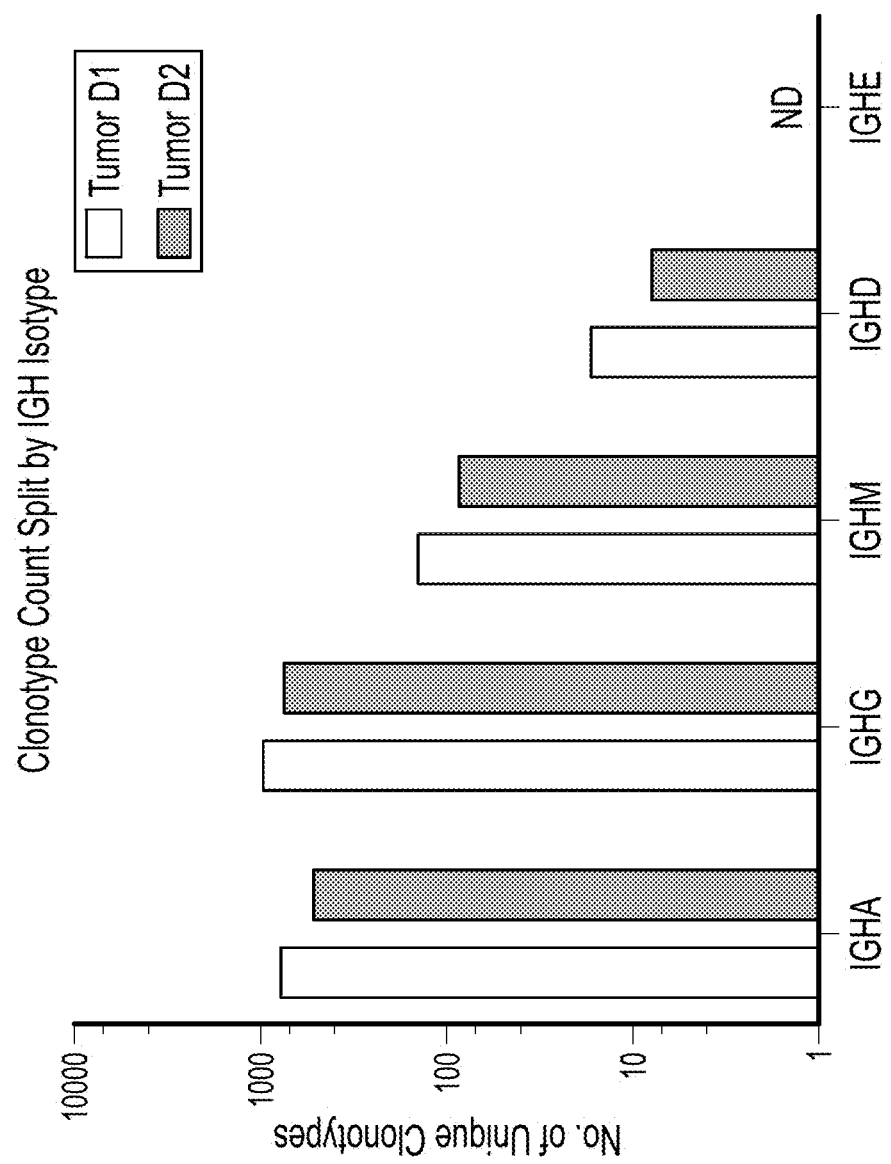
FIG. 19C is a graph showing clonotype count split by IGH isotype of the replicate breast tumor samples shown in FIG. 19A.

Target enrichment strategies as described herein were also tested on breast tumor tissue. Due to the high frequency of tumor cells and stromal cells in breast tumor tissue, it was expected that lymphocyte-associated transcripts would be less abundant, relative to tonsil tissue. Visium libraries were generated from two consecutive sections from breast tumor tissue, isolated from a HER2+ breast tumor patient. FIG. 19A shows the distribution of the clonotype (left) and UMI (right) count for two breast tumor sections. The number of clonotypes per spot ranged between 0 and 300. For each tonsil sample, we identified approximately 10,000 IGH, IGK and IGL clones (BCR) (FIG. 19B). Using the same approach, approximately 1000 IGH, IGK, and IGL clones and between 20-100 TCR clones from each breast tumor section were captured (FIGS. 19B and 19C). Fewer B and T cell clones were expected in the breast tumor samples relative to tonsil tissue, however, there were far fewer T cell clones relative to the B cell clones. Without wishing to be bound by theory, single-cell gene expression and VDJ libraries from the same tumor were prepared and 10-fold more T cells compared to B cell lineage cells (data not shown) were obtained from the single-cell data. Thus, the spatial methods described herein may be more efficient than single-cell approaches in capturing B cell expression and gene expression indicative of plasma, whereas single-cell techniques may be superior in capturing T cells, relative to spatial transcriptomics for antigen receptors.

Figure 20:
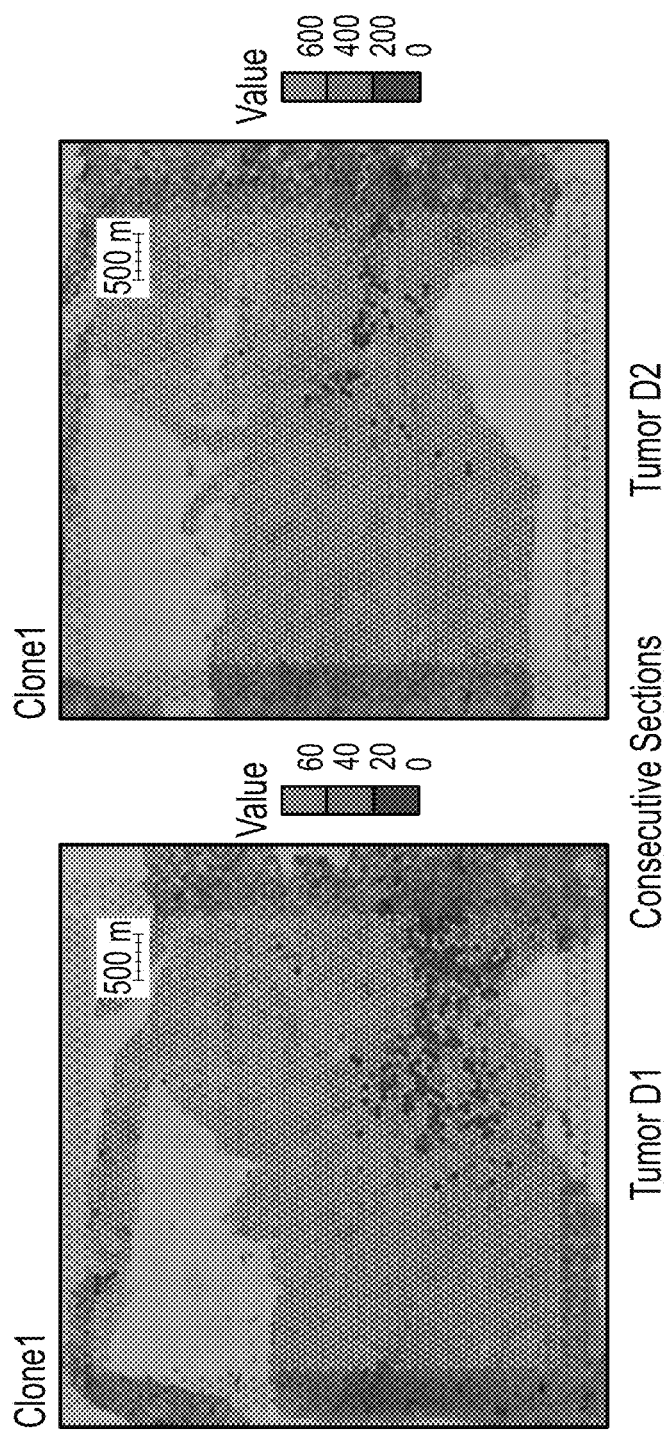
FIG. 20 shows the distribution of a representative IGH clonotypes of the replicate breast tumor samples shown in FIG. 19A.
Figure 21A:
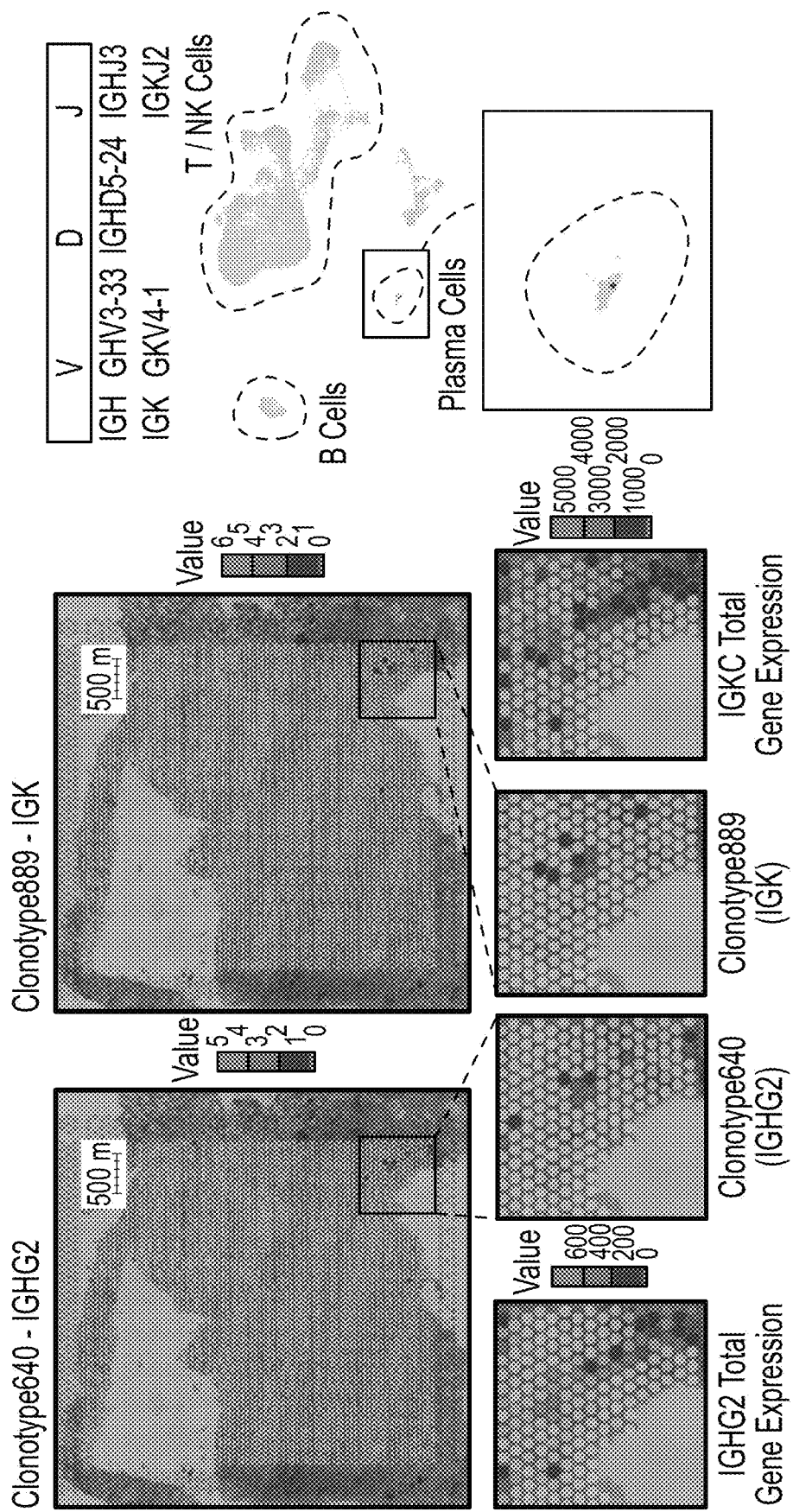
FIG. 21A shows spatial patterning of paired IG receptors (IGHG2 and IGK) (left) in breast tumor tissue and single-cell RNA-seq (right).
Figure 21B:
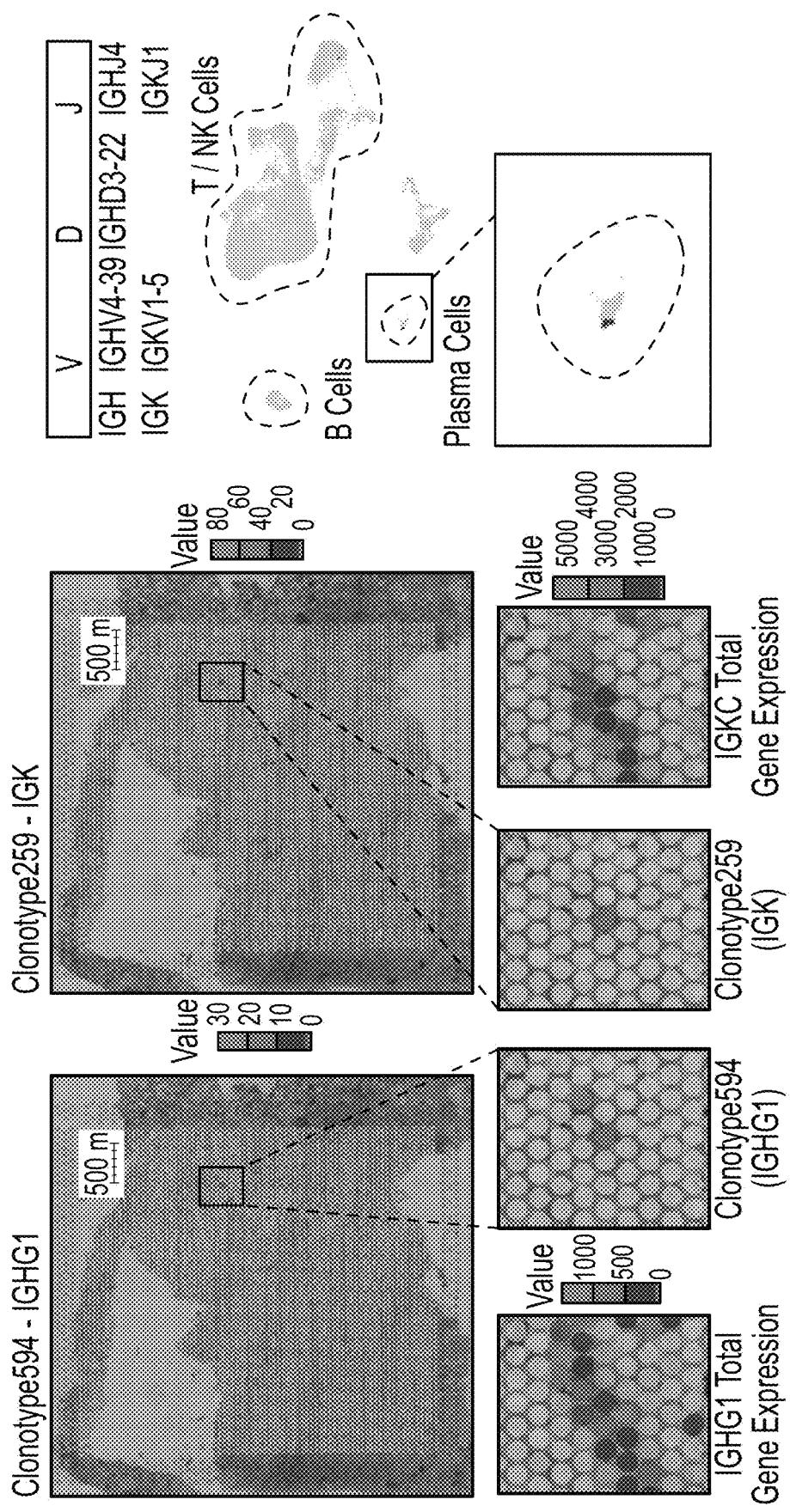
FIG. 21B shows spatial patterning of paired IG receptors (IGHG1 and IGK) (left) in breast tumor tissue and single-cell RNA-seq (right).
Figure 21C:
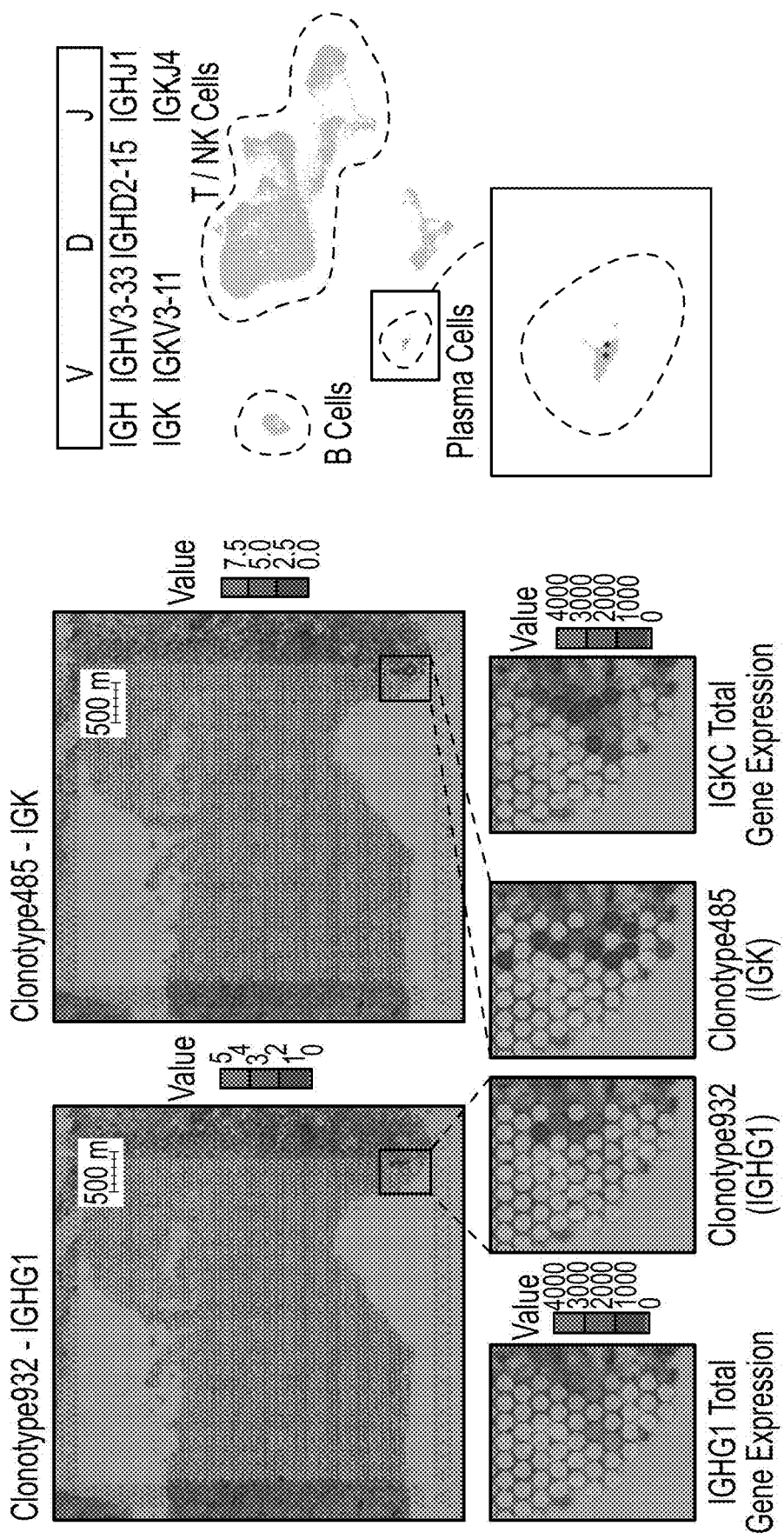
FIG. 21C shows spatial patterning of paired IG receptors (IGHG2 and IGK) (left) in breast tumor tissue and single-cell RNA-seq (right).

Spatial segregation of IGH clones (e.g., IGHV4-28, IGHD3-3, IGHD3-9, IGHJ4, IGHG1/IGHG3) within the breast tumor tissue was found consistent between two adjacent sections (See FIG. 20 for a representative example). Furthermore, since the linked single-cell VDJ data from the same tumor sample was available, detection of paired clones in the spatial clonotype data was also performed. While the single-cell data was processed from a much larger tissue section relative to the 10 μM tissue section used for spatial transcriptomic analysis, it was expected that large clones would be represented in both samples. By comparing the spatial transcriptomics for antigen receptor clonotype lists with the single-cell VDJ data, a total of 6 sets of paired BCR receptors were found in both datasets. The spatial gene expression of three such pairs are shown in FIGS. 21A-C. The similar spatial distribution for both chains for each clone and the concordance with the total respective IGH constant gene expression is demonstrated. For TCR clones, only two sets of paired receptors were found, with sparse UMI count (data not shown). The data show detection of paired receptors using spatial transcriptomics for antigen receptors and that these paired receptors are expressed in a spatially concordant manner.

Target Enrichment for TCR Using Semi-Nested PCR

Figure 22:
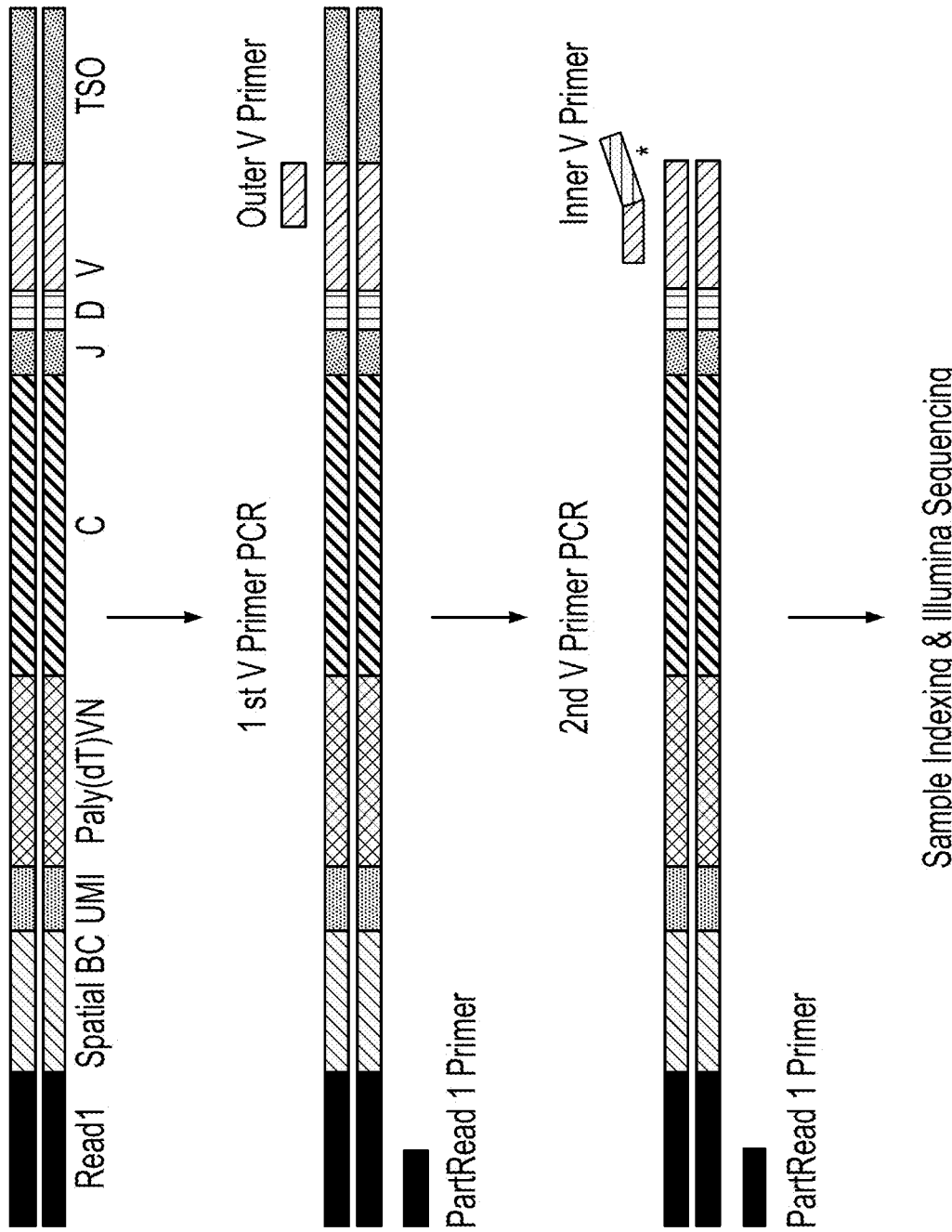
FIG. 22 shows an exemplary nested PCR strategy for additional TCR enrichment.

As described above, the hybridization probe approach was more efficient at capturing BCR clonotypes, most probably due to higher expression on a per cell basis than TCR clonotypes. In order to improve TCR capture, a second target enrichment step was introduced to increase the T cell clonotype yield and to prepare libraries compatible with ILLUMINA® (sequencing technology) sequencing. After hybridization probe capture and subsequent PCR amplification, TCR analytes were enriched using a semi-nested PCR approach as shown in FIG. 22. The PCR is a two-step PCR in which two sets of V (e.g., primer to the variable domain region "V") primers (e.g., "Outer" and "Inner") targeting the TRAV and TRBV genes, respectively, were combined with a universal primer targeting the partial Read1 present on transcripts in the Visium cDNA library. The "Outer" primer can be referred to as a second primer and the "Inner" primer can be referred to as a third primer. The outer primers target gene regions further away from the start of the CDR3 (e.g., between about 200-270 bp from the end of the coding V segment), whereas the inner primers target gene segments closer to the CDR3 (between about 20-25 bp from the end of the coding V segment).

The results show amplification of both TRA and TRB transcripts using the semi-nested PCR approach from breast tumor Visium libraries and that these libraries had the expected sizes (data not shown).

Collectively, the data demonstrate that spatial transcriptomics for antigen receptors can isolate high numbers of BCR and TCR clonotypes from tonsil and breast tumor tissue.

These clones segregate in the tissue in characteristic ways concordant with their biology and cell type gene expression patterns.

Embodiments

Embodiment 1 is a method for determining the presence and/or abundance of an immune cell clonotype at a location in a biological sample, the method comprising: (a) contacting a biological sample with an array comprising a plurality of capture probes, wherein a capture probe of the plurality of capture probes comprises (i) a spatial barcode and (ii) a capture domain that specifically binds to a nucleic acid encoding an immune cell receptor of the immune cell clonotype; and (b) determining (i) all or a portion of the sequence of the spatial barcode or a complement thereof, and (ii) all or a portion of the sequence of the nucleic acid encoding the immune cell receptor or a complement thereof, and using the determined sequences of (i) and (ii) to determine the presence and/or abundance of the immune cell clonotype at a location in the biological sample.

Embodiment 2 is the method of embodiment 1, wherein the immune cell clonotype is a T cell clonotype.

Embodiment 3. The method of embodiment 2, wherein the immune cell receptor is a T cell receptor alpha chain.

Embodiment 4 is the method of embodiment 3, wherein the capture domain binds specifically to a nucleic acid sequence encoding a constant region of the T cell receptor alpha chain.

Embodiment 5 is the method of embodiment 3 or 4, wherein step (b) comprises determining a sequence encoding CDR3 of the T cell receptor alpha chain.

Embodiment 6 is the method of embodiment 5, wherein step (b) further comprises determining a sequence encoding one or both of CDR1 and CDR2 of the T cell receptor alpha chain.

Embodiment 7 is the method of embodiment 5, wherein step (b) further comprises determining a sequence encoding a full-length variable domain of the T cell receptor alpha chain.

Embodiment 8 is the method of embodiment 2, wherein the immune cell receptor is a T cell receptor beta chain.

Embodiment 9 is the method of embodiment 8, wherein the capture domain binds specifically to a nucleic acid sequence encoding a constant region of the T cell receptor beta chain.

Embodiment 10 is the method of embodiment 8 or 9, wherein step (b) comprises determining a sequence encoding CDR3 of the T cell receptor beta chain.

Embodiment 11 is the method of embodiment 10, wherein step (b) further comprises determining a sequence encoding one or both of CDR1 and CDR2 of the T cell receptor beta chain.

Embodiment 12 is the method of embodiment 10, wherein step (b) further comprises determining a full-length variable domain of the T cell receptor beta chain.

Embodiment 13 is the method of embodiment 1, wherein the immune cell clonotype is a B cell clonotype.

Embodiment 14 is the method of embodiment 13, wherein the immune cell receptor is an immunoglobulin kappa light chain.

Embodiment 15 is the method of embodiment 14, wherein the capture domain binds specifically to a nucleic acid sequence encoding a constant region of the immunoglobulin kappa light chain.

Embodiment 16 is the method of embodiment 14 or 15, wherein step (b) comprises determining a sequence encoding CDR3 of the immunoglobulin kappa light chain.

Embodiment 17 is the method of embodiment 16, wherein step (b) further comprises determining a sequence encoding one or both of CDR1 and CDR2 of the immunoglobulin kappa light chain.

Embodiment 18 is the method of embodiment 16, wherein step (b) further comprises determining a sequence encoding a full-length variable domain of the immunoglobulin kappa light chain.

Embodiment 19 is the method of embodiment 13, wherein the immune cell receptor is an immunoglobulin lambda light chain.

Embodiment 20 is the method of embodiment 19, wherein the capture domain binds specifically to a nucleic acid sequence encoding a constant region of the immunoglobulin lambda light chain.

Embodiment 21 is the method of embodiment 19 or 20, wherein step (b) comprises determining a sequence encoding CDR3 of the immunoglobulin lambda light chain.

Embodiment 22 is the method of embodiment 21, wherein step (b) further comprises determining a sequence encoding one or both of CDR1 and CDR2 of the immunoglobulin lambda light chain.

Embodiment 23 is the method of embodiment 21, wherein step (b) further comprises determining a sequence encoding a full-length variable domain of the immunoglobulin lambda light chain.

Embodiment 24 is the method of embodiment 13, wherein the immune cell receptor is an immunoglobulin heavy chain.

Embodiment 25 is the method of embodiment 24, wherein the capture domain binds specifically to a nucleic acid sequence encoding a constant region of the immunoglobulin heavy chain.

Embodiment 26 is the method of embodiment 24 or 25, wherein step (b) comprises determining a sequence encoding CDR3 of the immunoglobulin heavy chain.

Embodiment 27 is the method of embodiment 26, wherein step (b) further comprises determining a sequence encoding one or both of CDR1 and CDR2 of the immunoglobulin heavy chain.

Embodiment 28 is the method of embodiment 26, wherein step (b) further comprises determining a sequence encoding a full-length variable domain of the immunoglobulin heavy chain.

Embodiment 29 is the method of any one of embodiments 1-28, wherein step (b) comprises the capture probe using the nucleic acid encoding the immune cell receptor as a template, thereby generating an extended capture probe.

Embodiment 30 is the method of embodiment 29, wherein step (b) comprises extending a 3' end of the capture probe.

Embodiment 31 is the method of embodiment 29 or 30, wherein step (b) further comprises generating a second strand of nucleic acid that comprises (i) a sequence that is complementary to all or a portion of the spatial barcode, and (ii) a sequence that corresponds to all or a portion of the sequence of the nucleic acid encoding the immune cell receptor.

Embodiment 32 is the method of any one of embodiments 1-31, wherein the capture probe further comprises a cleavage domain, a functional domain, a unique molecular identifier, or any combination thereof.

Embodiment 33 is the method of any one of embodiments 1-30, wherein the capture probe further comprises a functional domain.

Embodiment 34 is the method of embodiment 33, wherein step (b) further comprises generating a second strand of nucleic acid that comprises (i) a sequence that is complementary to all or a portion of the functional domain, (ii) a sequence that is complementary to all or a portion of the spatial barcode, and (iii) a sequence that corresponds to all or a portion of the sequence of the nucleic acid encoding the immune cell receptor.

Embodiment 35 is the method of embodiment 34, wherein step (b) further comprises amplifying the second strand of nucleic acid using (i) a first primer comprising all or a portion of the functional domain, wherein the functional domain is 5' to the spatial barcode in the second strand of nucleic acid, and (ii) a second primer comprising a sequence that is substantially complementary to a portion of a sequence encoding a variable region of the immune cell receptor.

Embodiment 36 is the method of any one of embodiments 1-35, wherein the biological sample comprises a tissue sample.

Embodiment 37 is the method of embodiment 36, wherein the tissue sample is a tissue section.

Embodiment 38 is the method of embodiment 37, wherein the tissue section is a fixed tissue section.

Embodiment 39 is the method of embodiment 38, wherein the fixed tissue section is a formalin-fixed paraffin-embedded tissue section.

Embodiment 40 is the method of any one of embodiments 37-39, wherein the tissue section comprises a tumor region.

Embodiment 41 is the method of any one of embodiments 1-40, wherein the nucleic acid encoding the immune cell receptor comprises RNA.

Embodiment 42 is the method of embodiment 41, wherein the RNA is mRNA.

Embodiment 43 is the method of any one of embodiments 1-40, wherein the nucleic acid encoding the immune cell receptor comprises DNA.

Embodiment 44 is the method of embodiment 43, wherein the DNA is genomic DNA.

Embodiment 45 is the method of any one of embodiments 1-44, wherein the method further comprises, prior to step (b), contacting the biological sample with ribosomal RNA depletion probes and mitochondrial RNA depletion probes.

Embodiment 46 is the method of any one of embodiments 1-45, wherein the method further comprises imaging the biological sample.

Embodiment 47 is the method of any one of embodiments 1-46, wherein the determining in step (b) comprises sequencing (i) all or a portion of the sequence of the spatial barcode or a complement thereof, and (ii) all or a portion of the sequence of the nucleic acid encoding the immune cell receptor or a complement thereof.

Embodiment 48 is the method of any one of embodiments 1-47, wherein step (b) comprises determining the presence of the immune cell clonotype at a location in the biological sample.

Embodiment 49 is the method of any one of embodiments 1-47, wherein step (b) comprises determining the abundance of the immune cell clonotype at a location in the biological sample.

Embodiment 50 is the method of any one of embodiments 1-47, wherein step (b) comprises determining the presence and abundance of the immune cell clonotype at a location in the biological sample.

Embodiment 51 is the method of any one of embodiments 1-47, wherein step (b) comprises determining the presence of two or more immune cell clonotypes at a location in the biological sample.

Embodiment 52 is the method of any one of embodiments 1-47, wherein step (b) comprises determining the abundance of two or more immune cell clonotypes at a location in the biological sample.

Embodiment 53 is the method of any one of embodiments 1-47, wherein step (b) comprises determining the presence and abundance of two or more immune cell clonotypes at a location in the biological sample.

Embodiment 54 is the method of any one of embodiments 51-53, wherein the method further comprises comparing the two or more immune cell clonotypes.

Embodiment 55 is the method of any one of embodiments 51-54, wherein the two or more immune cell clonotypes are each a B cell clonotype.

Embodiment 56 is the method of any one of embodiments 51-54, wherein the two or more immune cell clonotypes are each a T cell clonotype.

Embodiment 57 is the method of any one of embodiments 51-54, wherein the two or more immune cell clonotypes comprise at least one T cell clonotype and at least one B cell clonotype.

Embodiment 58 is a method for determining the presence and/or abundance of an immune cell receptor at a location in a biological sample, the method comprising: (a) contacting a biological sample with an array comprising a plurality of capture probes, wherein a capture probe of the plurality of capture probes comprises (i) a spatial barcode and (ii) a capture domain that specifically binds to a nucleic acid encoding an immune cell receptor; and (b) determining (i) all or a portion of the sequence of the spatial barcode or a complement thereof, and (ii) all or a portion of the sequence of the nucleic acid encoding the immune cell receptor or a complement thereof, and using the determined sequences of (i) and (ii) to determine the presence and/or abundance of the immune cell receptor at a location in the biological sample.

Embodiment 59 is the method of embodiment 58, wherein the immune cell receptor is a T cell receptor alpha chain.

Embodiment 60 is the method of embodiment 59, wherein the capture domain binds specifically to a nucleic acid sequence encoding a constant region of the T cell receptor alpha chain.

Embodiment 61 is the method of embodiment 59 or 60, wherein step (b) comprises determining a sequence encoding CDR3 of the T cell receptor alpha chain.

Embodiment 62 is the method of embodiment 61, wherein step (b) further comprises determining a sequence encoding one or both of CDR1 and CDR2 of the T cell receptor alpha chain.

Embodiment 63 is the method of embodiment 61, wherein step (b) further comprises determining a sequence encoding a full-length variable domain of the T cell receptor alpha chain.

Embodiment 64 is the method of embodiment 58, wherein the immune cell receptor is a T cell receptor beta chain.

Embodiment 65 is the method of embodiment 64, wherein the capture domain binds specifically to a nucleic acid sequence encoding a constant region of the T cell receptor beta chain.

Embodiment 66 is the method of embodiment 64 or 65, wherein step (b) comprises determining a sequence encoding CDR3 of the T cell receptor beta chain.

Embodiment 67 is the method of embodiment 66, wherein step (b) further comprises determining a sequence encoding one or both of CDR1 and CDR2 of the T cell receptor beta chain.

Embodiment 68 is the method of embodiment 66, wherein step (b) further comprises determining a full-length variable domain of the T cell receptor beta chain.

Embodiment 69 is the method of embodiment 58, wherein the immune cell receptor is an immunoglobulin kappa light chain.

Embodiment 70 is the method of embodiment 69, wherein the capture domain binds specifically to a nucleic acid sequence encoding a constant region of the immunoglobulin kappa light chain.

Embodiment 71 is the method of embodiment 69 or 70, wherein step (b) comprises determining a sequence encoding CDR3 of the immunoglobulin kappa light chain.

Embodiment 72 is the method of embodiment 71, wherein step (b) further comprises determining a sequence encoding one or both of CDR1 and CDR2 of the immunoglobulin kappa light chain.

Embodiment 73 is the method of embodiment 71, wherein step (b) further comprises determining a sequence encoding a full-length variable domain of the immunoglobulin kappa light chain.

Embodiment 74 is the method of embodiment 58, wherein the immune cell receptor is an immunoglobulin lambda light chain.

Embodiment 75 is the method of embodiment 74, wherein the capture domain binds specifically to a nucleic acid sequence encoding a constant region of the immunoglobulin lambda light chain.

Embodiment 76 is the method of embodiment 74 or 75, wherein step (b) comprises determining a sequence encoding CDR3 of the immunoglobulin lambda light chain.

Embodiment 77 is the method of embodiment 76, wherein step (b) further comprises determining a sequence encoding one or both of CDR1 and CDR2 of the immunoglobulin lambda light chain.

Embodiment 78 is the method of embodiment 76, wherein step (b) further comprises determining a sequence encoding a full-length variable domain of the immunoglobulin lambda light chain.

Embodiment 79 is the method of embodiment 58, wherein the immune cell receptor is an immunoglobulin heavy chain.

Embodiment 80 is the method of embodiment 79, wherein the capture domain binds specifically to a nucleic acid sequence encoding a constant region of the immunoglobulin heavy chain.

Embodiment 81 is the method of embodiment 79 or 80, wherein step (b) comprises determining a sequence encoding CDR3 of the immunoglobulin heavy chain.

Embodiment 82 is the method of embodiment 81, wherein step (b) further comprises determining a sequence encoding one or both of CDR1 and CDR2 of the immunoglobulin heavy chain.

Embodiment 83 is the method of embodiment 81, wherein step (b) further comprises determining a sequence encoding a full-length variable domain of the immunoglobulin heavy chain.

Embodiment 84 is the method of any one of embodiments 58-83, wherein step (b) comprises extending an end of the capture probe using the nucleic acid encoding the immune cell receptor as a template, thereby generating an extended capture probe.

Embodiment 85 is the method of embodiment 84, wherein step (b) comprises extending a 3' end of the capture probe.

Embodiment 86 is the method of embodiment 84 or 85, wherein step (b) further comprises generating a second strand of nucleic acid that comprises (i) a sequence that is complementary to all or a portion of the spatial barcode, and (ii) a sequence that corresponds to all or a portion of the sequence of the nucleic acid encoding the immune cell receptor.

Embodiment 87 is the method of any one of embodiments 58-86, where the capture probe further comprises a cleavage domain, a functional domain, a unique molecular identifier, or any combination thereof.

Embodiment 88 is the method of any one of embodiments 58-85, wherein the capture probe further comprises a functional domain.

Embodiment 89 is the method of embodiment 88, wherein step (b) further comprises generating a second strand of nucleic acid that comprises (i) a sequence that is complementary to all or a portion of the functional domain, (ii) a sequence that is complementary to all or a portion of the spatial barcode, and (iii) a sequence that corresponds to all or a portion of the sequence of the nucleic acid encoding the immune cell receptor.

Embodiment 90 is the method of embodiment 89, wherein step (b) further comprises amplifying the second strand of nucleic acid using (i) a first primer comprising all or a portion of the functional domain, wherein the functional domain is 5' to the spatial barcode in the second strand of nucleic acid, and (ii) a second primer comprising a sequence that is substantially complementary to a portion of a sequence encoding a variable region of the immune cell receptor.

Embodiment 91 is the method of any one of embodiments 58-90, wherein the biological sample comprises a tissue sample.

Embodiment 92 is the method of embodiment 91, wherein the tissue sample is a tissue section.

Embodiment 93 is the method of embodiment 92, wherein the tissue section is a fixed tissue section.

Embodiment 94 is the method of embodiment 93, wherein the fixed tissue section is a formalin-fixed paraffin-embedded tissue section.

Embodiment 95 is the method of any one of embodiments 92-94, wherein the tissue section comprises a tumor region.

Embodiment 96 is the method of any one of embodiments 58-95, wherein the nucleic acid encoding the immune cell receptor comprises RNA.

Embodiment 97 is the method of embodiment 96, wherein the RNA is mRNA.

Embodiment 98 is the method of any one of embodiments 58-95, wherein the nucleic acid encoding the immune cell receptor comprises DNA.

Embodiment 99 is the method of embodiment 98, wherein the DNA is genomic DNA.

Embodiment 100 is the method of any one of embodiments 58-99, wherein the method further comprises, prior to step (b), contacting the biological sample with ribosomal RNA depletion probes and mitochondrial RNA depletion probes.

Embodiment 101 is the method of any one of embodiments 58-100, wherein the method further comprises imaging the biological sample.

Embodiment 102 is the method of any one of embodiments 58-101, wherein the determining in step (b) comprises sequencing (i) all or a portion of the sequence of the spatial barcode or a complement thereof, and (ii) all or a portion of the sequence of the nucleic acid encoding the immune cell receptor or a complement thereof.

Embodiment 103 is the method of any one of embodiments 58-102, wherein step (b) comprises determining the presence of the immune cell receptor at a location in the biological sample.

Embodiment 104 is the method of any one of embodiments 58-102, wherein step (b) comprises determining the abundance of the immune cell receptor at a location in the biological sample.

Embodiment 105 is the method of any one of embodiments 58-102, wherein step (b) comprises determining the presence and abundance of the immune cell receptor at a location in the biological sample.

Embodiment 106 is the method of any one of embodiments 58-102, wherein step (b) comprises determining the presence of two or more immune cell receptors at a location in the biological sample.

Embodiment 107 is the method of any one of embodiments 58-102, wherein step (b) comprises determining the abundance of two or more immune cell receptors at a location in the biological sample.

Embodiment 108 is the method of any one of embodiments 58-102, wherein step (b) comprises determining the presence and abundance of two or more immune cell receptors at a location in the biological sample.

Embodiment 109 is the method of any one of embodiments 106-108, wherein the method further comprises comparing the two or more immune cell receptors.

Embodiment 110 is the method of any one of embodiments 106-109, wherein the two or more immune cell clonotypes are each an immune cell receptor of a B cell.

Embodiment 111 is the method of any one of embodiments 106-109, wherein the two or more immune cell clonotypes are each an immune cell receptor of a T cell.

Embodiment 112 is the method of any one of embodiments 106-109, wherein the two or more immune cell clonotypes comprise at least one immune cell receptor of a T cell and at least one immune cell receptor from a B cell.

Embodiment 113 is an array comprising a plurality of capture probes, wherein a capture probe of the plurality of capture probes comprises (i) a spatial barcode and (ii) a capture domain that specifically binds to a nucleic acid encoding an immune cell receptor of an immune cell clonotype.

Embodiment 114 is the array of embodiment 113, wherein the immune cell clonotype is a T cell clonotype.

Embodiment 115 is the array of embodiment 114, wherein the immune cell receptor is a T cell receptor alpha chain.

Embodiment 116 is the array of embodiment 115, wherein the capture domain binds specifically to a nucleic acid sequence encoding a constant region of the T cell receptor alpha chain.

Embodiment 117 is the array of embodiment 114, wherein the immune cell receptor is a T cell receptor beta chain.

Embodiment 118 is the array of embodiment 117, wherein the capture domain binds specifically to a nucleic acid sequence encoding a constant region of the T cell receptor beta chain.

Embodiment 119 is the array of embodiment 113, wherein the immune cell clonotype is a B cell clonotype.

Embodiment 120 is the array of embodiment 119, wherein the immune cell receptor is an immunoglobulin kappa light chain.

Embodiment 121 is the array of embodiment 120, wherein the capture domain binds specifically to a nucleic acid sequence encoding a constant region of the immunoglobulin kappa light chain.

Embodiment 122 is the array of embodiment 119, wherein the immune cell receptor is an immunoglobulin lambda light chain.

Embodiment 123 is the array of embodiment 122, wherein the capture domain binds specifically to a nucleic acid sequence encoding a constant region of the immunoglobulin lambda light chain.

Embodiment 124 is the array of embodiment 119, wherein the immune cell receptor is an immunoglobulin heavy chain.

Embodiment 125 is the array of embodiment 124, wherein the capture domain binds specifically to a nucleic acid sequence encoding a constant region of the immunoglobulin heavy chain.

Embodiment 126 is the array of any one of embodiments 113-125, where the capture probe further comprises a cleavage domain, a functional domain, a unique molecular identifier, or any combination thereof.

Embodiment 127. A kit comprising: an array of any one of embodiments 113-126; and one or both of ribosomal RNA depletion probes and mitochondrial RNA depletion probes.

Embodiment 128 is a method for determining the presence and/or abundance of an immune cell clonotype at a location in a biological sample, the method comprising: (a) contacting a biological sample with an array comprising a plurality of capture probes, wherein a capture probe of the plurality of capture probes comprises (i) a spatial barcode and (ii) a capture domain that binds to a nucleic acid encoding an immune cell receptor of the immune cell clonotype; (b) determining (i) all or a portion of the sequence of the spatial barcode or a complement thereof, and (ii) all or a portion of the sequence of the nucleic acid encoding the immune cell receptor or a complement thereof, and using the determined sequences of (i) and (ii) to determine the presence and/or abundance of the immune cell clonotype at a location in the biological sample.

Embodiment 129 is the method of embodiment 1, wherein step (b) comprises extending the capture probe using the nucleic acid encoding the immune cell receptor as a template, thereby generating an extended capture probe.

Embodiment 130 is the method of embodiment 129, wherein step (b) comprises extending a 3' end of the capture probe.

Embodiment 131 is the method of embodiment 129 or 130, wherein step (b) further comprises generating a second strand of nucleic acid that comprises (i) a sequence that is complementary to all or a portion of the spatial barcode, and (ii) a sequence that corresponds to all or a portion of the sequence of the nucleic acid encoding the immune cell receptor.

Embodiment 132 is the method of any one of embodiments 128-131, wherein the capture probe further comprises a cleavage domain, a functional domain, a unique molecular identifier, or any combination thereof.

Embodiment 133 is the method of any one embodiments 128-132, wherein the capture domain comprises a poly(T) sequence.

Embodiment 134 is the method of any one of embodiments 128-133, wherein the capture probe further comprises a functional domain.

Embodiment 135 is the method of embodiment 134, wherein step (b) further comprises generating a second strand of nucleic acid that comprises (i) a sequence that is complementary to all or a portion of the functional domain, (ii) a sequence that is complementary to all or a portion of the spatial barcode, and (iii) a sequence that corresponds to all or a portion of the sequence of the nucleic acid encoding the immune cell receptor.

Embodiment 136 is the method of embodiment 135, wherein step (b) further comprises amplifying the second strand of nucleic acid using (i) a first primer comprising all or a portion of the functional domain, wherein the functional domain is 5' to the spatial barcode in the second strand of nucleic acid, and (ii) a second primer comprising a sequence that is substantially complementary to a portion of a sequence encoding a variable region of the immune cell receptor.

Embodiment 137 is the method of any one of embodiments 128-136, wherein the immune cell clonotype is a T cell clonotype.

Embodiment 138 is the method of embodiment 137, wherein the immune cell receptor is a T cell receptor alpha chain.

Embodiment 139 is the method of embodiment 138, wherein step (b) comprises determining a sequence encoding CDR3 of the T cell receptor alpha chain.

Embodiment 140 is the method of embodiment 139, wherein step (b) further comprises determining a sequence encoding one or both of CDR1 and CDR2 of the T cell receptor alpha chain.

Embodiment 141 is the method of embodiment 139, wherein step (b) further comprises determining a sequence encoding a full-length variable domain of the T cell receptor alpha chain.

Embodiment 142 is the method of embodiment 137, wherein the immune cell receptor is a T cell receptor beta chain.

Embodiment 143 is the method of embodiment 142, wherein step (b) comprises determining a sequence encoding CDR3 of the T cell receptor beta chain.

Embodiment 144 is the method of embodiment 143, wherein step (b) further comprises determining a sequence encoding one or both of CDR1 and CDR2 of the T cell receptor beta chain.

Embodiment 145 is the method of embodiment 143, wherein step (b) further comprises determining a full-length variable domain of the T cell receptor beta chain.

Embodiment 146 is the method of any one of embodiments 128-136, wherein the immune cell clonotype is a B cell clonotype.

Embodiment 147 is the method of embodiment 146, wherein the immune cell receptor is an immunoglobulin kappa light chain.

Embodiment 148 is the method of embodiment 147, wherein step (b) comprises determining a sequence encoding CDR3 of the immunoglobulin kappa light chain.

Embodiment 149 is the method of embodiment 148, wherein step (b) further comprises determining a sequence encoding one or both of CDR1 and CDR2 of the immunoglobulin kappa light chain.

Embodiment 150 is the method of embodiment 148, wherein step (b) further comprises determining a sequence encoding a full-length variable domain of the immunoglobulin kappa light chain.

Embodiment 151 is the method of embodiment 146, wherein the immune cell receptor is an immunoglobulin lambda light chain.

Embodiment 152 is the method of embodiment 151, wherein step (b) comprises determining a sequence encoding CDR3 of the immunoglobulin lambda light chain.

Embodiment 153 is the method of embodiment 152, wherein step (b) further comprises determining a sequence encoding one or both of CDR1 and CDR2 of the immunoglobulin lambda light chain.

Embodiment 154 is the method of embodiment 152, wherein step (b) further comprises determining a sequence encoding a full-length variable domain of the immunoglobulin lambda light chain.

Embodiment 155 is the method of embodiment 146, wherein the immune cell receptor is an immunoglobulin heavy chain.

Embodiment 156 is the method of embodiment 155, wherein step (b) comprises determining a sequence encoding CDR3 of the immunoglobulin heavy chain.

Embodiment 157 is the method of embodiment 156, wherein step (b) further comprises determining a sequence encoding one or both of CDR1 and CDR2 of the immunoglobulin heavy chain.

Embodiment 158 is the method of embodiment 156, wherein step (b) further comprises determining a sequence encoding a full-length variable domain of the immunoglobulin heavy chain.

Embodiment 159 is the method of any one of embodiments 128-158, wherein the biological sample comprises a tissue sample.

Embodiment 160 is the method of embodiment 159, wherein the tissue sample is a tissue section.

Embodiment 161 is the method of embodiment 160, wherein the tissue section is a fixed tissue section.

Embodiment 162 is the method of embodiment 161, wherein the fixed tissue section is a formalin-fixed paraffin-embedded tissue section.

Embodiment 163 is the method of any one of embodiments 160-162, wherein the tissue section comprises a tumor region.

Embodiment 164 is the method of any one of embodiments 128-163, wherein the nucleic acid encoding the immune cell receptor comprises RNA.

Embodiment 165 is the method of embodiment 164, wherein the RNA is mRNA.

Embodiment 166 is the method of any one of embodiments 128-163, wherein the nucleic acid encoding the immune cell receptor comprises DNA.

Embodiment 167 is the method of embodiment 166, wherein the DNA is genomic DNA.

Embodiment 168 is the method of any one of embodiments 128-167, wherein the method further comprises, prior to step (b), contacting the biological sample with ribosomal RNA depletion probes and mitochondrial RNA depletion probes.

Embodiment 169 is the method of any one of embodiments 128-168, wherein the method further comprises imaging the biological sample.

Embodiment 170 is the method of any one of embodiments 128-169, wherein the determining in step (b) comprises sequencing (i) all or a portion of the sequence of the spatial barcode or a complement thereof, and (ii) all or a portion of the sequence of the nucleic acid encoding the immune cell receptor or a complement thereof.

Embodiment 171 is the method of any one of embodiments 128-170, wherein step (b) comprises determining the presence of the immune cell clonotype at a location in the biological sample.

Embodiment 172 is the method of any one of embodiments 128-171, wherein step (b) comprises determining the abundance of the immune cell clonotype at a location in the biological sample.

Embodiment 173 is the method of any one of embodiments 128-172, wherein step (b) comprises determining the presence and abundance of the immune cell clonotype at a location in the biological sample.

Embodiment 174 is the method of any one of embodiments 128-173, wherein step (b) comprises determining the presence of two or more immune cell clonotypes at a location in the biological sample.

Embodiment 175 is the method of any one of embodiments 128-174, wherein step (b) comprises determining the abundance of two or more immune cell clonotypes at a location in the biological sample.

Embodiment 176 is the method of any one of embodiments 128-174, wherein step (b) comprises determining the presence and abundance of two or more immune cell clonotypes at a location in the biological sample.

Embodiment 177 is the method of any one of embodiments 174-176, wherein the method further comprises comparing the two or more immune cell clonotypes.

Embodiment 178 is the method of any one of embodiments 174-177, wherein the two or more immune cell clonotypes are each a B cell clonotype.

Embodiment 179 is the method of any one of embodiments 174-177, wherein the two or more immune cell clonotypes are each a T cell clonotype.

Embodiment 180 is the method of any one of embodiments 174-177, wherein the two or more immune cell clonotypes comprise at least one T cell clonotype and at least one B cell clonotype.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

All publications, patent applications, patents, and other references mentioned herein are incorporated by reference in their entirety. In case of conflict, the present specification, including definitions, will control. In addition section headings, the materials, methods, and examples are illustrative only and not intended to be limiting.

What is claimed is:

1. A method for determining the presence of an immune cell clonotype at a location in a biological sample, the method comprising:

(a) contacting a biological sample with an array comprising a plurality of capture probes, wherein a capture probe of the plurality of capture probes comprises (i) a spatial barcode and (ii) a capture domain that hybridizes to a poly(A) sequence of a nucleic acid encoding an immune cell receptor of the immune cell clonotype;

(b) hybridizing the capture domain to the nucleic acid encoding the immune cell receptor of the immune cell clonotype;

(c) extending the capture probe using the nucleic acid encoding the immune cell receptor as a template to generate an extended capture probe comprising a sequence encoding a CDR3, or a complement thereof, of the immune cell receptor of the immune cell clonotype;

(d) hybridizing one or more probes to the extended capture probe, or a complement thereof, in a portion encoding a constant region of the immune cell receptor of the immune cell clonotype, wherein the one or more probes comprises a binding moiety capable of binding a capture moiety;
- (e) enriching the extended capture probe or the complement thereof via an interaction between the binding moiety in the one or more probes and the capture moiety; and
- (f) determining (i) the sequence of the spatial barcode or a complement thereof, and (ii) all or a portion of the sequence of the nucleic acid encoding the immune cell receptor of the immune cell clonotype or a complement thereof, and using the determined sequences of (i) and (ii) to determine the presence of the immune cell clonotype at a location in the biological sample.

2. The method of claim 1, wherein the immune cell clonotype is a T cell clonotype, the immune cell receptor of the immune cell clonotype is a T cell receptor alpha chain, and the one or more probes hybridizes to a nucleic acid sequence encoding a constant region of the T cell receptor alpha chain, or a complement thereof.

3. The method of claim 2, wherein step (f) comprises determining a sequence encoding one or more of CDR1, CDR2, and CDR3 of the T cell receptor alpha chain and, optionally, determining a sequence encoding a full-length variable domain of the T cell receptor alpha chain.

4. The method of claim 1, wherein the immune cell clonotype is a T cell clonotype, the immune cell receptor of the immune cell clonotype is a T cell receptor beta chain, and the one or more probes hybridizes to a nucleic acid sequence encoding a constant region of the T cell receptor beta chain, or a complement thereof.

5. The method of claim 4, wherein step (f) comprises determining a sequence encoding one or more of CDR1, CDR2, and CDR3 of the T cell receptor beta chain, and optionally, determining a sequence encoding a full-length variable domain of the T cell receptor beta chain.

6. The method of claim 1, wherein the immune cell clonotype is a B cell clonotype, the immune cell receptor of the immune cell clonotype is an immunoglobulin kappa light chain, and the one or more probes hybridizes to a nucleic acid sequence encoding a constant region of the immunoglobulin kappa light chain, or a complement thereof.

7. The method of claim 6, wherein step (f) comprises determining a sequence encoding one or more of CDR1, CDR2, and CDR3 of the immunoglobulin kappa light chain, and optionally, determining a sequence encoding a full-length variable domain of the immunoglobulin kappa light chain.

8. The method of claim 1, wherein the immune cell clonotype is a B cell clonotype, the immune cell receptor of the immune cell clonotype is an immunoglobulin lambda light chain, and the one or more probes hybridizes to a nucleic acid sequence encoding a constant region of the immunoglobulin lambda light chain, or a complement thereof.

9. The method of claim 8, wherein step (f) comprises determining a sequence encoding one or more of CDR1, CDR2, and CDR3 of the immunoglobulin lambda light chain, and optionally, determining a sequence encoding full-length variable domain of the immunoglobulin lambda light chain.

10. The method of claim 1, wherein the immune cell clonotype is a B cell clonotype, the immune cell receptor of the immune cell clonotype is an immunoglobulin heavy chain, and the one or more probes hybridizes to a nucleic acid sequence encoding a constant region of the immunoglobulin heavy chain, or a complement thereof.

11. The method of claim 10, wherein step (f) comprises determining a sequence encoding one or more of CDR1, CDR2, and CDR3 of the immunoglobulin heavy chain, and optionally, determining a sequence encoding a full-length variable domain of the immunoglobulin heavy chain.

12. The method of claim 1, wherein the capture domain comprises a poly(T) sequence.

13. The method of claim 1, wherein the capture probe further comprises a cleavage domain, a functional domain, a unique molecular identifier, or any combination thereof.

14. The method of claim 1, further comprising generating the complement of the extended capture probe using the extended capture probe as a template, wherein the complement of the extended capture probe comprises (i) a sequence that is complementary to the spatial barcode, and (ii) a sequence that corresponds to all or a portion of the sequence of the nucleic acid encoding the immune cell receptor of the immune cell clonotype.

15. The method of claim 14, wherein the step of generating the complement of the extended capture probe comprises use of a template switch oligonucleotide.

16. The method of claim 14, wherein the generating the complement of the extended capture probe is performed with the extended capture probe attached to the substrate.

17. The method of claim 1, wherein the binding moiety comprises biotin and the capture moiety comprises streptavidin.

18. The method of claim 1, wherein the biological sample comprises a tissue sample or a tissue section.

19. The method of claim 18, wherein the tissue section is a fresh frozen tissue section.

20. The method of claim 1, wherein the nucleic acid encoding the immune cell receptor of the immune cell clonotype comprises mRNA.

21. The method of claim 1, wherein the method further comprises imaging the biological sample.

22. The method of claim 1, wherein step (f) comprises sequencing the extended capture probe or the complement thereof to determine (i) the sequence of the spatial barcode, or the complement thereof, and (ii) all or a portion of the sequence of the nucleic acid encoding the immune cell receptor of the immune cell clonotype or the complement thereof.

23. The method of claim 22, wherein the sequencing comprises long read sequencing.

24. The method of claim 1, wherein the method comprises determining the presence of two or more immune cell clonotypes at a location in the biological sample, and optionally, wherein the method further comprises comparing the two or more immune cell clonotypes.

25. The method of claim 1, wherein the capture probe further comprises an functional domain and the method further comprises after step (e), performing a polymerase chain reaction using i) a first primer complementary to the functional domain of the capture probe, and ii) a second primer complementary to a portion of a nucleic acid sequence encoding a variable region of the immune cell receptor of the immune cell clonotype.

26. The method of claim 25, wherein the second primer is complementary to a nucleic acid sequence 5' to the sequence encoding CDR3 of the immune cell receptor of the immune cell clonotype.

27. The method of claim 25, wherein the immune cell clonotype is a T cell clonotype, and the immune cell receptor is a T cell receptor.

* * * * *